US006794518B1

(12) United States Patent
Rajopadhye et al.

(10) Patent No.: US 6,794,518 B1
(45) Date of Patent: *Sep. 21, 2004

(54) VITRONECTIN RECEPTOR ANTAGONIST PHARMACEUTICALS

(75) Inventors: Milind Rajopadhye, Westford, MA (US); Thomas D. Harris, Salem, NH (US); Edward H. Cheesman, Lunenberg, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/466,588

(22) Filed: Dec. 17, 1999

Related U.S. Application Data

(60) Provisional application No. 60/112,829, filed on Dec. 18, 1998.

(51) Int. Cl.$^7$ .................... C07D 231/54; A61K 31/416; A61K 51/04; A61M 36/00
(52) U.S. Cl. ................. 548/361.1; 548/362.1; 548/362.5; 548/364.5; 548/312.4; 548/127; 548/128; 548/131; 548/134; 548/136; 548/143; 548/146; 548/215; 544/179; 544/180; 544/182; 544/295; 544/238; 544/358; 544/336; 546/187; 546/256; 514/405; 514/241; 514/242; 514/247; 514/252.01; 514/252.12; 514/252.1; 514/256; 514/362; 514/363; 514/359; 514/365; 514/372; 514/374; 514/378; 514/379; 514/383; 514/385; 514/396
(58) Field of Search ................... 548/361.1, 362.1, 548/362.5, 364.5, 312.4, 361.2

(56) References Cited

U.S. PATENT DOCUMENTS

| 4,248,802 A | 2/1981 | Kuntz .................. 568/454 |
| 4,472,509 A | 9/1984 | Gansow et al. .............. 424/1 |

(List continued on next page.)

FOREIGN PATENT DOCUMENTS

| AU | 5314694 | 7/1994 |
| CA | 2113245 | 6/1988 |
| CA | 2039259 | 10/1991 |
| CA | 2156620 | 10/1994 |
| CA | 2232315 | 4/1997 |
| DE | 4311023 | 10/1994 |
| DE | 19536781 | 3/1997 |
| DE | 19536785 | 3/1997 |
| DE | 19725368 | 12/1998 |
| EP | 0 095 906 | 12/1983 |
| EP | 0107734 | 7/1987 |
| EP | 0359347 | 3/1990 |
| EP | 0436005 | 10/1991 |
| EP | 0606683 | 7/1994 |
| EP | 0727225 | 8/1996 |
| EP | 0 819 431 A1 | 1/1998 |
| WO | 8101145 | 4/1981 |
| WO | 9003801 | 4/1990 |
| WO | 9005539 | 5/1990 |
| WO | 9012585 | 11/1990 |
| WO | 9013300 | 11/1990 |
| WO | 9101144 | 2/1991 |
| WO | 9114460 | 10/1991 |
| WO | 9115244 | 10/1991 |
| WO | 9212729 | 8/1992 |
| WO | 9217215 | 10/1992 |
| WO | 9405328 | 4/1994 |
| WO | 9411499 | 5/1994 |
| WO | 9422497 | 10/1994 |
| WO | 9525543 | 9/1995 |
| WO | 9600574 | 1/1996 |
| WO | 9601653 | 1/1996 |
| WO | 9631243 | 10/1996 |
| WO | 9641803 | 12/1996 |
| WO | 9708145 | 3/1997 |
| WO | 9716474 | 5/1997 |
| WO | 9718207 | 5/1997 |
| WO | 9723480 | 7/1997 |
| WO | 9323074 | 9/1997 |
| WO | 9814220 | 4/1998 |
| WO | 9816256 | 4/1998 |
| WO | 9847541 | 10/1998 |

(List continued on next page.)

OTHER PUBLICATIONS

Remington's Pharmaceutical Sciences, 17$^{th}$ ed., Mack Publishing Company, Easton, PA, 1985, p. 1418.

(List continued on next page.)

*Primary Examiner*—Richard L. Raymond
*Assistant Examiner*—Venkataraman Balasubramanian
(74) *Attorney, Agent, or Firm*—Maureen P. O'Brien; Paul D. Golian; Wookcock Washburn LLP

(57) ABSTRACT

The present invention describes novel compounds of the formula:

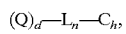

$(Q)_d$—$L_n$—$C_h$, useful for the diagnosis and treatment of cancer, methods of imaging tumors in a patient, and methods of treating cancer in a patient. The present invention also provides novel compounds useful for monitoring therapeutic angiogenesis treatment and destruction of new angiogenic vasculature. The present invention also provides novel compounds useful for imaging atherosclerosis, restenosis, cardiac ischemia, and myocardial reperfusion injury. The present invention also provides novel compounds useful for the treatment of rheumatoid arthritis. The pharmaceuticals are comprised of a targeting moiety that binds to a receptor that is upregulated during angiogenesis, an optional linking group, and a therapeutically effective radioisotope or diagnostically effective imageable moiety. The imageable moiety is a gamma ray or positron emitting radioisotope, a magnetic resonance imaging contrast agent, an X-ray contrast agent, or an ultrasound contrast agent.

3 Claims, No Drawings

U.S. PATENT DOCUMENTS

| | | | |
|---|---|---|---|
| 4,536,387 A | 8/1985 | Sakamoto et al. | 424/14 |
| 4,859,777 A | 8/1989 | Toner | 546/256 |
| 4,988,827 A | 1/1991 | Bergstein et al. | 549/551 |
| 5,021,236 A | 6/1991 | Gries et al. | 424/9 |
| 5,064,956 A | 11/1991 | Kruper et al. | 540/474 |
| 5,087,440 A | 2/1992 | Cacheris et al. | 424/9 |
| 5,155,215 A | 10/1992 | Ranney | 534/16 |
| 5,183,900 A | 2/1993 | Galardy et al. | 514/323 |
| 5,189,178 A | 2/1993 | Galardy et al. | 548/495 |
| 5,268,384 A | 12/1993 | Galardy et al. | 548/495 |
| 5,281,704 A | 1/1994 | Love et al. | 540/165 |
| 5,342,757 A | 8/1994 | Garin-Chesa et al. | 464/85.8 |
| 5,350,837 A | 9/1994 | Bridger et al. | 534/14 |
| 5,376,356 A | 12/1994 | Morgan, Jr. | 424/1.1 |
| 5,382,654 A | 1/1995 | Lyle et al. | 530/311 |
| 5,395,609 A | 3/1995 | Stuttle | 424/1.45 |
| 5,403,713 A | 4/1995 | Bevilacqua et al. | 530/391.3 |
| 5,412,148 A | 5/1995 | Keana | 424/9 |
| 5,417,959 A | 5/1995 | Wallace | 424/9 |
| 5,520,904 A | 5/1996 | Nosco et al. | 423/263 |
| 5,556,939 A | 9/1996 | Flanagan et al. | 530/311 |
| 5,567,411 A | 10/1996 | Keana et al. | 562/561 |
| 5,650,134 A | 7/1997 | Albert et al. | 424/1.69 |
| 5,659,013 A | 8/1997 | Senger et al. | 530/350 |
| 5,659,041 A | 8/1997 | Pollak et al. | 546/306 |
| 5,660,827 A | 8/1997 | Thorpe et al. | 424/152.1 |
| 5,679,810 A | 10/1997 | Love et al. | 560/171 |
| 5,696,147 A | 12/1997 | Galardy et al. | 548/495 |
| 5,760,028 A | 6/1998 | Jadhav et al. | 514/211 |
| 5,760,191 A | 6/1998 | Snow et al. | 534/10 |
| 5,766,591 A | 6/1998 | Brooks et al. | 424/1.84 |
| 5,776,427 A | 7/1998 | Thorpe et al. | 424/1.49 |
| 5,801,228 A | 9/1998 | Hollister et al. | 534/15 |
| 5,804,161 A | 9/1998 | Long et al. | 556/21 |
| 5,855,866 A | 1/1999 | Thorpe et al. | 530/391.7 |
| 5,863,538 A | 1/1999 | Thorpe et al. | 424/136.1 |
| 6,040,311 A | 3/2000 | Duggan et al. | 544/362 |
| 6,051,207 A | 4/2000 | Klaveness et al. | 424/9.1 |
| 6,051,230 A | 4/2000 | Thorpe et al. | 424/178 |
| 6,056,973 A | 5/2000 | Allen et al. | 424/450 |
| 6,143,274 A | 11/2000 | Tweedle et al. | |
| 6,322,770 B1 * | 11/2001 | Rajopadhye et al. | 548/361.1 |

FOREIGN PATENT DOCUMENTS

| | | |
|---|---|---|
| WO | 9906049 | 2/1999 |
| WO | WO 99/06347 | 2/1999 |
| WO | 9913329 | 3/1999 |
| WO | 9940947 | 8/1999 |
| WO | WO 99/58162 | 11/1999 |
| WO | WO 00/18439 | 4/2000 |
| WO | WO 00/35488 | 6/2000 |

OTHER PUBLICATIONS

Greene and Wuts, "Protective Groups in Organic Synthesis" John Wiley & Sons, New York (1991).

Batt, et al., Abstracts of papers American Chemical Society, 1998, 216, 1–3, pp MEDI 66.

J. Denekamp et al., 1982, Br. J. Cancer, 45, 136–139.

Denekamp et al., 1982, Br. J. Cancer, 46, 711–720.

Ghose et al., 1983, Meth. Enzymology, 93, 280–333.

J. Denekamp, 1984, Acta Radiologica Oncology, 23 Fasc. 4, 217–225.

Hans–Hermann Hagemeier et al., 1986, Int. J. Cancer, 38, 481–488.

Bevilacqua et al., 1987, Proc. Natl. Acad Sci., 84, 9238–9242.

Knowles et al., 1987, Analytical Biochemistry, 160, 440–443.

DiZio et al., Bioconjugate Chem., 1991, 2, 353–366.

Wellicome et al., 1990, J. Immunol, 144, 7, 2558–2565.

Juliana Denekamp, 1990, Cancer Meta. Rev. 9, 267–282.

Clauss et al., 1990, Journal of Biological Chemistry, 265, 12, 7078–7083.

Dvorak et al., 1991, Cancer Cells, 3, 77–85.

Orlando et al. J. of Biological Chemistry, Oct. 1991, 266, 29, 19543–19550.

F. J. Burrows et al, 1992, Cancer Research, 52, 5954–5962.

Mueller et al., 1992, Proc. Natl. Acad Sci USA, 89, 11832–11836.

Burrows et al., Jan. 1994, Journal of Controlled Release, 28, 1, 195–202.

Hu et al., 1994, Oncology Research, 6, 7, 321–327.

Thorpe et al., 1995, Breast Cancer Research & Treatment, 36, 2, 237–251.

Abstract, May 1995, Nucl. Med., Proceeding of the 42$^{nd}$ Annual Meeting, 36, 5, No. 287, 71P.

Horton et al., May 1997, Int. J. Biochem. Cell. Biol., 29, 5, 721–725.

Haubner, V313 Nuclear–Medizin, Mar. 1997.

Sellke et al., Drugs, 1999, 58, 3, 391–396.

DeNardo et al, Feb. 2000, Cancer Biotherapy & Radiopharm, 15, 1, 71–79.

Van Waes et al., 2000, International Journal of Oncology, 16, 1189–1195.

Batt et al., 2000, J. Med. Chem. 43, 41–58.

Baker et al., Life Sci., 1991, 49, 1583–91.

Krenning et al., Eur. J. Nucl. Med., 1993, 20. 716–31.

Krenning et al., Digestion, 1996, 57, 57–61.

Folkman, J., Nature Medicine, 1995, 1, 27–31.

O'Reilly et al., Cell, 1994, 79, 315–328.

O'Reilly et al., Cell, 1997, 88, 277–285.

(Clin. Can. Res., 1995, 1, 1623–1634).

Takeshita, S., et al., J. Clin. Invest., 1994, 93, 662–670.

Schaper, W. and Schaper, J., Collateral Circulation: Heart, Brain, Kidney, Limbs, Kluwer Academic Publishers, Boston, 1993.

Henry, T. et al., (J. Amer. College Cardiology, 1998, 31, 65A).

CRC Handbook of Chemistry and Physics, 65$^{th}$ Edition, CRS Press, Boca Raton, Fla, 1984.

Cheresh et al., Science, 1995, 270, 1500–2.

Senger, et al., Proc. Natl. Acad, Sci USA, 1997, 94, 13612–7.

Brinkley, M., Bioconjugate Chemistry, 1992, 3(1).

Margerstadt et al., Magn. Reason. Med., 1986, 3, 808.

Brechbiel, M. and Gansow, O., Bioconjugate Chem. 1991, 2, 187.

Deshpande, S., et al, J. Nucl. Med. 1990, 31, 473.

Runge et al., Radiology, 1988, 166, 835.

Bousquet et al., Radiology, 1988, 166, 693.

DeGrado and Kaiser, J. Org. Chem. 1980, 45, 1295.

Tet. Lett. 1997, 53, 11937–11952.

J. Org. Chem. 1996, 61, 903–908.

Copy of the PCT International Search Report dated Jul. 26, 2002 (PCT/US01/19794).

* cited by examiner

VITRONECTIN RECEPTOR ANTAGONIST PHARMACEUTICALS

This application claims benefit of U.S. Provisional Application No. 60/112,829, filed on Dec. 18, 1998.

FIELD OF THE INVENTION

The present invention provides novel pharmaceuticals useful for the diagnosis and treatment of cancer, methods of imaging tumors in a patient, and methods of treating cancer in a patient. The pharmaceuticals are comprised of a targeting moiety that binds to the vitronectin receptor that is expressed in tumor vasculature, an optional linking group, and a therapeutically effective radioisotope or diagnostically effective imageable moiety. The therapeutically effective radioisotope emits a gamma ray or alpha particle sufficient to be cytotoxic. The imageable moiety is a gamma ray or positron emitting radioisotope, a magnetic resonance imaging contrast agent, an X-ray contrast agent, or an ultrasound contrast agent.

BACKGROUND OF THE INVENTION

Cancer is a major public health concern in the United States and around the world. It is estimated that over 1 million new cases of invasive cancer will be diagnosed in the United States in 1998. The most prevalent forms of the disease are solid tumors of the lung, breast, prostate, colon and rectum. Cancer is typically diagnosed by a combination of in vitro tests and imaging procedures. The imaging procedures include X-ray computed tomography, magnetic resonance imaging, ultrasound imaging and radionuclide scintigraphy. Frequently, a contrast agent is administered to the patient to enhance the image obtained by X-ray CT, MRI and ultrasound, and the administration of a radiopharmaceutical that localizes in tumors is required for radionuclide scintigraphy.

Treatment of cancer typically involves the use of external beam radiation therapy and chemotherapy, either alone or in combination, depending on the type and extent of the disease. A number of chemotherapeutic agents are available, but generally they all suffer from a lack of specificity for tumors versus normal tissues, resulting in considerable side-effects. The effectiveness of these treatment modalities is also limited, as evidenced by the high mortality rates for a number of cancer types, especially the more prevalent solid tumor diseases. More effective and specific treatment means continue to be needed.

Despite the variety of imaging procedures available for the diagnosis of cancer, there remains a need for improved methods. In particular, methods that can better differentiate between cancer and other pathologic conditions or benign physiologic abnormalities are needed. One means of achieving this desired improvement would be to administer to the patient a metallopharmaceutical that localizes specifically in the tumor by binding to a receptor expressed only in tumors or expressed to a significantly greater extent in tumors than in other tissue. The location of the metallopharmaceutical could then be detected externally either by its imageable emission in the case of certain radiopharmaceuticals or by its effect on the relaxation rate of water in the immediate vicinity in the case of magnetic resonance imaging contrast agents.

This tumor specific metallopharmaceutical approach can also be used for the treatment of cancer when the metallopharmaceutical is comprised of a particle emitting radioisotope. The radioactive decay of the isotope at the site of the tumor results in sufficient ionizing radiation to be toxic to the tumor cells. The specificity of this approach for tumors minimizes the amount of normal tissue that is exposed to the cytotoxic agent and thus may provide more effective treatment with fewer side-effects.

Previous efforts to achieve these desired improvements in cancer imaging and treatment have centered on the use of radionuclide labeled monoclonal antibodies, antibody fragments and other proteins or polypeptides that bind to tumor cell surface receptors. The specificity of these radiopharmaceuticals is frequently very high, but they suffer from several disadvantages. First, because of their high molecular weight, they are generally cleared from the blood stream very slowly, resulting in a prolonged blood background in the images. Also, due to their molecular weight they do not extravasate readily at the site of the tumor and then only slowly diffuse through the extravascular space to the tumor cell surface. This results in a very limited amount of the radiopharmaceutical reaching the receptors and thus very low signal intensity in imaging and insufficient cytotoxic effect for treatment.

Alternative approaches to cancer imaging and therapy have involved the use of small molecules, such as peptides, that bind to tumor cell surface receptors. An In-111 labeled somatostatin receptor binding peptide, In-111-DTPA-D-Phe$^1$-octeotide, is in clinical use in many countries for imaging tumors that express the somatostatin receptor (Baker, et al. Life Sci., 1991, 49, 1583–91 and Krenning, et al., Eur. J. Nucl. Med., 1993, 20, 716–31). Higher doses of this radiopharmaceutical have been investigated for potential treatment of these types of cancer (Krenning, et al., Digestion, 1996, 57, 57–61). Several groups are investigating the use of Tc-99m labeled ananlogs of In-111-DTPA-D-Phe$^1$-octeotide for imaging and Re-186 labeled analogs for therapy (Flanagan, et al., U.S. Pat. No. 5,556,939, Lyle, et al., U.S. Pat. No. 5,382,654, and Albert et al., U.S. Pat. No. 5,650,134).

Angiogenesis is the process by which new blood vessels are formed from pre-existing capillaries or post capillary venules; it is an important component of a variety of physiological processes including ovulation, embryonic development, wound repair, and collateral vascular generation in the myocardium. It is also central to a number of pathological conditions such as tumor growth and metastasis, diabetic retinopathy, and macular degeneration. The process begins with the activation of existing vascular endothelial cells in response to a variety of cytokines and growth factors. Tumor released cytokines or angiogenic factors stimulate vascular endothelial cells by interacting with specific cell surface receptors for the factors. The activated endothelial cells secrete enzymes that degrade the basement membrane of the vessels. The endothelial cells then proliferate and invade into the tumor tissue. The endothelial cells differentiate to form lumens, making new vessel offshoots of pre-existing vessels. The new blood vessels then provide nutrients to the tumor permitting further growth and a route for metastasis.

Under normal conditions, endothelial cell proliferation is a very slow process, but it increases for a short period of time during embryogenesis, ovulation and wound healing. This temporary increase in cell turnover is governed by a combination of a number of growth stimulatory factors and growth suppressing factors. In pathological angiogenesis, this normal balance is disrupted resulting in continued increased endothelial cell proliferation. Some of the proangiogenic factors that have been identified include basic fibroblast growth factor (bFGF), angiogenin, TGF-alpha, TGF-beta, and vascular endothelium growth factor (VEGF). While interferon-alpha, interferon-beta and thrombospondin are examples of angiogenesis suppressors.

The proliferation and migration of endothelial cells in the extracellular matrix is mediated by interaction with a variety of cell adhesion molecules (Folkman, J., Nature Medicine, 1995, 1, 27–31). Integrins are a diverse family of heterodimeric cell surface receptors by which endothelial cells attach to the extracellular matrix, each other and other cells. The integrin $\alpha_v\beta_3$ is a receptor for a wide variety for a wide variety of extracellular matrix proteins with an exposed tripeptide Arg-Gly-Asp moiety and mediates cellular adhesion to its ligand: vitronectin, fibronectin, and fibrinogen, among others. The integrin $\alpha_v\beta_3$ is minimally expressed on normal blood vessels, but is significantly upregulated on vascular cells within a variety of human tumors. The role of the $\alpha_v\beta_3$ receptors is to mediate the interaction of the endothelial cells and the extracellular matrix and facilitate the migration of the cells in the direction of the angiogenic signal, the tumor cell population. Angiogenesis induced by bFGF or TNF-alpha depend on the agency of the integrin $\alpha_v\beta_3$, while angiogenesis induced by VEGF depends on the integrin $\alpha_v\beta_3$ (Cheresh et. al., Science, 1955, 270, 1500–2). Induction of expression of the integrins $\alpha_1\beta_1$ and $\alpha_2\beta_1$ on the endothelial cell surface is another important mechanism by which VEGF promotes angiogenesis (Senger, et. al., Proc. Natl. Acad, Sci USA, 1997, 84, 13612–7).

Angiogenic factors interact with endothelial cell surface receptors such as the receptor tyrosine kinases EGFR, FGFR, PDGFR, Flk-1/KDR, Flt-1, Tek, tie, neuropilin-1, endoglin, endosialin, and Axl. The receptors Flk-1/KDR, neuropilin-1, and Flt-1 recognize VEGF and these interactions play key roles in VEGF-induced angiogenesis. The Tie subfamily of receptor tyrosine kinases are also expressed prominently during blood vessel formation.

Because of the importance of angiogenesis to tumor growth and metastasis, a number of chemotherapeutic approaches are being developed to interfere with or prevent this process. One of these approaches, involves the use of anti-angiogenic proteins such as angiostatin and endostatin. Angiostatin is a 38 kDa fragment of plasminogen that has been shown in animal models to be a potent inhibitor of endothelial cell proliferation. (O'Reilly et. al., Cell, 1994, 79, 315–328) Endostatin is a 20 kDa C-terminal fragment of collagen XVIII that has also been shown to be a potent inhibitor. (O'Reilly et. al., Cell, 1997, 88, 277–285) Systemic therapy with endostatin has been shown to result in strong anti-tumor activity in animal models. However, human clinical trials of these two chemotherapeutic agents of biological origin have been hampered by lack of availability.

Another approach to anti-angiogenic therapy is to use targeting moieties that interact with endothelial cell surface receptors expressed in the angiogenic vasculature to which are attached chemotherapeutic agents. Burrows and Thorpe (Proc. Nat. Acad. Sci, USA, 1993, 90, 8996–9000) described the use of an antibody-immunotoxin conjugate to eradicate tumors in a mouse model by destroying the tumor vasculature. The antibody was raised against an endothelial cell class II antigen of the major histocompatibility complex and was then conjugated with the cytotoxic agent, deglycosylated ricin A chain. The same group (Clin. Can. Res., 1995, 1, 1623–1634) investigated the use of antibodies raised against the endothelial cell surface receptor, endoglin, conjugated to deglycosylated ricin A chain. Both of these conjugates exhibited potent anti-tumor activity in mouse models. However, both still suffer drawbacks to routine human use. As with most antibodies or other large, foreign proteins, there is considerable risk of immunologic toxicity which could limit or preclude administration to humans. Also, while the vasculature targeting may improve the local concentration of the attached chemotherapeutic agents, the agents still must be cleaved from the antibody carrier and be transported or diffuse into the cells to be cytotoxic.

Thus, it is desirable to provide anti-angiogenic pharmaceuticals and tumor or new vasculature imaging agents which do not suffer from poor diffusion or transportation, possible immunologic toxicity, limited availability, and/or a lack of specificity.

Another application of anti-angiogenic therapy is in treating rheumatoid arthritis (RA). In RA, the ingrowth of a highly vascularized pannus is caused by the excessive production of angiogenic factors by the infiltrating macrophages, immune cells, or inflammatory cells. Therefore, it is desirable to have new pharmaceuticals to destroy the highly vascularized pannus that results and thus treat the disease.

There is also a growing interest in therapeutic angiogenesis to improve blood flow in regions of the body that have become ischemic or poorly perfused. Several investigators are using growth factors administered locally to cause new vasculature to form either in the limbs or the heart. The growth factors VEGF and bFGF are the most common for this application. Recent publications include: Takeshita, S., et. al., J. Clin. Invest., 1994, 93, 662–670; and Schaper, W. and Schaper, J., Collateral Circulation: Heart, Brain, Kidney, Limbs, Kluwer Academic Publishers, Boston, 1993. The main applications that are under investigation in a number of laboratories are for improving cardiac blood flow and in improving peripheral vessal blood flow in the limbs. For example, Henry, T. et. al. (J. Amer. College Cardiology, 1998, 31, 65A) describe the use of recombinant human VEGF in patients for improving myocardial perfusion by therapeutic angiogenesis. Patients received infusions of rhVEGF and were monitored by nuclear perfusion imaging 30 and 60 days post treatment to determine improvement in myocardial perfusion. About 50% of patients showed improvement by nuclear perfusion imaging whereas 5/7 showed new collatoralization by angiography. Thus, it is desirable to discover a method of monitoring improved cardiac blood flow which is targeted to new collateral vessels themselves and not, as in nuclear perfusion imaging, a regional consequence of new collateral vessels.

The detection, imaging and diagnosis of a number of cardiovascular diseases need to be improved, including restenosis, atherosclerosis, myocardial reperfusion injury, and myocardial ischemia, stunning or infarction. It has recently been determined that in all of these disease conditions, the integrin receptor $\alpha_v\beta_3$ plays an important role.

For example, in the restenosis complication that occurs in ~30–50% of patients having undergone angioplasty or stent placement, neointimal hyperplasia and ultimate reocclusion is caused by aggressively proliferating vascular smooth muscle cells that express $\alpha_v\beta_3$. (Cardiovascular Res., 1997, 36, 408–428; DDT, 1997, 2, 187–199; Current Pharm. Design, 1997, 3, 545–584).

Atherosclerosis proceeds from an intial endothelial damage that results in the recruitment and subintimal migration of monocytes at the site of the injury. Growth factors are released which induce medial smooth muscle cells to proliferate and migrate to the intimal layer. The migrating smooth muscle cells express $\alpha_v\beta_3$.

In reperfusion injury, neutrophil transmigration is integrin dependent and the integrins moderate initial infiltration into the viable border zone. The induction of $\alpha_5\beta_1$, $\alpha_4\beta_1$ and $\alpha_v\beta_5$ in infiltrating neutrophils occurs within 3 to 5 hours after reperfusion as neutrophils move from the border zone to the area of necrosis. (Circulation, 1999, 100, I-275).

Acute or chronic occlusion of a coronary artery is known to result in angiogenesis in the heart as native collateral vessels are recruited to attempt to relieve the ischemia. However, even a gradual occlusion usually results in areas of infarction as the resulting angiogenesis is not sufficient to prevent damage. Cardiac angiogenesis has been associated with increased expression of the growth factors VEGF and FGF and the upregulation of the growth factor receptors flt-1 and flk-1/KDR. (Drugs, 1999, 58, 391–396).

SUMMARY OF THE INVENTION

It is one object of the present invention to provide improved anti-angiogenic pharmaceuticals, comprised of a targeting moiety that binds to the vitronectin receptor that is expressed in tumor neovasculature, an optional linking group, and a radioisotope. The vitronectin receptor binding compounds target the radioisotope to the tumor neovasculature. The beta or alpha-particle emitting radioisotope emits a cytotoxic amount of ionizing radiation which results in cell death. The penetrating ability of radiation obviates the requirement that the cytotoxic agent diffuse or be transported into the cell to be cytotoxic.

It is another object of the present invention to provide pharmaceuticals to treat rheumatoid arthritis. These pharmaceuticals comprise a targeting moiety that binds to a receptor that is upregulated during angiogenesis, an optional linking group, and a radioisotope that emits cytotoxic radiation (i.e., beta particles, alpha particles and Auger or Coster-Kronig electrons). In rheumatoid arthritis, the ingrowth of a highly vascularized pannus is caused by the excessive production of angiogenic factors by the infiltrating macrophages, immune cells, or inflammatory cells. Therefore, the radiopharmaceuticals of the present invention that emit cytotoxic radiation could be used to destroy the new angiogenic vasculature that results and thus treat the disease.

It is another object of the present invention to provide imaging agents, comprised of vitronectin receptor binding compounds conjugated to an imageable moiety, such as a gamma ray or positron emitting radioisotope, a magnetic resonance imaging contrast agent, an X-ray contrast agent, or an ultrasound contrast agent. These imaging agents are useful for imaging tumor neovasculature, therapeutic angiogenesis interventions in the heart, natural angiogenic processes in response to acute or chronic coronary vessel occlusion, restenosis post-angioplasty, atherosclerosis and plaque formation, and reperfusion injury.

It is another object of the present invention to provide compounds useful for preparing the pharmaceuticals of the present invention. These compounds are comprised of a non-peptide indazole containing targeting moiety that binds to a receptor that is upregulated during angiogenesis or during cardiovascular diseases, Q, an optional linking group, $L_n$, and a metal chelator or bonding moiety, $C_h$. The compounds may have one or more protecting groups attached to the metal chelator or bonding moiety. The protecting groups provide improved stability to the reagents for long-term storage and are removed either immediately prior to or concurrent with the synthesis of the radiopharmaceuticals. Alternatively, the compounds of the present invention are comprised of a peptide or peptidomimetic targeting moiety that binds to a receptor that is upregulated during angiogenesis or during cardiovascular diseases, Q, an optional linking group, $L_n$, and a surfactant, $S_f$.

The pharmaceuticals of the present invention may be used for diagnostic and/or therapeutic purposes. Diagnostic radiopharmaceuticals of the present invention are pharmaceuticals comprised of a diagnostically useful radionuclide (i.e., a radioactive metal ion that has imageable gamma ray or positron emissions). Therapeutic radiopharmaceuticals of the present invention are pharmaceuticals comprised of a therapeutically useful radionuclide, a radioactive metal ion that emits ionizing radiation such as beta particles, alpha particles and Auger or Coster-Kronig electrons.

The pharmaceuticals comprising a gamma ray or positron emitting radioactive metal ion are useful for imaging tumors and by gamma scintigraphy or positron emission tomography. The pharmaceuticals comprising a gamma ray or positron emitting radioactive metal ion are also useful for imaging therapeutic angiogenesis, natural angiogenic processes in response to acute or chronic coronary vessel occlusion, restenosis post-angioplasty, atherosclerosis and plaque formation, and reperfusion injury by gamma scintigraphy or positron emission tomography. The pharmaceuticals comprising a particle emitting radioactive metal ion are useful for treating cancer by delivering a cytotoxic dose of radiation to the tumors. The pharmaceuticals comprising a particle emitting radioactive metal ion are also useful for treating rheumatoid arthritis by destroying the formation of angiogenic vasculature. The pharmaceuticals comprising a paramagnetic metal ion are useful as magnetic resonance imaging contrast agents. The pharmaceuticals comprising one or more X-ray absorbing or "heavy" atoms of atomic number 20 or greater are useful as X-ray contrast agents. The pharmaceuticals comprising a microbubble of a biocompatible gas, a liquid carrier, and a surfactant microsphere, are useful as ultrasound contrast agents.

DETAILED DESCRIPTION OF THE INVENTION

Thus, in a first embodiment, the present invention provides a novel compound, comprising: a targeting moiety and a chelator, wherein the targeting moiety is bound to the chelator, is a indazole nonpeptide, and binds to a receptor that is upregulated during angiogenesis and the compound has 0–1 linking groups between the targeting moiety and chelator.

In a preferred embodiment, the receptor is the integrin $\square_v\square_3$ or $\square_v\square_5$ and the compound is of the formula:

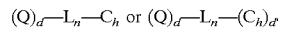

wherein,

Q is independently a compound of Formula (Ia) or (Ib):

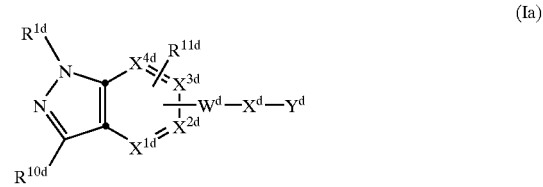

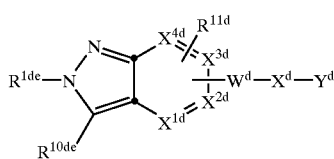

(Ib)

including stereoisomeric forms thereof, or mixtures of stereoisomeric forms thereof, or pharmaceutically acceptable salt or prodrug forms thereof wherein:

$X^{1d}$ is N, CH, C—$W^d$—$X^d$—$Y^d$, or C—$L_n$;

$X^{2d}$ is N, CH, or C—$W^d$—$X^d$—$Y^d$;

$X^{3d}$ is N, $CR^{11d}$, or C—$W^d$—$X^d$—$Y^d$;

$X^{4d}$ is N or $CR^{11d}$;

provided that when $R^{1d}$ is $R^{1de}$ then one of $X^{1d}$ and $X^{2d}$ is C—$W^d$—$X^d$—$Y^d$, and when $R^{10d}$ is $R^{1de}$ then $X^{3d}$ is C—$W^d$—$X^d$—$Y^d$;

$R^{1d}$ is selected from: $R^{1de}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{1de}$ is selected from:

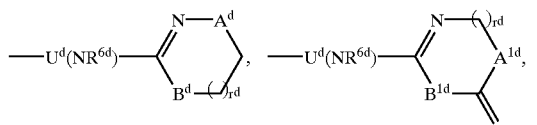

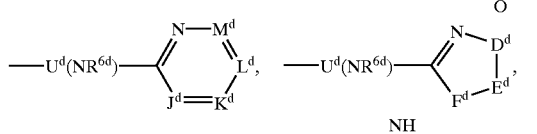

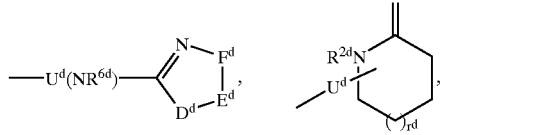

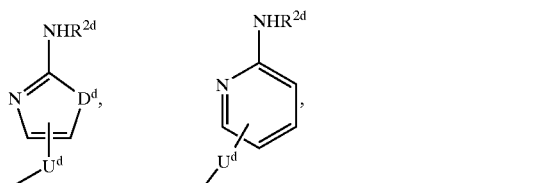

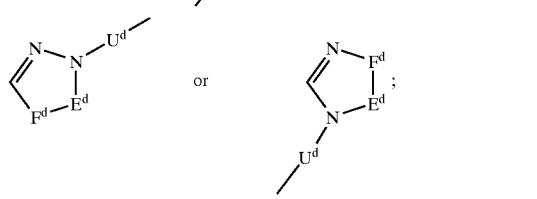

$A^d$ and $B^d$ are independently —$CH_2$—, —O—, —N($R^{2d}$)—, or —C(=O)—;

$A^{1d}$ and $B^{1d}$ are independently —$CH_2$— or —N($R^{3d}$)—;

$D^d$ is —N($R^{2d}$)—, —O—, —S—, —C(=O)— or —$SO_2$—;

$E^d$–$F^d$ is —C($R^{4d}$)=C($R^{5d}$)—, —N=C($R^{4d}$)—, —C($R^{4d}$)=N—, or —C($R^{4d}$)$_2$C($R^{5d}$)$_2$—;

$J^d$, $K^d$, $L^d$ and $M^d$ are independently selected from —C($R^{4d}$)—, —C($R^{5d}$)— and —N—, provided that at least one of $J^d$, $K^d$, $L^d$ and $M^d$ is not —N—;

$R^{2d}$ is selected from: H, $C_1$–$C_6$ alkyl, ($C_1$–$C_6$ alkyl)carbonyl, ($C_1$–$C_6$ alkoxy)carbonyl; ($C_1$–$C_6$ alkyl)aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl($C_1$–$C_6$ alkyl)-, ($C_1$–$C_6$ alkyl)carbonyl-, arylcarbonyl-, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group: $C_1$–$C_4$ alkyl, $C_1$–$C_4$ alkoxy, halo, $CF_3$, and nitro;

$R^{3d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;

$R^{4d}$ and $R^{5d}$ are independently selected from: H, $C_1$–$C_4$ alkoxy, $NR^{2d}R^{3d}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl)carbonyl, ($C_1$–$C_6$ alkoxy)carbonyl, and arylcarbonyl, or alternatively, when substituents on adjacent atoms, $R^{4d}$ and $R^{5d}$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, and $NO_2$;

$U^d$ is selected from: —$(CH_2)_n^d$—, —$(CH_2)_n^d$ $(CR^{7d}$=$CR^{8d})(CH_2)_m^d$—, —$(CH_2)_n^d$(C≡C) $(CH_2)_m^d$—, —$(CH_2)_t^d Q(CH_2)_m^d$—, —$(CH_2)_n^d$O $(CH_2)_m^d$—, —$(CH_2)_n^d N(R^{6d})(CH_2)_m^d$—, —$(CH_2)_n^d C$ (=O)$(CH_2)_m^d$—, —$(CH_2)_n^d$(C=O)N($R^{6d}$)$(CH_2)_m^d$—, —$(CH_2)_n^d N(R^{6d})$(C=O)$(CH_2)_m^d$—, and —$(CH_2)_n^d S$ $(O)_p^d(CH_2)_m^d$—;

wherein one or more of the methylene groups in $U^d$ is optionally substituted with $R^{7d}$;

$Q^d$ is selected from 1,2-cycloalkylene, 1,2-phenylene, 1,3-phenylene, 1,4phenylene, 2,3-pyridinylene, 3,4-pyridinylene, 2,4-pyridinylene, and 3,4-pyridazinylene;

$R^{6d}$ is selected from: H, $C_1$–$C_4$ alkyl, and benzyl;

$R^{7d}$ and $R^{8d}$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_0$–$C_6$ alkyl)-;

$R^{10d}$ is selected from: H, $R^{1de}$, $C_1$–$C_4$ alkoxy substituted with 0–1 $R^{21d}$, N($R^{6d}$)$_2$, halogen, $NO_2$, CN, $CF_3$, $CO_2R^{17d}$, C(=O)$R^{17d}$, $CONR^{17d}R^{20d}$, —$SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{10de}$ is selected from: H, $C_1$–$C_4$ alkoxy substituted with 0–1 $R^{21d}$, N($R^{6d}$)$_2$, halogen, $NO_2$, CN, $CF_3$, $CO_2R^{17d}$, C(=O)$R^{17d}$, $CONR^{17d}R^{20d}$, —$SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1

R$^{15d}$ or 0–1 R$^{21d}$, C$_3$–C$_7$ cycloalkyl substituted with 0–1 R$^{15d}$ or 0–1 R$^{21d}$, C$_1$–C$_{11}$ cycloalkylalkyl substituted with 0–1 R$^{15d}$ or 0–1 R$^{21d}$, aryl substituted with 0–1 R$^{15d}$ or 0–2 R$^{11d}$ or 0–1 R$^{21d}$, and aryl(C$_1$–C$_6$ alkyl)- substituted with 0–1 R$^{15d}$ or 0–2 R$^{11d}$ or 0–1 R$^{21d}$;

R$^{11d}$ is selected from H, halogen, CF$_3$, CN, NO$_2$, hydroxy, NR$^{2d}$R$^{3d}$, C$_1$–C$_4$ alkyl substituted with 0–1 R$^{21d}$, C$_1$–C$_4$ alkoxy substituted with 0–1 R$^{21d}$, aryl substituted with 0–1 R$^{21d}$, aryl(C$_1$–C$_6$ alkyl)- substituted with 0–1 R$^{21d}$, (C$_1$–C$_4$ alkoxy)carbonyl substituted with 0–1 R$^{21d}$, (C$_1$–C$_4$ alkyl)carbonyl substituted with 0–1 R$^{21d}$, C$_1$–C$_4$ alkylsulfonyl substituted with 0–1 R$^{21d}$, and C$_1$–C$_4$ alkylaminosulfonyl substituted with 0–1 R$^{21d}$;

W$^d$ is selected from: —(C(R$^{12d}$)$_2$)$_q{}^d$C(=O)N(R$^{13d}$)—, and —C(=O)—N(R$^{13d}$)—(C(R$^{12d}$)$_2$)$_q{}^d$—;

X$^d$ is —C(R$^{12d}$)(R$^{14d}$)—C(R$^{12d}$)(R$^{15d}$)—; or alternatively, W$^d$ and X$^d$ can be taken together to be

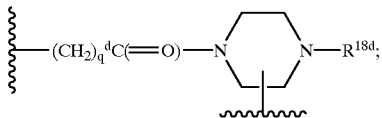

R$^{12d}$ is selected from H, halogen, C$_1$–C$_6$ alkyl, C$_2$–C$_6$ alkenyl, C$_2$–C$_6$ alkynyl, C$_3$–C$_7$ cycloalkyl, C$_4$–C$_{10}$ cycloalkylalkyl, (C$_1$–C$_4$ alkyl)carbonyl, aryl, and aryl (C$_1$–C$_6$ alkyl)-;

R$^{13d}$ is selected from H, C$_1$–C$_6$ alkyl, C$_3$–C$_7$ cycloalkylmethyl, and aryl(C$_1$–C$_6$ alkyl)-;

R$^{14d}$ is selected from: H, C$_1$–C$_6$ alkylthio(C$_1$–C$_6$ alkyl)-, aryl(C$_1$–C$_{10}$ alkylthioalkyl)-, aryl(C$_1$–C$_{10}$ alkoxyalkyl)-, C$_1$–C$_{10}$ alkyl, C$_1$–C$_{10}$ alkoxyalkyl, C$_1$–C$_6$ hydroxyalkyl, C$_2$–C$_{10}$ alkenyl, C$_2$–C$_{10}$ alkynyl, C$_3$–C$_{10}$ cycloalkyl, C$_3$–C$_{10}$ cycloalkylalkyl, aryl (C$_1$–C$_6$ alkyl)-, heteroaryl(C$_1$–C$_6$ alkyl)-, aryl, heteroaryl, CO$_2$R$^{17d}$, C(=O)R$^{17d}$, and CONR$^{17d}$R$^{20d}$, provided that any of the above alkyl, cycloalkyl, aryl or heteroaryl groups may be unsubstituted or substituted independently with 0–1 R$^{16d}$ or 0–2 R$^{11d}$;

R$^{15d}$ is selected from: H, R$^{16d}$, C$_1$–C$_{10}$ alkyl, C$_1$–C$_{10}$ alkoxyalkyl, C$_1$–C$_{10}$ alkylaminoalkyl, C$_1$–C$_{10}$ dialkylaminoalkyl, (C$_1$–C$_{10}$ alkyl)carbonyl, aryl (C$_1$–C$_6$ alkyl)carbonyl, C$_1$–C$_{10}$ alkenyl, C$_1$–C$_{10}$ alkynyl, C$_3$–C$_{10}$ cycloalkyl, C$_3$–C$_{10}$ cycloalkylalkyl, aryl(C$_1$–C$_6$ alkyl)-, heteroaryl(C$_1$–C$_6$ alkyl)-, aryl, heteroaryl, CO$_2$R$^{17d}$, C(=O)R$^{17d}$, CONR$^{17d}$R$^{20d}$, SO$_2$R$^{17d}$, and SO$_2$NR$^{17d}$R$^{20d}$, provided that any of the above alkyl, cycloalkyl, aryl or heteroaryl groups may be unsubstituted or substituted independently with 0–2 R$^{11d}$;

Y$^d$ is selected from: —COR$^{19d}$, —SO$_3$H, —PO$_3$H, tetrazolyl, —CONHNHSO$_2$CF$_3$, —CONHSO$_2$R$^{17d}$, —CONHSO$_2$NHR$^{17d}$, —NHCOCF$_3$, —NHCONHSO$_2$R$^{17d}$, —NHSO$_2$R$^{17d}$, —OPO$_3$H$_2$, —OSO$_3$H, —PO$_3$H$_2$, —SO$_3$H, —SO$_2$NHCOR$^{17d}$, —SO$_2$NHCO$_2$R$^{17d}$,

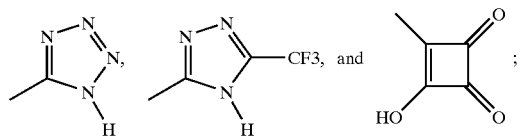

R$^{16d}$ is selected from: —N(R$^{20d}$)—C(=O)—O—R$^{17d}$, —N(R$^{20d}$)—C(=O)—R$^{17d}$, —N(R$^{20d}$)—C(=O)—NH—R$^{17d}$, —N(R$^{20d}$)SO$_2$—R$^{17d}$, and —N(R$^{20d}$)SO$_2$—NR$^{20d}$R$^{17d}$;

R$^{17d}$ is selected from: C$_1$–C$_{10}$ alkyl optionally substituted with a bond to L$_n$, C$_3$–C$_{11}$ cycloalkyl optionally substituted with a bond to L$_n$, aryl(C$_1$–C$_6$ alkyl)- optionally substituted with a bond to L$_n$, (C$_1$–C$_6$ alkyl)aryl optionally substituted with a bond to L$_n$, heteroaryl (C$_1$–C$_6$ alkyl)- optionally substituted with a bond to L$_n$, (C$_1$–C$_6$ alkyl)heteroaryl optionally substituted with a bond to L$_n$, biaryl(C$_1$–C$_6$ alkyl)- optionally substituted with a bond to L$_n$, heteroaryl optionally substituted with a bond to L$_n$, aryl optionally substituted with a bond to L$_n$, biaryl optionally substituted with a bond to L$_n$, and a bond to L$_n$, wherein said aryl, biaryl or heteroaryl groups are also optionally substituted with 0–3 substituents selected from the group consisting of: C$_1$–C$_4$ alkyl, C$_1$–C$_4$ alkoxy, aryl, heteroaryl, halo, cyano, amino, CF$_3$, and NO$_2$;

R$^{18d}$ is selected from: —H, —C(=O)—O—R$^{17d}$, —C(=O)—R$^{17d}$, —C(=O)—NH—R$^{17d}$, —SO$_2$—R$^{17d}$, and —SO$_2$—NR$^{20d}$R$^{17d}$;

R$^{19d}$ is selected from: hydroxy, C$_1$–C$_{10}$ alkyloxy, C$_3$–C$_{11}$ cycloalkyloxy, aryloxy, aryl(C$_1$–C$_6$ alkoxy)-, C$_3$–C$_{10}$ alkylcarbonyloxyalkyloxy, C$_3$–C$_{10}$ alkoxycarbonyloxyalkyloxy, C$_2$–C$_{10}$ alkoxycarbonylalkyloxy, C$_5$–C$_{10}$ cycloalkylcarbonyloxyalkyloxy, C$_5$–C$_{10}$ cycloalkoxycarbonyloxyalkyloxy, C$_5$–C$_{10}$ cycloalkoxycarbonylalkyloxy, C$_7$–C$_{11}$ aryloxycarbonylalkyloxy, C$_8$–C$_{12}$ aryloxycarbonyloxyalkyloxy, C$_8$–C$_{12}$ arylcarbonyloxyalkyloxy, C$_5$–C$_{10}$ alkoxyalkylcarbonyloxyalkyloxy, C$_5$–C$_{10}$ (5-alkyl-1,3-dioxa-cyclopenten-2-one-yl)methyloxy, C$_{10}$–C$_{14}$ (5-aryl-1,3-dioxa-cyclopenten-2-one-yl)methyloxy, and (R$^{11d}$)(R$^{12d}$)N—(C$_1$–C$_{10}$ alkoxy)-;

R$^{20d}$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, and heteroaryl(C$_1$–C$_6$ alkyl);

R$^{21d}$ is selected from: COOH and NR$^{6d}{}_2$;

m$^d$ is 0–4;

n$^d$ is 0–4;

t$^d$ is 0–4;

p$^d$ is 0—2;

q$^d$ is 0—2; and r$^d$ is 0—2;

with the following provisos:

(1) t$^d$, n$^d$, m$^d$ and q$^d$ are chosen such that the number of atoms connecting R$^{1d}$ and Y$^d$ is in the range of 10–14; and (2) n$^d$ and m$^d$ are chosen such that the value of n$^d$ plus m$^d$ is greater than one unless U$^d$ is —(CH$_2$)$_t{}^d$Q$^d$ (CH$_2$)$_m{}^d$—;

or Q is a peptide selected from the group:

R$^1$ is L-valine, D-valine or L-lysine optionally substituted on the ε amino group with a bond to L$_n$;

R$^2$ is L-phenylalanine, D-phenylalanine, D-1-naphthylalanine, 2-aminothiazole-4-acetic acid or tyrosine, the tyrosine optionally substituted on the hydroxy group with a bond to L$_n$;

R$^3$ is D-valine;

R$^4$ is D-tyrosine substituted on the hydroxy group with a bond to L$_n$;

provided that one of R$^1$ and R$^2$ in each Q is substituted with a bond to L$_n$, and further provided that when R$^2$ is 2-aminothiazole-4-acetic acid, K is N-methylarginine;

provided that at least one Q is a compound of Formula (Ia) or (Ib);

d is selected from 1, 2, 3, 4, 5, 6, 7, 8, 9, and 10;

d' is 1–100;

L$_n$ is a linking group having the formula:

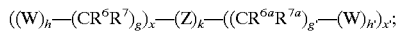

W is independently selected at each occurrence from the group: O, S, NH, NHC(=O), C(=O)NH, NR$^8$C(=O), C(=O)N R$^8$, C(=O), C(=O)O, OC(=O), NHC(=S)NH, NHC(=O)NH, SO$_2$, SO$_2$NH, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;

aa is independently at each occurrence an amino acid;

Z is selected from the group: aryl substituted with 0–3 R$^{10}$, C$_{3-10}$ cycloalkyl substituted with 0–3 R$^{10}$, and a 5–10 membered heterocyclic ring system containing 1–4 heteroatoms independently selected from N, S, and O and substituted with 0–3 R$^{10}$;

R$^6$, R$^{6a}$, R$^7$, R$^{7a}$, and R$^8$ are independently selected at each occurrence from the group: H, =O, COOH, SO$_3$H, PO$_3$H, C$_1$–C$_5$ alkyl substituted with 0–3 R$^{10}$, aryl substituted with 0–3 R$^{10}$, benzyl substituted with 0–3 R$^{10}$, and C$_1$–C$_5$ alkoxy substituted with 0–3 R$^{10}$, NHC(=O)R$^{11}$, C(=O)NHR$^{11}$, NHC(=O)NHR$^{11}$, NHR$^{11}$, R$^{11}$, and a bond to C$_h$;

R$^{10}$ is independently selected at each occurrence from the group: a bond to C$_h$, COOR$^{11}$, C(=O)NHR$^{11}$, NHC(=O)R$^{11}$, OH, NHR$^{11}$, SO$_3$H, PO$_3$H, —OPO$_3$H$_2$, —OSO$_3$H, aryl substituted with 0–3 R$^{11}$, C$_{1-5}$ alkyl substituted with 0–1 R$^{12}$, C$_{1-5}$ alkoxy substituted with 0–1 R$^{12}$, and a 5–10 membered heterocyclic ring system containing 1–4 heteroatoms independently selected from N, S, and O and substituted with 0–3 R$^{11}$;

R$^{11}$ is independently selected at each occurrence from the group: H, alkyl substituted with 0–1 R$^{12}$, aryl substituted with 0–1 R$^{12}$, a 5–10 membered heterocyclic ring system containing 1–4 heteroatoms independently selected from N, S, and O and substituted with 0–1 R$^{12}$, C$_{3-10}$ cycloalkyl substituted with 0–1 R$^{12}$, polyalkylene glycol substituted with 0–1 R$^{12}$, carbohydrate substituted with 0–1 R$^{12}$, cyclodextrin substituted with 0–1 R$^{12}$, amino acid substituted with 0–1 R$^{12}$, polycarboxyalkyl substituted with 0–1 R$^{12}$, polyazaalkyl substituted with 0–1 R$^{12}$, and peptide substituted with 0–1 R$^{12}$, wherein the peptide is comprised of 2–10 amino acids, 3,6-O-disulfo-B-D-galactopyranosyl, bis(phosphonomethyl)glycine, and a bond to C$_h$;

R$^{12}$ is a bond to C$_h$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

C$_h$ is a metal bonding unit having a formula selected from the group:

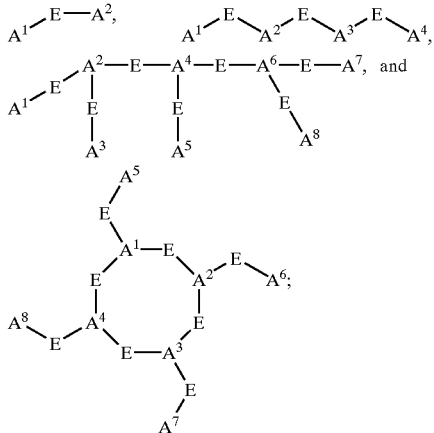

A$^1$, A$^2$, A$^3$, A$^4$, A$^5$, A$^6$, A$^7$, and A$^8$ are independently selected at each occurrence from the group: NR$^{13}$, NR$^{13}$R$^{14}$, S, SH, S(Pg), O, OH, PR$^{13}$, PR$^{13}$R$^{14}$, P(O)R$^{15}$R$^{16}$, and a bond to L$_n$;

E is a bond, CH, or a spacer group independently selected at each occurrence from the group: C$_1$–C$_{10}$ alkyl substituted with 0–3 R$^{17}$, aryl substituted with 0–3 R$^{17}$, C$_{3-10}$ cycloalkyl substituted with 0–3 R$^{17}$, heterocyclo-C$_{1-10}$ alkyl substituted with 0–3 R$^{17}$, wherein the heterocyclo group is a 5–10 membered heterocyclic ring system containing 1–4 heteroatoms independently selected from N, S, and O, C$_{6-10}$ aryl-C$_{1-10}$ alkyl substituted with 0–3 R$^{17}$, C$_{1-10}$ alkyl-C$_{6-10}$ aryl- substituted with 0–3 R$^{17}$, and a 5–10 membered heterocyclic ring system containing 1–4 heteroatoms independently selected from N, S, and O and substituted with 0–3 R$^{17}$;

R$^{13}$ and R$^{14}$ are each independently selected from the group: a bond to L$_n$, hydrogen, C$_1$–C$_{10}$ alkyl substituted with 0–3 R$^{17}$, aryl substituted with 0–3 R$^{17}$, C$_{1-10}$ cycloalkyl substituted with 0–3 R$^{17}$, heterocyclo-C$_{1-10}$ alkyl substituted with 0–3 R$^{17}$, wherein the heterocyclo group is a 5–10 membered heterocyclic ring system containing 1–4 heteroatoms independently selected from N, S, and O, C$_{6-10}$ aryl-C$_{1-10}$ alkyl substituted with 0–3 R$^{17}$, C$_{1-10}$ alkyl-C$_{6-10}$ aryl- substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form $=C(R^{20})(R^{21})$;

$R^{15}$ and $R^{16}$ are each independently selected from the group: a bond to $L_n$, —OH, $C_1$–$C_{10}$ alkyl substituted with 0–3 $R^{17}$, $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl- substituted with 0–3 $R^{17}$, and a 5–10 membered heterocyclic ring system containing 1–4 heteroatoms independently selected from N, S, and O and substituted with 0–3 $R^{17}$;

$R^{17}$ is independently selected at each occurrence from the group: a bond to $L_n$, =O, F, Cl, Br, I, —$CF_3$, —CN, —$CO_2R^{18}$, —$C(=O)R^{18}$, —$C(=O)N(R^{18})_2$, —CHO, —$CH_2OR^{18}$, —$OC(=O)R^{18}$, —$OC(=O)OR^{18a}$, —$OR^{18}$, —$OC(=O)N(R^{18})_2$, —$NR^{19}C(=O)R^{18}$, —$NR^{19}C(=O)OR^{18a}$, —$NR^{19}C(=O)N(R^{18})_2$, —$NR^{19}SO_2N(R^{18})_2$, —$NR^{19}SO_2R^{18a}$, —$SO_3H$, —$SO_2R^{18a}$, —$SR^{18}$, —$S(=O)R^{18a}$, —$SO_2N(R^{18})_2$, —$N(R^{18})_2$, —$NHC(=S)NHR^{18}$, =$NOR^{18}$, $NO_2$, —$C(=O)NHOR^{18}$, —$C(=O)NHNR^{18}R^{18a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{18}$, and a 5–10 membered heterocyclic ring system containing 1–4 heteroatoms independently selected from N, S, and O;

$R^{18}$, $R^{18a}$, and $R^{19}$ are independently selected at each occurrence from the group: a bond to $L_n$, H, $C_1$–$C_6$ alkyl, phenyl, benzyl, $C_1$–$C_6$ alkoxy, halide, nitro, cyano, and trifluoromethyl;

Pg is a thiol protecting group;

$R^{20}$ and $R^{21}$ are independently selected from the group: H, $C_1$–$C_{10}$ alkyl, —CN, —$CO_2R^{25}$, —$C(=O)R^{25}$, —$C(=O)N(R^{25})_2$, $C_2$–$C_{10}$ 1-alkene substituted with 0–3 $R^{23}$, $C_2$–$C_{10}$ 1-alkyne substituted with 0–3 $R^{23}$, aryl substituted with 0–3 $R^{23}$, unsaturated 5–10 membered heterocyclic ring system containing 1–4 heteroatoms independently selected from N, S, and O and substituted with 0–3 $R^{23}$, and unsaturated $C_{3-10}$ carbocycle substituted with 0–3 $R^{23}$;

alternatively, $R^{20}$ and $R^{21}$, taken together with the divalent carbon radical to which they are attached form:

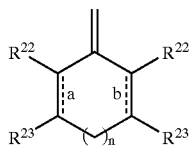

$R^{22}$ and $R^{23}$ are independently selected from the group: H, $R^{24}$, $C_1$–$C_{10}$ alkyl substituted with 0–3 $R^{24}$, $C_2$–$C_{10}$ alkenyl substituted with 0–3 $R^{24}$, $C_2$–$C_{10}$ alkynyl substituted with 0–3 $R^{24}$, aryl substituted with 0–3 $R^{24}$, a 5–10 membered heterocyclic ring system containing 1–4 heteroatoms independently selected from N, S, and O and substituted with 0–3 $R^{24}$, and $C_{3-10}$ carbocycle substituted with 0–3 $R^{24}$;

alternatively, $R^{22}$, $R^{23}$ taken together form a fused aromatic or a 5–10 membered heterocyclic ring system containing 1–4 heteroatoms independently selected from N, S, and O;

a and b indicate the positions of optional double bonds and n is 0 or 1;

$R^{24}$ is independently selected at each occurrence from the group: =O, F, Cl, Br, I, —$CF_3$, —CN, —$CO_2R^{25}$, —$C(=O)R^{25}$, —$C(=O)N(R^{25})_2$, —$N(R^{25})_3^+$, —$CH_2OR^{25}$, —$OC(=O)R^{25}$, —$OC(=O)OR^{25a}$, —$OR^{25}$, —$OC(=O)N(R^{25})_2$, —$NR^{26}C(=O)R^{25}$, —$NR^{26}C(=O)OR^{25a}$, —$NR^{26}C(=O)N(R^{25})_2$, —$NR^{26}SO_2N(R^{25})_2$, —$NR^{26}SO_2R^{25a}$, —$SO_3H$, —$SO_2R^{25a}$, —$SR^{25}$, —$S(=O)R^{25a}$, —$SO_2N(R^{25})_2$, —$N(R^{25})_2$, =$NOR^{25}$, —$C(=O)NHOR^{25}$, —$OCH_2CO_2H$, and 2-(1-morpholino)ethoxy; and, $R^{25}$, $R^{25a}$, and $R^{26}$ are each independently selected at each occurrence from the group: hydrogen and $C_1$–$C_6$ alkyl.

In a more preferred embodiment, the present invention provides a compound wherein:

$R^{1de}$ is selected from:

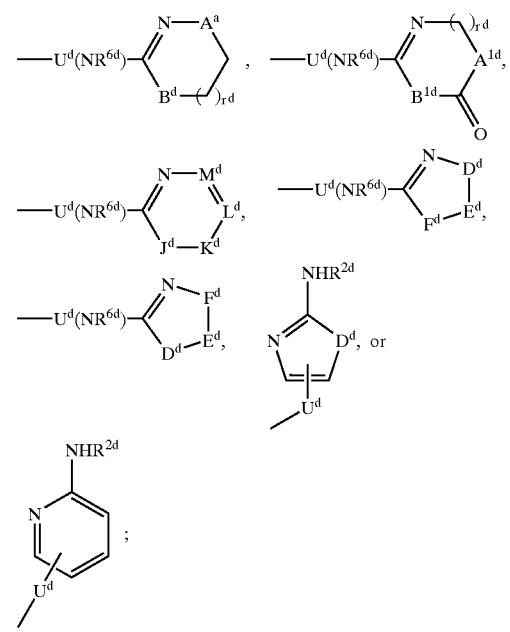

$A^d$ and $B^d$ are independently —$CH_2$—, —O—, —$N(R^{2d})$—, or —$C(=O)$—;

$A^{1d}$ and $B^{1d}$ are independently —$CH_2$— or —$N(R^{3d})$—;

D is —$N(R^{2d})$—, —O—, —S—, —$C(=O)$— or —$SO_2$—;

$E^d$—$F^d$ is —$C(R^{4d})=C(R^{5d})$—, —N=$C(R^{4d})$—, —$C(R^{4d})$=N—, or —$C(R^{4d})_2C(R^{5d})_2$—;

$J^d$, $K^d$, $L^d$ and $M^d$ are independently selected from: $C(R^{4d})$—, —$C(R^{5d})$— and —N—, provided that at least one of $J^d$, $K^d$, $L^d$ and $M^d$ is not —N—;

$R^{2d}$ is selected from: H, $C_1$–$C_6$ alkyl, ($C_1$–$C_6$ alkyl)carbonyl, ($C_1$–$C_6$ alkoxy)carbonyl, $C_1$–$C_6$ alkylaminocarbonyl, $C_3$–$C_6$ alkenyl, $C_3$–$C_7$ cycloalkyl, $C_4$–$C_{11}$ cycloalkylaLkyl, aryl, heteroaryl($C_1$–$C_6$ alkyl) carbonyl, heteroarylcarbonyl, aryl($C_1$–$C_6$ alkyl)-, ($C_1$–$C_6$ alkyl)carbonyl, arylcarbonyl, alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{3d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;

$R^{4d}$ and $R^{5d}$ are independently selected from: H, $C_1$–$C_4$ alkoxy, $NR^{2d}R^{3d}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, $C_2$–$C_7$ alkylcarbonyl, and arylcarbonyl;

alternatively, when substituents on adjacent atoms, $R^{4d}$ and $R^{5d}$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

$U^d$ is selected from: —$(CH_2)_n{}^d$—, —$(CH_2)_n{}^d(CR^{7d}{=}CR^{8d})(CH_2)_m{}^d$—, —$(CH_2)_t{}^dQ^d(CH_2)_m{}^d$—, —$(CH_2)_n{}^dO(CH_2)_m{}^d$—, —$(CH_2)_n{}^dN(R^{6d})(CH_2)_m{}^d$—, —$(CH_2)_n{}^dC({=}O)(CH_2)_m{}^d$—, and —$(CH_2)_n{}^dS(O)_p{}^d(CH_2)_m{}^d$—;

wherein one or more of the methylene groups in $U^d$ is optionally substituted with $R^{7d}$;

$Q^d$ is selected from 1,2-phenylene, 1,3-phenylene, 2,3-pyridinylene, 3,4-pyridinylene, and 2,4-pyridinylene;

$R^{6d}$ is selected from: H, $C_1$–$C_4$ alkyl, and benzyl;

$R^{7d}$ and $R^{8d}$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_0$–$C_6$ alkyl)-;

$W^d$ is —$C({=}O)$—$N(R^{13d})$—$(C(R^{12d})_2)_q{}^d$—;

$X^d$ is —$C(R^{12d})(R^{14d})$—$C(R^{12d})(R^{15d})$—;

alternatively, $W^d$ and $X^d$ can be taken together to be

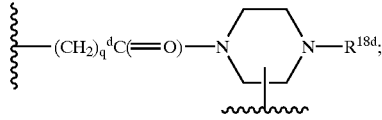

$R^{12d}$ is H or $C_1$–$C_6$ alkyl;

$Y^d$ is selected from: —$COR^{19d}$, —$SO_3H$,

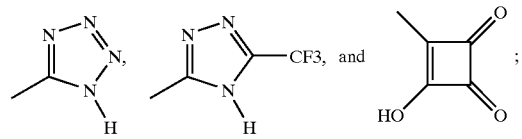

d is selected from 1, 2, 3, 4, and 5;

d' is 1–50;

W is independently selected at each occurrence from the group: O, NH, NHC(=O), C(=O)NH, $NR^8C$(=O), C(=O)N $R^8$, C(=O), C(=O)O, OC(=O), NHC(=S) NH, NHC(=O)NH, $SO_2$, $(OCH_2CH_2)_s$, $(CH_2CH_2O)_{s'}$, $(OCH_2CH_2CH_2)_{s''}$, $(CH_2CH_2CH_2O)_t$, and $(aa)_{t'}$;

aa is independently at each occurrence an amino acid;

Z is selected from the group: aryl substituted with 0–1 $R^{10}$, $C_{3–10}$ cycloalkyl substituted with 0–1 $R^{10}$, and a 5–10 membered heterocyclic ring system containing 1–4 heteroatoms independently selected from N, S, and O and substituted with 0–1 $R^{10}$;

$R^6$, $R^{6a}$, $R^7$, $R^{7a}$, and $R^8$ are independently selected at each occurrence from the group: H, =O, COOH, $SO_3H$, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)$R^{11}$, C(=O)NH$R^{11}$, NHC(=O)NH$R^{11}$, NH$R^{11}$, $R^{11}$, and a bond to $C_n$;

k is 0 or 1;

s is selected from 0, 1, 2, 3, 4, and 5;

s' is selected from 0, 1, 2, 3, 4, and 5;

s" is selected from 0, 1, 2, 3, 4, and 5;

t is selected from 0, 1, 2, 3, 4, and 5;

$A^1$, $A^2$, $A^3$, $A^4$, $A^5$, $A^6$, $A^7$, and $A^8$ are independently selected at each occurrence from the group: $NR^{13}$, $NR^{13}R^{14}$, S, SH, S(Pg), OH, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3–10}$ cycloalkyl substituted with 0–3 $R^{17}$, and a 5–10 membered heterocyclic ring system containing 1–4 heteroatoms independently selected from N, S, and O and substituted with 0–3 $R^{17}$;

$R^{13}$ and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form =$C(R^{20})(R^{21})$;

$R^{17}$ is independently selected at each occurrence from the group: a bond to $L_n$, =O, F, Cl, Br, I, —$CF_3$, —CN, —$CO_2R^{18}$, —C(=O)$R^{18}$, —C(=O)N($R^{18}$)$_2$, —$CH_2OR^{18}$, —OC(=O)$R^{18}$, —OC(=O)O$R^{18a}$, —O$R^{18}$, —OC(=O)N($R^{18}$)$_2$, —$NR^{19}$C(=O)$R^{18}$, —$NR^{19}$C(=O)O$R^{18a}$, —$NR^{19}$C(=O)N($R^{18}$)$_2$, —$NR^{19}SO_2N(R^{18})_2$, —$NR^{19}SO_2R^{18a}$, —$SO_3H$, —$SO_2R^{18a}$, —S(=O)$R^{18a}$, —$SO_2N(R^{18})_2$, —N($R^{18}$)$_2$, —NHC(=S)NH$R^{18}$, =NO$R^{18}$, —C(=O) NHN$R^{18}R^{18a}$, —$OCH_2CO_2H$, and 2-(1-morpholino) ethoxy;

$R^{18}$, $R^{18a}$, and $R^{19}$ are independently selected at each occurrence from the group: a bond to $L_n$, H, and $C_1$–$C_6$ alkyl;

$R^{20}$ and $R^{21}$ are independently selected from the group: H, $C_1$–$C_5$ alkyl, —$CO_2R^{25}$, $C_2$–$C_5$ 1-alkene substituted with 0–3 $R^{23}$, $C_2$–$C_5$ 1-alkyne substituted with 0–3 $R^{23}$, aryl substituted with 0–3 $R^{23}$, and unsaturated 5–10 membered heterocyclic ring system containing 1–4 heteroatoms independently selected from N, S, and O and substituted with 0–3 $R^{23}$;

alternatively, $R^{20}$ and $R^{21}$, taken together with the divalent carbon radical to which they are attached form:

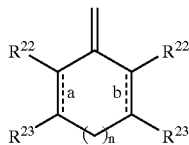

$R^{22}$ and $R^{23}$ are independently selected from the group: H, and $R^{24}$;

alternatively, $R^{22}$, $R^{23}$ taken together form a fused aromatic or a 5–10 membered heterocyclic ring system containing 1–4 heteroatoms independently selected from N, S, and O;

$R^{24}$ is independently selected at each occurrence from the group: $-CO_2R^{25}$, $-C(=O)N(R^{25})_2$, $-CH_2OR^{25}$, $-OC(=O)R^{25}$, $-OR^{25}$, $-SO_3H$, $-N(R^{25})_2$, and $-OCH_2CO_2H$; and, $R^{25}$ is independently selected at each occurrence from the group: H and $C_1$–$C_3$ alkyl.

In an even more preferred embodiment, the present invention provides a compound wherein:

$R^{10de}$ is selected from:

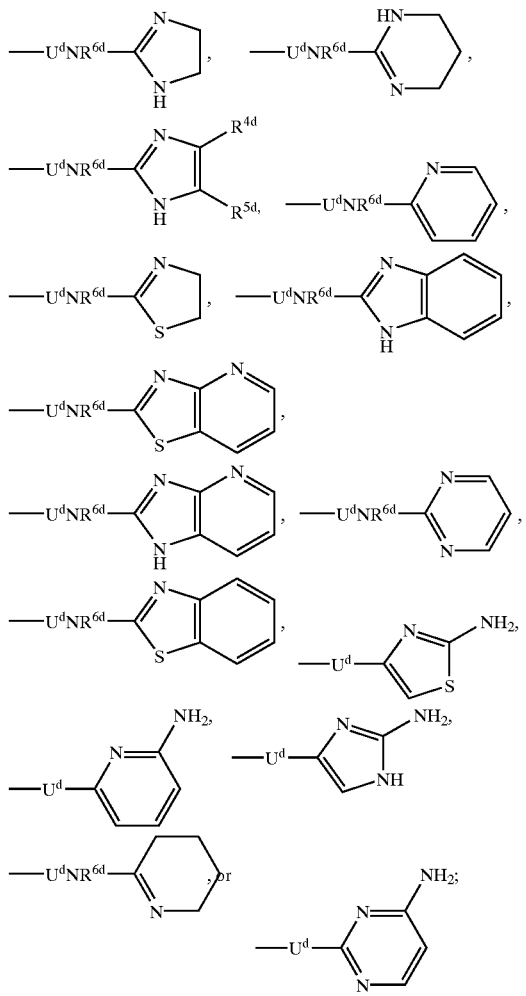

wherein the above heterocycles are optionally substituted with 0–2 substituents selected from the group: $NH_2$, halogen, $NO_2$, CN, $CF_3$, $C_1$–$C_4$ alkoxy, $C_1$–$C_6$ alkyl, and $C_3$–$C_7$ cycloalkyl;

$U^d$ is $-(CH_2)_{n^d}-$, $-(CH_2)_{t^d}Q^d(CH_2)_{m^d}-$ or $-C(=O)(CH_2)_{n^d-1}-$, wherein one of the methylene groups is optionally substituted with $R^{7d}$;

$R^{7d}$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, and heteroaryl($C_1$–$C_6$ alkyl);

$R^{10d}$ is selected from: H, $R^{1de}$, $C_1$–$C_4$ alkoxy substituted with 0–1 $R^{21d}$, halogen, $CO_2R^{17d}$, $CONR^{17d}R^{20d}$, $C_1$–$C_6$ alkyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{10de}$ is selected from: H, $C_1$–$C_4$ alkoxy substituted with 0–1 $R^{21d}$, halogen, $CO_2R^{17d}$, $CONR^{17d}R^{20d}$, $C_1$–$C_6$ alkyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$W^d$ is $-C(=O)-N(R^{13d})-$;

$X^d$ is $-CH(R^{14d})-CH(R^{15d})-$;

$R^{13d}$ is H or $CH_3$;

$R^{14d}$ is selected from: H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15d}$ is H or $R^{16d}$;

$Y^d$ is $-COR^{19d}$;

$R^{19d}$ is selected from: hydroxy, $C_1$–$C_{10}$ alkoxy, methylcarbonyloxymethoxy-, ethylcarbonyloxymethoxy-, t-butylcarbonyloxymethoxy-, cyclohexylcarbonyloxymethoxy-, 1-(methylcarbonyloxy)ethoxy-, 1-(ethylcarbonyloxy)ethoxy-, 1-(t-butylcarbonyloxy)ethoxy-, 1-(cyclohexylcarbonyloxy)ethoxy-, i-propyloxycarbonyloxymethoxy-, t-butyloxycarbonyloxymethoxy-, 1-(i-propyloxycarbonyloxy)ethoxy-, 1-(cyclohexyloxycarbonyloxy)ethoxy-, 1-(t-butyloxycarbonyloxy)ethoxy-, dimethylaminoethoxy-, diethylaminoethoxy-, (5-methyl-1,3-dioxacyclopenten-2-on-4-yl)methoxy-, (5-(t-butyl)-1,3-dioxacyclopenten-2-on-4-yl)methoxy-, (1,3-dioxa-5-phenyl-cyclopenten-2-on-4-yl)methoxy-, and 1-(2-(2-methoxypropyl)carbonyloxy)ethoxy-;

$R^{20d}$ is H or $CH_3$;

$m^d$ is 0 or 1;

$n^d$ is 1–4;

$t^d$ is 0 or 1;

$C_h$ is

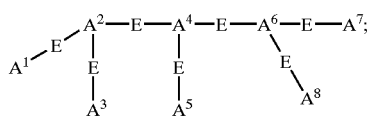

$A^1$ is selected from the group: OH, and a bond to $L_n$;

$A^2$, $A^4$, and $A^6$ are each N;

$A^3$, $A^5$, and $A^8$ are each OH;

$A^7$ is a bond to $L_n$ or NH-bond to $L_n$;

E is a $C_2$ alkyl substituted with 0–1 $R^{17}$;

$R^{17}$ is $=O$;

alternatively, $C_h$ is

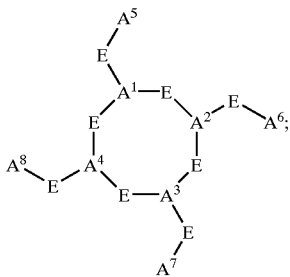

$A^1$ is selected from the group: OH and a bond to $L_n$;
$A^2$, $A^3$ and $A^4$ are each N;
$A^5$, $A^6$ and $A^8$ are each OH;
$A^7$ is a bond to $L_n$;
E is a $C_2$ alkyl substituted with 0–1 $R^{17}$;
$R^{17}$ is =O;
alternatively, $C_h$ is

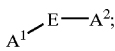

$A^1$ is $NH_2$ or $N=C(R^{20})(R^{21})$;
E is a bond;
$A^2$ is $NHR^{13}$;
$R^{13}$ is a heterocycle substituted with $R^{17}$, the heterocycle being selected from pyridine and pyrimidine;
$R^{17}$ is selected from a bond to $L_n$, $C(=O)NHR^{18}$ and $C(=O)R^{18}$;
$R^{18}$ is a bond to $L_n$;
$R^{24}$ is selected from the group: $-CO_2R^{25}$, $-OR^{25}$, $-SO_3H$, and $-N(R^{25})_2$; and,
$R^{25}$ is independently selected at each occurrence from the group: hydrogen and methyl.

In another even more preferred embodiment, the present invention provides a compound wherein:
$R^{1de}$ is selected from:

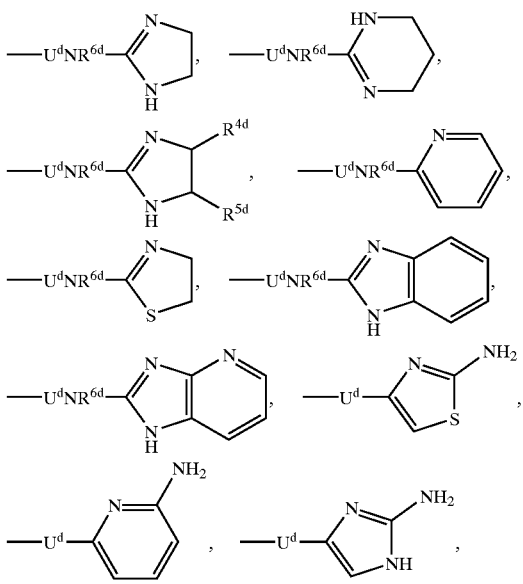

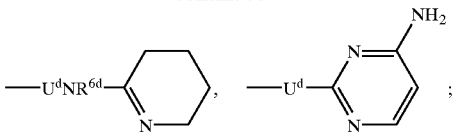

wherein the above heterocycles are optionally substituted with 0–2 substituents selected from the group: $NH_2$, halogen, $NO_2$, CN, $CF_3$, $C_1$–$C_4$ alkoxy, $C_1$–$C_6$ alkyl, and $C_3$–$C_7$ cycloalkyl.

In another preferred embodiment, the present invention provides a compound selected from the group:

2-(((4-(4-(((3-(2-(2-(3-((6-((1-aza-2-(2-sulfophenyl) vinyl)amino)(3-pyridyl))carbonylamino)propoxy) ethoxy)ethoxy)propyl)amino)sulfonyl)phenyl)phenyl) sulfonyl)amino)-3-((1-(3-(imidazole-2-ylamino) propyl)(1H-indazol-5-yl))carbonylamino)propanoic acid;

2-(2-aza-2-((5-(N-(1,3-bis(3-(2-(2-(3-(((4-(4-(((1-carboxy-2-((1-(3-(imidazol-2-ylamino)propyl)(1H-indazol-5-yl))carbonylamino)ethyl)amino)sulfonyl) phenyl)phenyl)sulfonyl)amino)propoxy)ethoxy) ethoxy)propyl)carbamoyl)propyl)carbamoyl)(2-pyridyl))amino)vinyl)benzenesulfonic acid;

2-((6-((1-aza-2-(sulfophenyl)vinyl)amino)(3-pyridyl)) carbonylamino)-4-(N-(3-(2-(2-(3-(((4-(4-(((1-carboxy-2-((1-(3-(imidazol-2-ylamino)propyl)(1H-indazol-5-yl))carbonylamino)ethyl)amino)sulfonyl)phenyl) phenyl)sulfonyl)amino)propoxy)ethoxy)ethoxy) propyl)carbamoyl)butanoic acid;

3-((1-(3-(imidazole-2-ylamino)propyl)(1H-indazol-5-yl)) carbonylamino)-2-(((4-(4-(((3-(2-(2-(3-(2-(1,4,7,10-tetraaza-4,7,10-tris(carboxyrnethyl)cyclododecyl) acetylamino)propoxy)ethoxy)ethoxy)propyl)amino) sulfonyl)phenyl)phenyl)sulfonyl)amino)propanoic acid;

2-(6-((6-((1-aza-2-(2-sulfophenyl)vinyl)-amino)(3-pyridyl))carbonylamino)hexanoylamino)-3-((1-(3-(imidazol-2-ylamino)propyl)(1H-indazol-5-yl)) carbonylamino)-propanoic acid;

2-((6-((1-aza-2-(2-sulfophenyl)vinyl)-amino)(3-pyridyl)) carbonylamino)-3-((1-(3-(imidazol-2-ylamino)propyl) (1H-indazol-5-yl))carbonylamino)propanoic acid;

[2-[[[5-[carbonyl]-2-pyridinyl]hydrazono]methyl]-benzenesulfonic acid]-Glu(2-(6-aminohexanoylamino)-3-((1-(3-(imidazol-2-ylaminopropyl)(1H-indazol-5-yl))carbonylamino) propanoic acid)(2-(6-aminohexanoylamino)-3-((1-(3-(imidazol-2-ylamino)propyl)(1H-indazol-5-yl)) carbonyl-amino)propanoic acid);

[2-[[[5-[carbonyl]-2-pyridinyl]hydrazono]methyl]-benzenesulfonic acid]-Glu-bis-[Glu(2-(6-Aminohexanoylamino)-3-((1-(3-(imidazol-2-ylamino) propyl)(1H-indazol-5-yl))carbonylamino)propanoic acid)(2-(6-aminohexanoylamino)-3-((1-(3-(imidazol-2-ylamino)propyl)(1H-indazol-5-yl))carbonyl-amino) propanoic acid)];

2-(1,4,7,10-tetraaza-4,7,10-tris(carboxyrnethyl)-1-cyclododecyl)acetyl-{2-(6-aminohexanoylamino)-3-((1-(3-(imidazol-2-ylamino)propyl)(1H-indazol-5-yl)) carbonylamino)propanoic acid};

2-(1,4,7,10-tetraaza-4,7,10-tris(carboxymethyl)-1-cyclododecyl)acetyl-Glu{2-(6-Aminohexanoylamino)-3-((1-(3-(imidazol-2-ylamino)propyl)(1H-indazol-5-yl))carbonylamino)propanoic acid}{2-(6-Aminohexanoylamino)-3-(1-(3-(imidazol-2-ylamino) propyl)(1H-indazol-5-yl))carbonyl-amino)propanoic acid};

21
22
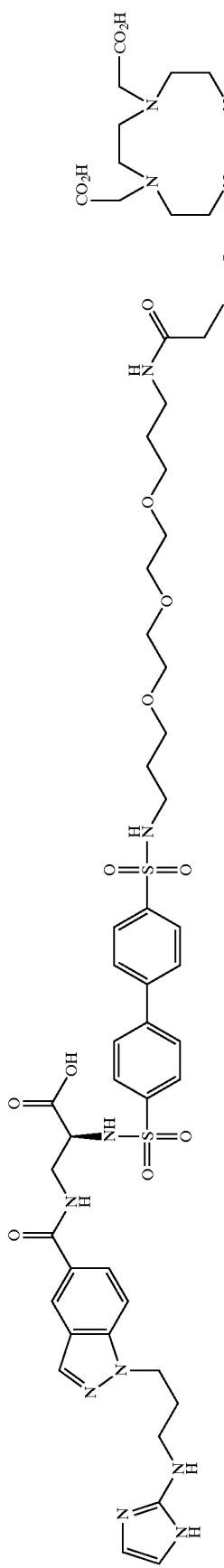
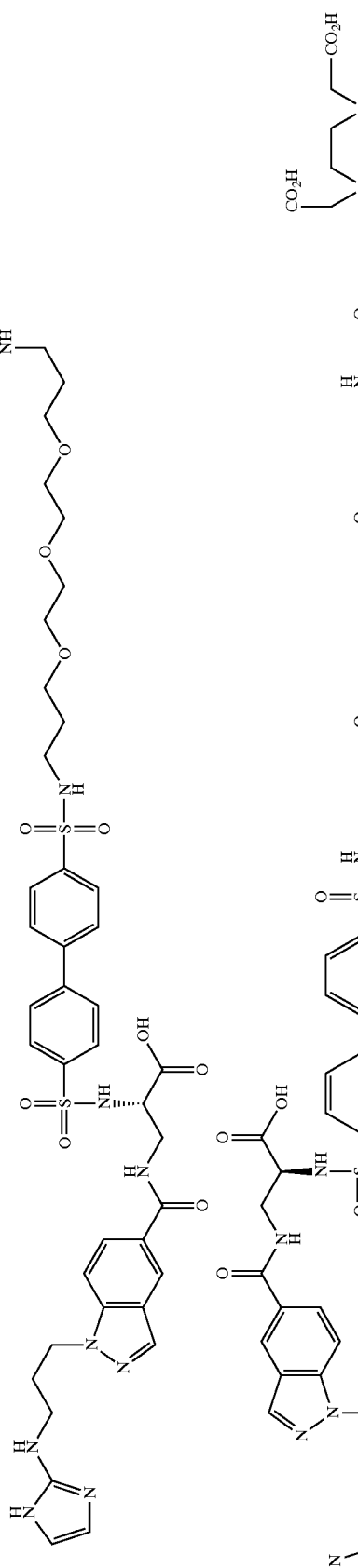
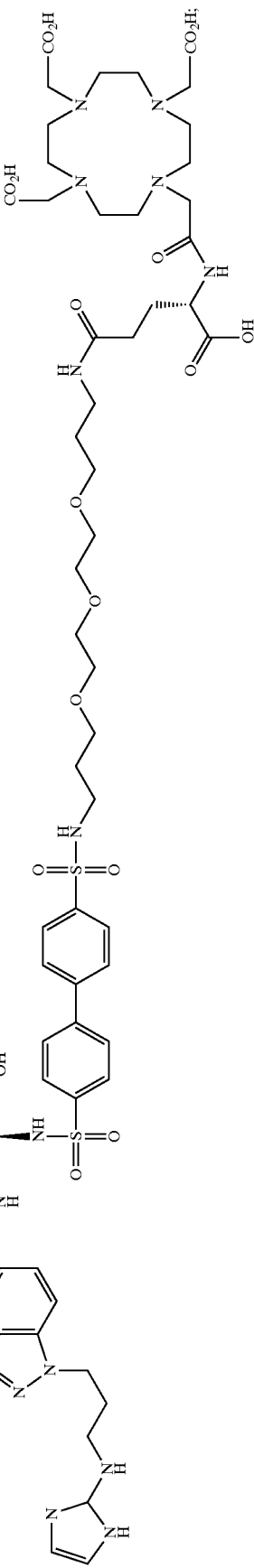

-continued
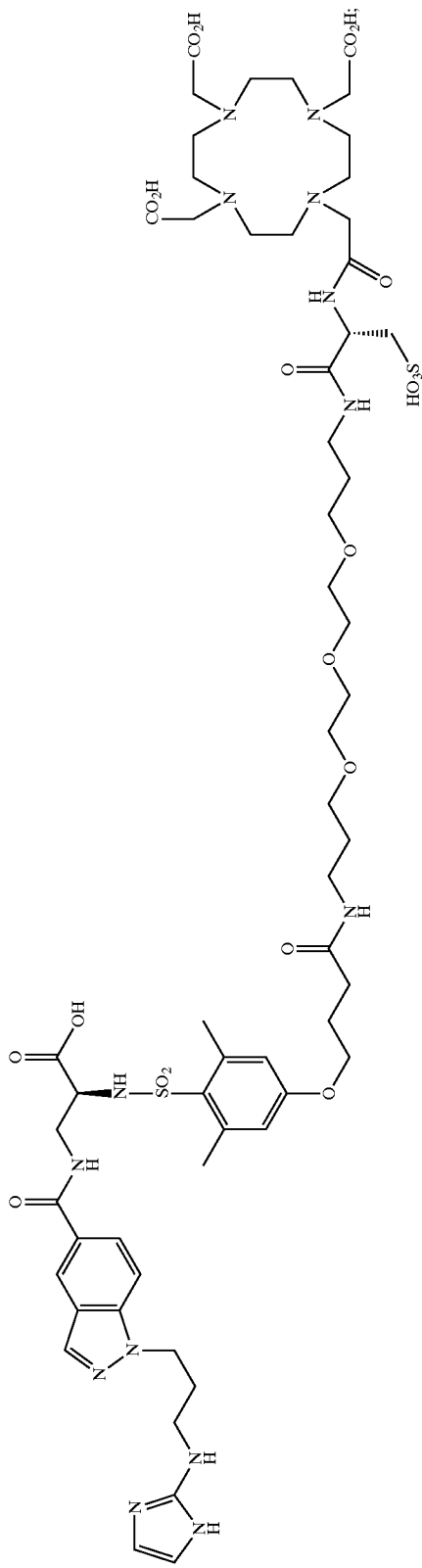
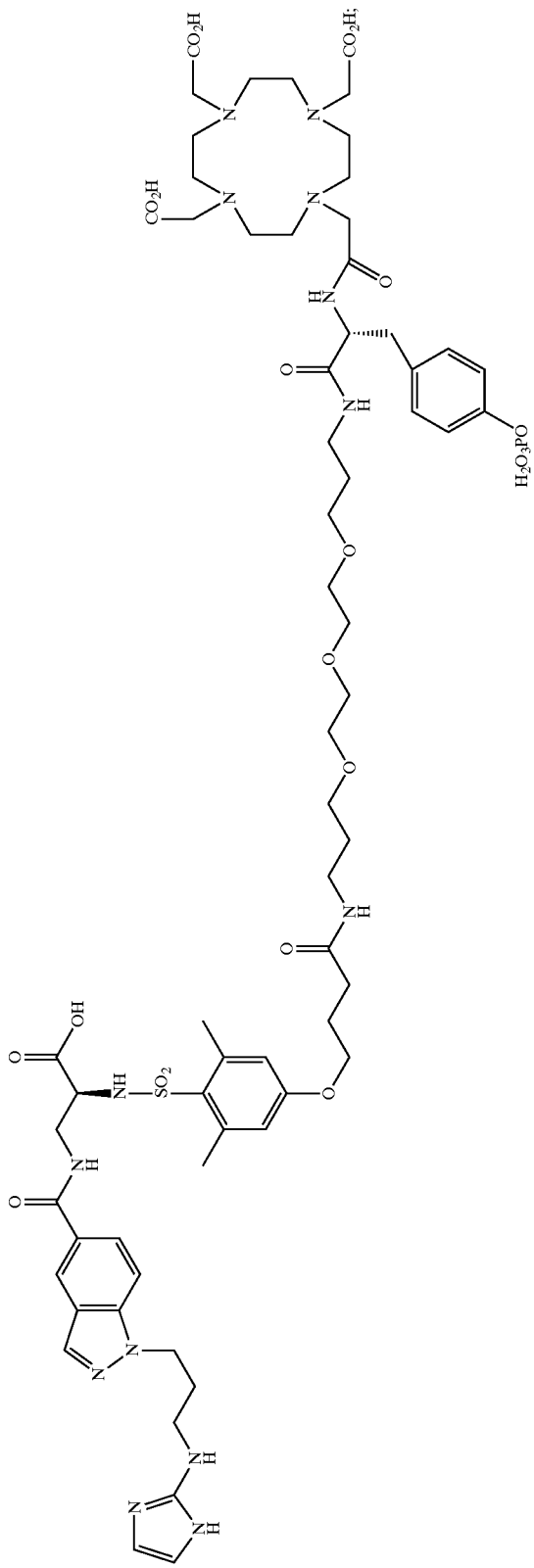

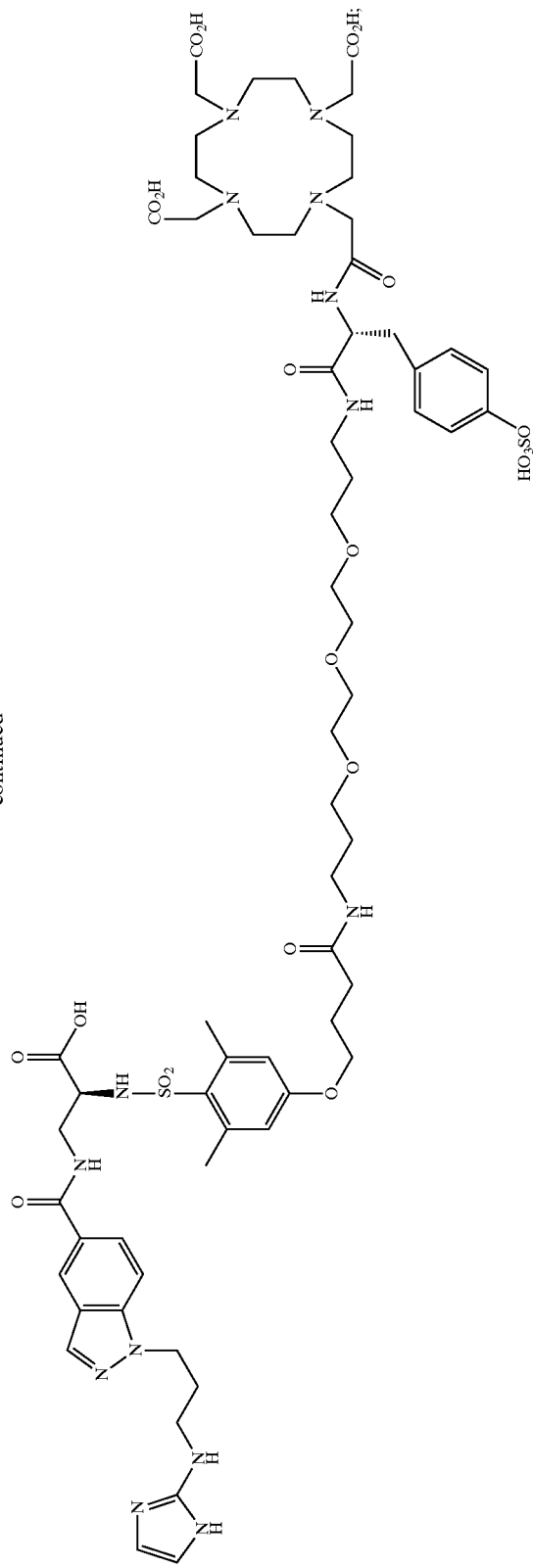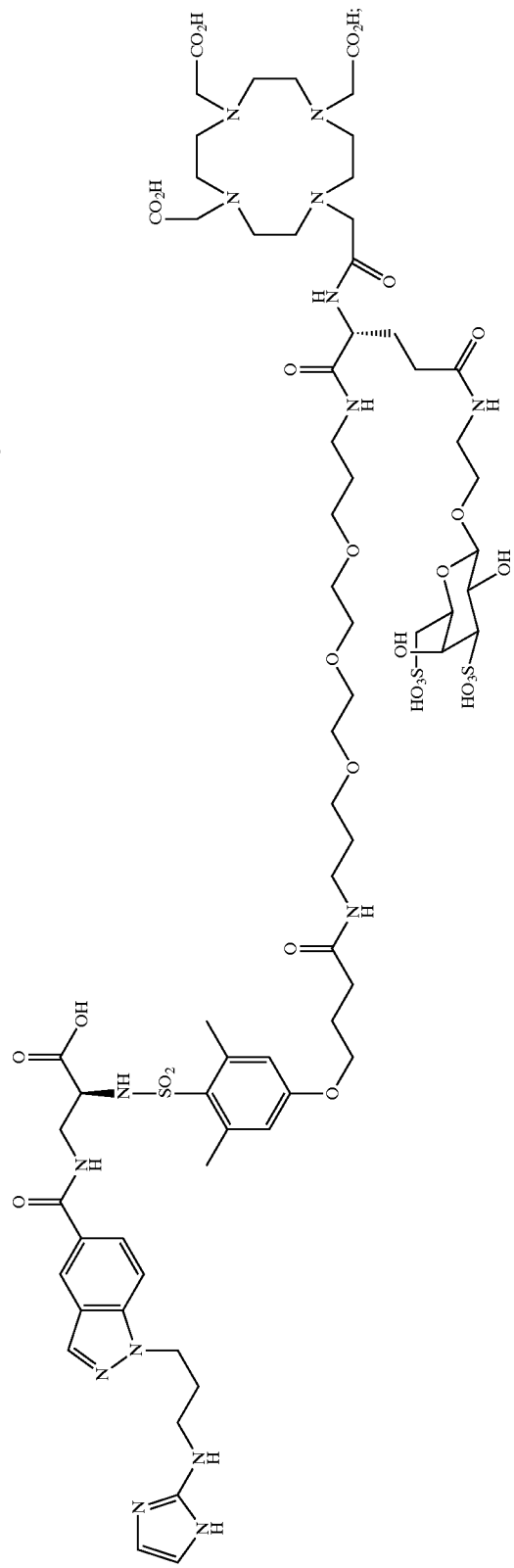

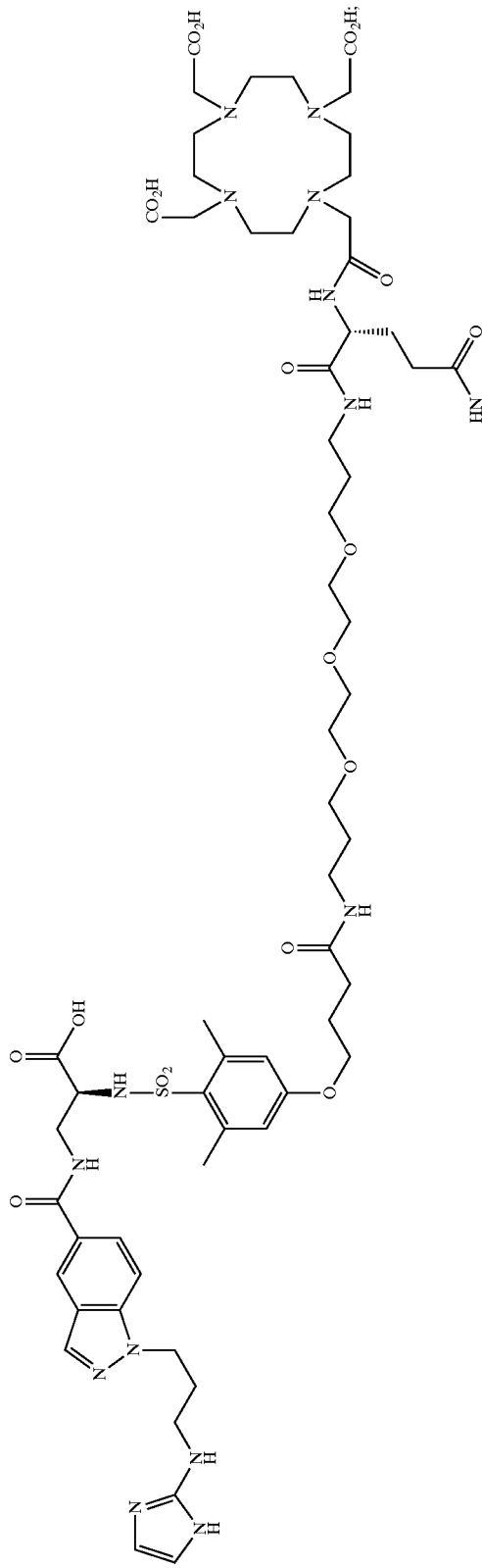
β-Cyclodextrin
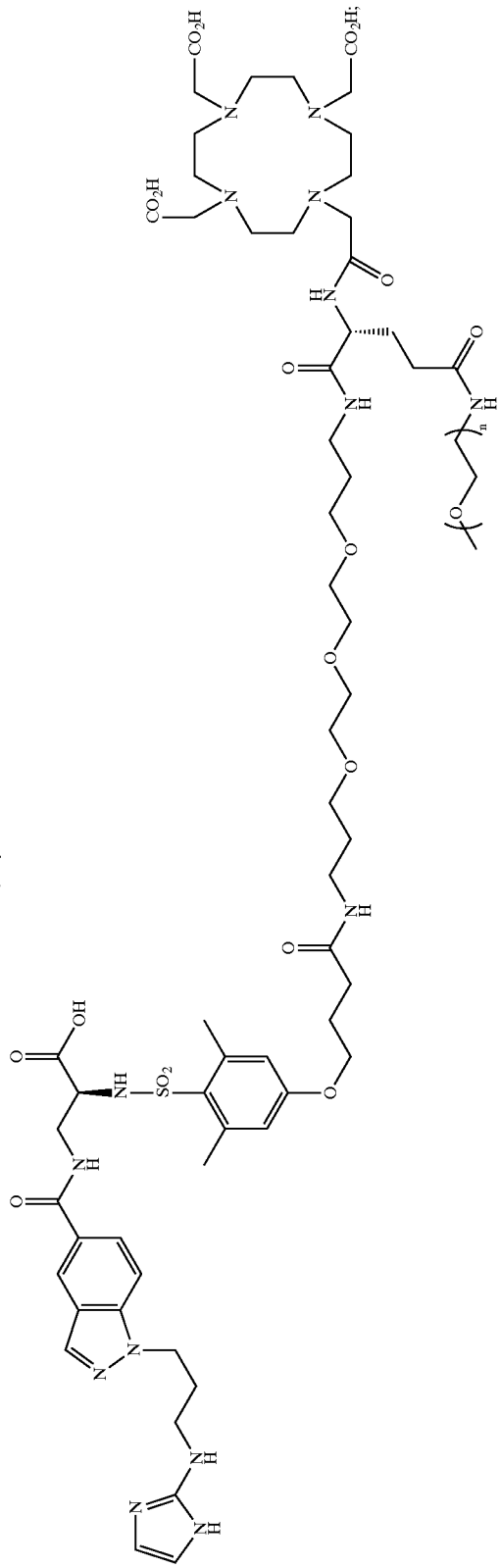
n = 114, ave 2-(((4-(3-(N-(3-(2-(2-(3-(2-(1,4,7,10-tetraaza-4,7,10-tris(carboxymethyl)cyclododecylacetylamino)-6aminohexanoylamino)propoxy)ethoxy)ethoxy)propyl)carbamnoyl)propoxy)-2,6-dimethylphenyl)sulfonyl)amino)-3-((1-(3-(imidazol-2-ylamino)propyl)(1H-indazol-5-yl))carbonylamino)propionic acid salt;

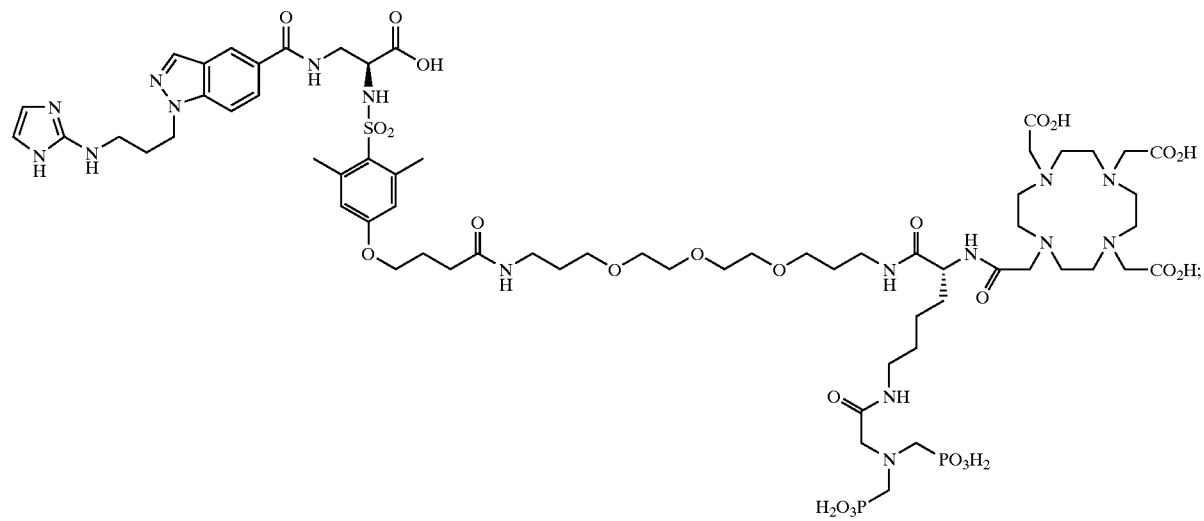

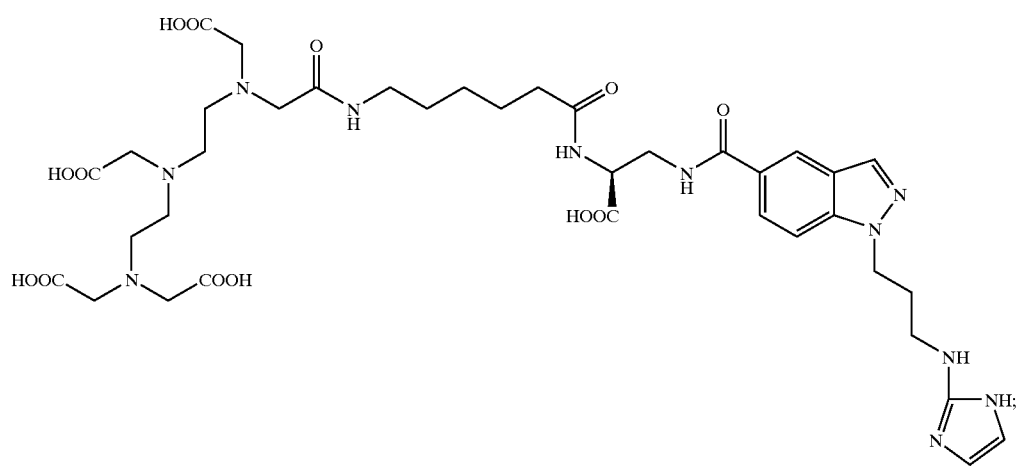

2-({[4-(3-{N-[2-((2R)-3-Sulfo-2-{2-[1,4,7,10-tetraaza-4,7,10-tris(carboxymethyl)cyclododecyl]acetylamino}propyl)ethyl]carbamoyl}propoxy)-2,6-dimethylphenyl]sulfonyl}amino)(2S)-3-({1-[3-(imidazol-2-ylamino)propyl](1H-indazol-5-yl)}carbonylamino)propanoic Acid;

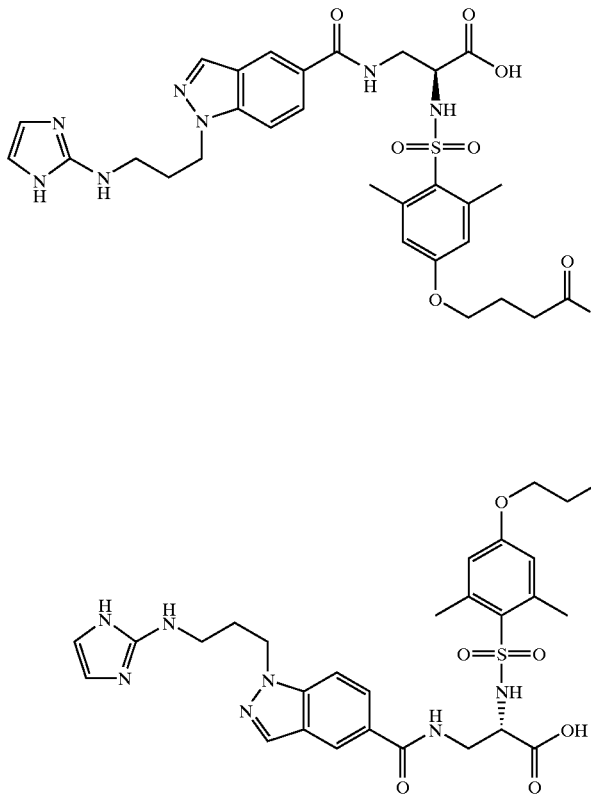
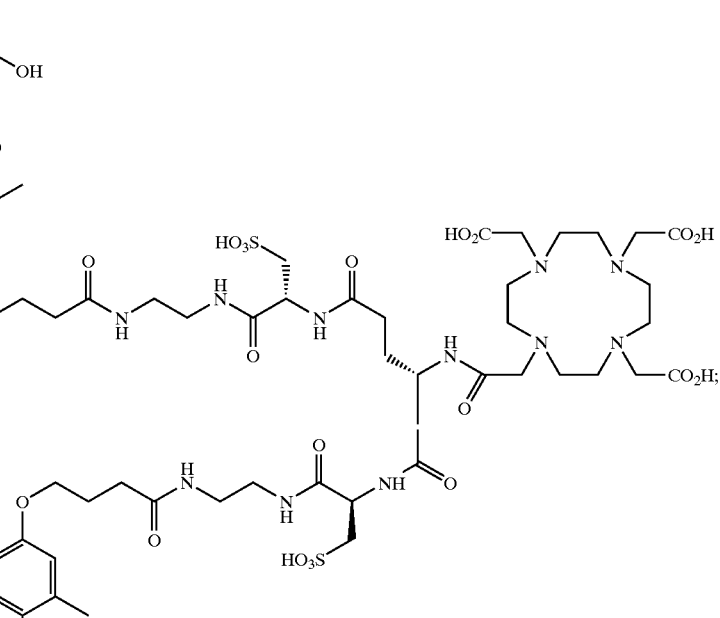

2-[({4-[4-({[2-((2R)-3-Sulfo-2-{2-[1,4,7,10-tetraaza-4,7,10-tris(carboxymethyl)cyclododecyl]acetylamino}propyl)ethyl]amino}sulfonyl)phenyl]phenyl}sulfonyl)amino](2S)-3-({1-[3-(imidazol-2-ylamino)propyl](1H-indazol-5-yl)}carbonylamino)propanoic Acid;

(4S)-4-(N-{1-[N-(2-{4-[4-({[(1S)-1-carboxy-2-({1-[3-(2-pyridylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid;

(4S)-4-(N-{1-[N-(2-{4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid;

(4S)-4-{N-[(1S)-1-(N-{1,3-bis[N-(2-{4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]propyl}carbarnoyl)-3-carboxypropyl]carbamoyl}-4-(6-{2-[1,4,7,10-tetraaza-4,7,10-tris(carboxymethyl)cyclododecyl]acetylamino}hexanoylamino)butanoic acid;

(4S)-4-(N-{1-[N-(2-{4-[4-({[(1S)-1-carboxy-2-({1-[3-(3,4,5,6-tetrahydropyrimidin-2-ylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid;

(4S)-4-(N-{1-[N-(2-{4-[4-({[(1S)-1-carboxy-2-({1-methyl-3-[3-2-3,4,5,6-tetrahydropyridylamino)propyl](1H-indazol-6-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tris(carboxymethyl)cyclododecyl]acetylamino}butanoic acid;

(4S)-4-(N-{(1S)-1-[N-(2-{4-[4-({[(1S)-1-carboxy-2-({1-[2-(2-3,4,5,6-tetrahydropyridylamino)ethyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid;

(2S)-2-{[(2,6-dimethyl-4-{3-[N-(2-{2-[1,4,7,10-tetraaza-4,7,10-tris(carboxymethyl)cyclododecyl]acetylamino}ethyl)carbamoyl]propoxy}phenyl)sulfonyl]amino}-3-({2-[2-(2-3,4,5,6-tetrahydropyridylamino)ethyl](2-hydro-1H-indazol-5-yl)}carbonylamino)propanoic acid;

(4S)-4-{N-[(1S)-1-(N-{2-[({4-[4-({[(1S)-1-carboxy-2-({1-[2-(2-3,4,5,6-tetrahydropyridylamino)ethyl](1H-indazol-5-yl)}carbonylamino)ethyl]amino}sulfonyl)phenyl]phenyl}sulfonyl)amino]ethyl}carbamoyl)-3-carboxypropyl]carbamoyl}-4-{2-[1,4,7,10-tetraaza-4,7,10-tris(carboxy-methyl)cyclododecyl]acetylamino}butanoic acid;

(4S)-4-{N-[(1S)-1-(N-{2-[({4-[4-({[(1S)-1-carboxy-2-({1-[3-(3,4,5,6-tetrahydropyrimidin-2-ylamino)propyl](1H-indazol-5-yl)}carbonylamino)ethyl]

amino}sulfonyl)phenyl]phenyl}sulfonyl)amino]
ethyl}carbamoyl)-3-carboxypropyl]carbamoyl}-4-{2-
[1,4,7,10-tetraaza-4,7,10-tris(carboxymethyl)
cyclododecyl]acetylamino)}butanoic acid;

(2S)-3-({3-[(imidazol-2-ylamino)methyl]-1-methyl(1H-
indazol-6-yl)}carbonylamino)-2-({[4-(4-{[(2-{2-[1,4,
7,10-tetraaza-4,7,10-tris(carboxymethyl)cyclododecyl]
acetylamino}ethyl)amino]sulfonyl}phenyl)phenyl]
sulfonyl}amino)propanoic acid;

3-[(7-{3-[(6-{[(1E)-1-aza-2-(2-sulfophenyl)vinyl]amino}
(3-pyridyl))carbonylamino]propoxy}-1-[3-(imidazol-
2-ylamino)propyl](1H-indazol-5-yl))-carbonylamino]
(2S)-2-{[(2,4,6-trimethylphenyl)sulfonyl]-
amino}propanoic acid; and 3-{[1-[3-(imidazol-2-ylamino)propyl]-7-(3-{2-[1,4,7,10-
tetraaza-4,7,10-tris(carboxymethyl)cyclododecyl]-
acetylamino}propoxy)(1H-indazol-5-yl)]
carbonylamino}-2-{[(2,4,6-trimethylphenyl)sulfonyl]
amino}propanoic acid;

or a pharmaceutically acceptable salt form thereof.

In a further preferred embodiment, the present invention provides a kit comprising a compound of the present invention, or a pharmaceutically acceptable salt form thereof and a pharmaceutically acceptable carrier.

In another preferred embodiment, the kit further comprises one or more ancillary ligands and a reducing agent.

In yet another preferred embodiment, the ancillary ligands are tricine and TPPTS.

In another preferred embodiment, the reducing agent is tin(II).

In a second embodiment, the present invention provides a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator.

In a preferred embodiment, the metallopharmaceutical is a diagnostic radiopharmaceutical, the metal is a radioisotope selected from the group: $^{99m}Tc$, $^{95}Tc$, $^{111}In$, $^{62}Cu$, $^{64}Cu$, $^{67}Ga$, and $^{68}Ga$, and the linking group is present between the targeting moiety and chelator.

In another preferred embodiment, the targeting moiety is an indazole and the receptor is $\alpha_v\beta_3$ or $\alpha_v\beta_5$.

In another preferred embodiment, the radioisotope is $^{99m}Tc$ or $^{95}Tc$, the radiopharmaceutical further comprises a first ancillary ligand and a second ancillary ligand capable of stabilizing the radiopharmaceutical.

In another preferred embodiment, the radioisotope is $^{99m}Tc$.

In another preferred embodiment, the radiopharmaceutical is selected from the group:

$^{99m}Tc$ ((((4-(4-(((3-(2-(2-(3-((6-(diazenido)(3-pyridyl))
carbonylamino)propoxy)ethoxy)ethoxy)propyl)amino)
sulfonyl)phenyl)phenyl)sulfonyl)amino)-3-((1-(3-
(imidazole-2-ylamino)propyl)(1H-indazol-5-yl))
carbonylamino)propanoic acid) (tricine)(TPPTS);

$^{99m}Tc$ (2-(2-((5-(N-(1,3-bis(3-(2-(2-(3-(((4-(4-(((1-
carboxy-2-((1-(3-(imidazol-2-ylamino)propyl)(1H-
indazol-5-yl))carbonylamino)ethyl)amino)sulfonyl)
phenyl)phenyl)sulfonyl)amino)propoxy)ethoxy)
ethoxy)propyl)carbamoyl)propyl)carbamoyl)(2-
pyridyl))2-diazenido) (tricine)(TPPTS);

$^{99m}Tc$ (2-((6-(diazenido)(3-pyridyl))carbonylamino)-4-
(N-(3-(2-(2-(3-(((4-(4-(((1-carboxy-2-((1-(3-
(imidazol-2-ylamino)propyl)(1H-indazol-5-yl))
carbonylamino)ethyl)amino)sulfonyl)phenyl)phenyl)
sulfonyl)amino)propoxy)ethoxy)ethoxy)propyl)
carbamoyl)butanoic acid) (tricine)(TPPTS);

$^{99m}Tc$ (2-(6-((6-(diazenido)(3-pyridyl))carbonylamino)
hexanoylamino)-3-((1-(3-(imidazol-2-ylamino)propyl)
(1H-indazol-5-yl))carbonylamino)-propanoic acid)
(tricine)(TPPTS);

$^{99m}Tc$ (2-((6-(diazenido)(3-pyridyl))carbonylamino)-3-
((1-(3-(imidazol-2-ylamino)propyl)(1H-indazol-5-yl))
carbonylamino)propanoic acid (tricine)(TPPTS);

$^{99m}Tc$ [2-[[[5-[carbonyl]-2-pyridinyl]diazenido]-Glu(2-
(6-aminohexanoylamino)-3-((1-(3-(imidazol-2-
ylamino)propyl)(1H-indazol-5-yl))carbonyl-amino)
propanoic acid)(2-(6-aminohexanoylamino)-3-((1-(3-
(imidazol-2-ylamino)propyl)(1H-indazol-5-yl))
carbonylamino)propanoic acid)) (tricine)(TPPTS);

$^{99m}Tc$ ([2-[[[5-[carbonyl]-2-pyridinyl]diazenido]-Glu-
bis-[Glu(2-(6-aminohexanoylamino)-3-((1-(3-
(imidazol-2-ylamino)propyl)(1H-indazol-5-yl))
carbonyl-amino)propanoic acid)(2-(6-
aminohexanoylamino)-3-((1-(3-(imidazol-2-ylamino)
propyl)(1H-indazol-5-yl))carbonyl-amino)propanoic
acid)]) (tricine)(TPPTS);

In another preferred embodiment, the radioisotope is $^{111}In$.

In another preferred embodiment, the radiopharmaceutical is selected from the group:

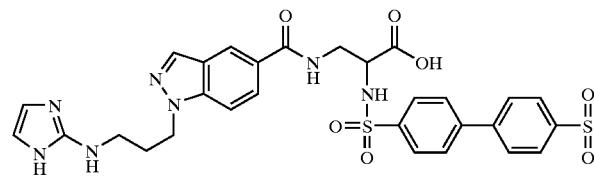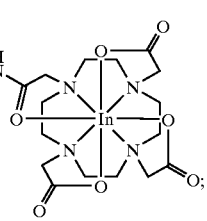

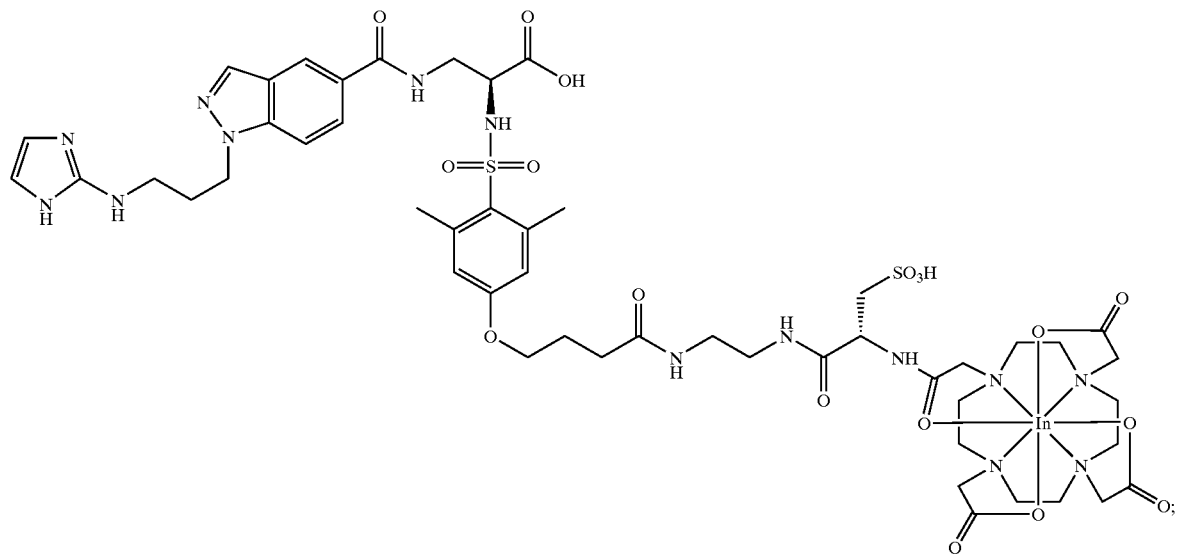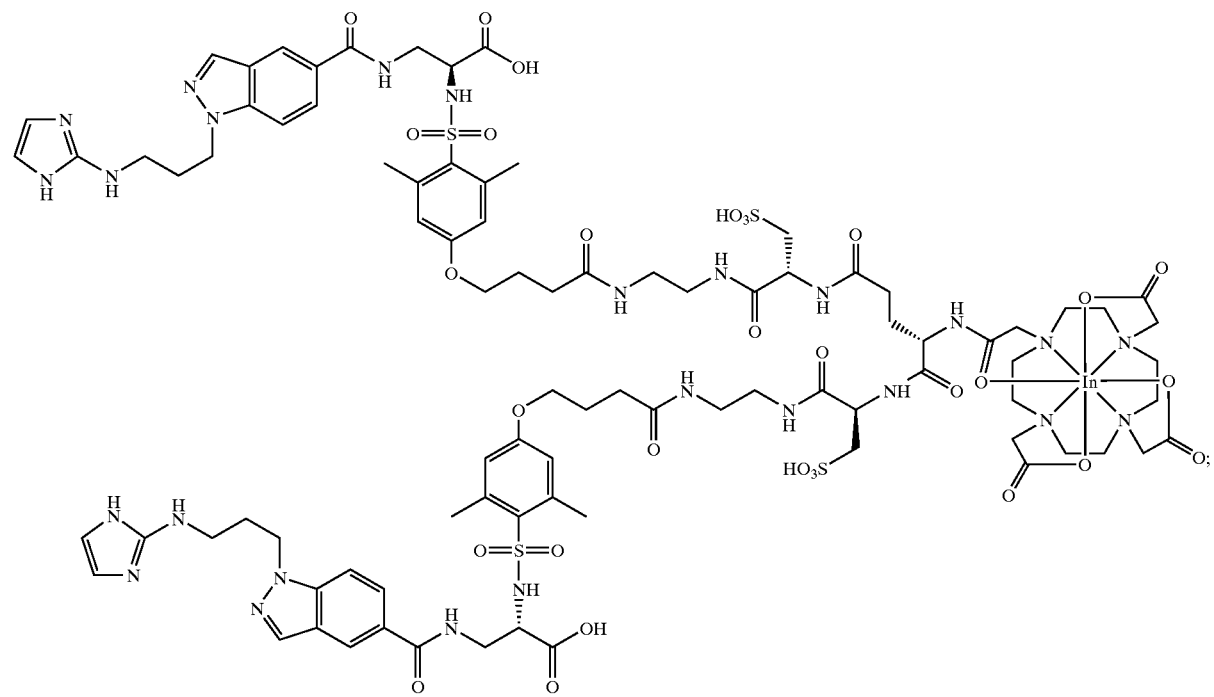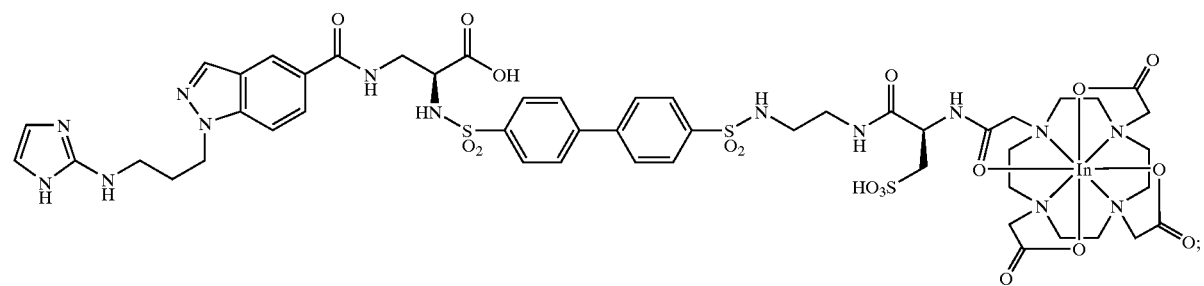

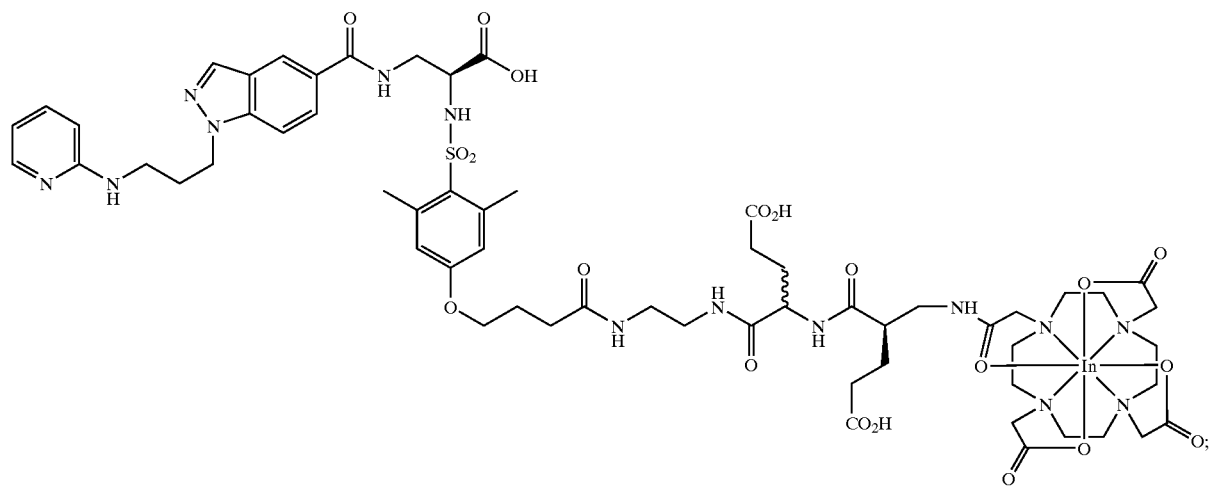
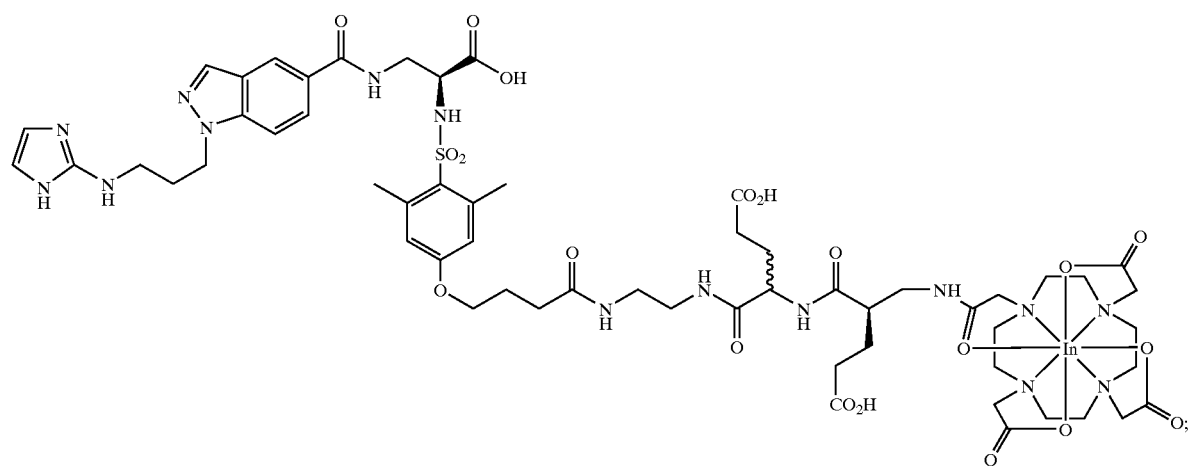
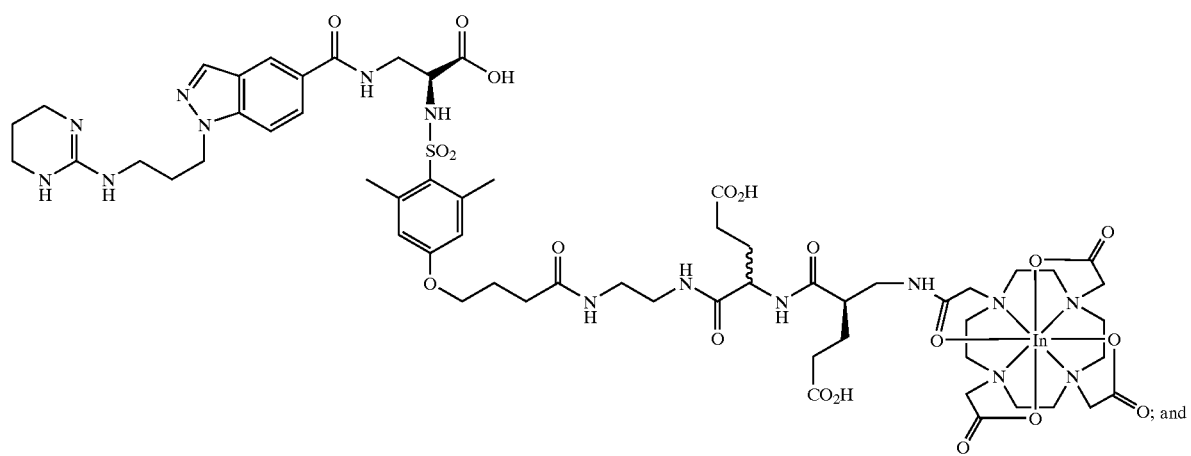

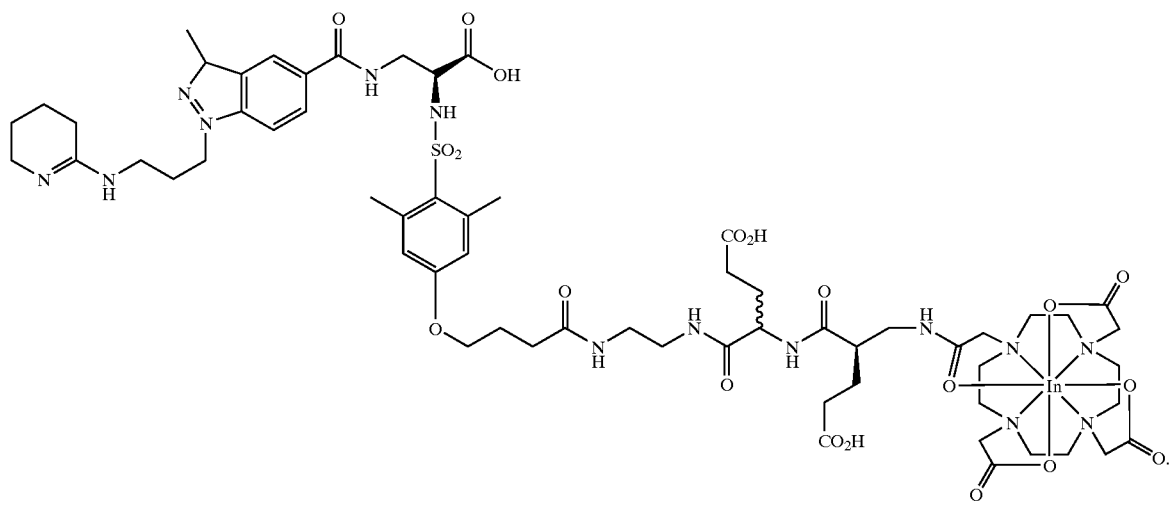

In another preferred embodiment wherein the metallopharmaceutical is a therapeutic radiopharmaceutical, the metal is a radioisotope selected from the group: $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir, the targeting moiety is an indazole nonpeptide and the linking group is present between the targeting moiety and chelator.

In another preferred embodiment, the targeting moiety is an indazole and the receptor is $\alpha_v\beta_3$ or $\alpha_v\beta_5$.

In another preferred embodiment, the radioisotope is $^{153}$Sm.

In another preferred embodiment, the radioisotope is $^{177}$Lu.

In another preferred embodiment, the radiopharmaceutical is

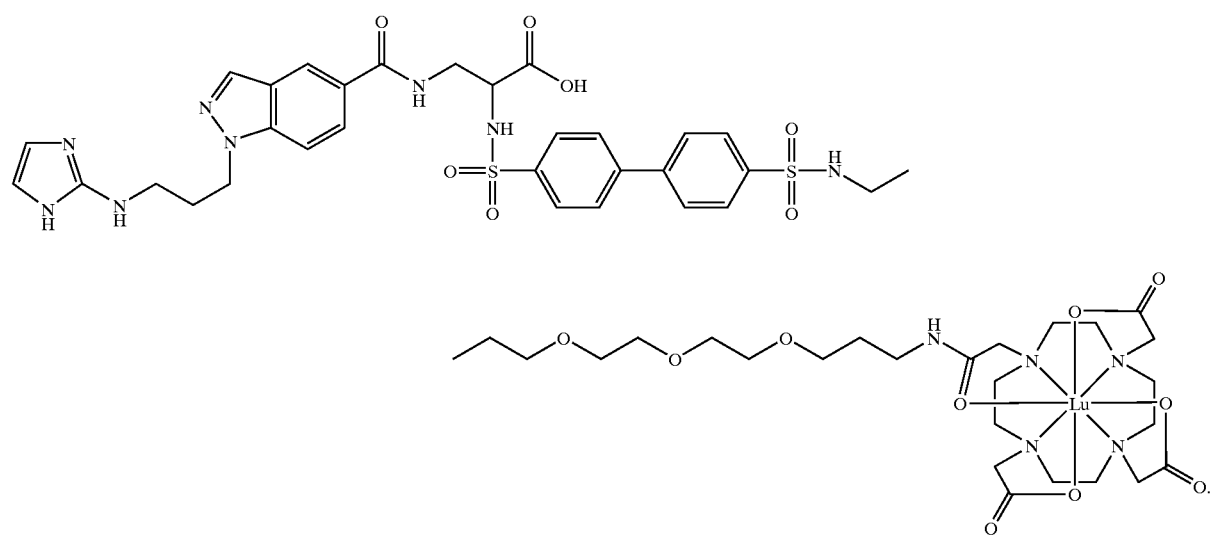

In another preferred embodiment, the radioisotope is $^{90}$Y.

In another preferred embodiment, the radiopharmaceutical is selected from the group:

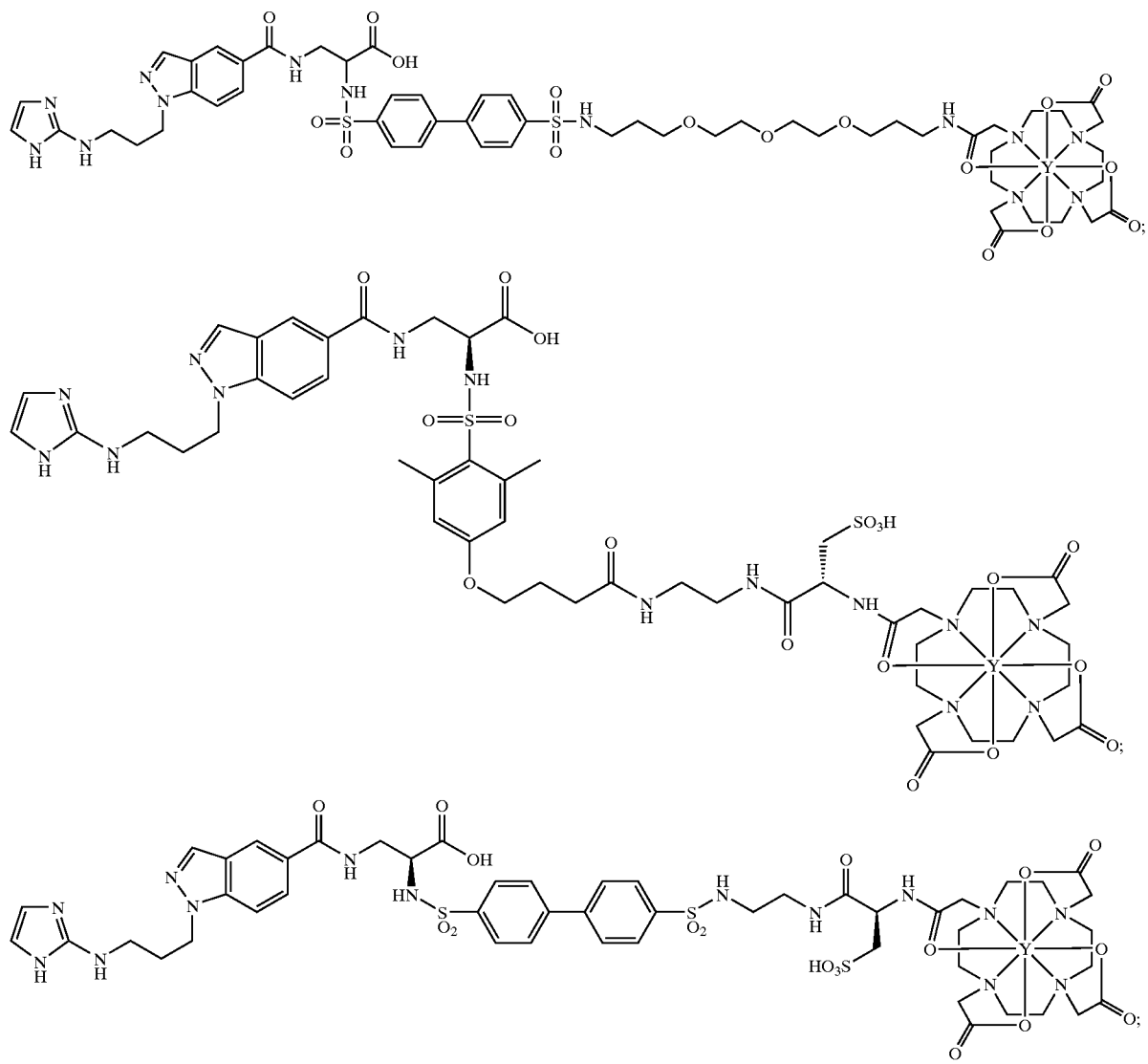
and
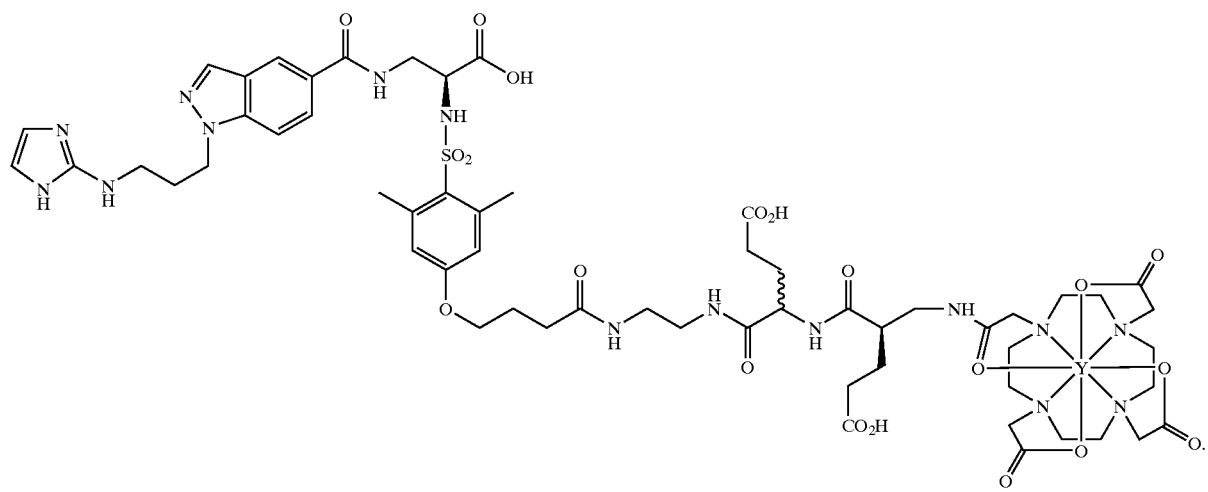
In another preferred embodiment wherein the metallopharmaceutical is a MRI contrast agent, the metal is a paramagnetic metal ion selected from the group: Gd(III), Dy(III), Fe(III), and Mn(II), the targeting moiety is an indazole nonpeptide and the linking group is present between the targeting moiety and chelator.

In another preferred embodiment, the targeting moiety is an indazole and the receptor is $\alpha_v\beta_3$ or $\alpha_v\beta_5$.

In another preferred embodiment, the metal ion is Gd(III).

In another preferred embodiment, the contrast agent is selected from the group: $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir, the targeting moiety is an indazole nonpeptide and the linking group is present between the targeting moiety and chelator by injection or infusion.

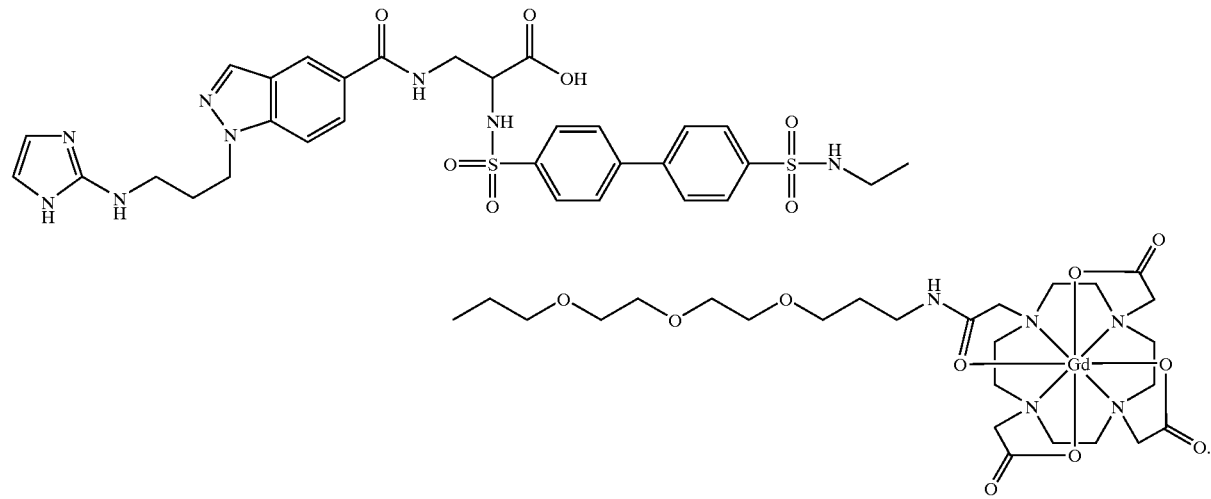

In another preferred embodiment wherein the metallopharmaceutical is a X-ray contrast agent, the metal is selected from the group: Re, Sm, Ho, Lu, Pm, Y, Bi, Pd, Gd, La, Au, Au, Yb, Dy, Cu, Rh, Ag, and Ir, the targeting moiety comprises an indazole, the receptor is $\alpha_v\beta_3$ or $\alpha_v\beta_5$, and the linking group is present between the targeting moiety and chelator.

In another preferred embodiment, the present invention provides a novel method of treating rheumatoid arthritis in a patient comprising: administering a therapeutic radiopharmaceutical comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator, wherein the metallopharmaceutical is a therapeutic radiopharmaceutical, the metal is a radioisotope selected from the group: $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir, the targeting moiety is an indazole nonpeptide and the linking group is present between the targeting moiety and chelator capable of localizing in new angiogenic vasculature to a patient by injection or infuision.

In another preferred embodiment, the present invention provides a novel method of treating cancer in a patient comprising: administering to a patient in need thereof a therapeutic radiopharmaceutical comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator, wherein the metallopharmaceutical is a therapeutic radiopharmaceutical, the metal is a radioisotope In another preferred embodiment, the present invention provides a novel method of treating restenosis in a patient comprising: administering to a patient, either systemically or locally, a therapeutic radiopharmaceutical comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator, wherein the metallopharrmaceutical is a therapeutic radiopharmaceutical, the metal is a radioisotope selected from the group: $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir, the targeting moiety is an indazole nonpeptide and the linking group is present between the targeting moiety and chelator capable of localizing in the restenotic area and delivering an effective dose of radiation.

In another preferred embodiment, the present invention provides a novel method of imaging therapeutic angiogenesis in a patient comprising: (1) administering a diagnostic radiopharmaceutical, a MRI contrast agent, or a X-ray contrast agent comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator to a patient by injection or infusion; (2) imaging the area of the patient wherein the desired formation of new blood vessels is located.

In another preferred embodiment, the present invention provides a novel method of imaging atherosclerosis in a patient comprising: (1) administering a diagnostic radiopharrmaccutical, a MRI contrast agent, or a X-ray contrast agent comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator to a patient by injection or infusion; (2) imaging the area of the patient wherein the atherosclerosis is located.

In another preferred embodiment, the present invention provides a novel method of imaging restenosis in a patient comprising: (1) administering a diagnostic radiopharmaceutical, a MRI contrast agent, or a X-ray contrast agent comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator to a patient by injection or infusion; (2) imaging the area of the patient wherein the restenosis is located.

In another preferred embodiment, the present invention provides a novel method of imaging cardiac ischemia in a patient comprising: (1) administering a diagnostic radiopharmaceutical, a MRI contrast agent, or a X-ray contrast agent comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator to a patient by injection or infusion; (2) imaging the area of the myocardium wherein the ischemic region is located.

In another preferred embodiment, the present invention provides a novel method of imaging myocardial reperfusion injury in a patient comprising: (1) administering a diagnostic radiopharmaceutical, a MRI contrast agent, or a X-ray contrast agent comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator to a patient by injection or infusion; (2) imaging the area of myocardium wherein the reperfusion injury is located.

In another preferred embodiment, the present invention provides a novel method of imaging cancer in a patient comprising: (1) administering a diagnostic radiopharmaceutical comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator, wherein the metallopharmaceutical is a diagnostic radiopharmaceutical, the metal is a radioisotope selected from the group: $^{99m}$Tc, $^{95}$Tc, $^{111}$In, $^{62}$Cu, $^{64}$Cu, $^{67}$Ga, and $^{68}$Ga, and the linking group is present between the targeting moiety and chelator to a patient by injection or infusion; (2) imaging the patient using planar or SPECT gamma scintigraphy, or positron emission tomography.

In another preferred embodiment, the present invention provides a novel method of imaging cancer in a patient comprising: (1) administering a MRI contrast agent comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator, wherein the metallopharmaceutical is a MRI contrast agent, the metal is a paramagnetic metal ion selected from the group: Gd(III), Dy(III), Fe(III), and Mn(II), the targeting moiety is an indazole nonpeptide and the linking group is present between the targeting moiety and chelator, and wherein the targeting moiety is an indazole and the receptor is $\alpha_v\beta_3$ or $\alpha_v\beta_5$; and (2) imaging the patient using magnetic resonance imaging.

In another preferred embodiment, the present invention provides a novel method of imaging cancer in a patient comprising: (1) administering a X-ray contrast agent comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator, wherein the metallopharmaceutical is a X-ray contrast agent, the metal is selected from the group: Re, Sm, Ho, Lu, Pm, Y, Bi, Pd, Gd, La, Au, Au, Yb, Dy, Cu, Rh, Ag, and Ir, the targeting moiety comprises an indazole, the receptor is $\alpha_v\beta_3$ or $\alpha_v\beta_5$, and the linking group is present between the targeting moiety and chelator; and (2) imaging the patient using X-ray computed tomography.

In a third embodiment, the present invention provides a novel compound, comprising: a targeting moiety and a surfactant, wherein the targeting moiety is bound to the surfactant, is an indazole nonpeptide, and binds to a receptor that is upregulated during angiogenesis and the compound has 0–1 linking groups between the targeting moiety and surfactant.

In a preferred embodiment, the linking group is present between the targeting moiety and surfactant.

In another preferred embodiment, the receptor is the integrin $\alpha_v\beta_3$ or $\alpha_v\beta_5$ and the compound is of the formula:

$$(Q)_d—L_n—S_f$$

wherein,

Q is a independently a compound of Formulae (Ia) or (Ib):

(Ia)

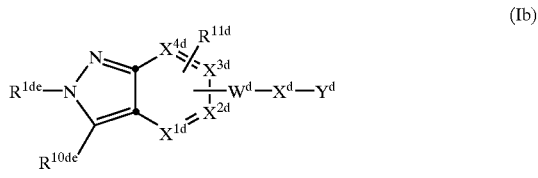
(Ib)

including stereoisomeric forms thereof, or mixtures of stereoisomeric forms thereof, or pharmaceutically acceptable salt or prodrug forms thereof wherein:

$X^{1d}$ is N, CH, C—$W^d$—$X^d$—$Y^d$, or C—$L_n$;

$X^{2d}$ is N, CH, or C—$W^d$—$X^d$—$Y^d$;

$X^{3d}$ is N, $CR^{11d}$, or C—$W^d$—$X^d$—$Y^d$;

$X^{4d}$ is N or $CR^{11d}$;

provided that when $R^{1d}$ is $R^{1de}$ then one of $X^{1d}$ and $X^{2d}$ is C—$W^d$—$X^d$—$Y^d$, and when $R^{10d}$ is $R^{1de}$ then $X^{3d}$ is C—$W^d$—$X^d$—$Y^d$;

$R^{1d}$ is selected from: $R^{1de}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{1de}$ is selected from:

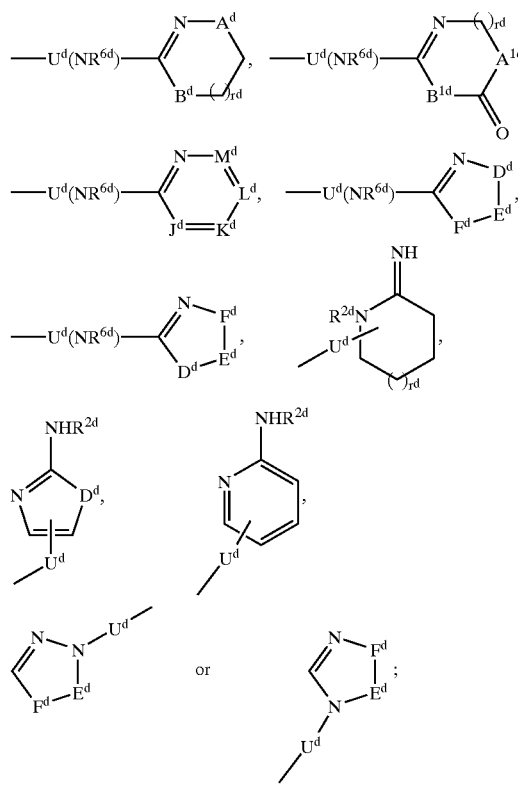

$A^d$ and $B^d$ are independently —$CH_2$—, —O—, —N($R^{2d}$)—, or —C(=O)—;

$A^{1d}$ and $B^{1d}$ are independently —$CH_2$— or —N($R^{3d}$)—;

$D^d$ is —N($R^{2d}$)—, —O—, —S—, —C(=O)— or —$SO_2$—;

$E^d$—$F^d$ is —C($R^{4d}$)=C($R^{5d}$)—, —N=C($R^{4d}$)—, —C($R^{4d}$)=N—, or —C($R^{4d}$)$_2$C($R^{5d}$)$_2$—;

$J^d$, $K^d$, $L^d$ and $M^d$ are independently selected from: —C($R^{4d}$)—, —C($R^{5d}$)— and —N—, provided that at least one of $J^d$, $K^d$, $L^d$ and $M^d$ is not —N—;

$R^{2d}$ is selected from: H, $C_1$–$C_6$ alkyl, ($C_1$–$C_6$ alkyl) carbonyl, ($C_1$–$C_6$ alkoxy)carbonyl; ($C_1$–$C_6$ alkyl) aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl($C_1$–$C_6$ alkyl)-, ($C_1$–$C_6$ alkyl)carbonyl-, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{3d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;

$R^{4d}$ and $R^{5d}$ are independently selected from: H, $C_1$–$C_4$ alkoxy, $NR^{2d}R^{3d}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl) carbonyl, ($C_1$–$C_6$ alkoxy)carbonyl, arylcarbonyl, or alternatively, when substituents on adjacent atoms, $R^{4d}$ and $R^{5d}$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, and $NO_2$;

$U^d$ is selected from: —$(CH_2)_n{}^d$—, —$(CH_2)_n{}^d$($CR^{7d}$=$CR^{8d}$)$(CH_2)_m{}^d$—, —$(CH_2)_n{}^d$(C≡C) $(CH_2)_m{}^d$—, —$(CH_2)_t{}^d$Q$(CH_2)_m{}^d$—, —$(CH_2)_n{}^d$O $(CH_2)_m{}^d$—, —$(CH_2)_n{}^d$N($R^{6d}$)$(CH_2)_m{}^d$—, —$(CH_2)_n{}^d$C (=O)$(CH_2)_m{}^d$—, —$(CH_2)_n{}^d$(C=O)N($R^{6d}$)$(CH_2)_m{}^d$—, —$(CH_2)_n{}^d$N($R^{6d}$)(C=O)$(CH_2)_m{}^d$—, and —$(CH_2)_n{}^d$S (O)$_p{}^d$$(CH_2)_m{}^d$—;

wherein one or more of the methylene groups in $U^d$ is optionally substituted with $R^{7d}$;

$Q^d$ is selected from 1,2-cycloalkylene, 1,2-phenylene, 1,3-phenylene, 1,4-phenylene, 2,3-pyridinylene, 3,4-pyridinylene, 2,4-pyridinylene, and 3,4-pyridazinylene;

$R^{6d}$ is selected from: H, $C_1$–$C_4$ alkyl, or benzyl;

$R^{7d}$ and $R^{8d}$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_0$–$C_6$ alkyl)-;

$R^{10d}$ is selected from: H, $R^{1de}$, $C_1$–$C_4$ alkoxy substituted with 0–1 $R^{21d}$, N($R^{6d}$)$_2$, halogen, $NO_2$, CN, $CF_3$, $CO_2R^{17d}$, C(=O)$R^{17d}$, $CONR^{17d}R^{20d}$, —$SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{10de}$ is selected from: H, $C_1$–$C_4$ alkoxy substituted with 0–1 $R^{21d}$, N($R^{6d}$)$_2$, halogen, $NO_2$, CN, $CF_3$, $CO_2R^{17d}$, C(=O)$R^{17d}$, $CONR^{17d}R^{20d}$, —$SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{11d}$ is selected from H, halogen, $CF_3$, CN, $NO_2$, hydroxy, $NR^{2d}R^{3d}$, $C_1$–$C_4$ alkyl substituted with 0–1 $R^{21d}$, $C_1$–$C_4$ alkoxy substituted with 0–1 $R^{21d}$, aryl substituted with 0–1 $R^{21d}$, aryl($C_1$–$C_6$ alkyl)- substituted with 0–1 $R^{21d}$, ($C_1$–$C_4$ alkoxy)carbonyl substituted with 0–1 $R^{21d}$, ($C_1$–$C_4$ alkyl)carbonyl substituted with 0–1 $R^{21d}$, $C_1$–$C_4$ alkylsulfonyl substituted with 0–1 $R^{21d}$, and $C_1$–$C_4$ alkylaminosulfonyl substituted with 0–1 $R^{21d}$;

$W^d$ is selected from: —$(C(R^{12d})_2)_q{}^d C(=O)N(R^{13d})$—, and —$C(=O)$—$N(R^{13d})$—$(C(R^{12d})_2)_q{}^d$—;

$X^d$ is —$C(R^{12d})(R^{14d})$—$C(R^{12d})(R^{15d})$—; or alternatively, $W^d$ and $X^d$ can be taken together to be

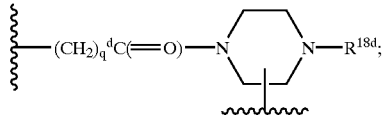

$R^{12d}$ is selected from H, halogen, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, and aryl ($C_1$–$C_6$ alkyl)-;

$R^{13d}$ is selected from H, $C_1$–$C_6$ alkyl, $C_3$–$C_7$ cycloalkylmethyl, and aryl($C_1$–$C_6$ alkyl)-;

$R^{14d}$ is selected from: H, $C_1$–$C_6$ alkylthio($C_1$–$C_6$ alkyl)-, aryl($C_1$–$C_{10}$ alkylthioalkyl), aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17d}$, $C(=O)R^{17d}$, and $CONR^{17d}R^{20d}$, provided that any of the above alkyl, cycloalkyl, aryl or heteroaryl groups may be unsubstituted or substituted independently with 0–1 $R^{16d}$ or 0–2 $R^{11d}$;

$R^{15d}$ is selected from: H, $R^{16d}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl ($C_1$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17d}$, $C(=O)R^{17d}$, $CONR^{17d}R^{20d}$, $SO_2R^{17d}$, and $SO_2NR^{17d}R^{20d}$, provided that any of the above alkyl, cycloalkyl, aryl or heteroaryl groups may be unsubstituted or substituted independently with 0–2 $R^{11d}$;

$Y^d$ is selected from: —$COR^{19d}$, —$SO_3H$, —$PO_3H$, tetrazolyl, —$CONHNHSO_2CF_3$, —$CONHSO_2R^{17d}$, —$CONHSO_2NHR^{17d}$, —$NHCOCF_3$, —$NHCONHSO_2R^{17d}$, —$NHSO_2R^{17d}$, —$OPO_3H_2$, —$OSO_3H$, —$PO_3H_2$, —$SO_3H$, —$SO_2NHCOR^{17d}$, —$SO_2NHCO_2R^{17d}$,

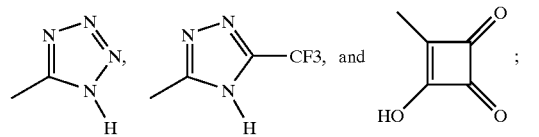

$R^{16d}$ is selected from: —$N(R^{20d})$—$C(=O)$—$O$—$R^{17d}$, —$N(R^{20d})$—$C(=O)$—$R^{17d}$, —$N(R^{20d})$—$C(=O)$—$NH$—$R^{17d}$, —$N(R^{20d})SO_2$—$R^{17d}$, and —$N(R^{20d})SO_2$—$NR^{20d}R^{17d}$;

$R^{17d}$ is selected from: $C_1$–$C_{10}$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, ($C_1$–$C_6$ alkyl)aryl optionally substituted with a bond to $L_n$, heteroaryl ($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl)- optionally substituted with a bond to $L_n$, heteroaryl optionally substituted with a bond to $L_n$, aryl optionally substituted with a bond to $L_n$, biaryl optionally substituted with a bond to $L_n$, and a bond to $L_n$, wherein said aryl, biaryl or heteroaryl groups are also optionally substituted with 0–3 substituents selected from the group: $C_1$–$C_4$ alkyl, $C_1$–$C_4$ alkoxy, aryl, heteroaryl, halo, cyano, amino, $CF_3$, and $NO_2$;

$R^{18d}$ is selected from: —H, —$C(=O)$—$O$—$R^{17d}$, —$C(=O)$—$R^{17d}$, —$C(=O)$—$NH$—$R^{17d}$, —$SO_2$—$R^{17d}$, and —$SO_2$—$NR^{20d}R^{17d}$;

$R^{19d}$ is selected from: hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$ alkylcarbonyloxyalkyloxy, $C_3$–$C_{10}$
alkoxycarbonyloxyalkyloxy, $C_2$–$C_{10}$
alkoxycarbonylalkyloxy, $C_5$–$C_{10}$
cycloalkylcarbonyloxyalkyloxy, $C_5$–$C_{10}$
cycloalkoxycarbonyloxyalkyloxy, $C_5$–$C_{10}$
cycloalkoxycarbonylalkyloxy, $C_7$–$C_{11}$
aryloxycarbonylalkyloxy, $C_8$–$C_{12}$
aryloxycarbonyloxyalkyloxy, $C_8$–$C_{12}$
arylcarbonyloxyalkyloxy, $C_5$–$C_{10}$
alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, and $(R^{11d})(R^{12d})N$—$(C_1$–$C_{10}$ alkoxy)-;

$R^{20d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl);

$R^{21d}$ is selected from: COOH and $NR^{6d}{}_2$;

$m^d$ is 0–4;

$n^d$ is 0–4;

$t^d$ is 0–4;

$p^d$ is 0–2;

$q^d$ is 0–2; and $r^d$ is 0–2;

with the following provisos:

(1) $t^d$, $n^d$, $m^d$ and $q^d$ are chosen such that the number of atoms connecting $R^{1d}$ and $Y^d$ is in the range of 10–14; and (2) $n^d$ and $m^d$ are chosen such that the value of $n^d$ and $m^d$ is greater than one unless $U^d$ is —$(CH_2)_t{}^d Q^d (CH_2)_m{}^d$—;

or Q is a peptide selected from the group:

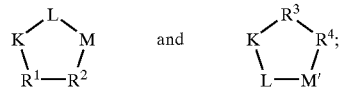

$R^1$ is L-valine, D-valine or L-lysine optionally substituted on the ☐ amino group with a bond to $L_n$;

$R^2$ is L-phenylalanine, D-phenylalanine, D-1-naphthylalanine, 2-aminothiazole-4-acetic acid or tyrosine, the tyrosine optionally substituted on the hydroxy group with a bond to $L_n$;

$R^3$ is D-valine;

$R^4$ is D-tyrosine substituted on the hydroxy group with a bond to $L_n$;

provided that one of $R^1$ and $R^2$ in each Q is substituted with a bond to $L_n$, and further provided that when $R^2$ is 2-aminothiazole-4-acetic acid, K is N-methylarginine;

provided that at least one Q is a compound of Formula Ia or Ib;

d is selected from 1, 2, 3,4, 5, 6, 7, 8, 9, and 10;

$L_n$ is a linking group having the formula:

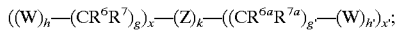

W is independently selected at each occurrence from the group: O, S, NH, NHC(=O), C(=O)NH, $NR^8C$(=O), C(=O)N $R^8$, C(=O), C(=O)O, OC(=O), NHC(=S) NH, NHC(=O)NH, $SO_2$, $SO_2NH$, $(OCH_2CH_2)_{20-200}$, $(CH_2CH_2O)_{20-200}$, $(OCH_2CH_2CH_2)_{20-200}$, $(CH_2CH_2CH_2O)_{20-200}$, and $(aa)_{t'}$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, and $R^8$ are independently selected at each occurrence from the group: H, =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)NH$R^{11}$, NHC(=O)NH$R^{11}$, NH$R^{11}$, $R^{11}$, and a bond to $S_f$;

$R^{10}$ is independently selected at each occurrence from the group: a bond to $S_f$, COO$R^{11}$, C(=O)NH$R^{11}$, NHC(=O)$R^{11}$, OH, NH$R^{11}$, $SO_3H$, $PO_3H$, —OP$O_3H_2$, —OS$O_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, and a bond to $S_f$;

$R^{12}$ is a bond to $S_f$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

$S_f$ is a surfactant which is a lipid or a compound of the formula:

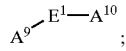

$A^9$ is selected from the group: OH and O$R^{27}$;

$A^{10}$ is O$R^{27}$;

$R^{27}$ is C(=O)$C_{1-20}$ alkyl;

$E^1$ is $C_{1-10}$ alkylene substituted with 1–3 $R^{28}$;

$R^{28}$ is independently selected at each occurrence from the group: $R^{30}$, —P$O_3H$—$R^{30}$, =O, —C$O_2R^{29}$, —C(=O) $R^{29}$, —C(=O)N$(R^{29})_2$, —$CH_2OR^{29}$, —O$R^{29}$, —N$(R^{29})_2$, $C_1$–$C_5$ alkyl, and $C_2$–$C_4$ alkenyl;

$R^{29}$ is independently selected at each occurrence from the group: $R^{30}$, H, $C_1$–$C_6$ alkyl, phenyl, benzyl, and trifluoromethyl;

$R^{30}$ is a bond to $L_n$;

and a pharmaceutically acceptable salt thereof.

In another preferred embodiment, the compound is of the formula:

wherein:

Q is a compound of Formula (Ia) or (Ib):

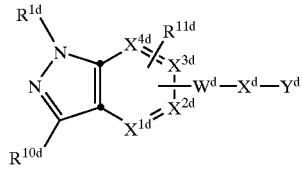

(Ia)

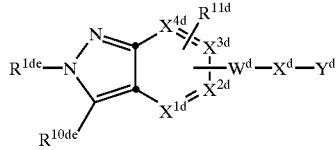

(Ib)

$R^{1de}$ is selected from:

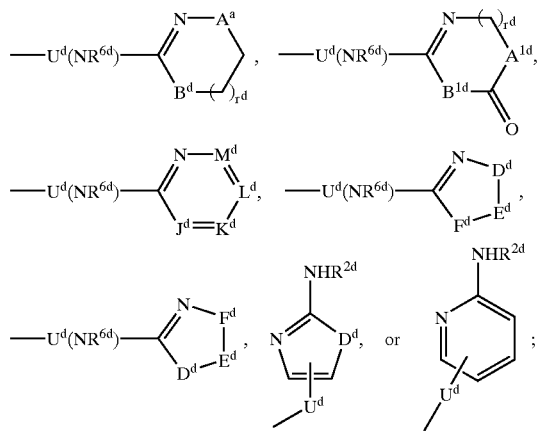

$A^d$ and $B^d$ are independently —$CH_2$—, —O—, —N$(R^{2d})$—, or —C(=O)—;

$A^{1d}$ and $B^{1d}$ are independently —$CH_2$— or —N$(R^{3d})$—;

$D^d$ is —N$(R^{2d})$—, —O—, —S—, —C(=O)— or —$SO_2$—;

$E^d$—$F^d$ is —C($R^{4d}$)=C($R^{1d}$)—, —N=C($R^{4d}$)—, —C($R^{4d}$)=N—, or —C($R^{4d}$)$_2$C($R^{5d}$)$_2$—;

$J^d$, $K^d$, $L^d$ and $M^d$ are independently selected from: —C($R^{4d}$)—, —C($R^{5d}$)— and —N—, provided that at least one of $J^d$, $K^d$, $L^d$ and $M^d$ is not —N—;

$R^{2d}$ is selected from: H, $C_1$—$C_6$ alkyl, ($C_1$—$C_6$ alkyl) carbonyl, ($C_1$–$C_6$ alkoxy)carbonyl, $C_1$–$C_6$ alkylaminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl($C_1$–$C_6$ alkyl)-, ($C_1$–$C_6$ alkyl)carbonyl, arylcarbonyl, alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl(C$_1$–C$_6$ alkoxy)carbonyl, wherein said aryl groups are substituted with 0–2 substituents selected from the group: C$_1$–C$_4$ alkyl, C$_1$–C$_4$ alkoxy, halo, CF$_3$, and nitro;

R$^{3d}$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, and heteroaryl(C$_1$–C$_6$ alkyl)-;

R$^{4d}$ and R$^{5d}$ are independently selected from: H, C$_1$–C$_4$ alkoxy, NR$^{2d}$R$^{3d}$, halogen, NO$_2$, CN, CF$_3$, C$_1$–C$_6$ alkyl, C$_3$–C$_6$ alkenyl, C$_3$–C$_7$ cycloalkyl, C$_4$–C$_{11}$ cycloalkylalkyl, aryl, aryl(C$_1$–C$_6$ alkyl)-, C$_2$–C$_7$ alkylcarbonyl, and arylcarbonyl or alternatively, when substituents on adjacent atoms, R$^{4d}$ and R$^{5d}$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: C$_1$–C$_4$ alkyl, C$_1$–C$_4$ alkoxy, halo, cyano, amino, CF$_3$, and NO$_2$;

U$^d$ is selected from: —(CH$_2$)$_n{}^d$—, —(CH$_2$)$_n{}^d$(CR$^{7d}$═CR$^{8d}$)(CH$_2$)$_m{}^d$—, —(CH$_2$)$_t{}^d$Q$^d$(CH$_2$)$_m{}^d$—, —(CH$_2$)$_n{}^d$O(CH$_2$)$_m{}^d$—, —(CH$_2$)$_n{}^d$N(R$^{6d}$)(CH$_2$)$_m{}^d$—, —(CH$_2$)$_n{}^d$C(═O)(CH$_2$)$_m{}^d$—, and —(CH$_2$)$_n{}^d$S(O)$_p$(CH$_2$)$_m{}^d$—;

wherein one or more of the methylene groups in U$^d$ is optionally substituted with R$^{7d}$;

Q$^d$ is selected from 1,2-phenylene, 1,3-phenylene, 2,3-pyridinylene, 3,4-pyridinylene, and 2,4-pyridinylene;

R$^{6d}$ is selected from: H, C$_1$–C$_4$ alkyl, and benzyl;

R$^{7d}$ and R$^{8d}$ are independently selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, and heteroaryl(C$_0$–C$_6$ alkyl)-;

W$^d$ is —C(═O)—N(R$^{13d}$)—(C(R$^{12d}$)$_2$)$_q{}^d$—;

X$^d$ is —C(R$^{12d}$)(R$^{14d}$)C(R$^{12d}$)(R$^{15d}$)—;

alternatively, W$^d$ and X$^d$ can be taken together to be

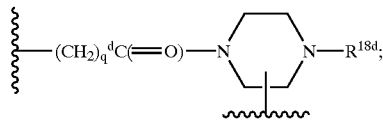

R$^{12d}$ is H or C$_1$–C$_6$ alkyl;

Y$^d$ is selected from: —COR$^{19d}$, —SO$_3$H,

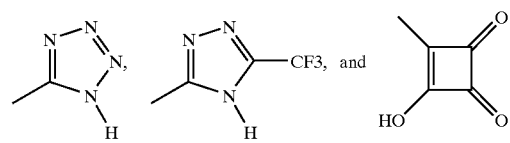

Z is selected from the group: aryl substituted with 0–1 R$^{10}$, C$_{3–10}$ cycloalkyl substituted with 0–1 R$^{10}$, and a 5–10 membered heterocyclic ring system containing 1–4 heteroatoms independently selected from N, S, and O and substituted with 0–1 R$^{10}$;

R$^6$, R$^{6a}$, R$^7$, R$^{7a}$, and R$^8$ are independently selected at each occurrence from the group: H, ═O, COOH, SO$_3$H, C$_1$–C$_5$ alkyl substituted with 0–1 R$^{10}$, aryl substituted with 0–1 R$^{10}$, benzyl substituted with 0–1 R$^{10}$, and C$_1$–C$_5$ alkoxy substituted with 0–1 R$^{10}$, NHC(═O)R$^{11}$, C(═O)NHR$^{11}$, NHC(═O)NHR$^{11}$, NHR$^{11}$, R$^{11}$, and a bond to S$_f$;

k is 0 or 1;

S$_f$ is a surfactant which is a lipid or a compound of the formula:

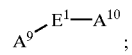

A$^9$ is OR$^{27}$;

A$^{10}$ is OR$^{27}$;

R$^{27}$ is C(═O)C$_{1–15}$ alkyl;

E$^1$ is C$_{1–4}$ alkylene substituted with 1–3 R$^{28}$;

R$^{28}$ is independently selected at each occurrence from the group: R$^{30}$, —PO$_3$H—R$^{30}$, ═O, —CO$_2$R$^{29}$, —C(═O)R$^{29}$, —CH$_2$OR$^{29}$, —OR$^{29}$, and C$_1$–C$_5$ alkyl;

R$^{29}$ is independently selected at each occurrence from the group: R$^{30}$, H, C$_1$–C$_6$ alkyl, phenyl, and benzyl;

R$^{30}$ is a bond to L$_n$;

and a pharmaceutically acceptable salt thereof.

In another preferred embodiment, the present invention provides a compound selected from the group:

DPPE-2-(6-aminohexanoylamino)-3-((1-(3-(imidazol-2-ylamino)propyl)(1H-indazol-5-yl))carbonyl-amino) propanoic acid-dodecanoate conjugate;

ω-amino-PEG$_{3400}$-2-(6-aminohexanoylamino)-3-((1-(3-imidazol-2-ylamino)propyl)(1H-indazol-5-yl)) carbonyl-amino)propanoic acid; and ω-amino-PEG$_{3400}$-Glu-(2-(6-aminohexanoylamino)-3-((1-(3-(imidazol-2-ylamino)-propyl)(1H-indazol-5-yl)) carbonyl-amino)propanoic acid)$_2$.

In another more preferred embodiment, the present invention provides a novel ultrasound contrast agent composition, comprising:

(a) a compound comprising: a targeting moiety and a surfactant, wherein the targeting moiety is bound to the surfactant, is an indazole nonpeptide, and binds to a receptor that is upregulated during angiogenesis and the compound has 0–1 linking groups between the targeting moiety and surfactant, wherein the linking group is present between the targeting moiety and surfactant, and the receptor is the integrin α$_v$β$_3$ or α$_v$β$_5$ and the compound is of the formula:

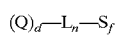

wherein,

Q is a independently a compound of Formulae (Ia) or (Ib):

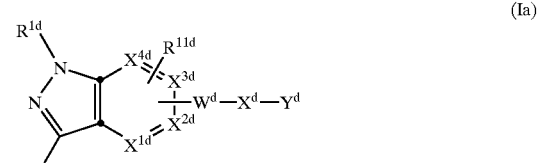

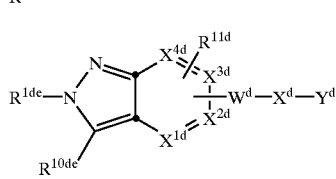

including stereoisomeric forms thereof, or mixtures of stereoisomeric forms thereof, or pharmaceutically acceptable salt or prodrug forms thereof wherein:

$X^{1d}$ is N, CH, C—$W^d$—$X^d$—$Y^d$, or C—$L_n$;
$X^{2d}$ is N, CH, or C—$W^d$—$X^d$—$Y^d$;
$X^{3d}$ is N, $CR^{11d}$, or C—$W^d$—$X^d$—$Y^d$;
$X^{4d}$ is N or $CR^{11d}$;
provided that when $R^{1d}$ is $R^{1de}$ then one of $X^{1d}$ and $X^{2d}$ is C—$W^d$—$X^d$—$Y^d$, and when $R^{10d}$ is $R^{1de}$ then $X^{3d}$ is C—$W^d$—$X^d$—$Y^d$;
$R^{1d}$ is selected from: $R^{1de}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{1de}$ is selected from:

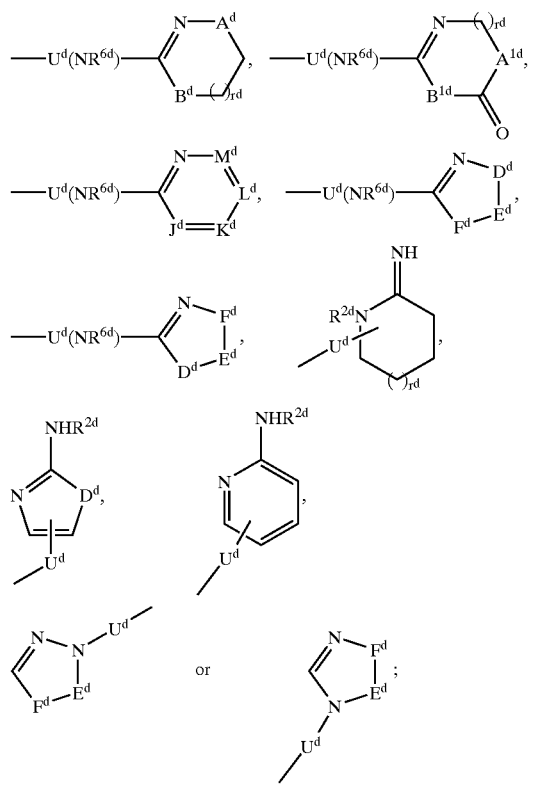

$A^d$ and $B^d$ are independently —$CH_2$—, —O—, —N($R^{2d}$)—, or —C(=O)—;
$A^{1d}$ and $B^{1d}$ are independently —$CH_2$— or —N($R^{3d}$)—;
$D^d$ is —N($R^{2d}$)—, —O—, —S—, —C(=O)— or —$SO_2$—;
$E^d$—$F^d$ is —C($R^{4d}$)=C($R^{5d}$)—, —N=C($R^{4d}$)—, —C($R^{4d}$)=N—, or —C$R^{4d}{}_2$C($R^{5d}$)$_2$—;
$J^d$, $K^d$, $L^d$ and $M^d$ are independently selected from: —C($R^{4d}$)—, —C($R^{5d}$)— and —N—, provided that at least one of $J^d$, $K^d$, $L^d$ and $M^d$ is not —N—;
$R^{2d}$ is selected from: H, $C_1$–$C_6$ alkyl, ($C_1$–$C_6$ alkyl)carbonyl, ($C_1$–$C_6$ alkoxy)carbonyl; ($C_1$–$C_6$ alkyl)aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl($C_1$–$C_6$ alkyl)-, ($C_1$–$C_6$ alkyl)carbonyl-, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;
$R^{3d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;
$R^{4d}$ and $R^{5d}$ are independently selected from: H, $C_1$–$C_4$ alkoxy, $NR^{2d}R^{3d}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl) carbonyl, ($C_1$–$C_6$ alkoxy)carbonyl, arylcarbonyl, or
alternatively, when substituents on adjacent atoms, $R^{4d}$ and $R^{5d}$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, and $NO_2$;
$U^d$ is selected from: —$(CH_2)_n{}^d$—, —$(CH_2)_n{}^d(CR^{7d}=CR^{8d})(CH_2)_m{}^d$—, —$(CH_2)_n{}^d(C\equiv C)(CH_2)_m{}^d$—, —$(CH_2)_t{}^dQ(CH_2)_m{}^d$—, —$(CH_2)_n{}^dO(CH_2)_m{}^d$—, —$(CH_2)_n{}^dN(R^{6d})(CH_2)_m{}^d$—, —$(CH_2)_n{}^dC(=O)(CH_2)_m{}^d$—, —$(CH_2)_n{}^d(C=O)N(R^{6d})(CH_2)_m{}^d$—, —$(CH_2)_n{}^dN(R^{6d})(C=O)(CH_2)_m{}^d$—, and —$(CH_2)_n{}^dS(O)_p{}^d(CH_2)_m{}^d$—;
wherein one or more of the methylene groups in $U^d$ is optionally substituted with $R^{7d}$;
$Q^d$ is selected from 1,2-cycloalkylene, 1,2-phenylene, 1,3-phenylene, 1,4-phenylene, 2,3-pyridinylene, 3,4-pyridinylene, 2,4pyridinylene, and 3,4-pyridazinylene;
$R^{6d}$ is selected from: H, $C_1$–$C_4$ alkyl, or benzyl;
$R^{7d}$ and $R^{8d}$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_0$–$C_6$ alkyl)-;
$R^{10d}$ is selected from: H, $R^{1de}$, $C_1$–$C_4$ alkoxy substituted with 0–1 $R^{21d}$, $N(R^{6d})_2$, halogen, $NO_2$, CN, $CF_3$, $CO_2R^{17d}$, C(=O)$R^{17d}$, $CONR^{17d}R^{20d}$, —$SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;
$R^{10de}$ is selected from: H, $C_1$–$C_4$ alkoxy substituted with 0–1 $R^{21d}$, $N(R^{6d})_2$, halogen, $NO_2$, CN, $CF_3$, $CO_2R^{17d}$, C(=O)$R^{17d}$, $CONR^{17d}R^{20d}$, —$SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;
$R^{11d}$ is selected from H, halogen, $CF_3$, CN, $NO_2$, hydroxy, $NR^{2d}R^{3d}$, $C_1$–$C_4$ alkyl substituted with 0–1 $R^{21d}$, $C_1$–$C_4$ alkoxy substituted with 0–1 $R^{21d}$, aryl substituted with 0–1 $R^{21d}$, aryl($C_1$–$C_6$ alkyl)- substituted with 0–1 $R^{21d}$, ($C_1$–$C_4$ alkoxy)carbonyl substituted with 0–1 $R^{21d}$, ($C_1$–$C_4$ alkyl)carbonyl substituted with 0–1 $R^{21d}$, $C_1$–$C_4$ alkylsulfonyl substituted with 0–1 $R^{21d}$, and $C_1$–$C_4$ alkylaminosulfonyl substituted with 0–1 $R^{21d}$;

$W^d$ is selected from: $-(C(R^{12d})_2)_q{}^dC(=O)N(R^{13d})-$, and $-C(=O)-N(R^{13d})-(C(R^{12d})_2)_q{}^d-$;

$X^d$ is $C(R^{12d})(R^{14d})-C(R^{12d})(R^{15d})-$; or alternatively, $W^d$ and $X^d$ can be taken together to be

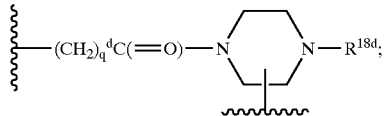

$R^{12d}$ is selected from H, halogen, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, and aryl ($C_1$–$C_6$ alkyl)-;

$R^{13d}$ is selected from H, $C_1$–$C_6$ alkyl, $C_3$–$C_7$ cycloalkylmethyl, and aryl($C_1$–$C_6$ alkyl)-;

$R^{14d}$ is selected from: H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17d}$, $C(=O)R^{17d}$, and $CONR^{17d}R^{20d}$, provided that any of the above alkyl, cycloalkyl, aryl or heteroaryl groups may be unsubstituted or substituted independently with 0–1 $R^{16d}$ or 0–2 $R^{11d}$;

$R^{15d}$ is selected from: H, $R^{16d}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl ($C_1$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17d}$, $C(=O)R^{17d}$, $CONR^{17d}R^{20d}$, $SO_2R^{17d}$, and $SO_2NR^{17d}R^{20d}$, provided that any of the above alkyl, cycloalkyl, aryl or heteroaryl groups may be unsubstituted or substituted independently with 0–2 $R^{11d}$;

$Y^d$ is selected from: $-COR^{19d}$, $-SO_3H$, $-PO_3H$, tetrazolyl, $-CONHNHSO_2CF_3$, $-CONHSO_2R^{17d}$, $-CONHSO_2NHR^{17d}$, $-NHCOCF_3$, $-NHCONHSO_2R^{17d}$, $-NHSO_2R^{17d}$, $-OPO_3H_2$, $-OSO_3H$, $-PO_3H_2$, $-SO_3H$, $-SO_2NHCOR^{17d}$, $-SO_2NHCO_2R^{17d}$,

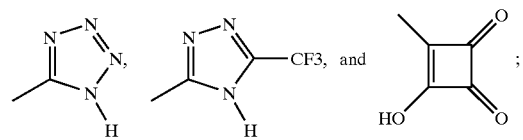

$R^{16d}$ is selected from: $-N(R^{20d})-C(=O)-O-R^{17d}$, $-N(R^{20d})-C(=O)-R^{17d}$, $-N(R^{20d})-C(=O)-NH-R^{17d}$, $-N(R^{20d})SO_2-R^{17d}$, and $-N(R^{20d})SO_2-NR^{20d}R^{17d}$;

$R^{17d}$ is selected from: $C_1$–$C_{10}$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, ($C_1$–$C_6$ alkyl)aryl optionally substituted with a bond to $L_n$, heteroaryl ($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl)- optionally substituted with a bond to $L_n$, heteroaryl optionally substituted with a bond to $L_n$, aryl optionally substituted with a bond to $L_n$, biaryl optionally substituted with a bond to $L_n$, and a bond to $L_n$, wherein said aryl, biaryl or heteroaryl groups are also optionally substituted with 0–3 substituents selected from the group: $C_1$–$C_4$ alkyl, $C_1$–$C_4$ alkoxy, aryl, heteroaryl, halo, cyano, amino, $CF_3$, and $NO_2$;

$R^{18d}$ is selected from: $-H$, $-C(=O)-O-R^{17d}$, $-C(=O)-R^{17d}$, $-C(=O)-NH-R^{17d}$, $-SO_2-R^{17d}$, and $-SO_2-NR^{20d}R^{17d}$;

$R^{19d}$ is selected from: hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, and $(R^{11d})(R^{12d})N-(C_1$–$C_{10}$ alkoxy)-;

$R^{20d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;

$R^{21d}$ is selected from: COOH and $NR^{6d}{}_2$;

$m^d$ is 0–4;

$n^d$ is 0–4;

$t^d$ is 0–4;

$p^d$ is 0–2;

$q^d$ is 0–2; and $r^d$ is 0–2;

with the following provisos:

(1) $t^d$, $n^d$, $m^d$ and $q^d$ are chosen such that the number of atoms connecting $R^{1d}$ and $Y^d$ is in the range of 10–14; and (2) $n^d$ and $m^d$ are chosen such that the value of $n^d$ and $m^d$ is greater than one unless $U^d$ is $-(CH_2)_t{}^dQ^d(CH_2)_m{}^d-$;

or Q is a peptide selected from the group:

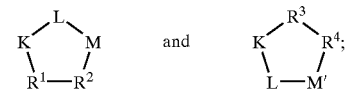

$R^1$ is L-valine, D-valine or L-lysine optionally substituted on the □ amino group with a bond to $L_n$;

$R^2$ is L-phenylalanine, D-phenylalanine, D-1-naphthylalanine, 2-aminothiazole-4-acetic acid or tyrosine, the tyrosine optionally substituted on the hydroxy group with a bond to $L_n$;

$R^3$ is D-valine;

$R^4$ is D-tyrosine substituted on the hydroxy group with a bond to $L_n$;

provided that one of $R^1$ and $R^2$ in each Q is substituted with a bond to $L_n$, and further provided that when $R^2$ is 2-aminothiazole-4-acetic acid, K is N-methylarginine;

provided that at least one Q is a compound of Formula Ia or Ib;

d is selected from 1, 2, 3, 4, 5, 6, 7, 8, 9, and 10;

$L_n$ is a linking group having the formula:

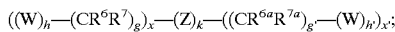

W is independently selected at each occurrence from the group: O, S, NH, NHC(=O), C(=O)NH, $NR^8$C(=O), C(=O)N $R^8$, C(=O), C(=O)O, OC(=O), NHC(=S) NH, NHC(=O)NH, $SO_2$, $SO_2$NH, $(OCH_2CH_2)_{20-200}$, $(CH_2CH_2O)_{20-200}$, $(OCH_2CH_2CH_2)_{20-200}$, $(CH_2CH_2CH_2O)_{20-200}$, and $(aa)_{t'}$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, and $R^8$ are independently selected at each occurrence from the group: H, =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)NH$R^{11}$, NHC(=O)NH$R^{11}$, NH$R^{11}$, $R^{11}$, and a bond to $S_f$;

$R^{10}$ is independently selected at each occurrence from the group: a bond to $S_f$, COO$R^{11}$, C(=O)NH$R^{11}$, NHC(=O)$R^{11}$, OH, NH$R^{11}$, $SO_3H$, $PO_3H$, —$OPO_3H_2$, —$OSO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, and a bond to $S_f$;

$R^{12}$ is a bond to $S_f$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

$S_f$ is a surfactant which is a lipid or a compound of the formula:

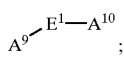

$A^9$ is selected from the group: OH and $OR^{27}$;

$A^{10}$ is $OR^{27}$;

$R^{27}$ is C(=O)$C_{1-20}$ alkyl;

$E^1$ is $C_{1-10}$ alkylene substituted with 1–3 $R^{28}$;

$R^{28}$ is independently selected at each occurrence from the group: $R^{30}$, —$PO_3H$—$R^{30}$, =O, —$CO_2R^{29}$, —C(=O) $R^{29}$, —C(=O)N($R^{29}$)$_2$, —$CH_2OR^{29}$, —$OR^{29}$, —N($R^{29}$)$_2$, $C_1$–$C_5$ alkyl, and $C_2$–$C_4$ alkenyl;

$R^{29}$ is independently selected at each occurrence from the group: $R^{30}$, H, $C_1$–$C_6$ alkyl, phenyl, benzyl, and trifluoromethyl;

$R^{30}$ is a bond to $L_n$;

and a pharmaceutically acceptable salt thereof, comprising: an indazole that binds to the integrin $\alpha_v\beta_3$ or $\alpha_v\beta_5$ a surfactant and a linking group between the indazole and the surfactant;

(b) a parenterally acceptable carrier; and, (c) an echogenic gas.

In another preferred embodiment, the present invention provides a novel ultrasound contrast agent composition, further comprising: 1,2-dipalmitoyl-sn-glycero-3-phosphatidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine.

In another preferred embodiment, the echogenic gas is a $C_{2-5}$ perfluorocarbon.

In another preferred embodiment, the present invention provides a method of imaging cancer in a patient comprising: (1) administering, by injection or infusion, a ultrasound contrast agent composition comprising: a targeting moiety and a surfactant, wherein the targeting moiety is bound to the surfactant, is an indazole nonpeptide, and binds to a receptor that is upregulated during angiogenesis and the compound has 0–1 linking groups between the targeting moiety and surfactant, wherein the linking group is present between the targeting moiety and surfactant, and the receptor is the integrin $\alpha_v\beta_3$ or $\alpha_v\beta_5$ and the compound is of the formula:

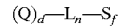

wherein,

Q is a independently a compound of Formulae (Ia) or (Ib):

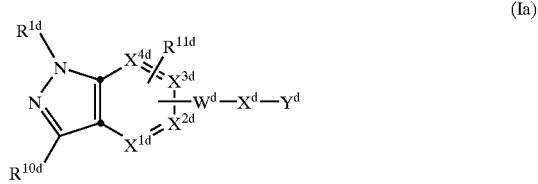

(Ia)

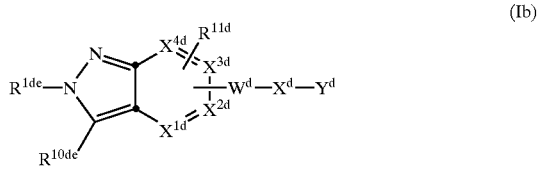

(Ib)

including stereoisomeric forms thereof, or mixtures of stereoisomeric forms thereof, or pharmaceutically acceptable salt or prodrug forms thereof wherein:

$X^{1d}$ is N, CH, C—$W^d$—$X^d$—$Y^d$, or C—$L_n$;

$X^{2d}$ is N, CH, or C—$W^d$—$X^d$—$Y^d$;

$X^{3d}$ is N, $CR^{11d}$, or C—$W^d$—$X^d$—$Y^d$;

$X^{4d}$ is N or $CR^{11d}$;

provided that when $R^{1d}$ is $R^{1de}$ then one of $X^{1d}$ and $X^{2d}$ is C—$W^d$—$X^d$—$Y^d$, and when $R^{10d}$ is $R^{1de}$ then $X^{3d}$ is C—$W^d$—$X^d$—$Y^d$;

$R^{1d}$ is selected from: $R^{1de}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{1de}$ is selected from:

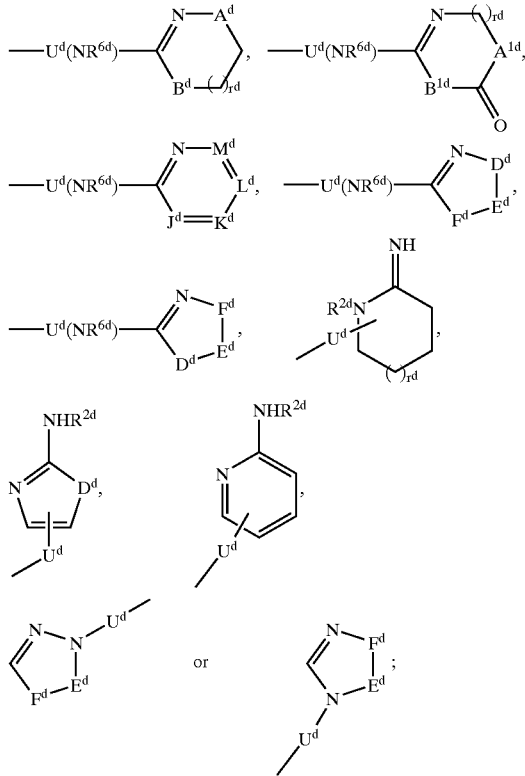

$A^d$ and $B^d$ are independently —$CH_2$—, —O—, —N($R^{2d}$)—, or —C(=O)—;

$A^{1d}$ and $B^{1d}$ are independently —$CH_2$— or —N($R^{3d}$)—;

$D^d$ is N($R^{2d}$)—, —O—, —S—, —C(=O)— or —$SO_2$—;

$E^d$—$F^d$ is —C($R^{4d}$)=C($R^{5d}$)—, —N=C($R^{4d}$), —C($R^{4d}$)=N—, or —C($R^{4d}$)$_2$C($R^{5d}$)$_2$—;

$J^d$, $K^d$, $L^d$ and $M^d$ are independently selected from: —C($R^{4d}$)—, —C($R^{5d}$)— and —N—, provided that at least one of $J^d$, $K^d$, $L^d$ and $M^d$ is not —N—;

$R^{2d}$ is selected from: H, $C_1$–$C_6$ alkyl, ($C_1$–$C_6$ alkyl) carbonyl, ($C_1$–$C_6$ alkoxy)carbonyl; ($C_1$–$C_6$ alkyl) aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl($C_1$–$C_6$ alkyl)-, ($C_1$–$C_6$ alkyl)carbonyl-, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{3d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;

$R^{4d}$ and $R^{5d}$ are independently selected from: H, $C_1$–$C_4$ alkoxy, $NR^{2d}R^{3d}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl) carbonyl, ($C_1$–$C_6$ alkoxy)carbonyl, arylcarbonyl, or alternatively, when substituents on adjacent atoms, $R^{4d}$ and $R^{5d}$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, and $NO_2$;

$U^d$ is selected from: —$(CH_2)_n{}^d$—, —$(CH_2)_n{}^d$($CR^{7d}$=$CR^{8d}$) $(CH_2)_m{}^d$—, —$(CH_2)_n{}^d$(C≡C)$(CH_2)_m{}^d$—, —$(CH_2)_n{}^d Q$ $(CH_2)_m{}^d$—, —$(CH_2)_n{}^d$O$(CH_2)_m{}^d$—, —$(CH_2)_n{}^d$N($R^{6d}$) $(CH_2)_m{}^d$—, —$(CH_2)_n{}^d$C(=O)$(CH_2)_m{}^d$—, —$(CH_2)_n{}^d$ (C=O)N($R^{6d}$)$(CH_2)_m{}^d$—, —$(CH_2)_n{}^d$N($R^{6d}$)(C=O) $(CH_2)_m{}^d$—, and —$(CH_2)_n{}^d$S(O)$_p{}^d(CH_2)_m{}^d$—;

wherein one or more of the methylene groups in $U^d$ is optionally substituted with $R^{7d}$;

$Q^d$ is selected from 1,2-cycloalkylene, 1,2-phenylene, 1,3-phenylene, 1,4phenylene, 2,3-pyridinylene, 3,4-pyridinylene, 2,4-pyridinylene, and 3,4-pyridazinylene;

$R^{6d}$ is selected from: H, $C_1$–$C_4$ alkyl, or benzyl;

$R^{7d}$ and $R^{8d}$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_0$–$C_6$ alkyl)-;

$R^{10d}$ is selected from: H, $R^{1de}$, $C_1$–$C_4$ alkoxy substituted with 0–1 $R^{21d}$, N($R^{6d}$)$_2$, halogen, $NO_2$, CN, $CF_3$, $CO_2R^{17d}$, C(=O)$R^{17d}$, $CONR^{17d}R^{20d}$, —$SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{10de}$ is selected from: H, $C_1$–$C_4$ alkoxy substituted with 0–1 $R^{21d}$, N($R^{6d}$)$_2$, halogen, $NO_2$, CN, $CF_3$, $CO_2R^{17d}$, C(=O)$R^{17d}$, $CONR^{17d}R^{20d}$, —$SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{11d}$ is selected from H, halogen, $CF_3$, CN, $NO_2$, hydroxy, $NR^{2d}R^{3d}$, $C_1$–$C_4$ alkyl substituted with 0–1 $R^{21d}$, $C_1$–$C_4$ alkoxy substituted with 0–1 $R^{21d}$, aryl substituted with 0–1 $R^{21d}$, aryl($C_1$–$C_6$ alkyl)- substituted with 0–1 $R^{21d}$, ($C_1$–$C_4$ alkoxy)carbonyl substituted with 0–1 $R^{21d}$, ($C_1$–$C_4$ alkyl)carbonyl substituted with 0–1 $R^{21d}$, $C_1$–$C_4$ alkylsulfonyl substituted with 0–1 $R^{21d}$, and $C_1$–$C_4$ alkylaminosulfonyl substituted with 0–1 $R^{21d}$;

$W^d$ is selected from: —$(C(R^{12d})_2)_q{}^d C(=O)N(R^{13d})$—, and —C(=O)—N($R^{13d}$)—$(C(R^{12d})_2)_q{}^d$;

$X^d$ is —C($R^{12d}$)($R^{14d}$)—C($R^{12d}$)($R^{15d}$)—; or alternatively, $W^d$ and $X^d$ can be taken together to be

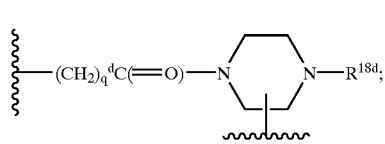

$R^{12d}$ is selected from H, halogen, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, and aryl ($C_1$–$C_6$ alkyl)-;

$R^{13d}$ is selected from H, $C_1$–$C_6$ alkyl, $C_3$–$C_7$ cycloalkylmethyl, and aryl($C_1$–$C_6$ alkyl)-;

$R^{14d}$ is selected from: H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl ($C_1$–$C_6$ alkyl)-, heteroaryl($C_1$–$C_6$ alkyl)-, aryl, heteroaryl, $CO_2R^{17d}$, $C(=O)R^{17d}$, and $CONR^{17d}R^{20d}$, provided that any of the above alkyl, cycloalkyl, aryl or heteroaryl groups may be unsubstituted or substituted independently with 0–1 $R^{16d}$ or 0–2 $R^{11d}$;

$R^{15d}$ is selected from: H, $R^{16d}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl ($C_1$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17d}$, $C(=O)R^{17d}$, $CONR^{17d}R^{20d}$, $SO_2R^{17d}$, and $SO_2NR^{17d}R^{20d}$, provided that any of the above alkyl, cycloalkyl, aryl or heteroaryl groups may be unsubstituted or substituted independently with 0–2 $R^{11d}$;

$Y^d$ is selected from: —$COR^{19d}$, —$SO_3H$, —$PO_3H$, tetrazolyl, —$CONHNHSO_2CF_3$, —$CONHSO_2R^{17d}$, —$CONHSO_2NHR^{17d}$, —$NHCOCF_3$, —$NHCONHSO_2R^{17d}$, —$NHSO_2R^{17d}$, —$OPO_3H_2$, —$OSO_3H$, —$PO_3H_2$, —$SO_3H$, —$SO_2NHCOR^{17d}$, —$SO_2NHCO_2R^{17d}$,

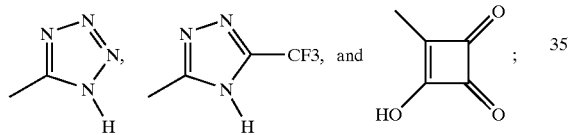

$R^{16d}$ is selected from: —$N(R^{20d})$—$C(=O)$—O—$R^{17d}$, —$N(R^{20d})$—$C(=O)$—$R^{17d}$, —$N(R^{20d})$—$C(=O)$—NH—$R^{17d}$, —$N(R^{20d})SO_2$—$R^{17d}$, and —$N(R^{20d})SO_2$—$NR^{20d}R^{17d}$;

$R^{17d}$ is selected from: $C_1$–$C_{10}$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, ($C_1$–$C_6$ alkyl)aryl optionally substituted with a bond to $L_n$, heteroaryl ($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl)- optionally substituted with a bond to $L_n$, heteroaryl optionally substituted with a bond to $L_n$, aryl optionally substituted with a bond to $L_n$, biaryl optionally substituted with a bond to $L_n$, and a bond to $L_n$, wherein said aryl, biaryl or heteroaryl groups are also optionally substituted with 0–3 substituents selected from the group: $C_1$–$C_4$ alkyl, $C_1$–$C_4$ alkoxy, aryl, heteroaryl, halo, cyano, amino, $CF_3$, and $NO_2$;

$R^{18d}$ is selected from: —H, —$C(=O)$—O—$R^{17d}$, —$C(=O)$—$R^{17d}$, —$C(=O)$—NH—$R^{17d}$, —$SO_2$—$R^{17d}$, and —$SO_2$—$NR^{20d}R^{17d}$;

$R^{19d}$ is selected from: hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, and $(R^{11d})(R^{12d})N$—($C_1$–$C_{10}$ alkoxy)-;

$R^{20d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;

$R^{21d}$ is selected from: COOH and $NR^{6d}_2$;

$m^d$ is 0–4;

$n^d$ is 0–4;

$t^d$ is 0–4;

$p^d$ is 0–2;

$q^d$ is 0–2; and $r^d$ is 0–2;

with the following provisos:
(1) $t^d$, $n^d$, $m^d$ and $q^d$ are chosen such that the number of atoms connecting $R^{1d}$ and $Y^d$ is in the range of 10–14; and
(2) $n^d$ and $m^d$ are chosen such that the value of $n^d$ and $m^d$ is greater than one unless $U^d$ is —$(CH_2)_t{}^d Q^d (CH_2)_m{}^d$—;

or Q is a peptide selected from the group:

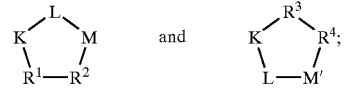

$R^1$ is L-valine, D-valine or D-lysine optionally substituted on the □ amino group with a bond to $L_n$;

$R^2$ is L-phenylalanine, D-phenylalanine, D-1-naphthylalanine, 2-aminothiazole-4-acetic acid or tyrosine, the tyrosine optionally substituted on the hydroxy group with a bond to $L_n$;

$R^3$ is D-valine;

$R^4$ is D-tyrosine substituted on the hydroxy group with a bond to $L_n$;

provided that one of $R^1$ and $R^2$ in each Q is substituted with a bond to $L_n$, and further provided that when $R^2$ is 2-aminothiazole-4-acetic acid, K is N-methylarginine;

provided that at least one Q is a compound of Formula Ia or Ib;

d is selected from 1, 2, 3, 4, 5, 6, 7, 8, 9, and 10;

$L_n$ is a linking group having the formula:

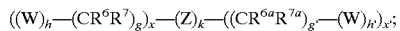

W is independently selected at each occurrence from the group: O, S, NH, NHC(=O), C(=O)NH, $NR^8C(=O)$, C(=O)N$R^8$, C(=O), C(=O)O, OC(=O), NHC(=S) NH, NHC(=O)NH, $SO_2$, $SO_2NH$, $(OCH_2CH_2)_{20-200}$, $(CH_2CH_2O)_{20-200}$, $(OCH_2CH_2CH_2)_{20-200}$, $(CH_2CH_2CH_2O)_{20-200}$, and $(aa)_r$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, and $R^8$ are independently selected at each occurrence from the group: H, =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, $NHC(=O)R^{11}$, $C(=O)NHR^{11}$, $NHC(=O)NHR^{11}$, $NHR^{11}$, $R^{11}$, and a bond to $S_f$;

$R^{10}$ is independently selected at each occurrence from the group: a bond to $S_f$, $COOR^{11}$, $C(=O)NHR^{11}$, $NHC(=O)R^{11}$, OH, $NHR^{11}$, $SO_3H$, $PO_3H$, —$OPO_3H_2$, —$OSO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, and a bond to $S_f$;

$R^{12}$ is a bond to $S_f$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

$S_f$ is a surfactant which is a lipid or a compound of the formula:

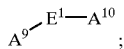

$A^9$ is selected from the group: OH and $OR^{27}$;

$A^{10}$ is $OR^{27}$;

$R^{27}$ is $C(=O)C_{1-20}$ alkyl;

$E^1$ is $C_{1-10}$ alkylene substituted with 1–3 $R^{28}$;

$R^{28}$ is independently selected at each occurrence from the group: $R^{30}$, —$PO_3H$—$R^{30}$, =O, —$CO_2R^{29}$, —$C(=O)R^{29}$, —$C(=O)N(R^{29})_2$, —$CH_2OR^{29}$, —$OR^{29}$, —$N(R^{29})_2$, $C_1$–$C_5$ alkyl, and $C_2$–$C_4$ alkenyl;

$R^{29}$ is independently selected at each occurrence from the group: $R^{30}$, H, $C_1$–$C_6$ alkyl, phenyl, benzyl, and trifluoromethyl;

$R^{30}$ is a bond to $L_n$;

and a pharmaceutically acceptable salt thereof to a patient; and (2) imaging the patient using sonography.

In another preferred embodiment, the present invention provides a method of imaging therapeutic angiogenesis in a patient comprising: (1) administering, by injection or infusion, an ultrasound contrast agent composition comprising: a targeting moiety and a surfactant, wherein the targeting moiety is bound to the surfactant, is an indazole nonpeptide, and binds to a receptor that is upregulated during angiogenesis and the compound has 0–1 linking groups between the targeting moiety and surfactant, wherein the linking group is present between the targeting moiety and surfactant to a patient; (2) imaging the area of the patient wherein the desired formation of new blood vessels is located.

In another preferred embodiment, the present invention provides a method of imaging atherosclerosis in a patient comprising: (1) administering, by injection or infusion, an ultrasound contrast agent composition comprising: a targeting moiety and a surfactant, wherein the targeting moiety is bound to the surfactant, is an indazole nonpeptide, and binds to a receptor that is upregulated during angiogenesis and the compound has 0–1 linking groups between the targeting moiety and surfactant, wherein the linking group is present between the targeting moiety and surfactant to a patient; (2) imaging the area of the patient wherein the atherosclerosis is located.

In another preferred embodiment, the present invention provides a method of imaging restenosis in a patient comprising: (1) administering, by injection or infusion, an ultrasound contrast agent composition comprising: a targeting moiety and a surfactant, wherein the targeting moiety is bound to the surfactant, is an indazole nonpeptide, and binds to a receptor that is upregulated during angiogenesis and the compound has 0–1 linking groups between the targeting moiety and surfactant, wherein the linking group is present between the targeting moiety and surfactant to a patient; (2) imaging the area of the patient wherein the restenosis is located.

In another preferred embodiment, the present invention provides a method of imaging cardiac ischemia in a patient comprising: (1) administering, by injection or infusion, an ultrasound contrast agent composition comprising: a targeting moiety and a surfactant, wherein the targeting moiety is bound to the surfactant, is an indazole nonpeptide, and binds to a receptor that is upregulated during angiogenesis and the compound has 0–1 linking groups between the targeting moiety and surfactant, wherein the linking group is present between the targeting moiety and surfactant to a patient; (2) imaging the area of the myocardium wherein the ischemic region is located.

In another preferred embodiment, the present invention provides a method of imaging myocardial reperfusion injury in a patient comprising: (1) administering, by injection or infusion, an ultrasound contrast agent composition comprising: a targeting moiety and a surfactant, wherein the targeting moiety is bound to the surfactant, is an indazole nonpeptide, and binds to a receptor that is upregulated during angiogenesis and the compound has 0–1 linking groups between the targeting moiety and surfactant, wherein the linking group is present between the targeting moiety and surfactant to a patient; (2) imaging the area of myocardium wherein the reperfusion injury is located.

In another preferred embodiment, the present invention provides a novel therapeutic radiopharmaceutical composition, comprising:

(a) a therapeutic radiopharmaceutical comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator, wherein the metallopharmnaceutical is a therapeutic radiopharmaceutical, the metal is a radioisotope selected from the group: $^{186}Re$, $^{188}Re$, $^{153}Sm$, $^{166}Ho$, $^{177}Lu$, $^{149}Pm$, $^{90}Y$, $^{212}Bi$, $^{103}Pd$, $^{109}Pd$, $^{159}Gd$, $^{140}La$, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir, the targeting moiety is an indazole nonpeptide and the linking group is present between the targeting moiety and chelator; and, (b) a parenterally acceptable carrier.

In another preferred embodiment, the present invention provides a novel diagnostic pharmaceutical composition, comprising:

(a) a diagnostic radiopharmaceutical, a MRI contrast agent, or a X-ray contrast agent comprising a novel diagnostic or therapeutic metallopharmaceutical composition, comprising: a metal, a chelator capable of chelating the metal and a targeting moiety, wherein the targeting moiety is bound to the chelator, is an indazole nonpeptide and binds to a receptor that is upregulated during angiogenesis and the compound has 0–1 linking groups between the targeting moiety and chelator; and, (b) a parenterally acceptable carrier.

Another embodiment of the present invention is diagnostic kits for the preparation of radiopharmaceuticals useful as imaging agents for cancer or imaging agents for imaging formation of new blood vessels. Diagnostic kits of the present invention comprise one or more vials containing the sterile, non-pyrogenic, formulation comprised of a predetermined amount of a reagent of the present invention, and optionally other components such as one or two ancillary ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The inclusion of one or two ancillary ligands is required for diagnostic kits comprising reagent comprising a hydrazine or hydrazone bonding moiety. The one or more vials that contain all or part of the formulation can independently be in the form of a sterile solution or a lyophilized solid.

Another aspect of the present invention are diagnostic kits for the preparation of radiopharmaceuticals useful as imaging agents for cancer. Diagnostic kits of the present invention comprise one or more vials containing the sterile, non-pyrogenic, formulation comprised of a predetermined amount of a reagent of the present invention, and optionally other components such as one or two ancillary ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The inclusion of one or two ancillary ligands is required for diagnostic kits comprising reagent comprising a hydrazine or hydrazone bonding moiety. The one or more vials that contain all or part of the formulation can independently be in the form of a sterile solution or a lyophilized solid.

Another aspect of the present invention contemplates a method of imaging cancer in a patient involving: (1) synthesizing a diagnostic radiopharmaceutical of the present invention, using a reagent of the present invention, capable of localizing in tumors; (2) administering said radiopharmaceutical to a patient by injection or infusion; (3) imaging the patient using planar or SPECT gamma scintigraphy, or positron emission tomography.

Another aspect of the present invention contemplates a method of imaging cancer in a patient involving: (1) administering a paramagnetic metallopharmaceutical of the present invention capable of localizing in tumors to a patient by injection or infusion; and (2) imaging the patient using magnetic resonance imaging.

Another aspect of the present invention contemplates a method of imaging cancer in a patient involving: (1) administering a X-ray contrast agent of the present invention capable of localizing in tumors to a patient by injection or infusion; and (2) imaging the patient using X-ray computed tomography.

Another aspect of the present invention contemplates a method of imaging cancer in a patient involving: (1) administering a ultrasound contrast agent of the present invention capable of localizing in tumors to a patient by injection or infusion; and (2) imaging the patient using sonography.

Another aspect of the present invention contemplates a method of treating cancer in a patient involving: (1) administering a therapeutic radiopharmaceutical of the present invention capable of localizing in tumors to a patient by injection or infusion.

DEFINITIONS

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present invention. The D and L-isomers of a particular amino acid are designated herein using the conventional 3-letter abbreviation of the amino acid, as indicated by the following examples: D-Leu, or L-Leu.

When any variable occurs more than one time in any substituent or in any formula, its definition on each occurrence is independent of its definition at every other occurrence. Thus, for example, if a group is shown to be substituted with 0–2 $R^{52}$, then said group may optionally be substituted with up to two $R^{52}$, and $R^{52}$ at each occurrence is selected independently from the defined list of possible $R^{52}$. Also, by way of example, for the group —N($R^{53}$)$_2$, each of the two $R^{53}$ substituents on N is independently selected from the defined list of possible $R^{53}$. Combinations of substituents and/or variables are permissible only if such combinations result in stable compounds. When a bond to a substituent is shown to cross the bond connecting two atoms in a ring, then such substituent may be bonded to any atom on the ring.

The term "nonpeptide" means preferably less than three amide bonds in the backbone core of the targeting moiety or preferably less than three amino acids or amino acid mimetics in the targeting moiety.

The term "metallopharmaceutical" means a pharmaceutical comprising a metal. The metal is the cause of the imageable signal in diagnostic applications and the source of the cytotoxic radiation in radiotherapeutic applications. Radiopharmaceuticals are metallopharmaceuticals in which the metal is a radioisotope.

By "reagent" is meant a compound of this invention capable of direct transformation into a metallopharmaceutical of this invention. Reagents may be utilized directly for the preparation of the metallopharmnaceuticals of this invention or may be a component in a kit of this invention.

The term "binding agent" means a metallopharmaceutical of this invention having affinity for and capable of binding to the vitronectin receptor. The binding agents of this invention have Ki<1000 nM.

By "stable compound" or "stable structure" is meant herein a compound that is sufficiently robust to survive isolation to a useful degree of purity from a reaction mixture, and formulation into an efficacious pharmaceutical agent.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the CRC Handbook of Chemistry and Physics, 65th Edition, CRC Press, Boca Raton, Fla., 1984, as any substance which yields ions, other than hydrogen or hydroxyl ions. As used herein, "pharmaceutically acceptable salts" refer to derivatives of the disclosed compounds modified by making acid or base salts. Examples of pharmaceutically acceptable salts include, but are not limited to, mineral or organic acid salts of basic residues such as amines; alkali or organic salts of acidic residues such as carboxylic acids; and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, tartaric, citric, ascorbic, pamoic, maleic, hydroxymaleic, phenylacetic, glutamic, benzoic, salicylic, sulfanilic, 2-acetoxybenzoic, furnaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

As used herein, "alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, hexyl, heptyl, octyl, nonyl, and decyl; "cycloalkyl" or "carbocycle" is intended to include saturated and partially unsaturated ring groups, including mono-, bi- or poly-cyclic ring systems, such as cyclopropyl, cyclobutyl, cyclopentyl, cyclohexyl, cycloheptyl, cyclooctyl and adamantyl; "bicycloalkyl" or "bicyclic" is intended to include saturated bicyclic ring groups such as [3.3.0]bicyclooctane, [4.3.0] bicyclononane, [4.4.0]bicyclodecane (decalin), [2.2.2] bicyclooctane, and so forth.

As used herein, the term "alkene" or "alkenyl" is intended to include hydrocarbon chains having the specified number of carbon atoms of either a straight or branched configuration and one or more unsaturated carbon-carbon bonds which may occur in any stable point along the chain, such as ethenyl, propenyl, and the like.

As used herein, the term "alkyne" or "alkynyl" is intended to include hydrocarbon chains having the specified number of carbon atoms of either a straight or branched configuration and one or more unsaturated carbon-carbon triple bonds which may occur in any stable point along the chain, such as propargyl, and the like.

As used herein, "aryl" or "aromatic residue" is intended to mean phenyl or naphthyl, which when substituted, the substitution can be at any position.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuiranyl, benzothiofliranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-arbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetaahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

As used herein, the term "alkaryl" means an aryl group bearing an alkyl group of 1–10 carbon atoms; the term "aralkyl" means an alkyl group of 1–10 carbon atoms bearing an aryl group; the term "arylalkaryl" means an aryl group bearing an alkyl group of 1–10 carbon atoms bearing an aryl group; and the term "heterocycloalkyl" means an alkyl group of 1–10 carbon atoms bearing a heterocycle.

A "polyalkylene glycol" is a polyethylene glycol, polypropylene glycol or polybutylene glycol having a molecular weight of less than about 5000, terminating in either a hydroxy or alkyl ether moiety.

A "carbohydrate" is a polyhydroxy aldehyde, ketone, alcohol or acid, or derivatives thereof, including polymers thereof having polymeric linkages of the acetal type.

A "cyclodextrin" is a cyclic oligosaccharide. Examples of cyclodextrins include, but are not limited to, α-cyclodextrin, hydroxyethyl-α-cyclodextrin, hydroxypropyl-α-cyclodextrin, β-cyclodextrin, hydroxypropyl-β-cyclodextrin, carboxymethyl-β-cyclodextrin, dihydroxypropyl-β-cyclodextrin, hydroxyethyl-β-cyclodextrin, 2,6 di-O-methyl-β-cyclodextrin, sulfated-β-cyclodextrin, γ-cyclodextrin, hydroxypropyl-γ-cyclodextrin, dihydroxypropyl-γ-cyclodextrin, hydroxyethyl-γ-cyclodextrin, and sulfated γ-cyclodextrin.

As used herein, the term "polycarboxyalkyl" means an alkyl group having between two and about 100 carbon atoms and a plurality of carboxyl substituents; and the term "polyazaalkyl" means a linear or branched alkyl group having between two and about 100 carbon atoms, interrupted by or substituted with a plurality of amine groups.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with a metal ion that is stable enough to prevent unwanted side-reactions but labile enough to be converted to a metallopharmaceutical. The formation of the intermediate complex is kinetically favored while the formation of the metallopharmaceutical is thermodynamically favored. Transfer ligands useful in the preparation of metallopharmaceuticals and in diagnostic kits useful for the preparation of diagnostic radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The term "donor atom" refers to the atom directly attached to a metal by a chemical bond.

"Ancillary" or "co-ligands" are ligands that are incorporated into a radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmraceutical comprised of two chelators or bonding units from one or two reagents and one ancillary or co-ligand are both considered to be comprised of binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmnaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "chelator" or "bonding unit" is the moiety or group on a reagent that binds to a metal ion through the formation of chemical bonds with one or more donor atoms.

The term "binding site" means the site in vivo or in vitro that binds a biologically active molecule.

A "diagnostic kit" or "kit" comprises a collection of components, termed the formulation, in one or more vials which are used by the practicing end user in a clinical or pharmacy setting to synthesize diagnostic radiopharmaceuticals. The kit provides all the requisite components to synthesize and use the diagnostic radiopharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

Therapeutic radiopharmaceuticals, X-ray contrast agent pharmaceuticals, ultrasound contrast agent pharmaceuticals and metallopharmaceuticals for magnetic resonance imaging contrast are provided to the end user in their final form in a formulation contained typically in one vial, as either a lyophilized solid or an aqueous solution. The end user reconstitutes the lyophilized with water or saline and withdraws the patient dose or just withdraws the dose from the aqueous solution formulation as provided.

A "lyophilization aid" is a component that has favorable physical properties for lyophilization, such as the glass transition temperature, and is added to the formulation to improve the physical properties of the combination of all the components of the formulation for lyophilization.

A "stabilization aid" is a component that is added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting preferentially with species that degrade other components or the metallopharmaceutical.

A "solubilization aid" is a component that improves the solubility of one or more other components in the medium required for the formulation.

A "bacteriostat" is a component that inhibits the growth of bacteria in a formulation either during its storage before use of after a diagnostic kit is used to synthesize a radiopharmaceutical.

The following abbreviations are used herein:

| | |
|---|---|
| Acm | acetamidomethyl |
| b-Ala, beta-Ala or bAla | 3-aminopropionic acid |
| ATA | 2-aminothiazole-5-acetic acid or 2-aminothiazole-5-acetyl group |
| Boc | t-butyloxycarbonyl |
| CBZ, Cbz or z | Carbobenzyloxy |
| Cit | citrulline |
| Dap | 2,3-diaminopropionic acid |
| DCC | dicyclohexylcarbodiimide |
| DIEA | diisopropylethylamine |
| DMAP | 4-dimethylaminopyridine |
| EOE | ethoxyethyl |
| HBTU | 2-(1H-Benzotriazol-1-yl)-1,1,3,3-tetramethyluronium hexafluorophosphate |
| hynic | boc-hydrazinonicotinyl group or 2-[carbonyl]-2-[[5-pyridinyl]hydrazono]methyl]-benzenesulfonic acid, |
| NMeArg or MeArga-N-methyl arginine | |
| NMeAsp | a-N-methyl aspartic acid |

-continued

| | |
|---|---|
| NMM | N-methylmorpholine |
| OcHex | O-cyclohexyl |
| OBzl | O-benzyl |
| oSu | O-succinimidyl |
| TBTU | 2-(1H-Benzotriazol-1-yl)-1,1,3,3-tetramethyluronium tetrafluoroborate |
| THF | tetrahydrofuranyl |
| THP | tetrahydropyranyl |
| Tos | tosyl |
| Tr | trityl |

The following conventional three-letter amino acid abbreviations are used herein; the conventional one-letter amino acid abbreviations are NOT used herein:

| | |
|---|---|
| Ala = | alanine |
| Arg = | arginine |
| Asn = | asparagine |
| Asp = | aspartic acid |
| Cys = | cysteine |
| Gln = | glutamine |
| Glu = | glutamic acid |
| Gly = | glycine |
| His = | histidine |
| Ile = | isoleucine |
| Leu = | leucine |
| Lys = | lysine |
| Met = | methionine |
| Nle = | norleucine |
| Orn = | ornithine |
| Phe = | phenylalanine |
| Phg = | phenylglycine |
| Pro = | proline |
| Sar = | sarcosine |
| Ser = | serine |
| Thr = | threonine |
| Trp = | tryptophan |
| Tyr = | tyrosine |
| Val = | valine |

As used herein, the term "bubbles", as used herein, refers to vesicles which are generally characterized by the presence of one or more membranes or walls surrounding an internal void that is filled with a gas or precursor thereto. Exemplary bubbles include, for example, liposomes, micelles and the like.

As used herein, the term "lipid" refers to a synthetic or naturally-occurring amphipathic compound which comprises a hydrophilic component and a hydrophobic component. Lipids include, for example, fatty acids, neutral fats, phosphatides, glycolipids, aliphatic alchols and waxes, terpenes and steroids.

As used herein, the term "lipid composition" refers to a composition which comprises a lipid compound. Exemplary lipid compositions include suspensions, emulsions and vesicular compositions.

As used herein, the term "lipid formulation" refers to a composition which comprises a lipid compound and a bioactive agent.

As used herein, the term "vesicle" refers to a spherical entity which is characterized by the presence of an internal void. Preferred vesicles are formulated from lipids, including the various lipids described herein. In any given vesicle, the lipids may be in the form of a monolayer or bilayer, and the mono- or bilayer lipids may be used to form one of more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

As used herein, the term "vesicular composition" refers to a composition which is formulate from lipids and which comprises vesicles.

As used herein, the term "vesicle formulation" refers to a composition which comprises vesicles and a bioactive agent.

As used herein, the term "lipsomes" refers to a generally spherical cluster or aggregate of amphipathic compounds, including lipid compounds, typically in the form of one or more concentric layers, for example, bilayers. They may also be referred to herein as lipid vesicles.

Angiogenesis is the process of formation of new capillary blood vessels from existing vasculature. It is an important component of a variety of physiological processes including ovulation, embryonic development, wound repair, and collateral vascular generation in the myocardium. It is also central to a number of pathological conditions such as tumor growth and metastasis, diabetic retinopathy, and macular degeneration. The process begins with the activation of existing vascular endothelial cells in response to a variety of cytokines and growth factors. The activated endothelial cells secrete enzymes that degrade the basement membrane of the vessels. The endothelial cells then proliferate and migrate into the extracellular matrix first forming tubules and subsequently new blood vessels.

Under normal conditions, endothelial cell proliferation is a very slow process, but it increases for a short period of time during embryogenesis, ovulation and wound healing. This temporary increase in cell turnover is governed by a combination of a number of growth stimulatory factors and growth suppressing factors. In pathological angiogenesis, this normal balance is disrupted resulting in continued increased endothelial cell proliferation. Some of the pro-angiogenic factors that have been identified include basic fibroblast growth factor (bFGF), angiogenin, TGF-alpha, TGF-beta, and vascular endothelium growth factor (VEGF), while interferon-alpha, interferon-beta and thrombospondin are examples of angiogenesis suppressors.

Angiogenic factors interact with endothelial cell surface receptors such as the receptor tyrosine kinases EGFR, FGFR, PDGFR, Flk-1/KDR, Flt-1, Tek, Tie, neuropilin-1, endoglin, endosialin, and Ax1. The receptors Flk-1/KDR, neuropilin-1, and Flk-1 recognize VEGF and these interactions play key roles in VEGF-induced angiogenesis. The Tie subfamily of receptor tyrosine kinases are also expressed prominently during blood vessel formation.

The proliferation and migration of endothelial cells in the extracellular matrix is mediated by interaction with a variety of cell adhesion molecules. Integrins are a diverse family of heterodimeric cell surface receptors by which endothelial cells attach to the extracellular matrix, each other and other cells. Angiogenesis induced by bFGF or TNF-alpha depend on the agency of the integrin avb3, while angiogenesis induced by VEGF depends on the integrin avb5 (Cheresh et. al., Science, 1995, 270, 1500–2). Induction of expression of the integrins a1b1 and a2b1 on the endothelial cell surface is another important mechanism by which VEGF promotes angiogenesis (Senger, et. al., Proc. Natl. Acad, Sci USA, 1997, 94, 13612–7).

The pharmaceuticals of the present invention are comprised of a non-peptide targeting moiety for the vitronectin receptor that is expressed or upregulated in angiogenic tumor vasculature.

The ultrasound contrast agents of the present invention comprise a plurality of vitronectin receptor targeting moieties attached to or incorporated into a microbubble of a biocompatible gas, a liquid carrier, and a surfactant microsphere, further comprising an optional linking moiety, $L_n$, between the targeting moieties and the microbubble. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein incorporated by reference. The term surfactant microsphere includes nanospheres, liposomes, vesicles and the like. The biocompatible gas can be air, or a fluorocarbon, such as a $C_3$–$C_5$ perfluoroalkane, which provides the difference in echogenicity and thus the contrast in ultrasound imaging. The gas is encapsulated or contained in the microsphere to which is attached the biodirecting group, optionally via a linking group. The attachment can be covalent, ionic or by van der Waals forces. Specific examples of such contrast agents include lipid encapsulated perfluorocarbons with a plurality of tumor neovasculature receptor binding peptides, polypeptides or peptidomimetics.

X-ray contrast agents of the present invention are comprised of one or more vitronectin receptor targeting moieties attached to one or more X-ray absorbing or "heavy" atoms of atomic number 20 or greater, further comprising an optional linking moiety, $L_n$, between the targeting moieties and the X-ray absorbing atoms. The frequently used heavy atom in X-ray contrast agents is iodine. Recently, X-ray contrast agents comprised of metal chelates (Wallace, R., U.S. Pat. No. 5,417,959) and polychelates comprised of a plurality of metal ions (Love, D., U.S. Pat. No. 5,679,810) have been disclosed. More recently, multinuclear cluster complexes have been disclosed as X-ray contrast agents (U.S. Pat. No. 5,804,161, PCT WO 91/14460, and PCT WO 92/17215).

MRI contrast agents of the present invention are comprised of one or more vitronectin receptor targeting moieties attached to one or more paramagnetic metal ions, further comprising an optional linking moiety, $L_n$, between the targeting moieties and the paramagnetic metal ions. The paramagnetic metal ions are present in the form of metal complexes or metal oxide particles. U.S. Pat. Nos. 5,412, 148, and 5,760,191, describe examples of chelators for paramagnetic metal ions for use in MRI contrast agents. U.S. Pat. No. 5,801,228, U.S. Pat. No. 5,567,411, and U.S. Pat. No. 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

The pharmaceuticals of the present invention have the formulae, $(Q)_d$—$L_n$—$(C_h$—$X)$, $(Q)_d$—$L_n$—$(C_h$—$X^1)_{d'}$, $(Q)_d$—$L_n$—$(X^2)_{d''}$, and $(Q)_d$—$L_n$—$(X^3)$, wherein Q represents a non-peptide that binds to a receptor expressed in angiogenic tumor vasculature, d is 1–10, $L_n$ represents an optional linking group, $C_h$ represents a metal chelator or bonding moiety, X represents a radioisotope, $X^1$ represents paramagnetic metal ion, $X^2$ represents a paramagnetic metal ion or heavy atom containing insoluble solid particle, d" is 1–100, and $X^3$ represents a surfactant microsphere of an echogenic gas. The interaction of the non-peptide recognition sequences of the vitronectin receptor binding portion of the pharmaceuticals with the □v□3 receptor results in localization of the pharmaceuticals in angiogenic tumor vasculature, which express the □v□3 receptor.

The pharmaceuticals of the present invention can be synthesized by several approaches. One approach involves the synthesis of the targeting non-peptide moiety, Q, and direct attachment of one or more moieties, Q, to one or more metal chelators or bonding moieties, $C_h$, or to a paramagnetic metal ion or heavy atom containing solid particle, or to an echogenic gas microbubble. Another approach involves the attachment of one or more moieties, Q, to the linking group, $L_n$, which is then attached to one or more metal chelators or bonding moieties, $C_h$, or to a paramagnetic metal ion or heavy atom containing solid particle, or to an echogenic gas microbubble. Another approach involves the synthesis of a non-peptide, Q, bearing a fragment of the linking group, $L_n$, one or more of which are then attached to the remainder of the linking group and then to one or more metal chelators or bonding moieties, $C_h$, or to a paramagnetic metal ion or heavy atom containing solid particle, or to an echogenic gas microbubble.

The non-peptide vitronectin binding moieties, Q, optionally bearing a linking group, $L_n$, or a fragment of the linking group, can be synthesized using standard synthetic methods known to those skilled in the art. Preferred methods include but are not limited to those methods described below.

The attachment of linking groups, $L_n$, to the non-peptides, Q; chelators or bonding units, $C_h$, to the non-peptides, , Q, or to the linking groups, $L_n$; and non-peptides, bearing a fragment of the linking group to the remainder of the linking group, in combination forming the moiety, $(Q)_d$—$L_n$, and then to the moiety $C_h$; can all be performed by standard techniques. These include, but are not limited to, amidation, esterification, alkylation, and the formation of ureas or thioureas. Procedures for performing these attachments can be found in Brinkley, M., *Bioconjugate Chemistiy* 1992, 3(1), which is incorporated herein by reference.

A number of methods can be used to attach the non-peptides, Q, to paramagnetic metal ion or heavy atom containing solid particles, $X^2$, by one of skill in the art of the surface modification of solid particles. In general, the targeting moiety Q or the combination $(Q)_d L_n$ is attached to a coupling group that react with a constituent of the surface of the solid particle. The coupling groups can be any of a number of silanes which react with surface hydroxyl groups on the solid particle surface, as described in co-pending U.S. patent application Ser. No. 09/356,178, and can also include polyphosphonates, polycarboxylates, polyphosphates or mixtures thereof which couple with the surface of the solid particles, as described in U.S. Pat. No. 5,520,904.

A number of reaction schemes can be used to attach the non-peptides, Q to the surfactant microsphere, $X^3$. These are illustrated in following reaction schemes where $S_f$ represents a surfactant moiety that forms the surfactant microsphere.

Acylation Reaction:

$S_f$—C(=O)—Y +

-continued

Q—$NH_2$ or ----> $S_f$—C(=O)—NH—Q

Q—OH or $S_f$—C(=O)—O—Q

Y is a leaving group or active ester

Disulfide Coupling:

$S_f$—SH + Q—SH ----> $S_f$—S—S—Q

Sulfonamide Coupling:

$S_f$—S(=O)$_2$—Y + Q—$NH_2$ ---->
$S_f$—S(=O)$_2$—NH—Q

Reductive Amidation:

$S_f$—CHO + Q—$NH_2$ ----> $S_f$—NH—Q

In these reaction schemes, the substituents $S_f$ and Q can be reversed as well.

The linking group $L_n$ can serve several roles. First it provides a spacing group between the metal chelator or bonding moiety, $C_h$, the paramagnetic metal ion or heavy atom containing solid particle, $X^2$, and the surfactant microsphere, $X^3$, and the one or more of the non-peptides, Q, so as to minimize the possibility that the moieties $C_h$—X, $C_h$—$X^1$, $X^2$, and $X^3$, will interfere with the interaction of the recognition sequences of Q with angiogenic tumor vasculature receptors. The necessity of incorporating a linking group in a reagent is dependent on the identity of Q, $C_h$—X, $C_h$—$X^1$, $X^2$, and $X^3$. If $C_h$—X, $C_h$—$X^1$, $X^2$, and $X^3$, cannot be attached to Q without substantially diminishing its affinity for the receptors, then a linking group is used. A linking group also provides a means of independently attaching multiple non-peptides, Q, to one group that is attached to $C_h$—X, $C_h$—$X^1$, $X^2$, or $X^3$.

The linking group also provides a means of incorporating a pharmacokinetic modifier into the pharmaceuticals of the present invention. The pharmacokinetic modifier serves to direct the biodistribution of the injected pharmaceutical other than by the interaction of the targeting moieties, Q, with the vitronectin receptors expressed in the tumor neovasculature. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route of elimination of the pharmaceuticals. Preferred pharmacokinetic modifiers are those that result in moderate to fast blood clearance and enhanced renal excretion.

The metal chelator or bonding moiety, $C_h$, is selected to form stable complexes with the metal ion chosen for the particular application. Chelators or bonding moieties for diagnostic radiopharmaceuticals are selected to form stable complexes with the radioisotopes that have imageable gamma ray or positron emissions, such as $^{99m}$Tc, $^{95}$Tc, 111In, $^{62}$Cu, $^{60}$Cu, $^{64}$Cu, $^{67}$Ga, $^{68}$Ga, $^{86}$Y.

Chelators for technetium, copper and gallium isotopes are selected from diaminedithiols, monoarine-monoamidedithiols, triamide-monothiols, monoamine-diamide-monothiols, diaminedioximes, and hydrazines. The chelators are generally tetradentate with donor atoms selected from nitrogen, oxygen and sulfur. Preferred reagents are comprised of chelators having amine nitrogen and thiol sulfur donor atoms and hydrazine bonding units. The thiol sulfur atoms and the hydrazines may bear a protecting group which can be displaced either prior to using the reagent to synthesize a radiopharmaceutical or preferably in situ during the synthesis of the radiopharmaceutical.

Exemplary thiol protecting groups include those listed in Greene and Wuts, "Protective Groups in Organic Synthesis" John Wiley & Sons, New York (1991), the disclosure of which is hereby incorporated by reference. Any thiol protecting group known in the art can be used. Examples of thiol protecting groups include, but are not limited to, the following: acetamidomethyl, benzamidomethyl, 1-ethoxyethyl, benzoyl, and triphenylmethyl.

Exemplary protecting groups for hydrazine bonding units are hydrazones which can be aldehyde or ketone hydrazones having substituents selected from hydrogen, alkyl, aryl and heterocycle. Particularly preferred hydrazones are described in co-pending U.S. Ser. No. 08/476,296 the disclosure of which is herein incorporated by reference in its entirety.

The hydrazine bonding unit when bound to a metal radionuclide is termed a hydrazido, or diazenido group and serves as the point of attachment of the radionuclide to the remainder of the radiopharmaceutical. A diazenido group can be either terminal (only one atom of the group is bound to the radionuclide) or chelating. In order to have a chelating diazenido group at least one other atom of the group must also be bound to the radionuclide. The atoms bound to the metal are termed donor atoms.

Chelators for $^{111}$In and $^{86}$Y are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic) acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-arinowmethoxyphenyl)-2,2':6',2"-terpyridine. Procedures for synthesizing these chelators that are not commercially available can be found in Brechbiel, M. and Gansow, O., *J. Chem. Soc. Perkin Trans.* 1992, 1, 1175; Brechbiel, M. and Gansow, O., *Bioconjugate Chem.* 1991, 2, 187; Deshpande, S., et. al., *J. Nucl. Med.* 1990, 31, 473; Kruper, J., U.S. Pat. No. 5,064,956, and Toner, J., U.S. Pat. No. 4,859,777, the disclosures of which are hereby incorporated by reference in their entirety.

The coordination sphere of metal ion includes all the ligands or groups bound to the metal. For a transition metal radionuclide to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If the chelator or bonding unit does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

Preferred technetium radiopharmaceuticals of the present invention are comprised of a hydrazido or diazenido bonding unit and an ancillary ligand, $A_{L1}$, or a bonding unit and two types of ancillary $A_{L1}$ and $A_{L2}$, or a tetradentate chelator comprised of two nitrogen and two sulfur atoms. Ancillary ligands $A_{L1}$ are comprised of two or more hard donor atoms such as oxygen and amine nitrogen (sp$^3$ hybridized). The donor atoms occupy at least two of the sites in the coordination sphere of the radionuclide metal; the ancillary ligand $A_{L1}$ serves as one of the three ligands in the ternary ligand system. Examples of ancillary ligands $A_{L1}$ include but are not limited to dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis (hydroxymethyl)propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bishydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine (tris (hydroxymethyl)methylglycine).

The most preferred technetium radiopharmaceuticals of the present invention are comprised of a hydrazido or diazenido bonding unit and two types of ancillary designated $A_{L1}$ and $A_{L2}$, or a diaminedithiol chelator. The second type of ancillary ligands $A_{L2}$ are comprised of one or more soft donor atoms selected from the group: phosphine phosphorus, arsine arsenic, imine nitrogen (sp$^2$ hybridized), sulfur (sp$^2$ hybridized) and carbon (sp hybridized); atoms which have p-acid character. Ligands $A_{L2}$ can be monodentate, bidentate or tridentate, the denticity is defined by the number of donor atoms in the ligand. One of the two donor atoms in a bidentate ligand and one of the three donor atoms in a tridentate ligand must be a soft donor atom. We have disclosed in co-pending U.S. Ser. No. 08/415,908, and U.S. Ser. Nos. 60/013360 and 08/646,886, the disclosures of which are herein incorporated by reference in their entirety, that radiopharmaceuticals comprised of one or more ancillary or co-ligands $A_{L2}$ are more stable compared to radiopharmaceuticals that are not comprised of one or more ancillary ligands, $A_{L2}$; that is, they have a minimal number of isomeric forms, the relative ratios of which do not change significantly with time, and that remain substantially intact upon dilution.

The ligands $A_{L2}$ that are comprised of phosphine or arsine donor atoms are trisubstituted phosphines, trisubstituted arsines, tetrasubstituted diphosphines and tetrasubstituted diarsines. The ligands $A_{L2}$ that are comprised of imine nitrogen are unsaturated or aromatic nitrogen-containing, 5 or 6-membered heterocycles. The ligands that are comprised of sulfur ($sp^2$ hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources. Isonitriles can be synthesized as described in European Patent 0107734 and in U.S. Pat. No. 4,988,827, herein incorporated by reference.

Preferred ancillary ligands $A_{L2}$ are trisubstituted phosphines and unsaturated or aromatic 5 or 6 membered heterocycles. The most preferred ancillary ligands $A_{L2}$ are trisubstituted phosphines and unsaturated 5 membered heterocycles.

The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands which may affect the biological properties of the radiopharmaceuticals, such as altering the distribution into non-target tissues, cells or fluids, and the mechanism and rate of elimination from the body.

Chelators or bonding moieties for therapeutic radiopharmaceuticals are selected to form stable complexes with the radioisotopes that have alpha particle, beta particle, Auger or Coster-Kronig electron emissions, such as $^{186}Re$, $^{188}Re$, $^{153}Sm$, $^{166}Ho$, $^{177}Lu$, $^{149}Pm$, $^{90}Y$, $^{212}Bi$, $^{103}Pd$, $^{109}Pd$, $^{159}Gd$, $^{140}La$, $^{198}Au$, $^{199}Au$, $^{169}Yb$, $^{175}Yb$, $^{165}Dy$, $^{166}Dy$, $^{67}Cu$, $^{105}Rh$, $^{111}Ag$, and $^{192}Ir$. Chelators for rhenium, copper, palladium, platinum, iridium, rhodium, silver and gold isotopes are selected from diaminedithiols, monoamine-monoamidedithiols, triamide-monothiols, monoamine-diamide-monothiols, diaminedioximes, and hydrazines. Chelators for yttrium, bismuth, and the lanthanide isotopes are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetrianinepentaacetic acid, 2-benzyl-6-methyl-DTPA, and 6,6"-bis[N,N,N",N"-tetra(carboxymethyl)aminomethyl)4'-(3-amino-4-methoxyphenyl)-2,2':6',2"-terpyridine.

Chelators for magnetic resonance imaging contrast agents are selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

The technetium and rhenium radiopharmaceuticals of the present invention comprised of a hydrazido or diazenido bonding unit can be easily prepared by admixing a salt of a radionuclide, a reagent of the present invention, an ancillary ligand $A_{L1}$, an ancillary ligand $A_{L2}$, and a reducing agent, in an aqueous solution at temperatures from 0 to 100° C. The technetium and rhenium radiopharmaceuticals of the present invention comprised of a tetradentate chelator having two nitrogen and two sulfur atoms can be easily prepared by admixing a salt of a radionuclide, a reagent of the present invention, and a reducing agent, in an aqueous solution at temperatures from 0 to 100° C.

When the bonding unit in the reagent of the present invention is present as a hydrazone group, then it must first be converted to a hydrazine, which may or may not be protonated, prior to complexation with the metal radionuclide. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator or bonding unit, or in the presence of the radionuclide in which case the reagent itself is combined with the radionuclide and the ancillary or co-ligand or ligands. In the latter case, the pH of the reaction mixture must be neutral or acidic.

Alternatively, the radiopharmaceuticals of the present invention comprised of a hydrazido or diazenido bonding unit can be prepared by first admixing a salt of a radionuclide, an ancillary ligand $A_{L1}$, and a reducing agent in an aqueous solution at temperatures from 0 to 100° C. to form an intermediate radionuclide complex with the ancillary ligand $A_{L1}$ then adding a reagent of the present invention and an ancillary ligand $A_{L2}$ and reacting further at temperatures from 0 to 100° C.

Alternatively, the radiopharmaceuticals of the present invention comprised of a hydrazido or diazenido bonding unit can be prepared by first admixing a salt of a radionuclide, an ancillary ligand $A_{L1}$, a reagent of the present invention, and a reducing agent in an aqueous solution at temperatures from 0 to 100° C. to form an intermediate radionuclide complex, and then adding an ancillary ligand $A_{L2}$ and reacting further at temperatures from 0 to 100° C.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnctate used to prepare the radiopharmaceuticals of the present invention can range from 0.1 mCi to 1 Ci, or more preferably from 1 to 200 mCi.

The amount of the reagent of the present invention used to prepare the technetium and rhenium radiopharmaceuticals of the present invention can range from 0.01 µg to 10 mg, or more preferably from 0.5 µg to 200 µg. The amount used will be dictated by the amounts of the other reactants and the identity of the radiopharmaceuticals of the present invention to be prepared.

The amounts of the ancillary ligands $A_{L1}$ used can range from 0.1 mg to 1 g, or more preferably from 1 mg to 100 mg.

The exact amount for a particular radiopharmaceutical is a function of identity of the radiopharmaceuticals of the present invention to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid.

The amounts of the ancillary ligands $A_{L2}$ used can range from 0.001 mg to 1 g, or more preferably from 0.01 mg to 10 mg. The exact amount for a particular radiopharmaceutical is a function of the identity of the radiopharmaceuticals of the present invention to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the reagent bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg.

The specific structure of a radiopharmaceutical of the present invention comprised of a hydrazido or diazenido bonding unit will depend on the identity of the reagent of the present invention used, the identity of any ancillary ligand $A_{L1}$, the identity of any ancillary ligand $A_{L2}$, and the identity of the radionuclide. Radiopharmaceuticals comprised of a hydrazido or diazenido bonding unit synthesized using concentrations of reagents of <100 µg/mL, will be comprised of one hydrazido or diazenido group. Those synthesized using >1 mg/mL concentrations will be comprised of two hydrazido or diazenido groups from two reagent molecules. For most applications, only a limited amount of the biologically active molecule can be injected and not result in undesired side-effects, such as chemical toxicity, interference with a biological process or an altered biodistribution of the radiopharmaceutical. Therefore, the radiopharmaceuticals which require higher concentrations of the reagents comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

The indium, copper, gallium, silver, palladium, rhodium, gold, platinum, bismuth, yttrium and lanthanide radiopharmaceuticals of the present invention can be easily prepared by admixing a salt of a radionuclide and a reagent of the present invention, in an aqueous solution at temperatures from 0 to 100° C. These radionuclides are typically obtained as a dilute aqueous solution in a mineral acid, such as hydrochloric, nitric or sulfuric acid. The radionuclides are combined with from one to about one thousand equivalents of the reagents of the present invention dissolved in aqueous solution. A buffer is typically used to maintain the pH of the reaction mixture between 3 and 10.

The gadolinium, dysprosium, iron and manganese metallopharmaceuticals of the present invention can be easily prepared by admixing a salt of the paramagnetic metal ion and a reagent of the present invention, in an aqueous solution at temperatures from 0 to 100° C. These paramagnetic metal ions are typically obtained as a dilute aqueous solution in a mineral acid, such as hydrochloric, nitric or sulfuric acid. The paramagnetic metal ions are combined with from one to about one thousand equivalents of the reagents of the present invention dissolved in aqueous solution. A buffer is typically used to maintain the pH of the reaction mixture between 3 and 10.

The total time of preparation will vary depending on the identity of the metal ion, the identities and amounts of the reactants and the procedure used for the preparation. The preparations may be complete, resulting in >80% yield of the radiopharmaceutical, in 1 minute or may require more time. If higher purity metallopharmaceuticals are needed or desired, the products can be purified by any of a number of techniques well known to those skilled in the art such as liquid chromatography, solid phase extraction, solvent extraction, dialysis or ultrafiltration.

Buffers useful in the preparation of metallopharmaceuticals and in diagnostic kits useful for the preparation of said radiopharmaceuticals include but are not limited to phosphate, citrate, sulfosalicylate, and acetate. A more complete list can be found in the United States Pharmacopeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of metallopharmaceuticals and in diagnostic kits useful for the preparation of radiopharmaceuticals include but are not limited to ascorbic acid, cysteine, monothioglycerol, sodium bisulfite, sodium metabisulfite, gentisic acid, and inositol.

Solubilization aids useful in the preparation of metallopharmaceuticals and in diagnostic kits useful for the preparation of radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of metallopharmaceuticals and in diagnostic kits useful for the preparation of radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Pat. No. 5,155,215; U.S. Pat. No. 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

The ultrasound contrast agents of the present invention are administered by intravenous injection in an amount of 10 to 30 µL of the echogenic gas per kg body weight or by infusion at a rate of approximately 3 µL/kg/min. Imaging is performed using known techniques of sonography.

Other features of the invention will become apparent in the course of the following descriptions of exemplary embodiments which are given for illustration of the invention and are not intended to be limiting thereof.

EXAMPLES

Representative materials and methods that may be used in preparing the compounds of the invention are described further below. 1-(3-((1-(triphenylmethyl)imidazol-2-yl)amino)propyl)-1H-indazole-5-carboxylic acid was synthesized as described in U.S. Pat. No. 5,760,028. All chemicals and solvents (reagent grade) were used as supplied from the vendors cited without further purification. t-Butyloxycarbonyl (Boc) amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). Boc-L-cysteic acid, Boc-L-cysteic acid N-hydroxyphenyl ester, and Boc-L-cysteic acid p-nitrophenyl ester were prepared as described in Liebigs Ann. Chem. 1979, 776–783. 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DEA), 1,2,4-triazole, stannous chloride dihydrate, 1-(3-dimethylaminopropyl)-3-ethylcarbodiimide hydrochloride (EDC), triethylsilane (Et$_3$SiH), and tris(3-sulfonatophenyl)phosphine trisodium salt (TPPTS) were purchased from Aldrich Chemical Company. Bis(3-sulfonatophenyl)phenylphosphine disodium salt (TPPDS) was prepared by the published procedure (Kuntz, E., U.S. Pat. No. 4,248,802). (3-Sulfonatophenyl)diphenylphosphine monosodium salt (TPPMS) was purchased from TCI America, Inc. Tricine was obtained from Research Organics, Inc. Technetium-99m-pertechnetate ($^{99m}$TcO$_4^-$) was obtained from a DuPont Pharma $^{99}$Mo/$^{99m}$Tc Technelite® generator. In-111-chloride (Indichlor®) was obtained from Amersham Medi-Physics, Inc. Sm-153-chloride and Lutetium-177-chloride were obtained from the University of Missouri Research Reactor (MURR). Yttrium-90 chloride was obtained from the Pacific Northwest Research Laboratories. Dimethylformamide (DMF), ethyl acetate, chloroform (CHCl$_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were commercially obtained. Absolute ethanol was obtained from Quantum Chemical Corporation. DOTA(OtBu)$_3$—OH was prepared as described or purchased from Macrocyclics, Inc (Texas).

Synthesis of Boc-Glu-(OTFP)-OTFP

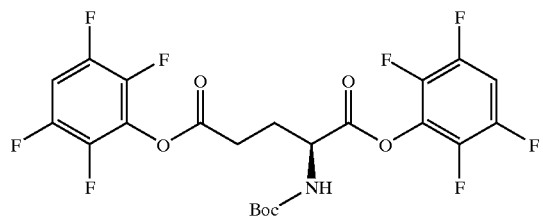

To a solution of Boc-Glu-OH (28.9 g, 117 mmol) in DMF (500 mL) at room temperature, and under nitrogen, was added a solution of 2,3,5,6-tetrafluorophenol (48.2 g, 290 mmol) in DMF (50 mL). After stirring for 10 min. EDC (55.6 g, 290 mmol) was added and the reaction mixture was stirred for about 96 h. The volatiles were removed in vacuo and the residue was triturated in 0.1 N HCl (750 mL). To this mixture was added ethyl acetate (600 mL), the layers separated. The aqueous layer was extracted with ethyl acetate (3×~500 mL), and all the ethyl acetate fractions were combined, washed with water (300 mL) and brine (300 mL), dried (MgSO$_4$), and concentrated to give a tan solid (62 g). The tan solid was washed with acetonitrile to give the title compound (45.5 g, 73%) in purified form.

ESMS: Calculated for C$_{22}$H$_{17}$F$_8$NO$_6$, 543.09; found, 566.0 [M+Na]$^{+1}$.

Example 1

Synthesis of 2-(((4-(4-(((3-(2-(2-(3-((6-((1-Aza-2-(2-sulfophenyl)vinyl)amino)(3-pyridyl))carbonylamino)propoxy)ethoxy)ethoxy)propyl)amino)sulfonyl)phenyl)phenyl)sulfonyl)amino)-3-((1-(3-(imidazole-2-ylamino)propyl)(1H-indazol-5-yl))carbonylamino)propanoic Acid

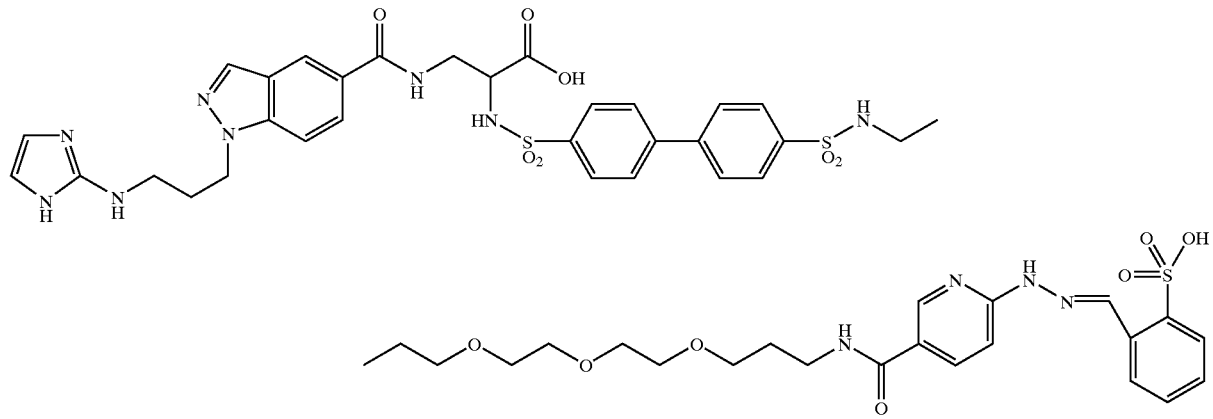

Part A—Preparation of N-(3-(2-(2-(3-aminopropoxy) ethoxy)ethoxy)propyl)(phenylmethoxy)formamide

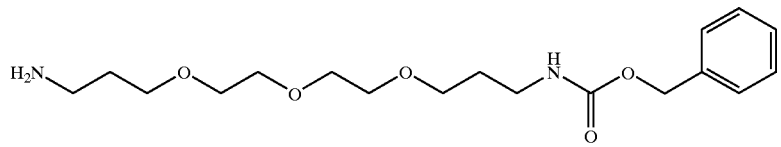

A solution of 4,7,10-trioxa-1,13-tridecanediamine (158 mL, 0.72 mol), TEA (16.7 mL, 0.12 mol), and MeOH (300 mL) in peroxide-free THF (1,000 mL) was placed in a 3 liter 3-neck flask fitted with a mechanical stirrer, a thermometer, and an addition funnel with nitrogen line. The addition funnel was charged with a solution of benzyl chloroformate (17.1 mL, 0.12 mol) in peroxide-free THF (1,000 mL). The contents of the flask were cooled below 5° C. The contents of the addition funnel were added to the flask with rapid stirring over 4 h while keeping the temperature below 5° C. The solution was stirred an additional 30 min and concentrated to give a thick syrup. This syrup was taken up in saturated NaCl (1800 mL) and 10% $Na_2CO_3$ (200 mL) and extracted with ether (3×1,000 mL). The combined ether extracts were washed with saturated NaCl (500 mL), dried ($MgSO_4$), and concentrated to give a pale yellow oil (36.74 g). Flash chromatography on a 7×29 cm silica gel column (DCM/MeOH/TEA, 20/15/0.5) gave the title compound as a colorless syrup (19.14 g, 45%). $^1$H NMR ($CDCl_3$): 7.33–7.25 (m, 5H), 5.59 (s, 1H), 5.06 (s, 2H), 3.62–3.45 (m, 12H), 3.32–3.25 (m, 2H), 2.74 (t, J=6.7 Hz, 2H), 1.75 (pentet, J=6.0 Hz, 2H), 1.67 (pentet, J=6.4 Hz, 2H), 1.33 (s, 2H); MS: m/e 355.4 [M+H]; High Resolution MS: Calcd for $C_{18}H_{31}N_2O_5$ [M+H]: 355.2233, Found: 355.2222.

Part B—Preparation of Methyl 3-((tert-Butoxy)carbonylamino)-2-(((4-(4-(((3-(2-(2-(3-((phenylmethoxy)carbonylamino)propoxy)ethoxy)ethoxy)propyl)amino)sulfonyl)phenyl)phenyl)sulfonyl)amino)propanoate

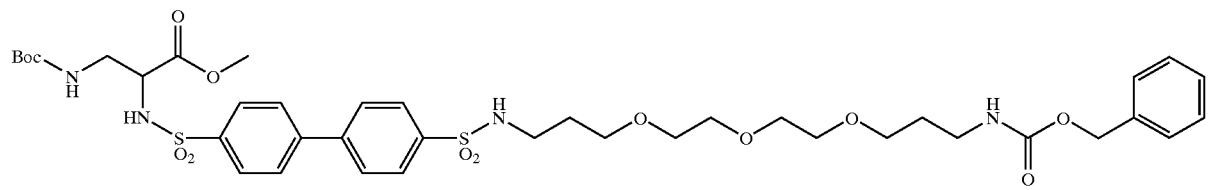

Biphenyl-4,4'-disulfonyl chloride (2.64 g, 7.5 mmol, freshly recrystallized from $CHCl_3$) and DCM (200 mL) were placed in a 500 mL 3-neck flask fitted with a thermometer, an addition fimnel, and a nitrogen line. The addition funnel was charged with a solution of N-(3-(2-(2-(3-aminopropoxy)ethoxy)ethoxy)propyl)(phenylmethoxy)formamide (1.77 g, 5.0 mmol) and DIEA (0.87 mL, 5.0 mmol) in DCM (40 mL). The contents of the flask were cooled below 5° C. The contents of the addition funnel were added to the flask with rapid stirring over 3 h while keeping the temperature of the flask below 5° C. The addition funnel was charged with a solution of N-β-Boc-L-α,β,-diaminopropionic acid methyl ester hydrochloride (2.55 g, 10 mmol) and DIEA (3.8 mL, 22 mmol) in DCM (25 mL). This solution was added to the flask with stirring at 5° C. over 15 min, and stirred at ambient temperatures for an additional 20 h. The reaction solution was washed consecutively with 0.1 N HCl (100 mL) and water (2×100 mL), dried ($MgSO_4$), and concentrated to give a viscous oil (5.79 g). Flash chromatography on a 5×21 cm silica gel column (85/15 EtOAc/hexanes, followed by 100% EtOAc) gave a colorless amorphous solid. Recrystallization from toluene (85 mL) gave the title compound as a colorless solid (2.52 g, 59%). MP: 104.5–106.5° C.; $^1$H NMR (CDCl$_3$): 8.00–7.90 (m, 4H), 7.72–7.64 (m, 4H), 7.46–7.24 (m, 5H), 5.96–5.88 (m, 1H), 5.86–5.73 (m, 1H), 5.41 (s, 1H), 5.16–5.00 (m, 3H), 4.15–4.02 (m, 1H), 3.68–3.39 (m, 17H), 3.34–3.22 (m, 2H), 3.13–3.03 (m, 2H), 1.80–1.62 (m, 4H), 1.39 (s, 9H); $^{13}$C NMR (CDCl$_3$): 170.2, 156.5, 156.1, 143.9, 143.0, 140.4, 139.4, 136.7, 128.4, 128.1, 128.0, 127.9, 127.9, 127.8, 127.3, 80.1, 70.6, 70.5, 70.2, 70.1, 70.0, 69.6, 66.5, 56.1, 52.9, 43.2, 42.4, 39.3, 29.4, 28.5, 28.2; MS: m/e 868.3 [M+NH$_4$]; High Resolution MS: Calcd for C$_{39}$H$_{55}$N$_4$O$_{13}$S$_2$ [M+H]: 851.3207, Found: 851.3226.

Part C—Preparation of Methyl 2-(((4-(4-(((3-(2-(2-(3-((Phenylmethoxy)carbonylamino)propoxy)ethoxy)ethoxy)propyl)amino)sulfonyl)phenyl)phenyl)sulfonyl)amino)-3-((1-(3-((1-(triphenylmethyl)imidazole-2-yl)amino)propyl)(1H-indazol-5-yl))carbonylamino)propanoate.

until basic to pH paper. In a separate flask, 1-(3-((1-(triphenylmethyl)imidazol-2-yl)amino)propyl)-1H-indazole-5-carboxylic acid (76 mg, 0.141 mmol), TEA (0.059 mL, 0.422 mmol), and HBTU (63.9 mg, 0.169 mmol) were dissolved in anhydrous DMF (3 mL). The resulting solution was stirred at ambient temperatures for 5 min and combined with the DMF solution from the TFA deprotection. The solution was concentrated after 2 h to give a viscous amber oil. The oil was dissolved in EtOAc (175 mL) and washed consecutively with water (50 mL), saturated NaHCO$_3$ (25 mL), and saturated NaCl (50 mL). The combined aqueous washings were back-extracted with EtOAc (50 mL). The combined EtOAc layers were dried (MgSO$_4$) and concentrated to give a viscous amber oil. Purification by flash chromatography on a 2×16 cm silica gel column using a EtOAc/MeOH step gradient (95/5, 93/7, 85/15) gave the title compound as a pale yellow foamy solid (86 mg, 48%). MS: m/e 1273.4 [M+H]; High Resolution MS: Calcd for C$_{68}$H$_{73}$N$_8$O$_{13}$S$_2$ [M+H]: 1273.4738, Found: 1273.4730.

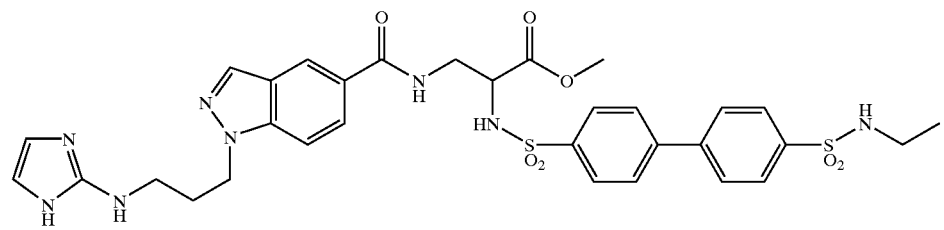

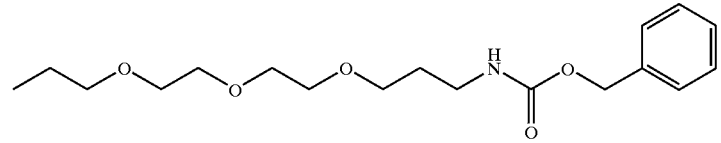

The product from Part B, above (141 mg, 0.166 mmol) was dissolved in 25/75 TFA/DCM (5 mL) and allowed to react at ambient temperatures for 15 min. The solution was concentrated to give a viscous amber oil. This oil was dissolved in anhydrous DMF (3 mL) and treated with TEA Part D—Preparation of 2-(((4-(4-(((3-(2-(2-(3-((Phenylmethoxy)carbonylamino)propoxy)ethoxy)ethoxy)propyl)amino)sulfonyl)phenyl)phenyl)sulfonyl)amino)-3-((1-(3-((1-(triphenylmethyl)imidazole-2-yl)amino)propyl)(1H-indazol-5-yl))carbonylamino)propanoic Acid

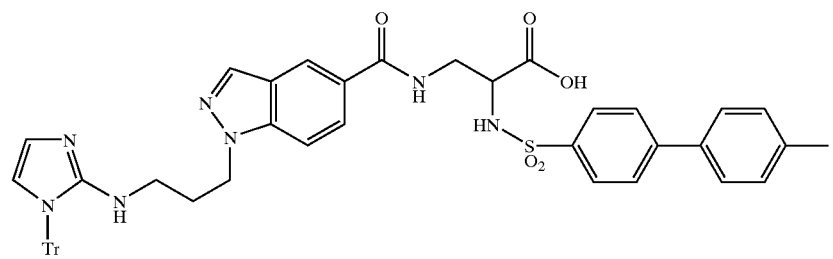

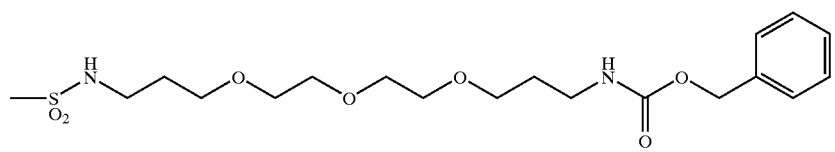

The product from Part C, above (200 mg, 0.159 mmol) was hydrolyzed in a mixture of peroxide-free THF (8.0 mL), 3 N LiOH (0.80 mL), and water (1.20 mL). The mixture was stirred at ambient temperatures under an atmosphere of nitrogen for 3 h. The THF was removed under reduced pressure and the resulting yellow solution was diluted with water (15 mL). The solution was adjusted to pH 5.0, and the resulting yellow ppt was extracted into DCM (4×25 mL). The combined DCM extracts were dried (MgSO$_4$), and concentrated to give the title compound as a yellow solid (174 mg, 88%). MS: m/e 1246.4 [M+H]; High Resolution MS: Calcd for $C_{66}H_{72}N_9O_{12}S_2$ [M+H]: 1246.4741, Found: 1246.4730.

Part E—Preparation of 2-(((4-(4-(((3-(2-(2-(3-Aminopropoxy)ethoxy)ethoxy)propyl)amino)sulfonyl)phenyl)phenyl)sulfonyl)amino)-3-((1-(3-(imidazole-2-ylamino)propyl)(1H-indazol-5-yl))carbonylamino)propanoic Acid.

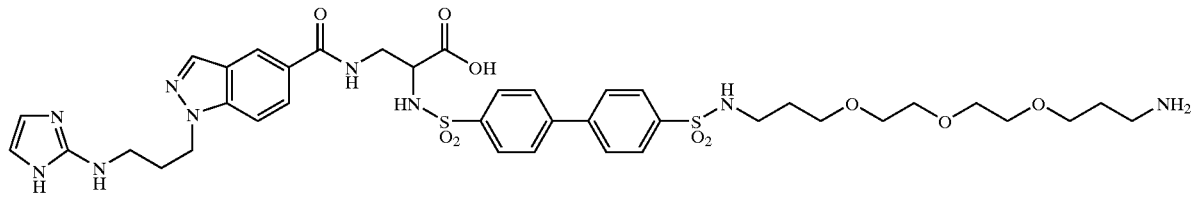

The product from Part D, above (154 mg, 0.124 mmol) was dissolved in degassed TFA (15 mL) and triethylsilane (0.10 mL, 0.626 mmol), and heated at 70° C. under an atmosphere of nitrogen for 1.5 h. The solution was concentrated and the resulting oily solid was dissolved in water (75 mL) and washed with ether (2×20 mL). The combined ether washings were back-extracted with water (10 mL). The two aqueous solutions were combined, and lyophilized to give the title compound as a hygroscopic off-white solid, (140 mg). MS: m/e 870.3 [M+H]; High Resolution MS: Calcd for $C_{39}H_{52}N_9O_{10}S_2$ [M+H]: 870.3278, Found: 870.3301.

Part F—Preparation of 2-(((4-4-(((3-(2-(2-(3-((6-((1-Aza-2-(2-sulfophenyl)vinyl)amino)(3-pyridyl))carbonylamino)propoxy)ethoxy)ethoxy)propyl)amino)sulfonyl)phenyl)phenyl)sulfonyl)amino)-3-((1-(3-(imidazole-2-ylamino)propyl)(1H-indazol-5-yl))carbonylamino)propanoic Acid.

The product from Part E, above (15 mg, 0.0137 mmol) was dissolved in anhydrous DMF (2.5 mL) and treated with TEA until basic to pH paper. The solution was treated with 2-(2-aza-2-((5-((2,5-dioxopyrrolidinyl)carbonyl)(2-pyridyl))amino)vinyl)benzenesulfonic acid (9.0 mg, 0.020 mmol) and stirred at ambient temperatures under a nitrogen atmosphere for 24 h. The DMF was removed under vacuum, and the resulting oil was dissolved in 50% ACN and purified by preparative HPLC on a Vydac C-18 column (22×250 mm) using a 2.52%/min gradient of 0 to 63% ACN containing 0.1% TFA at a flow rate of 20 mL/min. The main product peak eluting at 21.9 min was collected and lyophilized to give the title compound as a colorless powder (9.0 mg, 51%). MS: m/e 1173.4 [M+H]; High Resolution MS: Calcd for $C_{52}H_{61}N_{12}O_{14}S_3$ [M+H]: 1173.3592, Found: 1173.360.

Example 2

Synthesis of 2-(2-Aza-2-((5-(N-(1,3-bis(3-(2-(2-(3-(((4-(4-(((1-carboxy-2-((1-(3-(imidazol-2-ylamino)propyl)(1H-indazol-5-yl))carbonylamino)ethyl)amino)sulfonyl)phenyl)phenyl)sulfonyl)amino)propoxy)ethoxy)ethoxy)propyl)carbamoyl)prpyl)carbaroyl)(2-pyridyl))amino)vinyl)benzenesulfonic Acid

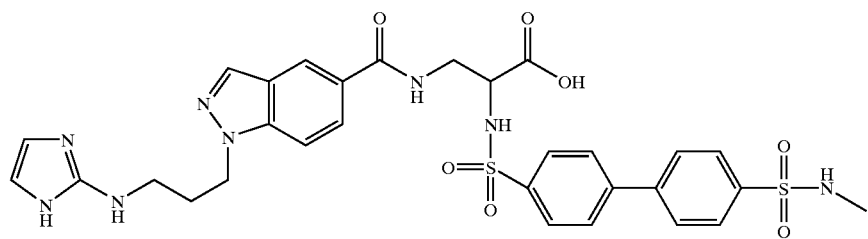
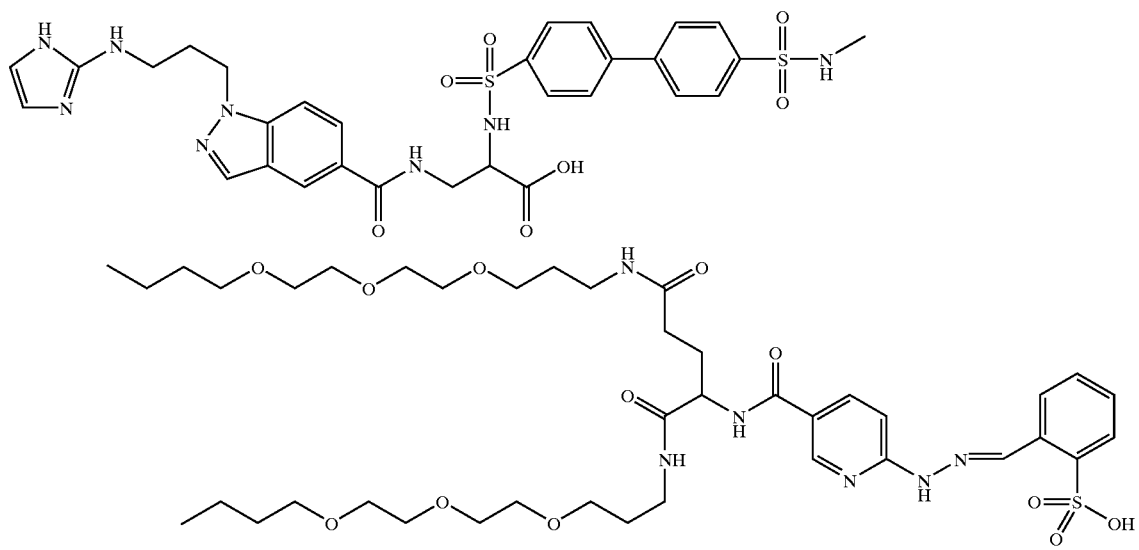
Part A—Preparation of N,N'-Bis(3-(2-(2-(3-(((4-(4-(((1-carboxy-2-((1-(3-(imidazol-2ylamino)propyl)(1H-indazol-5-yl))carbonylamino)ethyl)amino)sulfonyl)phenyl)phenyl)sulfonyl)amino)propoxy)ethoxy)ethoxy)propyl)-2-((tert-butoxy)carbonylamino)pentane-1,5-diamide.
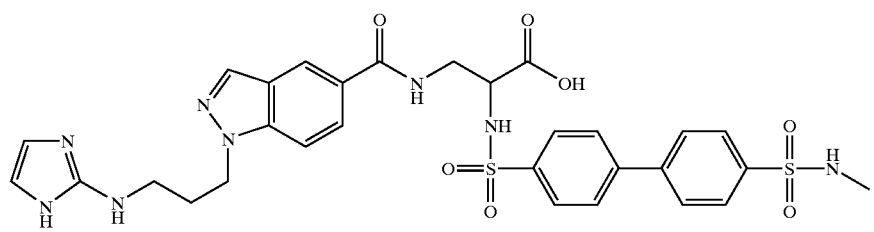
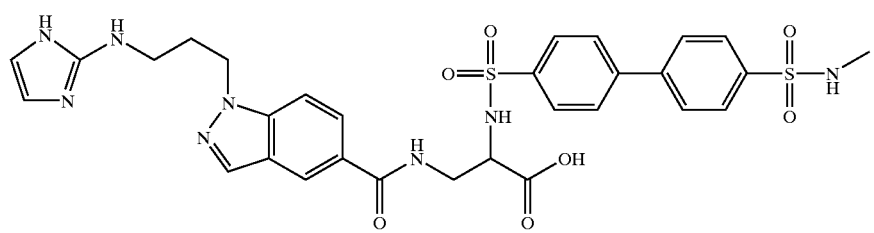

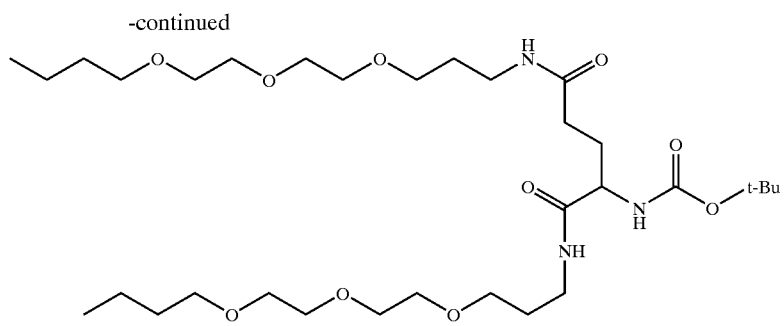

The product from Example 1, Part D (44 mg, 0.04 mmol) was dissolved in anhydrous DMF (5 mL) and made basic to pH paper with TEA. This solution was treated with the bis-N-hydroxysuccinimide ester of Boc-Glu-OH (7.9 mg, 0.018 mmol) and stirred at ambient temperatures under a nitrogen atmnosphere for 18 h. The DMF was removed under vacuum and the resulting oil was dissolved in 50% ACN and purified by preparative HPLC on a Vydac C-18 column (22×250 mm) using a 2.1%/min gradient of 0 to 63% ACN containing 0.1% TFA at a flow rate of 20 mL/min. The peak eluting at 21.1 min was collected and lyophilized to give the monomer 2-((tert-butoxy)carbonylamino)-4-(N-(3-(2-(2-(3-(((4-(4-(((1-carboxy-2-((1-(3-(imidazol-2-ylamino)propyl)(1H-indazol-5-yl))carbonylamino)ethyl) amino)sulfonyl)phenyl)phenyl)sulfonyl)amino)propoxy) ethoxy)ethoxy)propyl)carbamoyl)butanoic acid as a colorless solid in 82% purity A second HPLC purification using the above method gave 100% pure monomer (3.4 mg, 7.0%). MS: m/e 1099.5 [M+H], 550.5 [M+2H].

The dimeric product from Part A, above (11 mg. 0.0050 mmol) was dissolved in degassed TFA (2 mL) and stirred at ambient temperatures under a nitrogen atmosphere for 15 min and concentrated to a viscous amber oil. This oil was dissolved in anhydrous DMF (2 mL) and made basic with TEA. The solution was treated with 2-(2-aza-2-((5-((2,5-dioxopyrrolidinyl)carbonyl)(2-pyridyl))amino)vinyl) benzenesulfonic acid (0.024 mmol) and stirred at ambient temperatures under a nitrogen atmosphere for 56 h. The DMF was removed under vacuum, and the resulting oil was dissolved in 50% ACN and purified by preparative HPLC on a Vydac C-18 column (22×250 mm) using a 2.1%/min gradient of 0 to 63% ACN containing 0.1% TFA at a flow rate of 20 mL/min. The main product peak eluting at 20.7 min was collected and lyophilized to give the title compound as a colorless powder (5 mg, 42%). MS: m/e 1077.6 [M+2H], 719.0 [M+3H]; High Resolution MS: Calcd for $C_{96}H_{117}N_{22}O_{26}S_5$: 2153.7112, Found: 2153.7140.

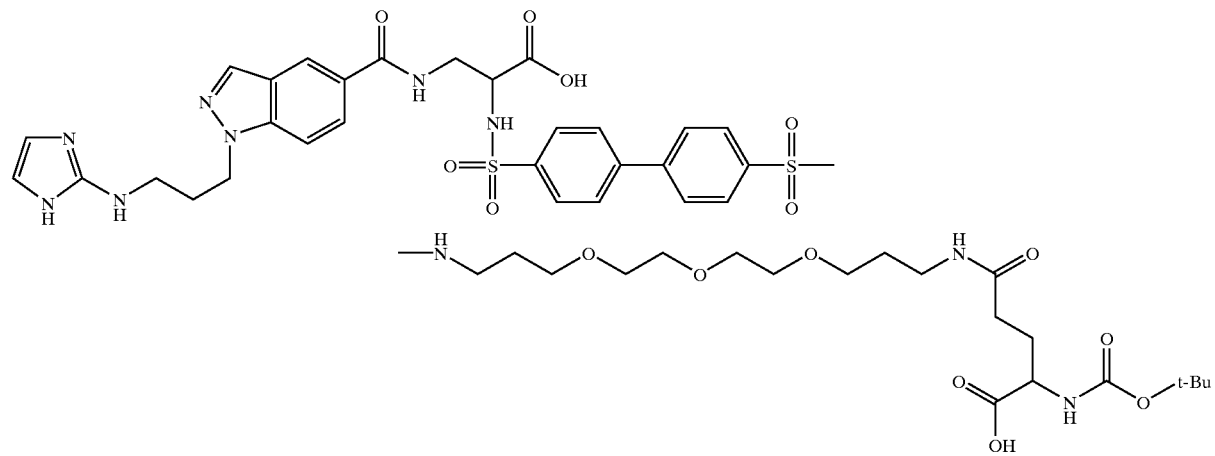

The main peak eluting at 22.4 min was collected and lyophilized to give the title compound as a colorless solid (11 mg, 25%). MS: m/e 1952.1 [M+H]; 976.9 [M+2H]; 651.6 [M+3H]; High Resolution MS: Calcd for $C_{88}H_{116}N_{19}O_{24}S_4$: 1950.7323, Found: 1950.7340.

Part B—Preparation of 2-(2-Aza-2-((5-(N-(1,3-bis(3-(2-(2-(3-(((4-(4-(((1-carboxy-2-((1-(3-(imidazol-2-ylamino) propyl)(1H-indazol-5-yl))carbonylamino)ethyl)amino) sulfonyl)phenyl)phenyl)sulfonyl)amino)propoxy)ethoxy) ethoxy)propyl)carbamoyl)propyl)carbaroyl)(2-pyridyl)) amino)vinyl)benzenesulfonic Acid Example 3

Synthesis of 2-((6-((1-Aza-2-(sulfophenyl)vinyl) amino)(3-pyridyl))carbonylamino)-4-(N-(3-(2-(2-(3-(((4-(4-(((1-carboxy-2-((1-(3-(imidazol-2-ylamino) propyl)(1H-indazol-5-yl))carbonylamino)ethyl) amino)sulfonyl)phenyl)phenyl)sulfonyl)amino) propoxy)ethoxy)ethoxy)propyl)carbamoyl)butanoic Acid

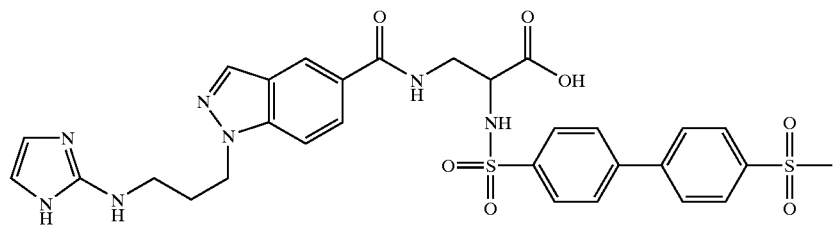

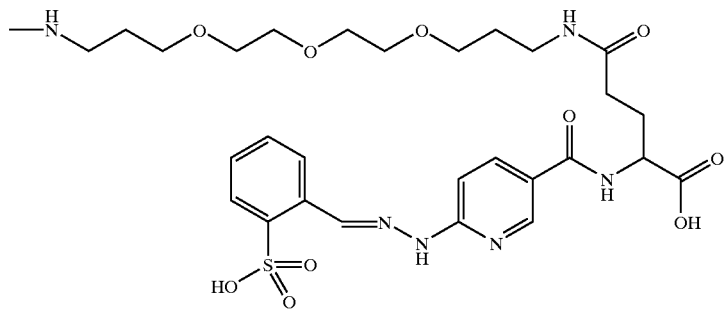

The monomeric product from Example 2, Part A (3.4 mg, 0.0031 mmol) was dissolved in TFA (1.5 mL) and allowed to react for 15 min at ambient temperatures, and concentrated to a viscous amber oil. This oil was dissolved in anhydrous DMF (2 mL) and made basic to pH paper with TEA. This solution was treated with 2-(2-aza-2-((5-((2,5-dioxopyrrolidinyl)carbonyl)(2-pyridyl))amino)vinyl)benzenesulfonic acid (5.3 mg, 0.012 mmol) and stirred at ambient temperatures under a nitrogen atmosphere for 7 days. The DMF was removed under vacuum and the resulting oil was dissolved in 50% ACN and purified by preparative HPLC on a Vydac C-18 column (22×250 mm) using a 2.1%/min gradient of 0 to 63% ACN containing 0.1% TFA at a flow rate of 20 mL/min. The main product peak eluting at 18.1 min was collected and lyophilized to give the title compound as a colorless powder (1.8 mg, 41%). MS: m/e 1302.5 [M+H], 651.9 [M+2H]; High Resolution MS: Calcd for $C_{57}H_{68}N_{13}O_{17}S_3$ [M+H]: 1302.4018, Found: 1302.4030.

Example 4

Synthesis of 3-((1-(3-(Imidazole-2-ylamino)propyl)(1H-indazol-5-yl))carbonylamino)-2-(((4-(4-(((3-(2-(2-(3-(2-(1,4,7,10-tetraaza-4,7,10-tris(carboxymethyl)cyclododecyl)acetylamino)propoxy)ethoxy)ethoxy)propyl)amino)sulfonyl)phenyl)phenyl)sulfonyl)amino)propanoic Acid Bis (trifluoroacetate) Salt

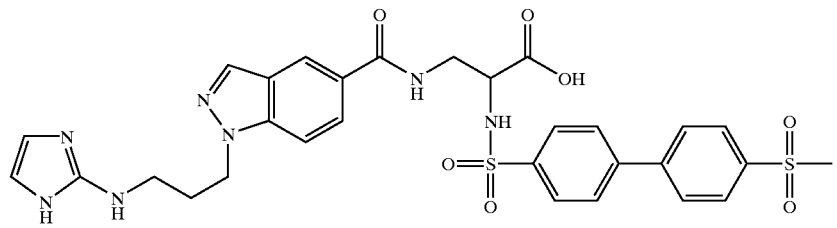

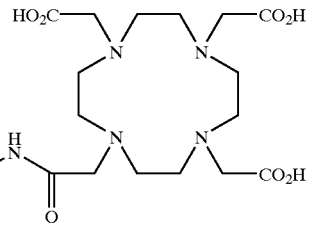

·2TFA

Part A—Phenylmethyl 2-(1,4,7,10-Tetraaza-4,7,10-tris (((tert-butyl)oxycarbonyl)methyl)cyclododecyl)acetate A solution of tert-butyl(1,4,7,10-tetraaza-4,7-bis(((tert-butyl)oxycarbonyl)methyl)cyclododecyl)acetate (0.922 g, 1.79 mmol), TEA (1.8 mL) and benzyl bromoacetate (0.86 mL, 5.37 mnol) in anhydrous DMF (24 mL) was stirred at ambient temperatures under a nitrogen atmosphere for 24 h. The DMF was removed under vacuum and the resulting oil was dissolved in EtOAc (300 mL). This solution was washed consecutively with water (2×50 mL) and saturated NaCl (50 mL), dried (MgSO₄), and concentrated to give the title compound as an amorphous solid (1.26 g). MS: m/e 663.5 [M+H].

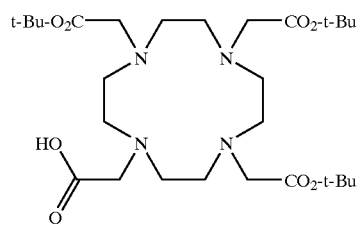

Part C—Preparation of 3-((1-(3-(Imidazole-2-ylamino) propyl)(1H-indazol-5-yl))carbonylamino)-2-(((4-(4-(((3-(2-(2-(3-(2-(1,4,7,10-tetraaza-4,7,10-tris(((tert-butyl) oxycarbonyl)methyl)cyclododecyl)acetylamino)propoxy) ethoxy)ethoxy)propyl)amino)sulfonyl)phenyl)phenyl) sulfonyl)amino)propanoic Acid Pentakis(trifluoroacetate) Salt

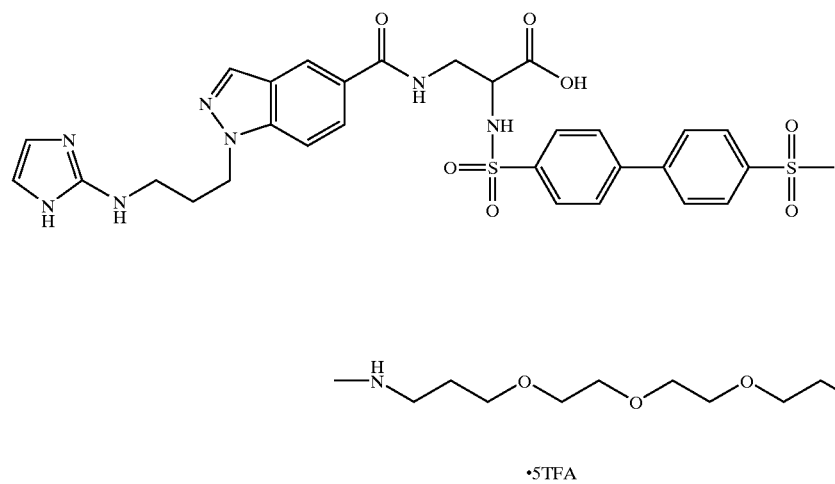

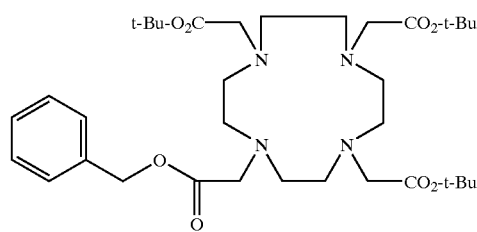

Part B—2-(1,4,7,10-tetraaza-4,7,10-tris(((tert-butyl) oxycarbonyl)methyl)cyclododecyl)acetic acid The product from Part A, above (165 mg, 0.25 mmol) was hydrogenolyzed over 10% Pd on carbon (50 mg) in EtOH (15 mL) at 60 psi for 24 h. The catalyst was removed by filtration through filter aid and washed with EtOH. The filtrates were concentrated to give the title compound as an amorphous solid (134 mg, 94%). MS: m/e 573.5 [M+H].

A solution of 2-(1,4,7,10-tetraaza-4,7,10-tris(((tert-butyl) oxycarbonyl)methyl)cyclododecyl)acetic acid (55 mg, 0.06 mmol), DIEA (0.063 mL, 0.36 mmol), and HBTU (17 mg, 0.045 mmol) in anhydrous DMF (3 mL) was stirred under nitrogen at ambient temperatures for 15 min and treated with the product of Example 1, Part E. Stirring was continued 1 h and the DMF was removed under vacuum. The resulting amber oil was dissolved in 10% ACN and purified by preparative HPLC on a Vydac C-18 column (22×250 mm) using a 2.1%/min gradient pof 0 to 63% ACN containing 0.1% TFA at a flow rate of 20 mL/min. The main product peak eluting at 23.0 min was collected and lyophilized to give the title compound as a colorless, hygroscopic solid (22 mg, 37%). MS: m/e 1424.8 [M+H]; 713.2 [M+2H].

Part D—Preparation of 3-((1-(3-(Imidazole-2-ylamino) propyl)(1H-indazol-5-yl))carbonylamino)-2-(((4-(4-(((3-(2-(2-(3-(2-(1,4,7,10-tetraaza-4,7,10-tris(carboxymethyl) cyclododecyl)acetylamino)propoxy)ethoxy)ethoxy)propyl) amino)sulfonyl)phenyl)phenyl)sulfonyl)amino)propanoic Acid Bis(trifluoroacetate) Salt The product of Part C, above, (10 mg, 0.005 mmol) and triethylsilane (0.10 mL) were dissolved in degassed TFA (2.0 mL) and heated at 50° C. under nitrogen for 1 h. The solution was concentrated under vacuum and the resulting solid was dissolved in 7% ACN and purified by preparative HPLC on a Vydac C-18 column (22×250 mm) using a 1.5%/min gradient of 0 to 45% ACN containing 0.1% TFA at a flow rate of 20 mL/min. The main product peak eluting at 19.3 min was collected and lyophilized to give the title compound as a colorless solid (3.0 mg, 40%). MS: m/e 1256.5 [M+H]; 629.0 [M+2H]; 419.9 [M+3H].

The analytical HPLC methods utilized for examples 5 and 6 are described below:

| Instrument: | HP1050 |
|---|---|
| Column: | Vydac C18 (4.6 × 250 mm) |
| Detector: | Diode array detector 220 nm/500 ref |
| Flow Rate: | 1.0 mL/min. |
| Column Temp: | 50° C. |
| Sample Size: | 15 uL |
| Mobile Phase: | A: 0.1% TFA in water |
| | B: 0.1% TFA in ACN/Water (9:1) |

| | Method A | | |
|---|---|---|---|
| Gradient: | Time (min) | % A | % B |
| | 0 | 80 | 20 |
| | 20 | 0 | 100 |
| | 30 | 0 | 100 |
| | 31 | 80 | 20 |

| | Method B | | |
|---|---|---|---|
| Gradient: | Time (min) | % A | % B |
| | 0 | 98 | 2 |
| | 16 | 63.2 | 36.8 |
| | 18 | 0 | 100 |
| | 28 | 0 | 100 |
| | 30 | 98 | 2 |

Example 5

Synthesis of 2-(6-((6-((1-Aza-2-(2-sulfophenyl)vinyl)-amino)(3-pyridyl))carbonylamino)hexanoylamino)-3-((1-(3-(imidazol-2-ylamino)propyl)(1H-indazol-5-yl))carbonylamino)-propanoic acid

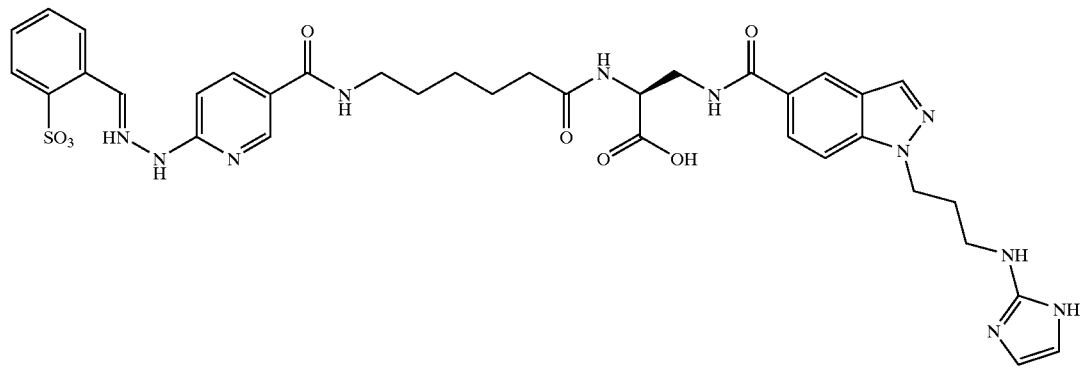

Part A. Preparation of Methyl 2-((phenylmethoxy)-carbonylamino-3-((1-3-((1-(triphenylmethyl)imidazol-2-yl)amino)propyl)(1H-indazol-5-yl))carbonylamino)propanoate

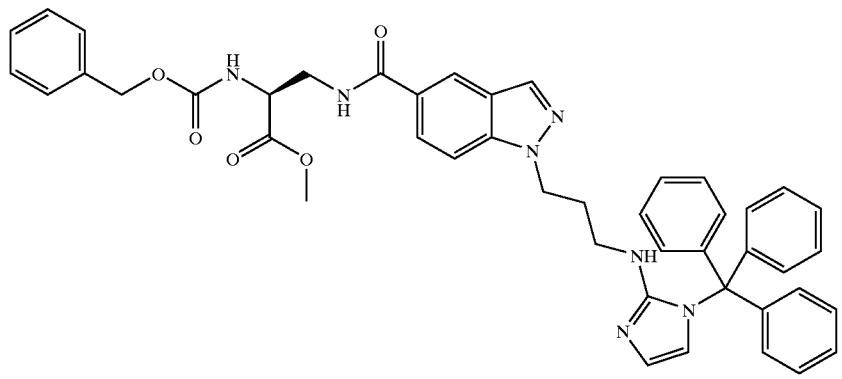

1-[3-[N-(-Triphenylmethylimidazo-2-yl)amino]propylyl]-5-carboxyindazole (0.950 g, 1.80 mmol), HBTU (0.751 g, 1.98 mmol), and methyl 3-amino-2(S)-(benzyloxycarbonylamino)propionate (0.624 g, 2.16 mmol) were dissolved in N,N-dimethylformamide (10 mL). Diisopropylethyl amine (94.1 μL, 5.40 mmmol) was added and the reaction mixture was stirred under $N_2$ for 18 h. The reaction mixture was then concentrated to an oil under high vacuum. The oil was brought up in water. The water layer was extracted with ethyl acetate. The organic layer was washed with brine, dried over magnesium sulfate, filtered and concentrated to a small volume. Product precipitated upon addition of hexane. The product was filtered, washed with hexane and dried under high vacuum to give 1.6128 g (117%) of product. ESMS: Calcd. for $C_{45}H_{43}N_7O_5$, 761.33; Found, 762.2 [M+H]+1.

Analytical HPLC, Method A, $R_t$=17.00 min, Purity=90%

Part B. Preparation of 2-((Phenylmethoxy)carbonylamino-3-((1-(3-((1-(triphenylmethyl)imidazol-2-yl)amino)propyl)(1H-indazol-5-yl))carbonylamino)propanoic acid

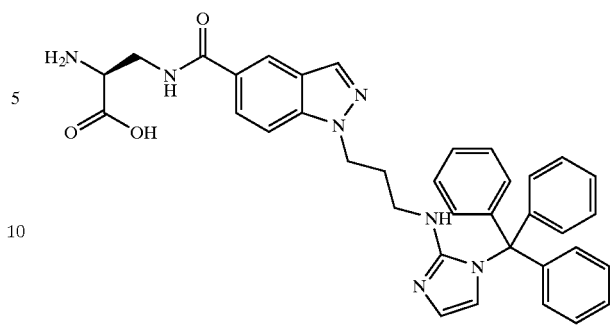

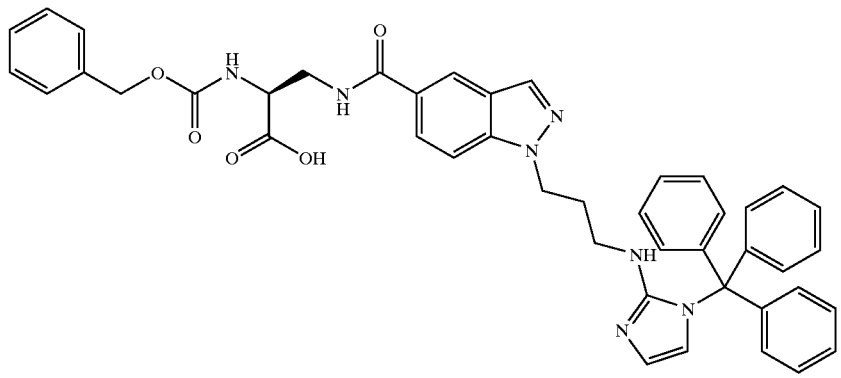

Methyl 2-((phenylmethoxy)-carbonylamino-3-((1-(3-((1-(triphenylmethyl)imidazol-2-yl)amino)propyl)(1H-indazol-5-yl))carbonylamino)propanoate (1.55 g, 2.03 mmol) was dissolved in tetrahydrofuran (20 mL). Lithium hydroxide monohydrate (1.71 g, 40.6 mmol) was dissolved in water and added to the reaction. The reaction was stirred overnight under $N_2$ for 18 h. The tetrahydrofuran was removed under high vacuum. The pH of the remaining aqueous layer was adjusted to 5 with 1N HCl. The aqueous layer was extracted with methylene chloride. The organic layer was washed with water, brine, dried over magnesium sulfate, filtered, and concentrated to an oil under high vacuum. The oil was recrystallized from hexane:ethyl acetate to give 800.9 mgs (53%) of product. ESMS: Calcd. for $C_{44}H_{41}N_7O_5$, 747.32; Found, 748.3 [M+H]+1

Analytical HPLC, Method A, $R_t$=15.66 min, Purity=94%

Part C. Preparation of 2-Amino-3-((1-(3-((1-(triphenylmethyl)imidazol-2-yl)amino)propyl)(1H-indazol-5-yl))carbonylamino)propanoic acid 2-((Phenylmethoxy)carbonylamino-3-((1-(3-((1-(triphenylmethyl)imidazol-2-yl)amino)propyl)(1H-indazol-5-yl))carbonylamino)propanoic acid (0.750 g, 1.00 mmol) was added to Pd/C (1.00 g) in ethanol (20 mL). The reaction was evacuated and purged with nitrogen twice. The reaction was then evacuated and purged with hydrogen twice, and then maintained under an atmosphere of hydrogen for 24 h. The reaction was filtered through celite. The filtrate was concentrated to an oil. The oil was recrystallized from hexane:ethyl acetate to give 215.6 mgs (35%) of product. ESMS: Calcd. for $C_{36}H_{35}N_7O_3$, 613.28; Found, 614.2 [M+H]+1

Analytical HPLC, Method A, $R_t$=12.26 min, Purity=90%

Part D. Preparation of 2-Amino-3-((1-(3-(imidazol-2-ylamino)propyl)(1H-indazol-5-yl))carbonylamino)propanoic acid

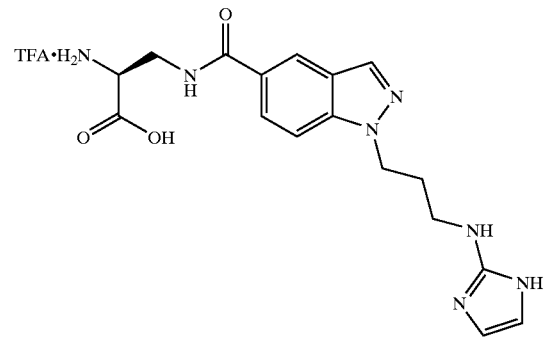

2-Amino-3-((1-(3-((1-(triphenylmethyl)imidazol-2-yl)amino)propyl)(1H-indazol-5-yl))carbonylamino)propanoic acid (0.203 g, 0.331 mmol) was dissolved in trifluoroacetic acid (3 mL), and the reaction was refluxed for 1 h. The reaction was concentrated to an oil under high vacuum. The oil was triturated with ether. The product was filtered, washed with ether, dissolved in 50/50 acetonitrile/water, and lyophilized to give 171.0 mgs (106%) of product. ESMS: Calcd. for $C_{17}H_{21}N_7O_3$, 371.17; Found, 372.0 [M+H]+1

Analytical HPLC, Method B, $R_t$=9.48 min, Purity=95%

Part E. Preparation of 2-(6-((Tert-butoxy)-carbonylamino)hexanoylamino)-3-((1-(3-(imidazol-2-ylamino)-propyl)(1H-indazol-5-yl))carbonylamino)propanoic acid Analytical HPLC, Method B, $R_t$=18.72 min, Purity=98%

| Preparative HPLC Method A: | |
|---|---|
| Instrument: | Rainin Rabbit; Dynamax software |
| Column: | Vyadac C-18 (21.2 min × 25 cm) |
| Detector: | Knauer VWM |
| Flow Rate: | 15 ml/min |
| Column Temp: | RT |
| Mobile Phase: | A: 0.1% TFA in $H_2O$ |
| | B: 0.1% TFA in ACN/$H_2O$ (9:1) |

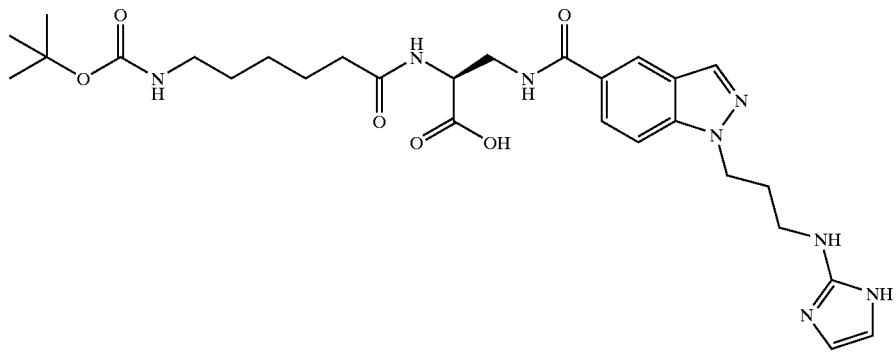

2-Amino-3-((1-(3-(imidazol-2-ylamino)propyl)(1H-indazol-5-yl))carbonylamino)propanoic acid (0.050 g, 0.103 mmol) was dissolved in N,N-dimethylformamide (2 mL). Triethylamine (43.1 μL, 0.309 mmol) was added and the reaction was stirred for 5 minutes. A precipitate formed so methyl sulfoxide (1 mL) was added. Succinimidyl N-boc-6-aminohexanoate (0.0406 g, 0.124 mmol) was added and the reaction was stirred under $N_2$ for 18 h. The reaction was then concentrated to an oil under high vacuum. The oil was purified by the following method (Preparative HPLC Method A) to give 39.9 mgs (66%) of product. ESMS: Calcd. for $C_{28}H_{40}N_8O_6$, 584.31; Found, 585.2 [M+H]+1.

-continued

| Preparative HPLC Method A: | | | |
|---|---|---|---|
| Gradient: | Time (min) | % A | % B |
| | 0 | 98 | 2 |
| | 16 | 63.2 | 36.8 |
| | 18 | 0 | 100 |
| | 28 | 0 | 100 |
| | 30 | 98 | 2 |

Part F. Preparation of 2-(6-Aminohexanoylamino)-3-((1-(3-(imidazol-2-ylamino)propyl)(1H-indazol-5-yl))carbonylamino)propanoic acid

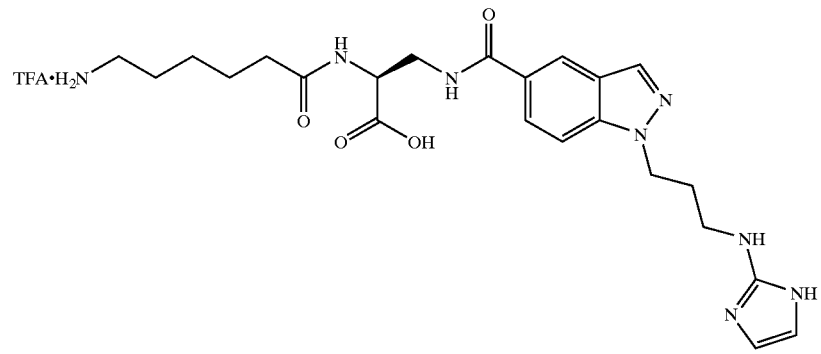

2-(6-((Tert-butoxy)-carbonylamino)hexanoylamino)-3-((1-(3-(imidazol-2-ylamino)-propyl)(1H-indazol-5-yl))carbonylamino)-propanoic acid (0.0322 g, 0.0551 mmol) was dissolved in methylene chloride (1 mL). Trifluoroacetic acid (1 mL) was added, and the reaction was stirred for 2 h. The reaction was concentrated to an oil under high vacuum. The oil was triturated with ether. The product was filtered, washed with ether, dissolved in 50/50 acetonitrile/water, and lyophilized to give 29.9 mgs (91%) of product. ESMS: Calcd. for $C_{23}H_{32}N_8O_4$, 464.25; Found, 485.2 [M+H]+1

Analytical HPLC, Method B, $R_t$=111.02 min, Purity=97%

Part G. Preparation of 2-(6-(((6-(((1-Aza-2-(2-sulfophenyl)vinyl)amino)(3-pyridyl))carbonylamino)-hexanoylamino)-3-((1-(3-(imidazol-2-ylamino)propyl)(1H-indazol-5-yl))carbonylamino)propanoic acid

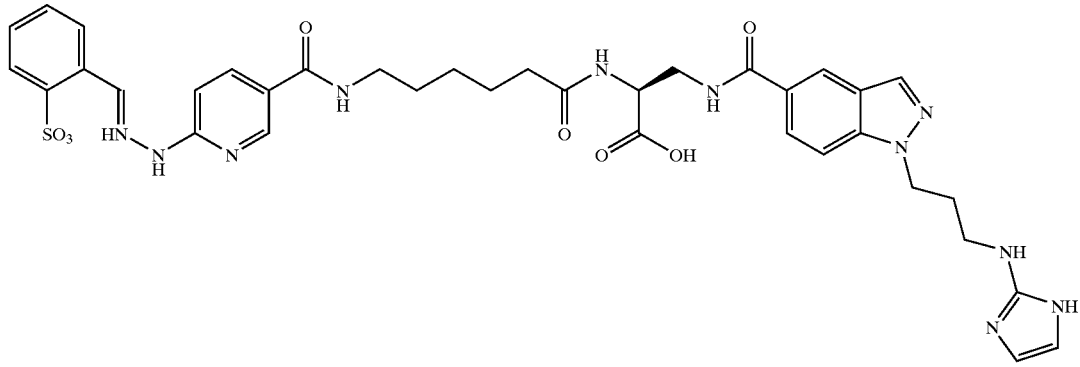

2-(6-Aminohexanoylamino)-3-((1-(3-(imidazol-2-ylamino)-propyl)(1H-indazol-5-yl))carbonylamino) propanoic acid (0.0265 g, 0.0443 mmol) was dissolved in N,N-dimethylformamide (2 mL). Triethylamine (18.5 μL, 0.133 mmol) was added, and the reaction was stirred for 5 min. 2-[[[5-[[(2,5-Dioxo-1-pyrrolidinyl)oxy]carbonyl]-2-pyridinyl]hydrazono]-methyl]-benzenesulfonic acid, monosodium salt (0.0234 g, 0.0532 mmol) was added, and the reaction was stirred for 4 days. The reaction was concentrated to an oil under high vacuum. The oil was purified by Preparative HPLC Method A to give 33.7 mgs (97%) of product. HRMS: Calcd. for $C_{36}H_{41}N_{11}O_8S$+H, 788.2938; Found, 788.2955.

Analytical HPLC, Method B, $R_t$=14.06 min, Purity=90%

Example 6

Synthesis of 2-((6-(((1-Aza-2-(2-sulfophenyl)vinyl)-amino)(3-pyridyl))carbonylamino)-3-((1-(3-(imidazol-2-ylamino)propyl)(1H-indazol-5-yl))carbonylamino)propanoic acid

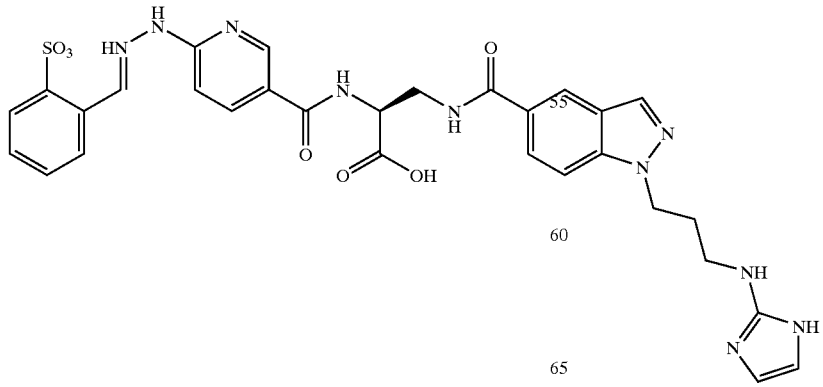

2-Amino-3-((1-(3-(imidazol-2-ylamino)propyl)(1H-indazol-5-yl))carbonylamino)propanoic acid (0.025 g, 0.0515 mmol) was dissolved in N,N-dimethylformamide (2 mL). Triethylamine (21.5 µL, 0.154 mmol) was added, and the reaction was stirred for 5 min. 2-[[[5-[[(2,5-Dioxo-1-pyrrolidinyl)oxy]carbonyl]-2-pyridinyl]hydrazono]-methyl]-benzenesulfonic acid, monosodium salt (0.0272 g, 0.0515 mmol) was added, and the reaction was stirred under nitrogen for 18 h. The reaction mixture was concentrated to an oil under high vacuum. The oil was purified by preparative HPLC using Preparative HPLC Method A to give 14.6 mgs (42%) of the desired product. ESMS: Calcd. for $C_{30}H_{30}N_{10}O_7S$, 674.20; Found, 697.1 [M+Na]+1.

Analytical HPLC, Method B, $R_t$=13.48 min, Purity=95%

Example 7

Synthesis of [2-[[[5-[carbonyl]-2-pyridinyl] hydrazono]methyl]-benzenesulfonic acid]-Glu(2-(6-Aminohexanoylamino)-3-((1-(3-(imidazol-2-ylamino)propyl)(1H-indazol-5-yl))carbonyl-amino) propanoic acid)(2-(6-aminohexanoylamino)-3-((1-(3-(imidazol-2-ylamino)propyl)(1H-indazol-5-yl)) carbonyl-amino)propanoic acid)

Part A. Preparation of Boc-Glu(OSu)-OSu

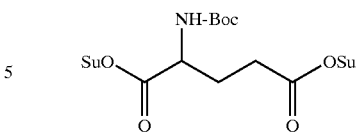

To a solution of Boc-Glu-OH (8.0 g, 32.25 mmol), N-hydroxysuccinimide (8.94 g, 77.64 mmol), and DMF (120 mL) was added 1-(3-dimethylaminopropyl)-3-ethylcarbodimide (14.88 g, 77.64 mmol). The reaction mixture was stirred at room temperature for 48 h. The mixture was concentrated under high vacuum and the residue was brought up in 0.1 N HCl and extracted with ethyl acetate (3×). The combined organic extracts were washed with water, saturated sodium bicarbonate and then saturated sodium chloride, dried over $MgSO_4$, and filtered. The filtrate was concentrated in vacuo and purified via reverse-phase HPLC (Vydac C18 column, 18 to 90% acetonitrile gradient containing 0.1% TFA, $R_t$=9.413 min) to afford 8.5 g (60%) of the desired product as a white powder. $^1$H NMR ($CDCl_3$): 2.98–2.70 (m, 11H), 2.65–2.25 (m, 2H), 1.55–1.40 (s, 9H); ESMS: Calculated for $C_{18}H_{23}N_3O_{10}$, 441.1383 Found 459.2 [M+$NH_4$]+1

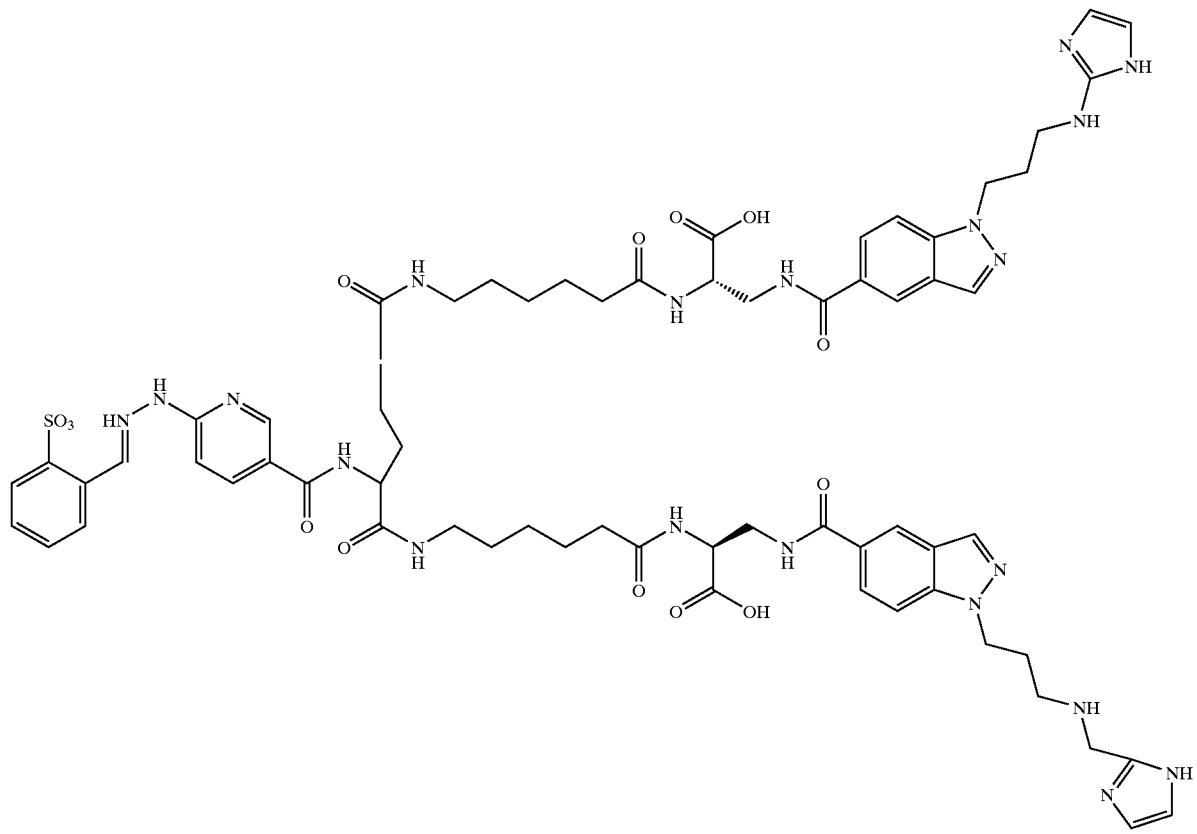

Part B. Preparation of Glu {2-6-aminohexanoylamino)-3-((1-(3-(imidazol-2-ylamino)propyl)(1H-indazol-5-yl))carbonyl-amino)propanoic acid}{2-(6-aminohexanoylamino)-3-((1-(3-(imidazol-2-ylamino)propyl)(1H-indazol-5-yl))carbonyl-amino)propanoic acid} propanoic acid)(2-(6-Aminohexanoylamino)-3-((1-(3-(imidazol-2-ylamino)propyl)(1H-indazol-5-yl))carbonyl-amino)propanoic acid) (0.0481 mmol) is dissolved in DMF (2 mL). Triethylamine (20.1 µL, 0.144 mmol) is added, and after 5 min of stirring 2-[[[5-[[(2,5-dioxo-1-pyrrolidinyl)

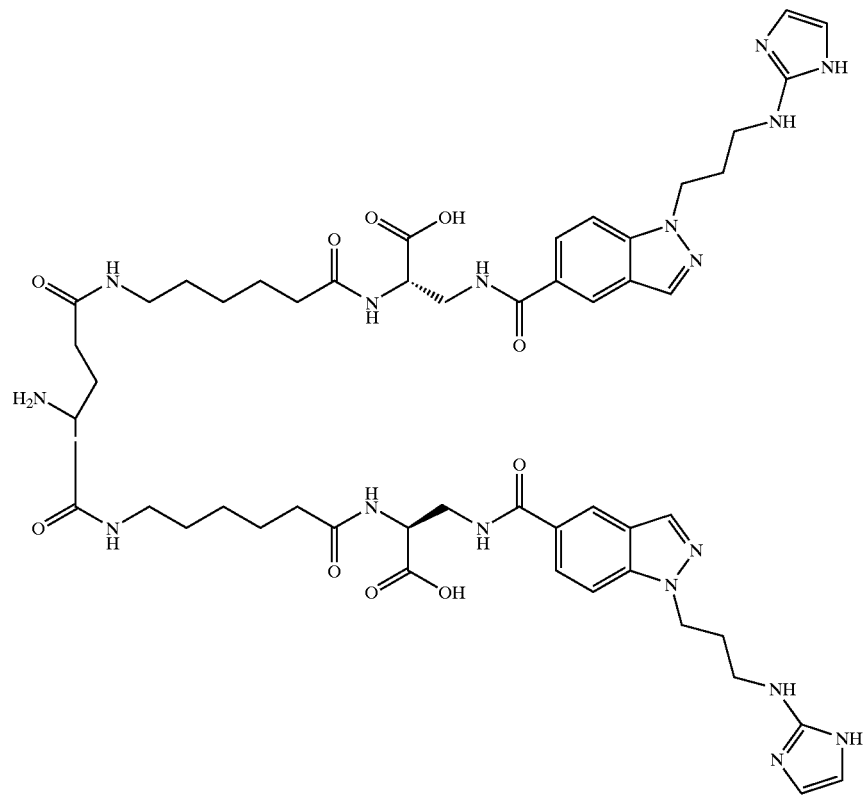

A solution of 2-(6-aminohexanoylamino)-3-((1-(3-(imidazol-2-ylamino)propyl)(1H-indazol-5-yl))carbonyl-amino)propanoic acid (1 mmol), diisopropylethylamine (3 mmol), and Boc-Glu(OSu)OSu (0.5 mmol) is dissolved in DMF (50 mL). The reaction mixture is stirred under nitrogen and at room temperature for 18 h. The solvents are removed in vacuo and the crude material is triturated in ethyl acetate, filtered and washed with ethyl acetate. The crude product thus obtained is dissolved in 50 mL of 50% TFA/DCM and the reaction mixture is stirred for 3 h at room temperature under nitrogen. TFA and DCM is then removed in vacuo and the title compound isolated and purified by preparative RP-HPLC.

Part C. Preparation of [2-[[[5-[carbonyl]-2-pyridinyl]hydrazono]methyl]-benzenesulfonic acid]-Glu(2-(6-Aminohexanoylamino)-3-((1-(3-(imidazol-2-ylamino)propyl)(1H-indazol-5-yl))carbonyl-amino)propanoic acid)(2-(6-Aminohexanoylamino)-3-((1-(3-(imidazol-2-ylamino)propyl)(1H-indazol-5-yl))carbonyl-amino)propanoic acid)

Glu(2-(6-Aminohexanoylamino)-3-((1-(3-(imidazol-2-ylamino)propyl)(11H-indazol-5-yl))carbonyl-amino)

oxy]carbonyl]-2-pyridinyl]hydrazono]-methyl]-benzenesulfonic acid, monosodium salt (0.0254 g, 0.0577 mmol) is added. The reaction mixture is stirred for 20 h and then concentrated to an oil under high vacuum. The oil is purified by preparative RP-HPLC to obtain the desired product.

Example 8

Synthesis of [2-[[[5-[carbonyl]-2-pyridinyl]hydrazono]methyl]-benzenesulfonic acid]-Glu-bis-[Glu(2-(6-Aminohexanoylamino)-3-((1-(3-(imidazol-2-ylamino)propyl)(1H-indazol-5-yl))carbonyl-amino)propanoic acid)(2-(6-Aminohexanoylamino)-3-((1-(3-(imidazol-2-ylamino)propyl)(1H-indazol-5-yl))carbonyl-amino)propanoic acid)]

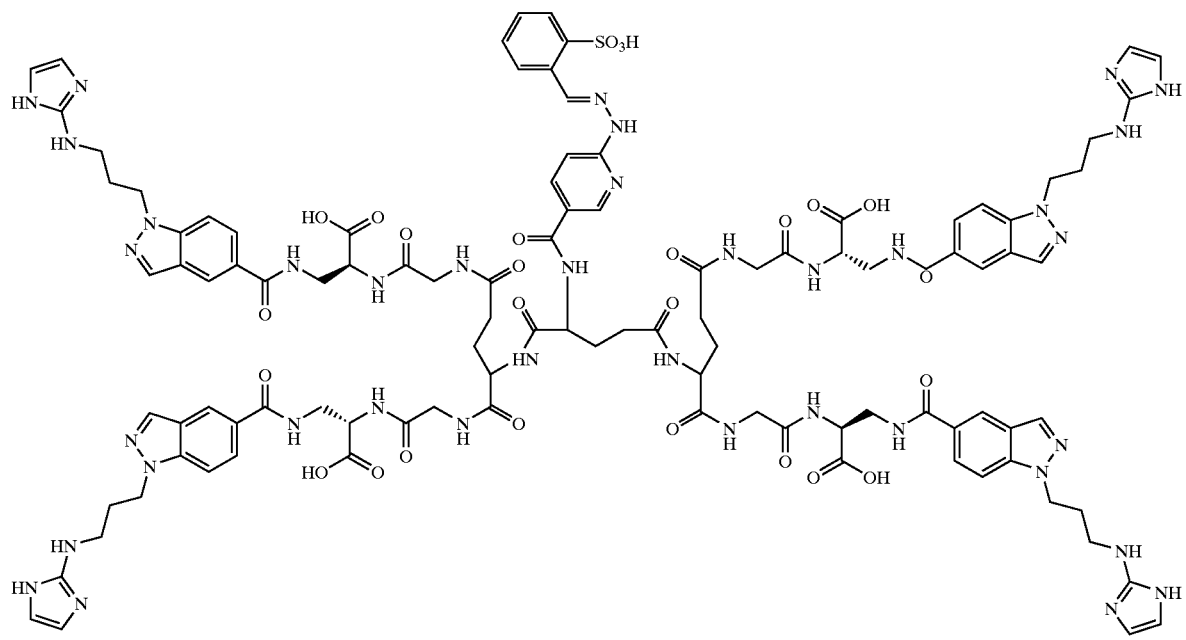

Part A. Preparation of Glu-Bis[Glu{2-(6-aminohexanoylamino)-3-((1-(3-(imidazol-2-ylamino)propyl)(1H-indazol-5-yl))carbonyl-amino)propanoic acid}{2-(6-aminohexanoylamino)-3-((1-(3-(imidazol-2-ylamino)propyl)(1H-indazol-5-yl))carbonyl-amino)propanoic acid}]

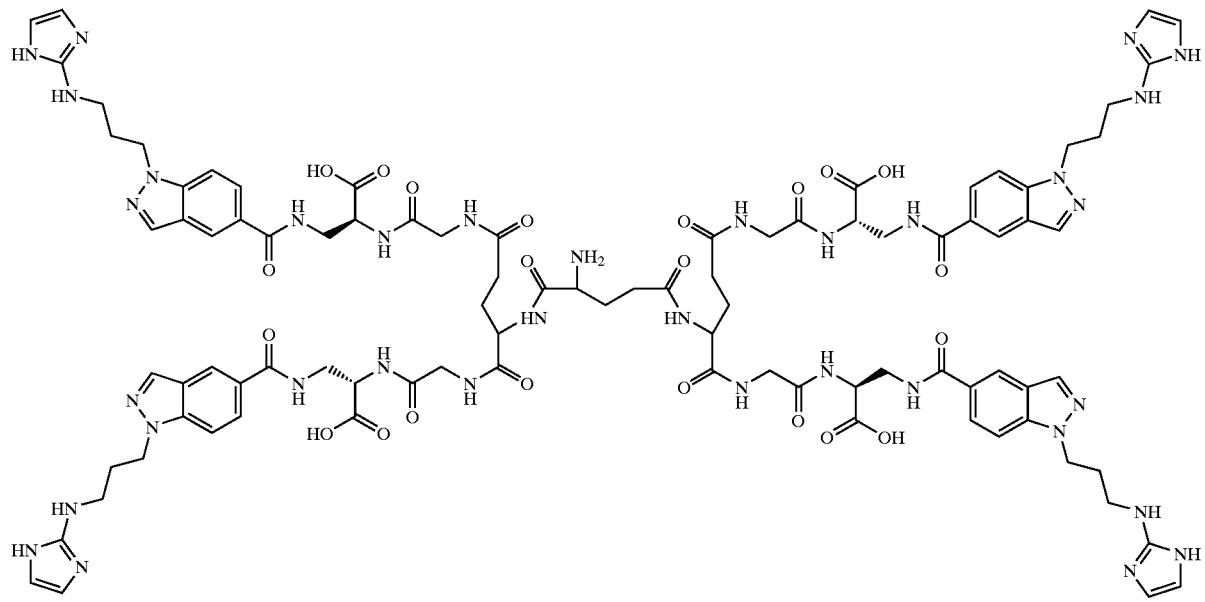

A solution of Glu{2-(6-aminohexanoylamino)-3-((1-(3-(imidazol-2-ylamino)propyl)(1H-indazol-5-yl))carbonyl-amino)propanoic acid}{2-(6-aminohexanoylamino)-3-((1-(3-(imidazol-2-ylamino)propyl)(1H-indazol-5-yl))carbonyl-amino)propanoic acid} (1 mmol), diisopropylethylamine (3 mmol), and Boc-Glu(OSu)OSu (0.5 mmol) is dissolved in DMF (50 mL). The reaction mixture is stirred under nitrogen and at room temperature for 18 h. The solvents are removed in vacuo and the crude material is triturated in ethyl acetate, filtered and washed with ethyl acetate. The crude product thus obtained is dissolved in 50 mL of 50% TFA/DCM and the reaction mixture is stirred for 3 h at room temperature under nitrogen. TFA and DCM is then removed in vacuo and the title compound isolated and purified by preparative RP-HPLC.

Part B: Preparation of [2-[[[5-[carbonyl]-2-pyridinyl]hydrazono]methyl]-benzenesulfonic acid]-Glu-bis-[Glu(2-(6-Aminohexanoylamino)-3-((1-(3-(imidazol-2-ylamino)propyl)(1H-indazol-5-yl))carbonyl-amino)propanoic acid)

(2-(6-Aminohexanoylamino)-3-((1-(3-(imidazol-2-ylamino)propyl)(1H-indazol-5-yl))carbonyl-amino)propanoic acid)]

Glu-bis-[Glu{2-(6-aminohexanoylamino)-3-((1-(3-(imidazol-2-ylamino)propyl)(1H-indazol-5-yl))carbonyl-amino)propanoic acid}{2-(6-aminohexanoylamino)-3-((1-(3-(imidazol-2-ylamino)propyl)(1H-indazol-5-yl))carbonyl-amino)propanoic acid}] (0.0481 mmol) is dissolved in DMF (2 mL). Triethylamine (20.1 µL, 0.144 mmol) is added, and after 5 min of stirring 2-[[[5-[[(2,5-dioxo-1-pyrrolidinyl)oxy]carbonyl]-2-pyridinyl]hydrazono]-methyl]-benzenesulfonic acid, monosodium salt (0.0254 g, 0.0577 mmol) is added. The reaction mixture is stirred for 20 h and then concentrated to an oil under high vacuum. The oil is purified by preparative RP-HPLC to obtain the desired product.

Example 9

Synthesis of of 2-(1,4,7,10-tetraaza-4,7,10-tris(carboxymethyl)-1-cyclododecyl)acetyl-{2-(6-aminohexanoylamino)-3-((1-(3-(imidazol-2-ylamino)propyl)(1H-indazol-5-yl))carbonyl-amino)propanoic acid}

To a solution of tris(t-butyl)-1,4,7,10-tetraazacyclododecane-1,4,7,10-tetraacetic acid (28 mg, 0.049 mmol) and Hunig's base (14 µL) in DMF (2 mL) is added HBTU (17 mg, 0.0456 mmol) and the mixture is stirred for 5 min. To this is added a solution of 2-(6-aminohexanoylamino)-3-((1-(3-(imidazol-2-ylamino)propyl)(1H-indazol-5-yl))carbonyl-amino)propanoic acid (0.0326 mmol) in DMF (1 mL) and the reaction mixture is allowed to stir under nitrogen at room temperature for 4 h. The solvent is removed in vacuo and the residue is purified by preparative RP-HPLC to obtain the product as a lyophilized solid.

Part B. Preparation of 2-(1,4,7,10-tetraaza-4,7,10-tris(carboxymethyl)-1-cyclododecyl)acetyl-{2-(6-aminohexanoylamino)-3-((1-(3-(imidazol-2-ylamino)propyl)(1H-indazol-5-yl))carbonyl-amino)propanoic acid}

A solution of 2-(1,4,7,10-tetraaza-4,7,10-tris(t-butoxycarbonylmethyl)-1-cyclododecyl)acetyl-2-6-Aminohexanoylamino)-3-((1-(3-(imidazol-2-ylamino)propyl)(1H-indazol-5-yl))carbonyl-amino)propanoic acid (8.71 mmol) in TFA (3 mL) is stirred at room temperature under nitrogen for 5 h. The solution is concentrated in vacuo and the residue is purified by preparative RP-HPLC to obtain the desired product as the lyophilized solid.

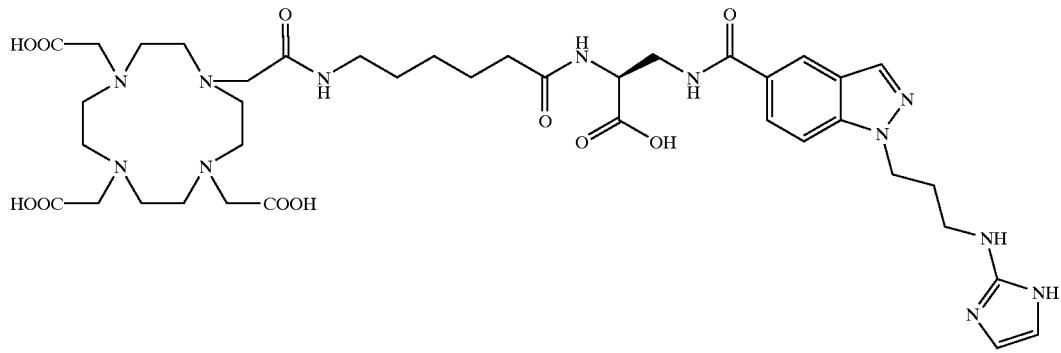

Part A. Preparation of 2-(1,4,7,10-tetraaza-4,7,10-tris(t-butoxycarbonylmethyl)-1-cyclododecyl)acetyl-{2-(6-aminohexanoylamino)-3-((1-(3-(imidazol-2-ylamino)propyl)(1H-indazol-5-yl))carbonyl-amino)propanoic acid}

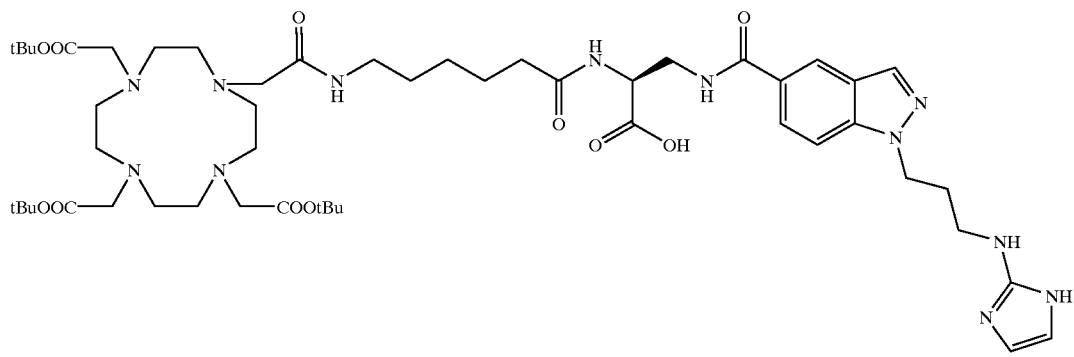

Example 10

Synthesis of 2-(1,4,7,10-tetraaza-4,7,10-tris(carboxymethyl)-1-cyclododecyl)acetyl-Glu{2-(6-Aminohexanoylamino)-3-((1-(3-(imidazol-2-ylamino)propyl)(1H-indazol-5-yl))carbonyl-amino)propanoic acid}{2-(6-Aminohexanoylamino)-3-((1-(3-(imidazol-2-ylamino)propyl)(1H-indazol-5-yl))carbonyl-amino)propanoic acid}

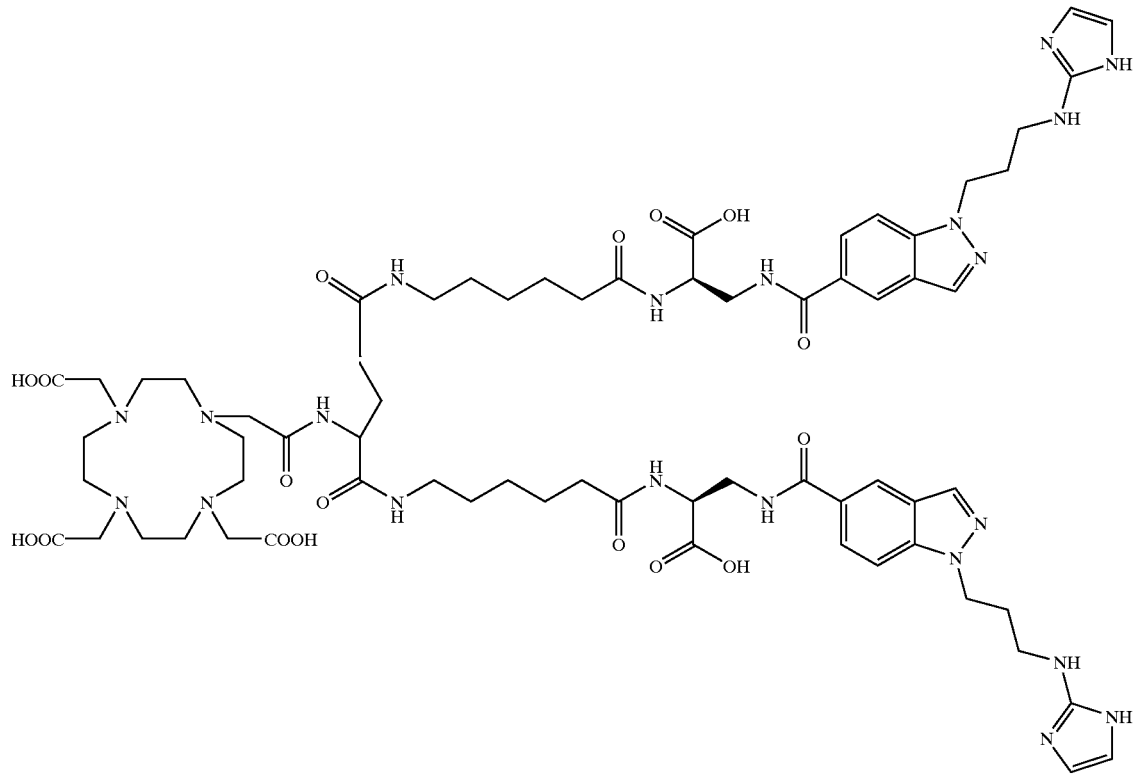

Part A. Preparation of 2-(1,4,7,10-tetraaza-4,7,10-tris(t-butoxycarbonylmnethyl)-1-cyclododecyl)acetyl-Glu{2-(6-Aminohexanoylamino)-3-((1-(3-(imidazol-2-ylamino)propyl)(1H-indazol-5-yl))carbonyl-amino)propanoic acid}{2-(6-Aminohcxanoylamino)-3-((1-(3-(imidazol-2-ylamino)propyl)(1H-indazol-5-yl))carbonyl-amino)propanoic acid}

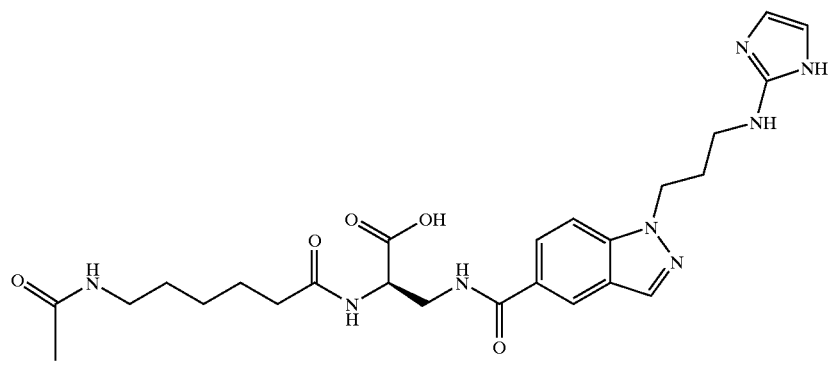

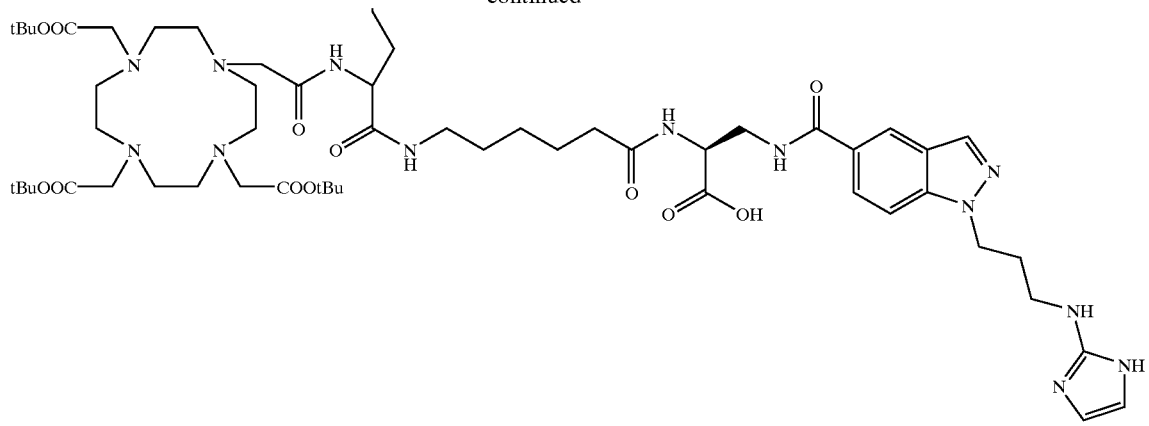

To a solution of tris(t-butyl)-1,4,7,10-tetra-azacyclododecane-1,4,7,10-tetraacetic acid (28 mg, 0.049 mmol) and Hunig's base (14 μL) in DMF (2 mL) is added HBTU (17 mg, 0.0456 mmol) and the mixture is stirred for 5 min. To this is added a solution of Glu{2-(6-Aminohexanoylamino)-3-((1-(3-(imidazol-2-ylamino)propyl)(1H-indazol-5-yl))carbonyl-amino)propanoic acid}{2-(6-Aminohexanoylamino)-3-((1-(3-(imidazol-2-ylamino)propyl)(1H-indazol-5-yl))carbonyl-amino)propanoic acid} (0.0326 mmol) in DMF (1 mL) and the reaction mixture is allowed to stir under nitrogen at room temperature for 4 h. The solvent is removed in vacuo and the residue is purified by preparative RP-HPLC to obtain the product as a lyophilized solid.

Part B. Preparation of 2-(1,4,7,10-tetraaza-4,7,10-tris(carboxymethyl)-1-cyclododecyl)acetyl-Glu{2-(6-Aminohexanoylamino)-3-((1-(3-(imidazol-2-ylamino)propyl)(1H-indazol-5-yl))carbonyl-amino)propanoic acid}{2-(6-Aminohexanoylamino)-3-((1-(3-(imidazol-2-ylamino)propyl)(1H-indazol-5-yl))carbonyl-amino)propanoic acid).

A solution of 2-(1,4,7,10-tetraaza-4,7,10-tris(t-butoxycarbonylmethyl)-1-cyclododecyl)acetyl-Glu{2-(6-Aminohexanoylamino)-3-((1-(3-(imidazol-2-ylamino)propyl)(1H-indazol-5-yl))carbonyl-amino)propanoic acid}{2-(6-Aminohexanoylamino)-3-((1-(3-(imidazol-2-ylamino)propyl)(1H-indazol-5-yl))carbonyl-amino)propanoic acid} (8.71 mmol) in TFA (3 mL) is stirred at room temperature under nitrogen for 5 h. The solution is concentrated in vacuo and the residue is purified by preparative RP-HPLC to obtain the desired product as the lyophilized solid.

Example 11

Synthesis of DOTA/N,N'-Bis(3-(2-(2-(3-(((4-(4-(((1-carboxy-2-((1-(3-(imidazol-2-ylamino)propyl)(1H-indazol-5-yl))carbonylamino)ethyl)amino)sulfonyl)phenyl)phenyl)sulfonyl)amino)propoxy)ethoxy)ethoxy)propyl)-2-(amino)pentane-1,5-diamide Tris(trifluoroacetate) Salt Conjugate

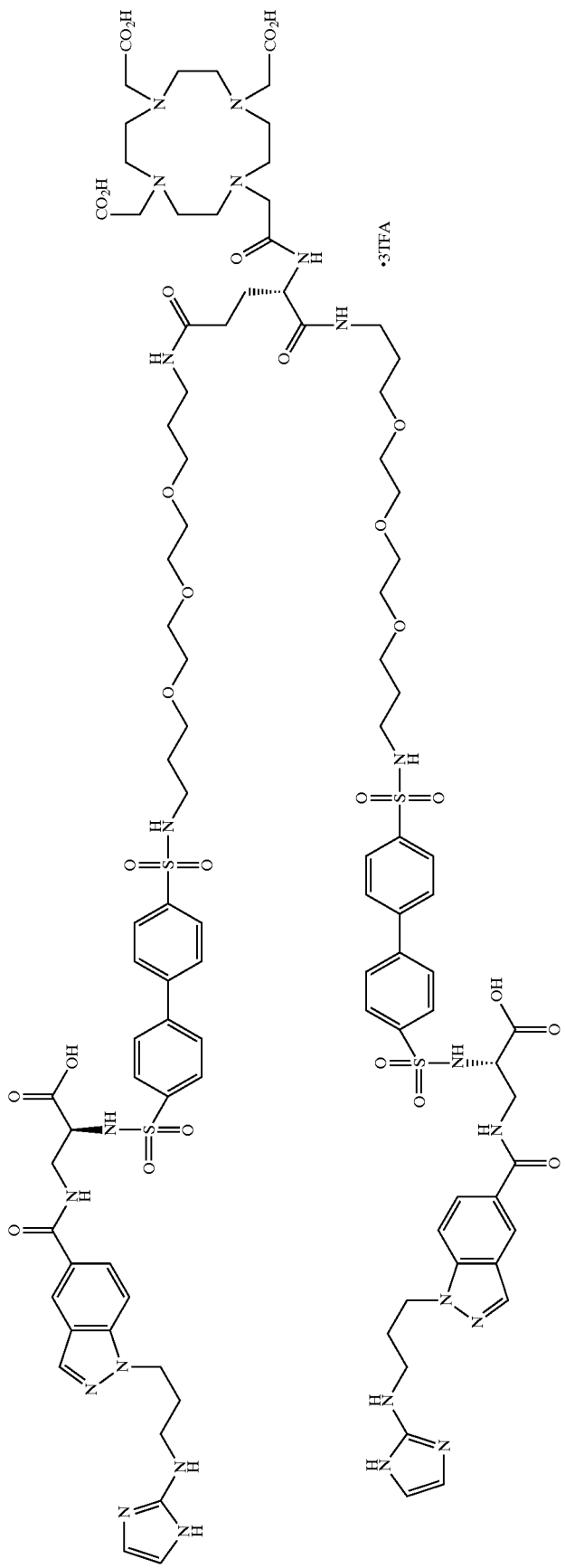

Part A—Preparation of DOTA Tris-t-Butyl Ester/N,N'-Bis (3-(2-(2-(3-(((4-(4-(((1-carboxy-2-((1-(3-(imidazol-2-ylamino)propyl)(1H-indazol-5-yl))carbonylamino)ethyl)amino)sulfonyl)phenyl)phenyl)sulfonyl)amino)propoxy)ethoxy)ethoxy)propyl)-2-(amino)pentane-1,5-diamide Hexakis(trifluoroacetate) Salt Conjugate A solution of the product from Example 2, Part A in degassed TFA is allowed to stand at ambient temperatures under nitrogen for 15 min. The solution is concentrated and the resulting oil is dissolved in 50% ACN. The TFA salt is converted to the free base by treatment with an ion exchange resin such as Bio-Rad AG-3X$^4$A, hydroxide form, until the pH of the solution is raised to 6.5. The resin is removed by filtration and the filtrate is lyophilized to give the free base of the deprotected dimer.

A solution of DOTA tris-t-butyl ester and DIEA in anhydrous DMF are treated with HBTU and allowed to react 15 min at ambient temperatures under nitrogen. The deprotected dimer from above is added to this solution and stirring is continued at ambient temperatures under nitrogen for 18 h. The DMF is removed under vacuum and the resulting oil is purified by preparative HPLC on a C18 column using a water:ACN:0.1% TFA gradient. The product fraction is lyophilized to give the title compound.

Part B—Preparation of DOTA/N,N'-Bis(3-2-(2-(3-(((4-(4-(((1-carboxy-2-((1-(3-(imidazol-2-ylamino)propyl)(1H-indazol-5-yl))carbonylamino)ethyl)amino)sulfonyl)phenyl)phenyl)sulfonyl)amino)propoxy)ethoxy)ethoxy)propyl)-2-(amino)pentane-1,5-diamide Tris(trifluoroacetate) Salt Conjugate The product of Part A, above, and Et$_3$SiH are dissolved in degassed TFA and heated at 50° C. under nitrogen for 1 h. The solution is concentrated and the resulting residue is purified by preparative HPLC on a C18 column using a water:ACN:0.1% TFA gradient. The product fraction is lyophilized to give the title compound.

Example 12

Synthesis of DOTA/2-Amino-4-(N-(3-(2-(2-(3-(((4-(4-(((1-carboxy-2-((1-(3-(imidazol-2-ylamino)propyl)(1H-indazol-5-yl))carbonylamino)ethyl)amino)sulfonyl)phenyl)phenyl)sulfonyl)amino)propoxy)ethoxy)ethoxy)propyl)carbamoyl)butanoic Acid Bis(trifluoroacetate) Salt

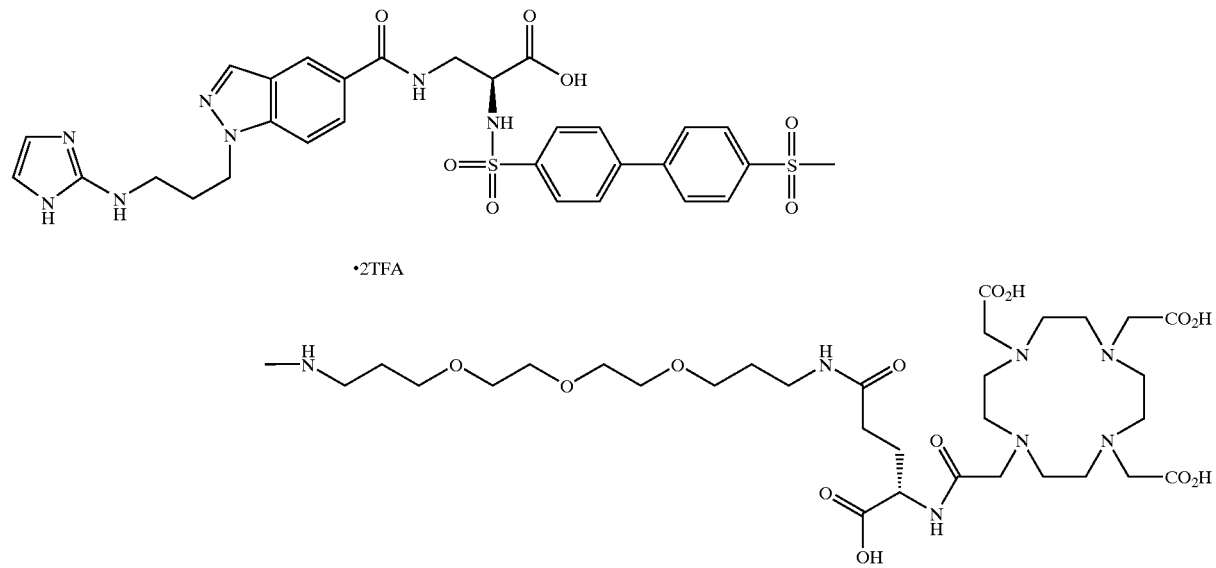

The title compound is prepared by the procedure described for Example 11 by substituting the monomeric product of Example 2, Part A for the dimeric product of Example 2, Part A.

Example 13

Synthesis of DOTA/2-(((4-(3-(N-(3-(2-(2-(3-(2-Amino-3-sulfopropyl)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Bis(trifluoroacetate) Salt Conjugate

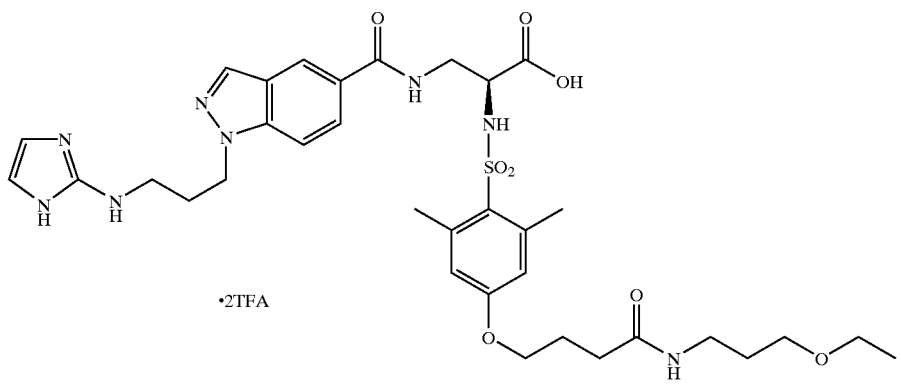

·2TFA

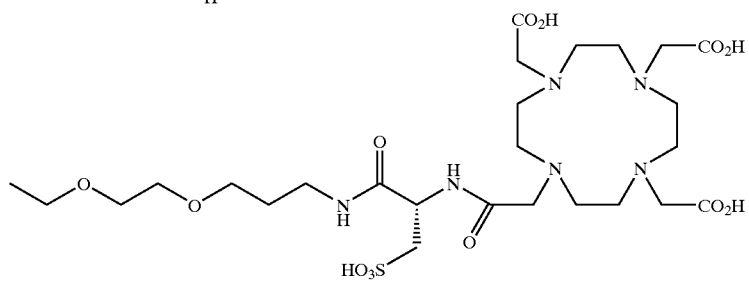

Part A—Ethyl 4-(3,5-Dimethylphenoxy)butanoate

Sodium metal (17.12 g, 0.744 mol) was added to anhydrous EtOH (350 mL) and stirred until dissolved. 3,5-Dimethylphenol was added and the solution was stirred 15 min at ambient temperatures. Ethyl 4-bromoacetate (58.7 mL, 0.41 mol) was added and the solution was stirred at ambient temperatures under a nitrogen atmosphere for 28 h. The EtOH was removed under vacuum and the oily solid was partitioned between water (1 L) and EtOAc (500 mL). The aqueous layer was extracted with additional EtOAc (500 mL). The combined EtOAc extracts were washed consecutively with saturated NaHCO$_3$ (300 mL) and saturated NaCl (300 mL), dried (MgSO$_4$), and concentrated to give an amber liquid. This liquid was vacuum fractional distilled through a 15 cm Vigreux column. The main fraction was collected from 91–117° C./6 mm Hg to gave the title compound as a colorless liquid (77.77 g, 89%). $^1$H NMR (CDCl$_3$): 6.59 (s, 1H), 6.52 (s, 2H), 4.16 (q, J=7.16 Hz, 2H), 3.98 (t, J=6.14 Hz, 2H), 2.49 (t, J=7.34 Hz, 2H), 2.28 (s, 6H), 2.11–2.07 (m, 2H), 1.26 (t, J=7.16 Hz, 3H); Anal. calcd for C$_{14}$H$_{20}$O$_3$: C, 71.16; H, 8.53, Found: C, 71.35; H, 8.59.

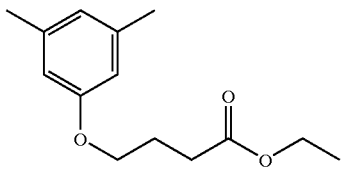

Part B—4-(3,5-Dimethylphenoxy)butanoic Acid

The product of part A, above (75.52 g, 0.320 mol) and KOH pellets (38.5 g, 0.584 mol) were dissolved in absolute EtOH (1.50 L) and heated at reflux for 3 h. The solution was concentrated to a colorless solid, which was taken up in water (2.0 L) and washed with ether (2×750 mL). The aqueous layer was adjusted to pH 1 with concd HCl (55 mL) and the resulting oily ppt was extracted into EtOAc (2×500 mL). The combined EtOAc extracts were washed consecutively with water (300 mL) and saturated NaCl, dried (MgSO$_4$), and concentrated to give a colorless solid (64.13 g). Recrystallization from hexanes (500 mL) gave the title compound as a colorless solid (59.51 g, 89%). MP: 66–68.5° C.; $^1$H NMR (CDCl$_3$): 11.70 (bs, 1H), 6.59 (s, 1H), 6.52 (s, 2H), 3.99 (t, J=6.06 Hz, 2H), 2.57 (t, J=7.29 Hz, 2H), 2.28 (s, 6H), 2.12–2.08 (m, 2H); Anal. calcd for C$_{12}$H$_{16}$O$_3$: C, 69.21; H, 7.74, Found: C, 69.23; H, 7.40.

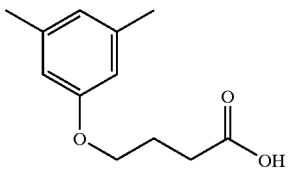

Part C—4-(4-(Chlorosulfonyl)-3,5-dimethylphenoxy) butanoic Acid

A solution of the product of Part B, above (20.8 g, 0.100 mol) in CHCl$_3$ (100 mL) was cooled to 0° C. and treated with chlorosulfonic acid (36 mL, 0.54 mol) dropwise and with rapid stirring while keeping the temperature of the reaction at 0° C. The resulting gelatinous mixture was stirred an additional 10 min and poured onto an ice/water mixture (600 mL). The resulting solid ppt was collected by filtration, washed with water (3×75 mL), and dried under vacuum to give a colorless solid (12.52 g). MP: 114–115° C. (with decomp); $^1$H NMR (CDCl$_3$): 13.84 (bs, 1H), 6.50 (s, 2H), 3.91 (t, J=6.48 Hz, 2H), 2.48 (s, 6H), 2.32 (t, J=7.32 Hz, 2H), 1.89–1.84 (m, 2H); IR (KBr cm$^{-1}$): 1705 (s), 1370 (s), 1175 (s); MS: m/e 305.1 [M−H].

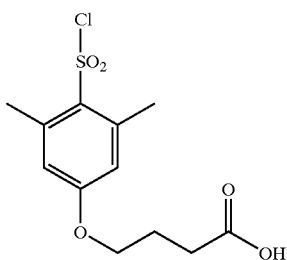

Part D—4-(4-(((2-((tert-Butoxy)carbonylamino)-1-(methoxycarbonyl)ethyl)amino)sulfonyl)-3,5-dimethylphenoxy)butanoic Acid A solution of N-β-Boc-L-α,β,-diaminopropionic acid methyl ester hydrochloride (568 mg, 2.10 mmol) and DIEA (0.73 mL, 4.2 mmol) in DCM (5 mL) was cooled to 0° C. and treated with a suspension of the product of Part C, above (656 mg, 2.10 mmol) in DCM (20 mL) in small portions over a 15 min period. The reaction was stirred at ambient temperatures under a nitrogen atmosphere for 18 h. The reaction was diluted with DCM (100 mL) and washed with water (3×75 mL). The organic phase was dried (MgSO$_4$), and concentrated to give crude product (698 mg), which was purified by preparative HPLC on a Vydac C-18 column (50×250 mm) using a 0.96%/min gradient of 18 to 58.5% ACN containing 0.1% TFA at a flow rate of 80 mL/min. The main product fraction eluting at 23.8 min was collected adjusted to pH 3, partially concentrated to remove ACN, and extracted with DCM (2×100 mL). The DCM extracts were dried (MgSO$_4$) and concentrated to give the title compound as a colorless solid (297 mg, 29%). $^1$H NMR (CDCl$_3$): δ 6.61 (s, 2H), 5.66 (d, J=7.2 Hz, 1H), 4.90 (s, 1H), 4.03 (bs, 2H), 3.86 (bs, 1H), 3.59 (s, 3H), 3.49 (bs, 2H), 2.62 (s, 6H), 2.58–2.51 (m, 2H), 2.18–2.07 (m, 2H), 1.41 (s, 9H); MS: m/e 489.4 [M+H]; High Resolution MS: Calcd for C$_{21}$H$_{33}$N$_2$O$_9$S [M+Na]: 511.1726, Found: 511.1747; Anal. calcd for C$_{21}$H$_{32}$N$_2$O$_9$S: C, 51.62; H, 6.61; N, 5.74, Found: C, 51.47; H, 6.27; N, 5.48.

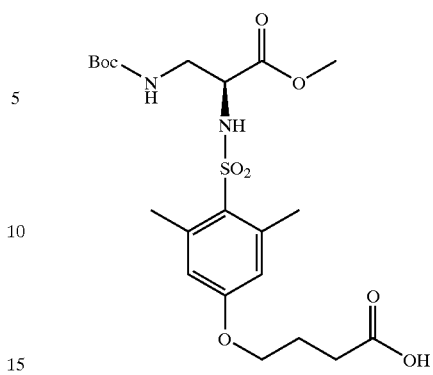

Part E—Methyl 3-((tert-Butoxy)carbonylamino)-2-(((2,6-dimethyl-4-(3-(N-(3-(2-(2-(3-((phenylmethoxy)carbonylamino)propoxy)ethoxy)ethoxy)propyl)carbamoyl)propoxy)phenyl)sulfonyl)amino)propanoate A solution of the product from Part D, above (233 mg, 0.477 mmol), the product of Example 1, Part A (190 mg, 0.536 mmol), TEA (0.2 mL, 1.43 mmol), and HBTU (226 mg, 0.701 mmmol) in anhydrous DMF (8 mL) was stirred at ambient temperatures under a nitrogen atmosphere for 1 h. The DMF was removed under vacuum and the oily residue was taken up in EtOAc (50 mL) and washed consecutively with 0.1 N HCl (35 mL), water (35 mL), and saturated NaCl (35 mL), dried (MgSO$_4$), and concentrated to give crude product as a yellow viscous oil. Flash chromatography on a 3×18 cm silica gel column (EtOAc/MeOH, 95/5) gave the title compound as a colorless viscous oil (393 mg, 100%). $^1$H NMR (CDCl$_3$): δ 7.34–7.28 (m, 5H), 6.60 (s, 2H), 6.26 (bs, 1H), 5.67 (bs, 1H), 5.29 (bs, 1H), 5.08 (s, 2H), 4.88 (bs, 1H), 3.99 (t, J=6.1 Hz, 2H), 3.88–3.84 (m, 1H), 3.62–3.40 (m, 17H), 3.37–3.26 (m, 4H), 2.62 (s, 6H), 2.32 (t, J=7.2 Hz, 2H), 2.08 (t, J=6.3 Hz, 2H), 1.79–1.70 (m, 4H), 1.41 (s, 9H); MS: m/e 825.5 [M+H]; High Resolution MS: Calcd for C$_{39}$H$_{61}$N$_4$O$_{13}$S [M+H]: 825.3955, Found: 825.3940.

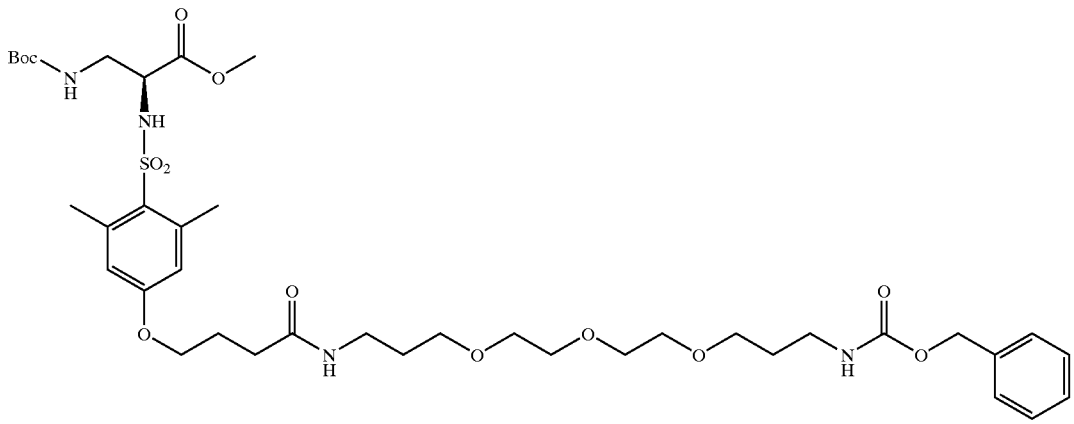

Part F—Methyl 3-Amino-2-(((2,6-dimethyl-4-(3-(N-(3-(2-(2-(3-((phenylmethoxy)carbonylamino)propoxy)ethoxy)ethoxy)propyl)carbamoyl)propoxy)phenyl)sulfonyl)amino)propanoate The product of Part E, above (750 mg, 0.91 mmol) was dissolved in 4 M HCl/dioxane (25 mL) and stirred at ambient temperatures for 1 h. The solution was diluted with ether (500 mL) and the resulting gummy ppt was triturated with fresh ether (2×250 mL). The gummy solid was dissolved in water (100 mL) and adjusted to pH 9 with NaHCO₃, causing an oily ppt to form. This ppt was extracted into DCM (2×75 mL). The DCM extracts were dried (MgSO₄) and concentrated to give the title compound as a colorless oil (386 mg, 56%). MS: m/e 725.5 [M+H].

propanoate, DIEA, and HBTU in anhydrous DMF are stirred at ambient temperatures under nitrogen for 4 h. The DMF is removed under vacuum and the resulting residue is dissolved in EtOAc and washed with water, saturated NaHCO3, and saturated NaCl. The EtOAc layer is dried (MgSO₄) and concentrated to dryness. The crude product is purified by flash chromatography on silica gel using EtOAc/MeOH.

Part H—Preparation of 2-(((4-3-(N-(3-(2-(2-(3-(2-((tert-Butoxy)carbonylamino)-3-sulfopropyl)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Trifluoroacetate Salt

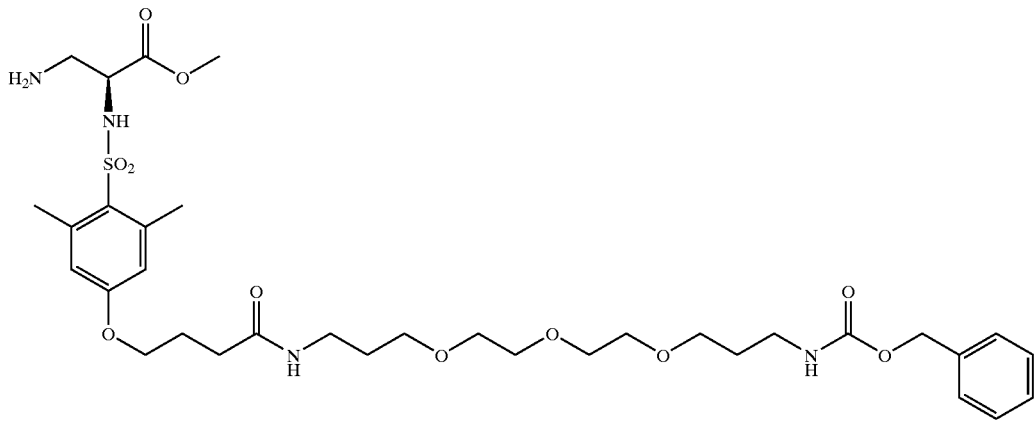

Part G—Preparation of Methyl 2-(((2,6Dimethyl-4-(3-(N-(3-(2-(2-(3-((phenylmethoxy)carbonylamino)propoxy)ethoxy)ethoxy)propyl)carbamoyl)propoxy)phenyl)sulfonyl)amino)-3-((1-(3-((1-(triphenylmethyl)imidazol-2-yl)amino)propyl)(1H-indazol-5-yl))carbonylamino)propionate

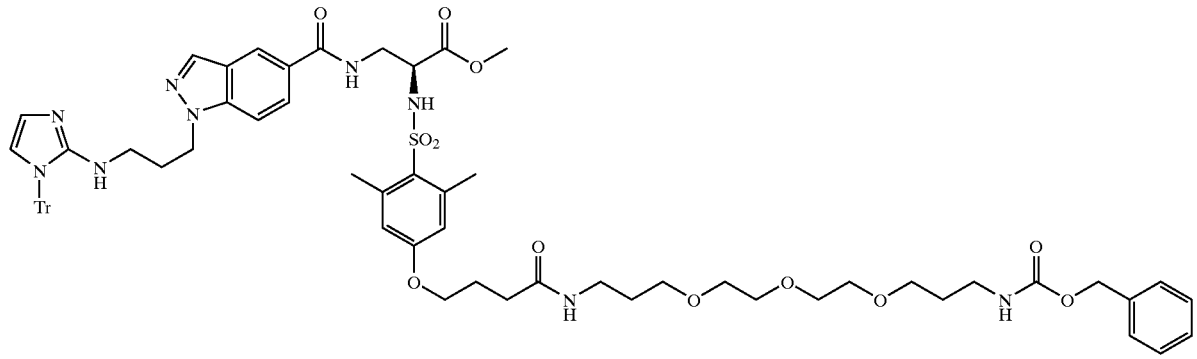

A solution of 1-(3-((1-(triphenylmethyl)imidazol-2-yl)amino)propyl)-1H-indazole-5-carboxylic acid, methyl 3-amino-2-(((2,6-dimethyl-4-(3-(N-(3-(2-(2-(3-((phenylmethoxy)carbonylamino)propoxy)ethoxy)ethoxy)propyl)carbamoyl)propoxy)phenyl)sulfonyl)amino)

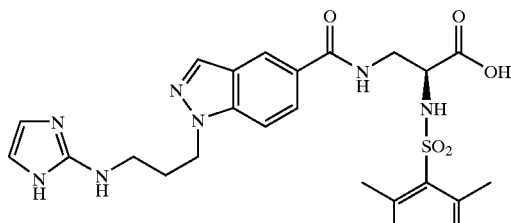

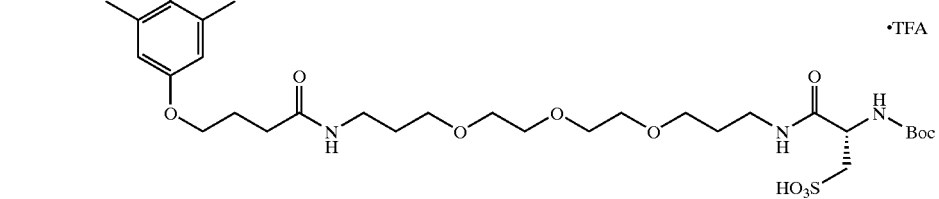

The product from Part G, above is hydrolyzed in a mixture of peroxide-free THF, water, and 3 N LiOH at ambient temperatures under nitrogen for 6 h. The THF is removed under vacuum and the resulting mixture is diluted with water and adjusted to pH 3 using 0.1 N HCl. The mixture is extracted with EtOAc, and the combined extracts are dried (MgSO$_4$) and concentrated.

A solution of the hydrolysis product from above and Et$_3$SiH in degassed TFA is heated at 70° C. under nitrogen for 1 h. The solution is concentrated and the resulting residue is dissolved in 50% ACN. The TFA salt is converted to the free base by treatment with an ion exchange resin such as Bio-Rad AG-3X4A, hydroxide form, until the pH of the solution is raised to 6.5. The resin is removed by filtration and the filtrate is lyophilized to give the free base.

The above material is dissolved in anhydrous DMF, and treated with the N-hydroxysuccinimide ester of Boc-cysteic acid (as described in *Liebigs Ann. Chem.* 1979, 776–783) and DIEA. The solution is stirred at ambient temperatures under nitrogen for 18 h, and the DMF is removed under vacuum. The resulting residue is purified by preparative HPLC on a C18 column using a water:ACN:0.1% TFA gradient. The product fraction is lyophilized to give the title compound.

Part I—Preparation of DOTA Tri-t-butyl Ester/2-(((4-(3-(N-(3-(2-(2-(3-(2-Amino-3-sulfopropyl)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Pentakis (trifluoroacetate) Salt Conjugate

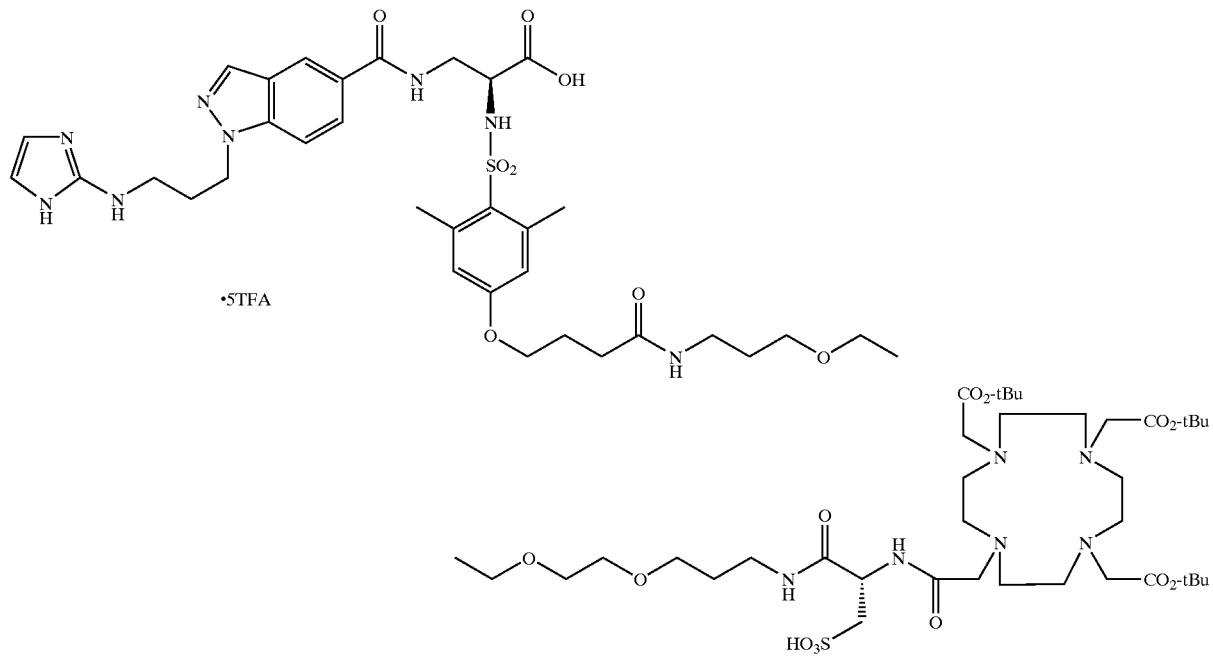

The product of Part H, above is dissolved in degassed TFA and stirred at ambient temperatures for 15 min. The solution is concentrated under vacuum, and the resulting residue is dissolved in 50% ACN and lyophilized to remove the last traces of TFA.

In a separate flask, a solution of DOTA tris-t-butyl ester and DIEA in anhydrous DMF are treated with HBTU and allowed to react 15 min at ambient temperatures under nitrogen. The deprotected product from above is added to this solution and stirring is continued at ambient temperatures under nitrogen for 18 h. The DMF is removed under vacuum and the resulting residue is purified by preparative HPLC on a C18 column using a water:ACN:0.1% TFA gradient. The product fraction is lyophilized to give the title compound.

Part J—Preparation of DOTA/2-(((4-(3-(N-(3-(2-2-(3-(2-Amino-3-sulfopropyl)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Bis(trifluoroacetate) Salt Conjugate The product of Part I, above, and Et$_3$SiH are dissolved in degassed TFA and heated at 50° C. under nitrogen for 1 h. The solution is concentrated and the resulting residue is purified by preparative HPLC on a C18 column using a water:ACN:0.1% TFA gradient. The product fraction is lyophilized to give the title compound.

Example 14

Synthesis of DOTA/2-(((4-(3-(N-(3-(2-(2-(3-(2-Amino-3-(4-(phosphonooxy)phenyl)propanoylamino)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Trifluoroacetate Salt Conjugate Example 15

Synthesis of DOTA/2-(((4-(3-(N-(3-(2-(2-(3-(2-Amino-3-(4-(sulfooxy)phenyl)propanoylamino)propoxy)ethoxy)ethoxy)propyl)carbanoyl)propoxy)-2,6-dimethylphenyl)sulfonyl)amino)-3-((1-(3-(imidazol-2-ylamino)propyl)(1H-indazol-5-yl))carbonylamino)propionic Acid Trifluoroacetate Salt Conjugate The title compound is prepared by the procedure described for Example 13 by substituting Boc-Tyr(SO$_3$H)-OSu for Boc-Cys(O$_3$H)-OSu.

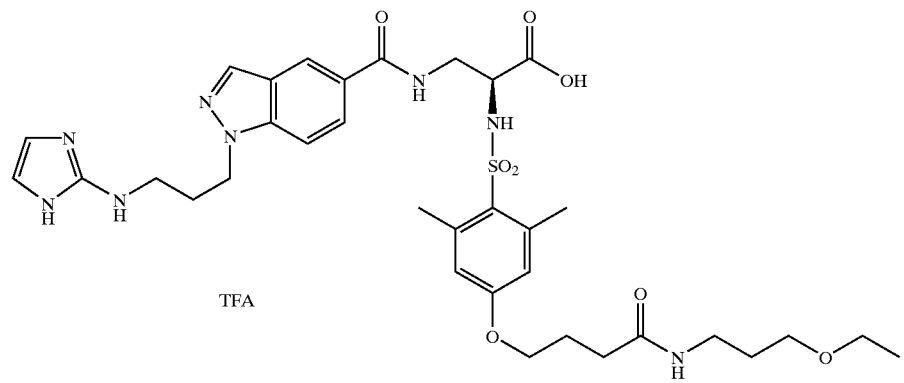

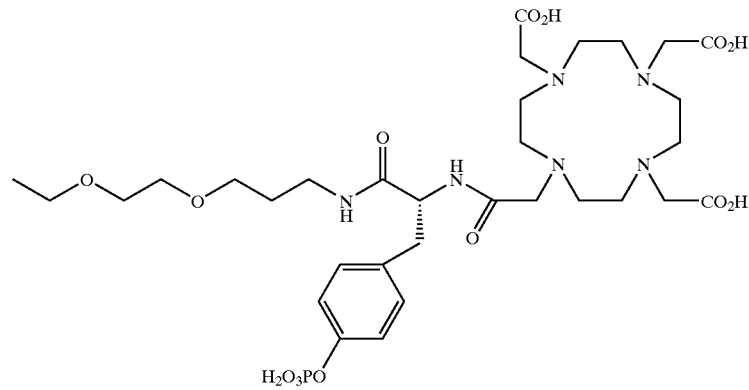

The title compound is prepared by the procedure described for Example 13 by substituting Boc-Tyr(PO$_3$H$_2$)-OSu for Boc-Cys(O$_3$H)-OSu.

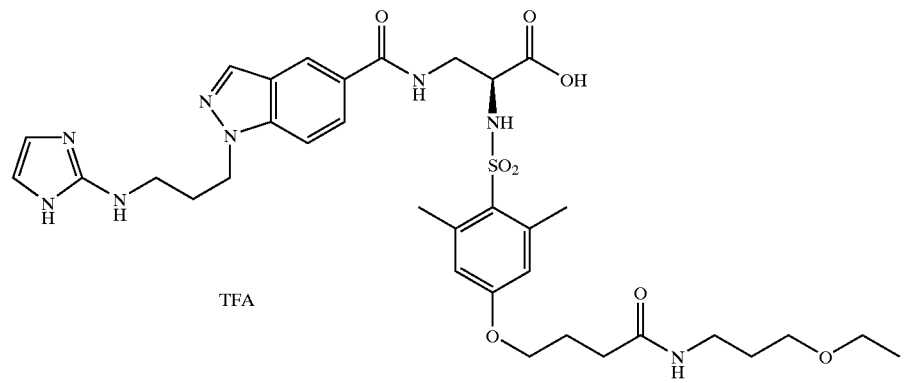
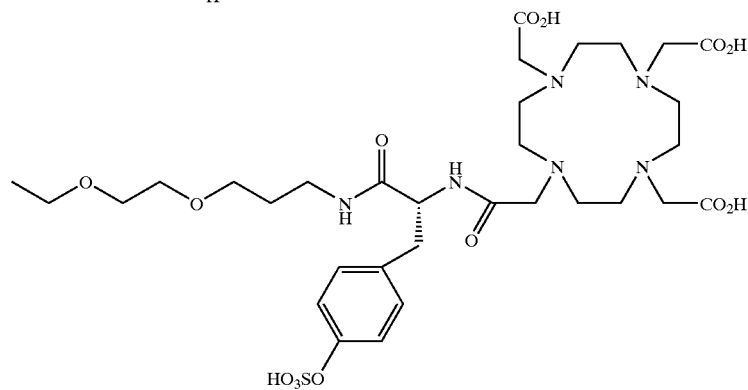
Example 16
Synthesis of DOTA/2-(((4-(3-(N-(3-(2-(2-(3-(2-Amino-4-(N-(ethyl-3,6-O-disulfo-β-D-galactopyranosyl)carbamoyl)butanoylamino)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Conjugate
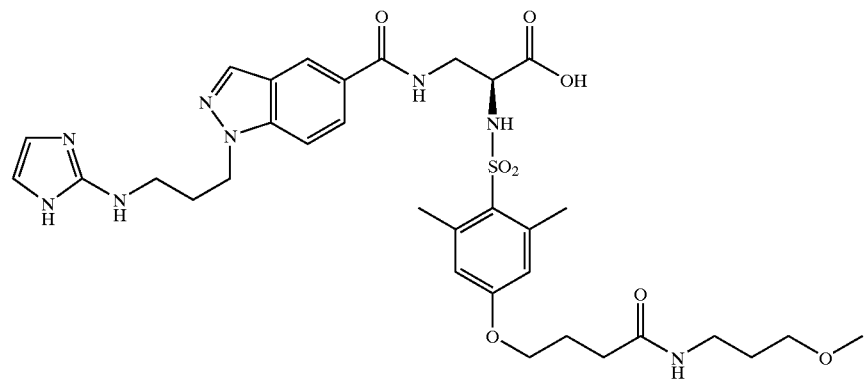

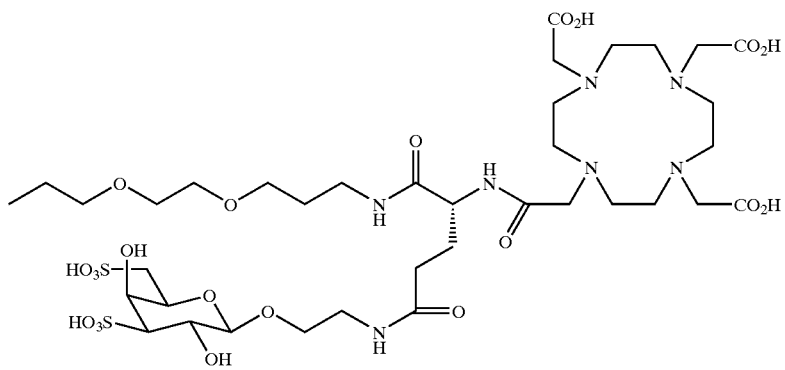

Part A—Preparation of Boc-Glu(aminoethyl-3,6-O-disulfo-β-D-galactopyranosyl)-OSu A solution of Boc-Glu-OMe, aminoethyl-3,6-O-disulfo-.-D-galactopyranoside (as described in *Tet. Lett.* 1997, 53, 11937–11952), DIEA, and HBTU in anhydrous DMF is stirred at ambient temperatures under nitrogen for 18 h. The DMF is removed under vacuum and the resulting residue is hydrolyzed using aqueous NaOH. The reaction solution is adjusted to pH 7 and purified by preparative anion exchange chromatography using a resin such as DEAE Cellulose and a Et₃NH₂CO₃ gradient. The product fraction is treated with a cation exchange resin, sodium form, to give the intermediate carboxylic acid as the sodium salt.

The above compound, N-hydroxysuccinimide, and DCC are dissolved in anhydrous DMF and stirred at ambient temperatures under nitrogen for 18 h. The DMF is removed under vacuum and the resulting residue is purified by preparative anion exchange chromatography as above to give the title compound as the triethylammonium salt.

Part B—Preparation of DOTA/2-(((4-(3-(N-(3-(2-(2-(3-(2-Amino-4-(N-(ethyl-3,6-O-disulfo-β-D-galactopyranosyl)carbamoyl)butanoylamino)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Conjugate The title compound is prepared by the procedure described for Example 13 by substituting Boc-Glu(aminoethyl-3,6-O-disulfo-β-D-galactopyranosyl)-OSu for Boc-Cys(O₃H)-OSu.

Example 17

Synthesis of DOTA/2-(((4-(3-(N-(3-(2-(2-(3-(2-Amino-4-(N-(6-deoxy-β-cyclodextryl)carbamoyl)butanoylamino)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Bis(trifluoroacetate) Conjugate

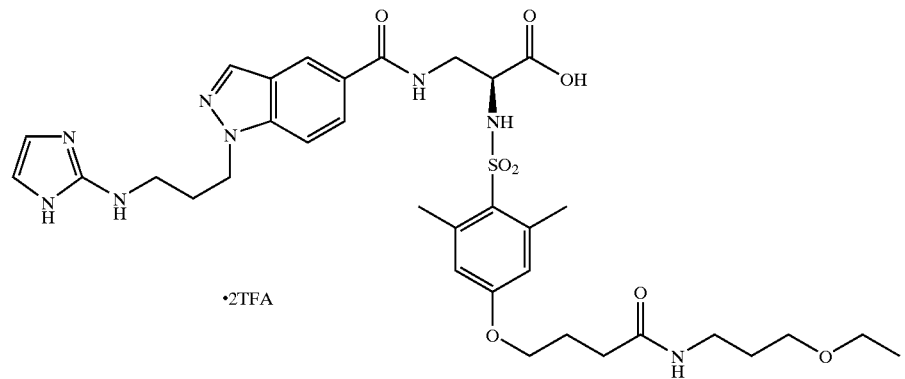

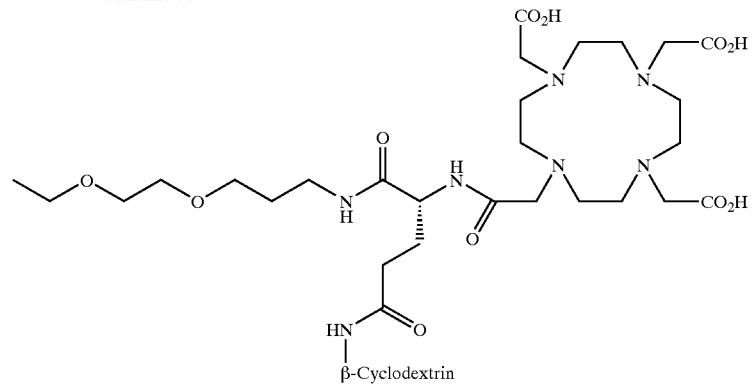

Part A—Preparation of Boc-Glu(6-amino-6-deoxy-β-cyclodextryl)-OMe

A solution of Boc-Glu-OMe, 6-amino-6-deoxy-β-cyclodextrin (as described in *J. Org. Chem.* 1996, 61, 903–908), DIEA, and HBTU in anhydrous DMF is stirred at ambient temperatures under nitrogen for 18 h. The DMF is removed under vacuum and the resulting residue is purified by preparative HPLC on a C18 column using a water-:ACN:0.1% TFA gradient. The product fraction is lyophilized to give the title compound.

Part B—Preparation of Boc-Glu(6-amino-6-deoxy-β-cyclodextryl)-OSu

The product of Part A, above, is hydrolyzed by stirring in a mixture of LiOH, THF, and water at ambient temperatures under nitrogen for 4 h. The THF is removed under vacuum and the resulting mixture is diluted with water and adjusted to pH 3 using 0.1 N HCl. The mixture is extracted with EtOAc, and the combined extracts are dried (MgSO$_4$) and concentrated. The resulting material is dissolved in anhydrous DMF along with N-hydroxysuccinimide, and DCC, and stirred at ambient temperatures under nitrogen for 18 h. The DMF is removed under vacuum and the resulting residue is purified by preparative HPLC on a C18 column using a water:ACN:0.1% TFA gradient. The product fraction is lyophilized to give the title compound.

Part C—Preparation of DOTA/2-(((4-(3-(N-(3-(2-(2-(3-(2-Amino-4-(N-(6-deoxy-β-cyclodextryl)carbamoyl)butanoylamino)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Bis(trifluoroacetate) Conjugate The title compound is prepared by the procedure described for Example 13 by substituting Boc-Glu(6-amino-6-deoxy-β-cyclodextryl)-OSu for Boc-Cys(O$_3$H)-OSu.

Example 18

Synthesis of DOTA/2-(((4-(3-(N-(3-(2-(2-(3-2-Amino-4-(N-((ω-methoxypolyethylene(5,000)glycoxyethyl)carbamoyl)butanoylamino)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Bis(trifluoroacetate) Conjugate

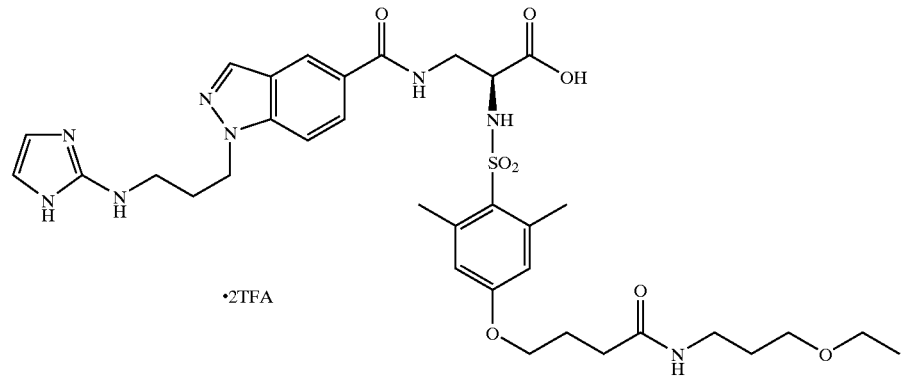

-continued

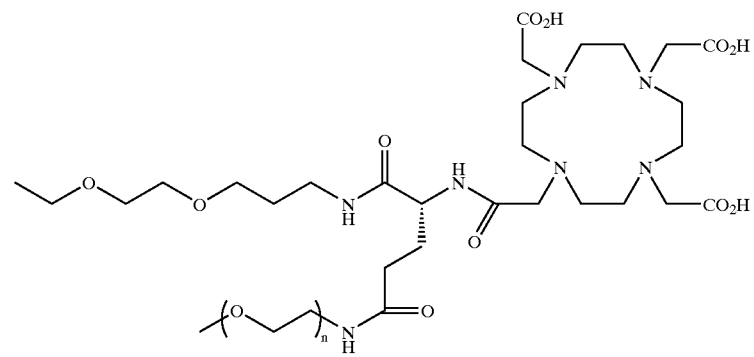

Part A—Preparation of Boc-Glu(amino-ω-methoxypolyethylene glycol)-OMe

A solution of Boc-Glu-OMe, amino-ω-methoxypolyethylene glycol, (MW=5,000), DIEA, and HBTU in anhydrous DMF is stirred at ambient temperatures under nitrogen for 18 h. The DMF is removed under vacuum and the resulting residue is purified by preparative HPLC on a C18 column using a water:ACN:0.1% TFA gradient. The product fraction is lyophilized to give the title compound.

Part B—Preparation of Boc-Glu(amino-ω-methoxypolyethylene glycol)-OSu

The product of Part A, above, is hydrolyzed by stirring in a mixture of LiOH, THF, and water at ambient temperatures under nitrogen for 4 h. The THF is removed under vacuum and the resulting solution is adjusted to pH 7 using 0.1 N HCl. The solution is desalted using a Sephadex PD-10 desalting column and the product eluant is lyophilized. The resulting material is dissolved in anhydrous DMF along with N-hydroxysuccinimide, and DCC, and stirred at ambient temperatures under nitrogen for 18 h. The DMF is removed under vacuum and the resulting residue is purified by preparative HPLC on a C18 column using a water-:ACN:0.1% TFA gradient. The product fraction is lyophilized to give the title compound.

Part C—Preparation of DOTA/2-(((4-(3-(N-(3-(2-(2-(3-(2-Amino-4-(N-(ω-methoxypolyethylene(5,000)glycoxyethyl)carbamoyl)butanoylamino)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Bis(trifluoroacetate) Salt Conjugate The title compound is prepared by the procedure described for Example 13 by substituting Boc-Glu(amino-ω-methoxypolyethylene glycol)-OSu for Boc-Cys(O₃H)-OSu.

Example 19

Synthesis of 2-(((4-(3-(N-(3-(2-(2-(3-(2-(1,4,7,10-Tetraaza-4,7,10-tris(carboxymethyl)cyclododecylacetylamino)-6-aminohexanoylamino)propoxy)ethoxy)ethoxy)propyl)carbamoyl)propoxy)-2,6-dimethylphenyl)sulfonyl)amino)-3-((1-(3-imidazol-2-ylamino)propyl)(1H-indazol-5-yl))carbonylamino)propionic Acid Tris(trifluoroacetate) Salt

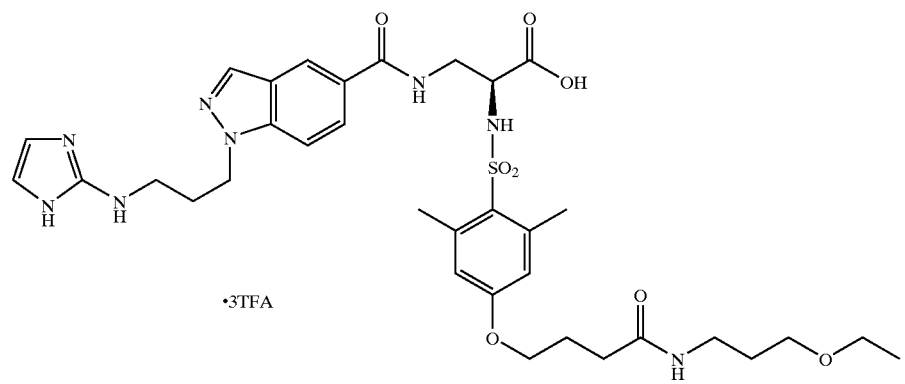

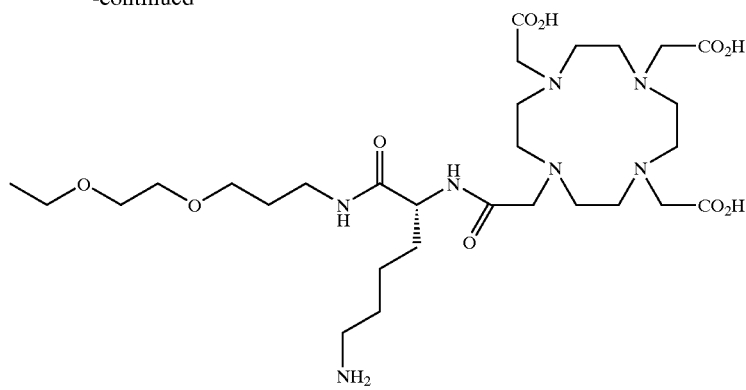

The title compound is prepared by the procedure described for Example 13 by substituting Boc-Lys(Cbz)-OSu for Boc-Cys(O₃H)-OSu.

Example 20

Synthesis of the DOTA/2-(((4-3-(N-(3-(2-(2-(3-(2-Amino-6-(2-(bis(phosphonomethyl)amino)acetylamino)hexanolylamino)propoxy)ethoxy)ethoxy)propyl)carbamoyl)propoxy)-2,6-dimethylphenyl)sulfonyl)amino)-3-((1-(3-(imidazol-2-ylamino)propyl)(1H-indazol-5-yl))carbonylamino)propionic Acid Trifluoroacetate Salt Conjugate

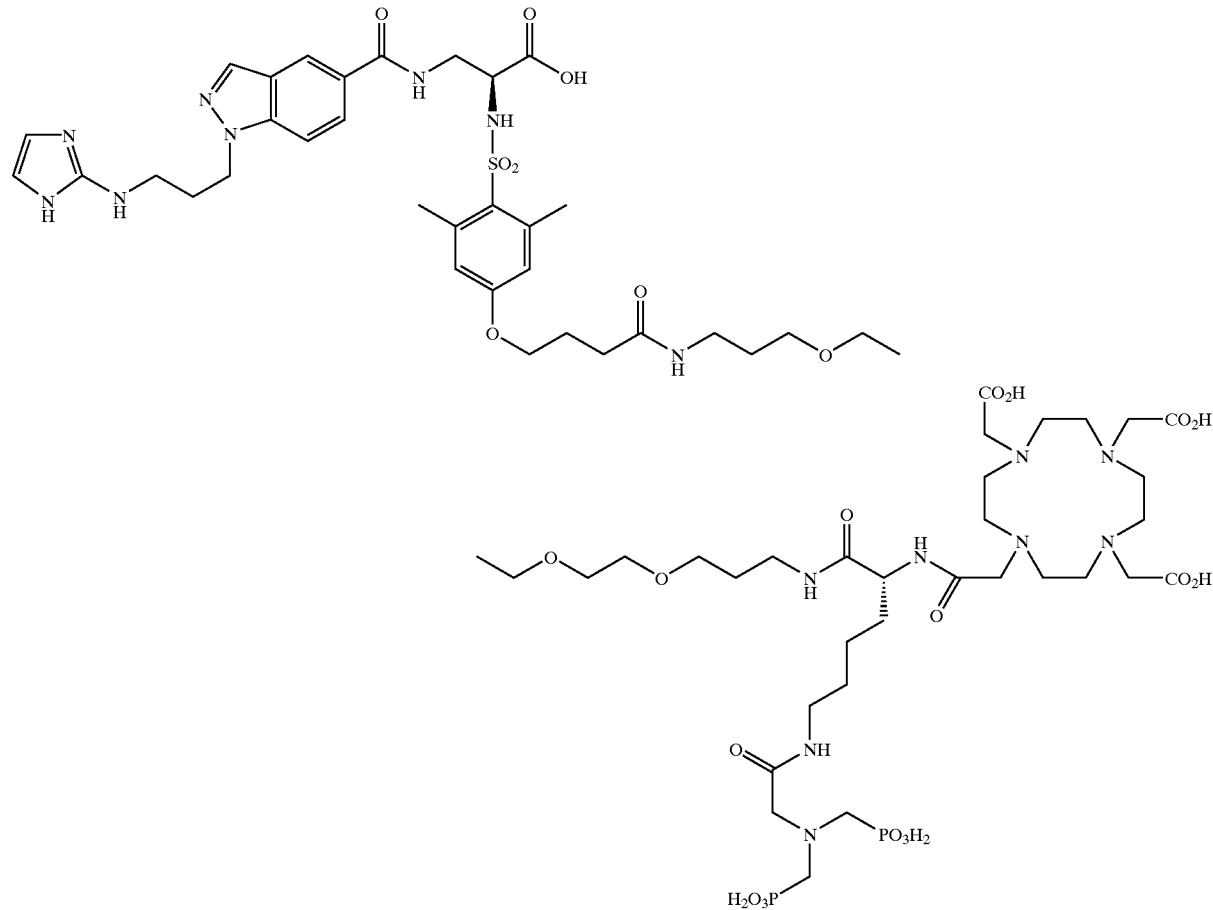

A solution of bis(phosphonomethyl)glycine, DIBA, and HBTU in anhydrous DMF is stirred at ambient temperatures under nitrogen for 15 min, and treated with the product of Example 19. Stirring is continued for 18 h and the DMF is removed under vacuum. The resulting residue is purified by ion exchange chromatography.

Example 21

Synthesis of DTPA adduct of 2-(6-Aminohexanoylamino)-3-((1-(3-(imidazol-2-ylamino)propyl)(1H-indazol-5-yl))carbonyl-amino)propanoic acid

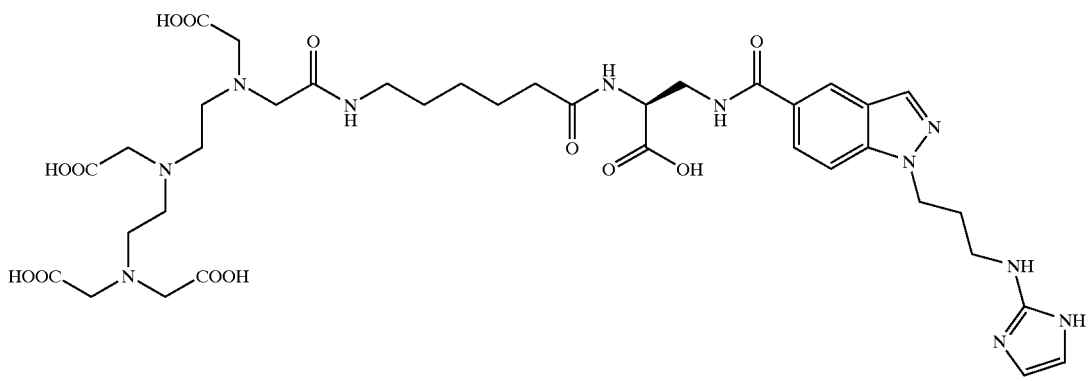

To a solution of DTPA dianhydride (3 mmol), triethylamine (3 mmol) in DMF 20 mL is added a solution of 2-(6-aminohexanoylamino)-3-((1-(3-(imidazol-2-ylamino)propyl)(1H-indazol-5-yl))carbonyl-amino)propanoic acid (1 mmol) in DMF 5 mL dropwise. The reaction mixture is stirred for 18 h at room temperature under nitrogen, the volatiles are removed and the title compound is obtained after purification and isolation using preparative RP-HPLC.

The following procedure describe the synthesis of radiopharmaceuticals of the present invention of the formula $^{99m}$Tc(VnA)(tricine)(phosphine), in which (VnA) represents a vitronectin receptor antagonist compound of the present invention bonded to the Tc through a diazenido (—N═N—) or hydrazido (═N—NH—) moiety. The diazenido or hydrazido moiety results from the reaction of the hydrazinonicotinamido group, present either as the free hydrazine or protected as a hydrazone, with the Tc-99m. The other two ligands in the Tc coordination sphere are tricine and a phosphine.

Examples 22–26

Synthesis of Complexes [$^{99m}$Tc(HYNIC-VnA)(tricine)(TPPTS)]

To a lyophilized vial containing 4.84 mg TPPTS, 6.3 mg tricine, 40 mg mannitol, succinic acid buffer, pH 4.8, and 0.1% Pluronic F-64 surfactant, was added 1.1 mL sterile water for injection, 0.2 mL (20 μg) of the appropriate HYNIC-conjugated vitronectin antagonist (VnA) in deionized water or 50% aqueous ethanol, and 0.2 mL of $^{99m}$TcO$_4^-$ (50±5 mCi) in saline. The reconstituted kit was heated in a 100° C. water bath for 15 minutes, and was allowed to cool 10 minutes at room temperature. A sample of the reaction mixture was analyzed by HPLC. The RCP results are listed in the table 1.

TABLE 1

Analytical and Yield Data for $^{99m}$Tc(VnA)(tricine) (TPPTS) Complexes

| Example No. | Reagent No. | Ret. Time (min) | % Yield |
|---|---|---|---|
| 22 | 1 | 18.6* | 50 |
| 23 | 2 | 13.2** | 55 |
| 24 | 3 | 17.0** | 71 |

TABLE 1-continued

Analytical and Yield Data for $^{99m}$Tc(VnA)(tricine) (TPPTS) Complexes

| Example No. | Reagent No. | Ret. Time (min) | % Yield |
|---|---|---|---|
| 25 | 5 | 10.3*** | 72 |
| 26 | 6 | 7.2* | 64 |

*The HPLC method using a reverse phase C$_{18}$ Zorbax column (4.6 mm × 25 cm, 80 Å pore size) at a flow rate of 1.0 mL/min with a gradient mobile phase from 100% A (10 mM pH 6.0 phosphate buffer) to 75% B (acetonitrile) at 20 min.
**The HPLC method using a reverse phase C$_{18}$ Zorbax column (4.6 mm × 25 cm, 80 Å pore size) at a flow rate of 1.0 mL/min with a gradient mobile phase from 100% A (10 mM pH 6.0 phosphate buffer) to 50% B (acetonitrile) at 20 min.
***The HPLC method using a reverse phase C$_{18}$ Zorbax column (4.6 mm × 25 cm, 80 Å pore size) at a flow rate of 1.0 mL/min with a gradient mobile phase from 100% A (10 mM pH 6.0 phosphate buffer) to 25% B (acetonitrile) at 20 min.

Example 27

Synthesis of the $^{177}$Lu Complex of 3-((1-(3-(Imidazole-2-ylamino)propyl)(1H-indazol-5-yl))carbonylamino)-2-(((4-(4-(((3-(2-(2-3-(2-(1,4,7,10-tetraaza-4,7,10-tris(carboxymethyl)cyclododecyl)acetylamino)propoxy)ethoxy)ethoxy)propyl)amino)sulfonyl)phenyl)phenyl)sulfonyl)amino)propanoic Acid To a clean sealed 5 mL vial was added 0.5 mL of a solution of the conjugate of Example 4 (200 μg/mL in 0.5 M ammonium acetate buffer, pH 6.9), followed by 0.05 mL of gentisic acid (sodium salt, 10 mg/mL in 0.5 M ammonium acetate buffer, pH 6.9) solution, 0.3 mL of 0.25 M ammonium acetate buffer (pH 7.0), and 0.010 mL of 177LuCl$_3$ solution (1000 mCi/mL) in 0.05 N HCl. The resulting mixture was heated at 100 C for 30 min. After cooling to room temperature, a sample of the resulting solution was analyzed by radio-HFLC and ITLC. The radiolabeling yield was 80%, and the retention time was 18.0 min.

| HPLC Method | | | | | | |
|---|---|---|---|---|---|---|
| Column: | Zorbax C18, 25 cm × 4.6 mm | | | | | |
| Flow rate: | 1.0 mL/min | | | | | |
| Solvent A: | 25 mM sodium phosphate buffer, pH 6.0 | | | | | |
| Solvent B: | 100% CH3CN | | | | | |
| t (min) | 0 | 20 | 21 | 25 | 26 | 32 |
| % Solvent B | 15 | 20 | 60 | 60 | 15 | 15 |

The instant thin layer chromatography (ITLC) method used Gelman Sciences silica-gel strips and a 1:1 mixture of acetone and saline as eluant.

Example 28

Synthesis of the $^{90}$Y Complex of 3-((1-(3-(Imidazole-2-ylamino)propyl)(1H-indazol-5-yl))carbonylamino)-2-(((4-(4-(((3-(2-(2-(3-(2-(1,4,7,10-tetraaza-4,7,10-tris(carboxymethyl)cyclododecyl)acetylamino)propoxy)ethoxy)ethoxy)propyl)amino)sulfonyl)phenyl)phenyl)sulfonyl)amino)propanoic Acid To a clean sealed 5 mL vial was added 0.5 mL of a solution of the conjugate of Example 4 (200 µg/mL in 0.5 M ammonium acetate buffer, pH 6.9), followed by 0.05 mL of gentisic acid (sodium salt, 10 mg/mL in 0.5 M ammonium acetate buffer, pH 6.9) solution, 0.3 mL of 0.25 M ammonium acetate buffer (pH 7.0), and 0.010 mL of $^{90}$YCl$_3$ solution (1000 mCi/mL) in 0.05 N HCl. The resulting mixture was heated at 100 C for 30 min. After cooling to room temperature, a sample of the resulting solution was analyzed by radio-HPLC and ITLC. The radiolabeling yield was 85%, and the retention time was 18.2 min.

| HPLC Method | | | | | | |
|---|---|---|---|---|---|---|
| Column: | Zorbax C18, 25 cm × 4.6 mm | | | | | |
| Flow rate: | 1.0 mL/min | | | | | |
| Solvent A: | 25 mM sodium phosphate buffer, pH 6.0 | | | | | |
| Solvent B: | 100% CH3CN | | | | | |
| t (min) | 0 | 20 | 21 | 25 | 26 | 32 |
| % Solvent B | 15 | 20 | 60 | 60 | 15 | 15 |

The instant thin layer chromatography (ITLC) method used Gelman Sciences silica-gel strips and a 1:1 mixture of acetone and saline as eluant.

Example 29

Synthesis of the $^{111}$In Complex of 3-((1-3-(Imidazole-2-ylamino)propyl)(1H-indazol-5-yl))carbonylamino)-2-(((4-(4-(((3-(2-(2-(3-(2-(1,4,7,10-tetraaza-4,7,10-tris(carboxymethyl)cyclododecyl)acetylamino)propoxy)ethoxy)ethoxy)propyl)amino)sulfonyl)phenyl)phenyl)sulfonyl)amino)propanoic Acid To a lead shielded and closed autosampler vial was added: 80 µg of the conjugate of Example 4 dissolved in 160 µL 0.4 M ammonium acetate at pH 4.7 and 3 mCi In-111-chloride in 12.5 µL 0.05 N HCl. The solution was heated at 100° C. for 35–40 minutes. After cooling to room temperature, a sample of the resulting solution was analyzed by radio-HPLC and ITLC. The radiolabeling yield was 95%, and the retention time was 9.5 min.

| HPLC Method | | | | | | |
|---|---|---|---|---|---|---|
| Column: | Zorbax C18, 25 cm × 4.6 mm | | | | | |
| Flow rate: | 1.0 mL/min | | | | | |
| Solvent A: | 25 mM sodium phosphate buffer, pH 6.0 | | | | | |
| Solvent B: | 100% CH3CN | | | | | |
| t (min) | 0 | 25 | 26 | 30 | 31 | 37 |
| % Solvent B | 16 | 18 | 60 | 60 | 16 | 16 |

The instant thin layer chromatography (ITLC) method used Gelman Sciences silica-gel strips and a 1:1 mixture of acetone and saline as eluant.

Example 30

Synthesis of the Gd Complex of 3-((1-(3-(Imidazole-2-ylamino)propyl)(1H-indazol-5-yl))carbonylamino)-2-(((4-(4-(((3-(2-(2-(3-(2-(1,4,7,10-tetraaza-4,7,10-tris(carboxymethyl)cyclododecyl)acetylamino)propoxy)ethoxy)ethoxy)propyl)amino)sulfonyl)phenyl)phenyl)sulfonyl)amino)propanoic Acid The gadolinium complex of the conjugate of Example 4 is prepared according to the following procedure. 3–3.5 mg of the conjugate is dissolved in 2 mL 1 M ammonium acetate buffer at pH 7.0, and one equivalent Gd(NO$_3$)$_3$ solution (0.02 M in water) is added to it. The reaction mixture is heated at 100 C for 30 minutes and the product is isolated by preparative HPLC. The fraction containing the complex is lyophilized. The identity of the complex is confirmed by mass spectroscopy.

The following examples describe the synthesis of ultrasound contrast agents of the present invention.

Example 31

Part A Synthesis of 1-(1,2-Dipalmitoyl-sn-glycero-3-phosphoethanolamino)-12-(2-(6-aminohexanoylamino)-3-((1-(3-(imidazol-2-ylamino)propyl)(1H-indazol-5-yl))carbonylamino)propanoic acid)-dodecane-1,12-dione

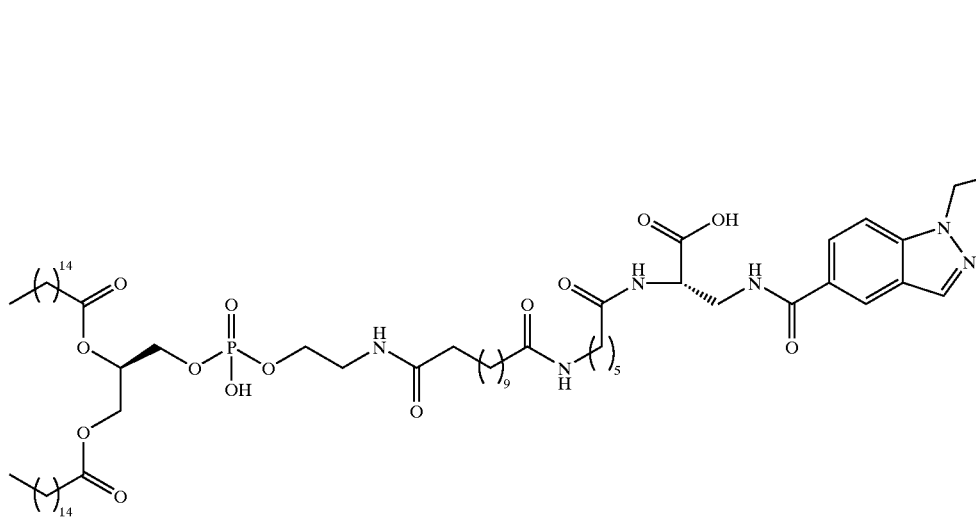

A solution of disuccinimidyl dodecane-1,12-dioate (0.424 g, 1 mmol), 1,2-dipalmitoyl-sn-glycero-3-phosphoethanolamine (1.489 g, 1 mmol) and 2-(6-aminohexanoylamino)-3-((1-(3-(imidazol-2-ylamino)propyl)(1H-indazol-5-yl))carbonylamino)propanoic acid TFA salt (1 mmol) in 25 ml chloroform is stirred for 5 min. Sodium carbonate (1 mmol) and sodium sulfate (1 mmol) are added and the solution is stirred at room temperature under nitrogen for 18 h. DMF is removed in vacuo and the crude product is purified to obtain the title compound.

Part B Preparation of Contrast Agent Composition

The 1-(1,2-Dipalmitoyl-sn-glycero-3-phosphoethanolamino)-12-(2-(6-aminohexanoylamino)-3-((1-(3-(imidazol-2-ylamino)propyl)(1H-indazol-5-yl))carbonylamino)propanoic acid)-dodecane-1,12-dione is admixed with three other lipids, 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine in relative amounts of 1 wt. %:6 wt. %:54 wt. %:41 wt. %. An aqueous solution of this lipid admixture (1 mg/mL), sodium chloride (7 mg/mL), glycerin (0.1 mL/mL), propylene glycol (0.1 mL/mL), at pH 6–7 is then prepared in a 2 cc glass vial. The air in the vial is evacuated and replaced with perfluoropropane and the vial is sealed. The ultrasound contrast agent composition is completed by agitating the sealed vial in a dental amalgamator for 30–45 sec. to form a milky white solution.

Example 32

Part A. Preparation of Preparation of ($\omega$-amino-PEG$_{3400}$-$\alpha$-carbonyl)-2-(6-aminohexanoylamino)-3-((1-(3-(imidazol-2-ylamino)propyl)(1H-indazol-5-yl))carbonylamino) propanoic acid

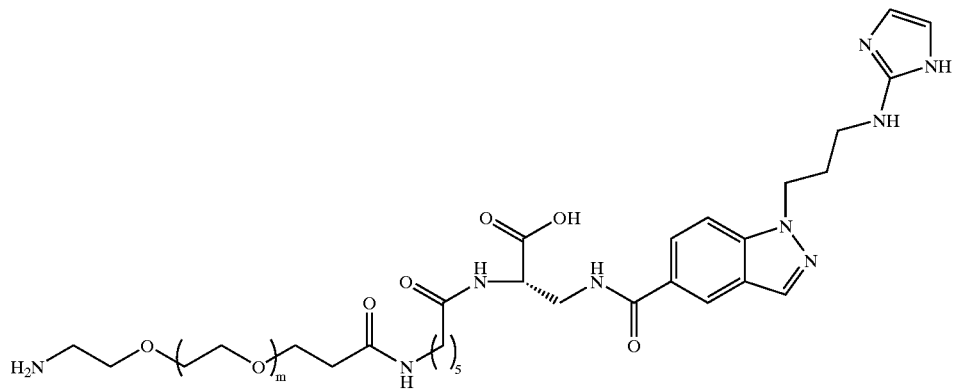

To a solution of N-Boc-$\omega$-amino-PEG$_{3400}$-$\alpha$-carboxylate sucinimidyl ester (1 mmol) and 2-(6-aminohexanoylamino)-3-((1-(3-(imidazol-2-ylamino)propyl)(1H-indazol-5-yl))carbonyl-amino)propanoic acid (1 mmol) in DMF (25 mL) is added triethylamine (3 mmol). The reaction mixture is stirred under nitrogen at room temperature overnight and the solvent is removed in vacuo. The crude product is dissolved in 50% trifluoroacetic acid/dichloromethane and is stirred for 4 h. The volatiles are removed and the title compound is isolated as the TFA salt via trituation in diethyl ether.

Part B. Preparation of 1-(1,2-Dipalmitoyl-sn-glycero-3-phosphoethanolamino)-12-(($\omega$-amino-PEG$_{3400}$-$\alpha$-carbonyl)-(2-(6-aminohexanoylamino)-3-((1-(3-(imidazol-2-ylamino)propyl)(1H-indazol-5-yl))carbonyl-amino) propanoic acid))-dodecane-1,12-dione A solution of disuccinimidyl dodecane-1,12-dioate (1 mmol), 1,2-dipalmitoyl-sn-glycero-3-phosphoethanolamine (1 mmol) and (ω-amino-PEG$_{3400}$-α-carbonyl)-cyclo(Arg-Gly-Asp-D-Phe-Lys) TFA salt (1 mmol) in 25 ml chloroform is stirred for 5 min. Sodium carbonate (1 mmol) and sodium sulfate (1 mmol) are added and the solution is stirred at room temperature under nitrogen for 18 h. DMF is removed in vacuo and the crude product is purified to obtain the title compound.

Part C Preparation of Contrast Agent Composition

The 1-(1,2-Dipalmitoyl-sn-glycero-3-phosphoethanolamino)-12-((ω-amino-PEG$_{3400}$-α-carbonyl)-(2-(6-aminohexanoylamino)-3-((1-(3-(imidazol-2-ylamino)propyl)(1H-indazol-5-yl))carbonyl-amino)propanoic acid))-dodecane-1,12-dione is admixed with three other lipids, 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine in relative amounts of 1 wt. %:6 wt. %:54 wt. %:41 wt. %. An aqueous solution of this lipid admixture (1 mg/mL), sodium chloride (7 mg/mL), glycerin (0.1 mL/mL), propylene glycol (0.1 mL/mL), at pH 6–7 is then prepared in a 2 cc glass vial. The air in the vial is evacuated and replaced with perfluoropropane and the vial is sealed. The ultrasound contrast agent composition is completed by agitating the sealed vial in a dental amalgamator for 30–45 sec. to form a milky white solution.

Example 33

Part A. Preparation of (ω-amino-PEG$_{3400}$-α-carbonyl)-Glu-(2-(6-aminohexanoylamino)-3-((1-(3-(imidazol-2-ylamino)-propyl)(1H-indazol-5-yl))carbonyl-amino)propanoic acid)$_2$

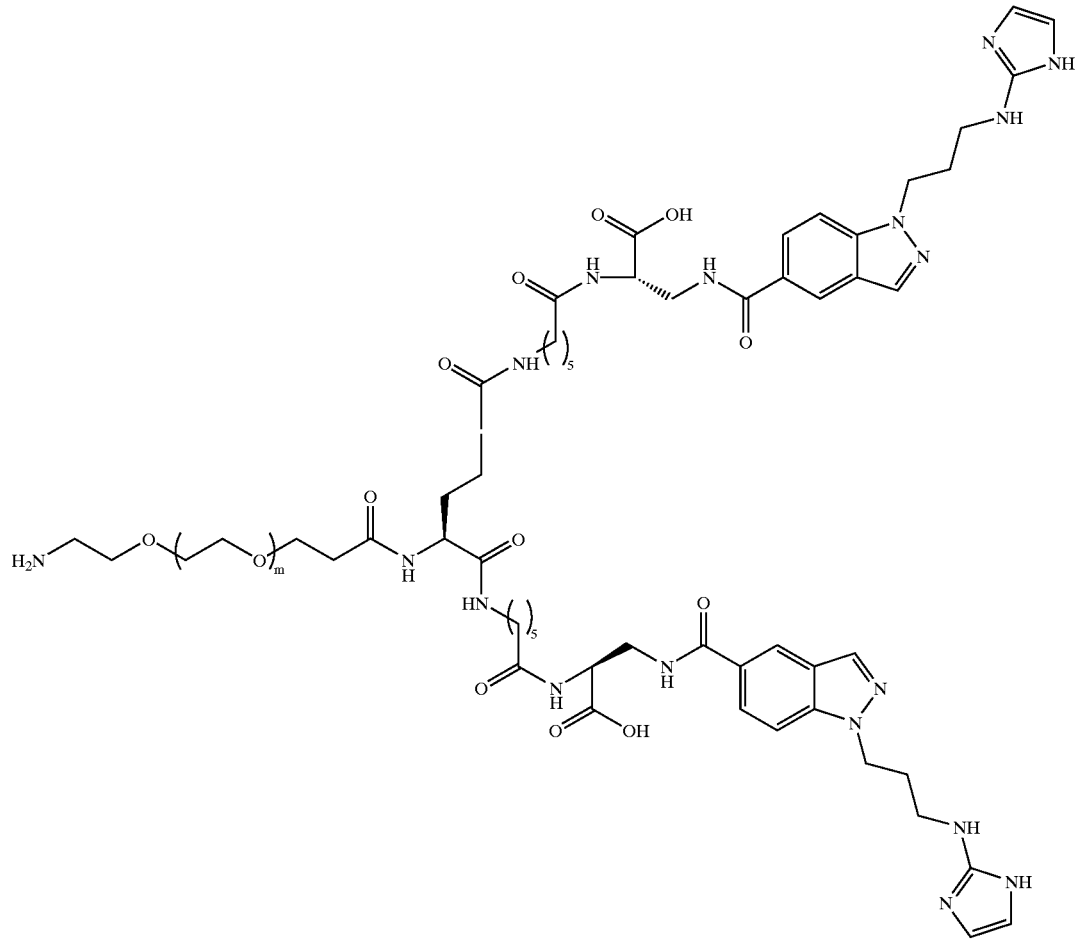

To a solution of N-Boc-ω-amino-PEG$_{3400}$-α-carboxylate sucinimidyl ester (1 mmol) and Glu-(2-(6-aminohexanoylamino)-3-((1-(3-(imidazol-2-ylamino)propyl)(1H-indazol-5-yl))carbonyl-amino)propanoic acid)$_2$ (1 mmol) in DMF (25 mL) is added triethylamine (3 mmol). The reaction mixture is stirred under nitrogen at room temperature overnight and the solvent is removed in vacuo. The crude product is dissolved in 50% trifluoroacetic acid/dichloromethane and is stirred for 4 h. The volatiles are removed and the title compound is isolated as the TFA salt via trituration in diethyl ether.

Part B. Preparation of 1-(1,2-Dipalmitoyl-sn-glycero-3-phosphoethanolamino)-12-(ω-amino-PEG$_{3400}$-α-carbonyl)-(Glu-(2-(6-aminohexanoylamino)-3-((1-(3-(imidazol-2-ylamino)propyl)(1H-indazol-5-yl))carbonyl-amino)propanoic acid)$_2$))-dodecane-1,12-dione A solution of disuccinimidyl dodecane-1,12-dioate (1 mmol), 1,2-dipalmitoyl-sn-glycero-3-phosphoethanolamine or DPPE (1 mmol) and (□-amino-PEG$_{3400}$-□-carbonyl)-Glu-(2-(6-aminohexanoylamino)-3-((1-(3-(imidazol-2- ylamino)propyl)(1H-indazol-5-yl))carbonyl-amino) propanoic acid)$_2$ TFA salt (1 mmol) in 25 ml chloroform is stirred for 5 min. Sodium carbonate (1 mmol) and sodium sulfate (1 mmol) are added and the solution is stirred at room temperature under nitrogen for 18 h. DMF is removed in vacuo and the crude product is purified to obtain the title compound.

Part C Preparation of Contrast Agent Composition

The 1-(1,2-Dipalmitoyl-sn-glycero-3-phosphoethanolamino)-12-((ω-amino-PEG$_{3400}$-α-carbonyl)-(Glu-(2-(6-aminohexanoylamino)-3-((1-(3-(imidazol-2-ylamino)propyl)(1H-indazol-5-yl))carbonyl-amino)propanoic acid)$_2$))-dodecane-1,12-dione is admixed with three other lipids, 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine in relative amounts of 1 wt. %:6 wt. %:54 wt. %:41 wt. %. An aqueous solution of this lipid admixture (1 mg/mL), sodium chloride (7 mg/mL), glycerin (0.1 mL/mL), propylene glycol (0.1 mL/mL), at pH 6–7 is then prepared in a 2 cc glass vial. The air in the vial is evacuated and replaced with perfluoropropane and the vial is sealed. The ultrasound contrast agent composition is completed by agitating the sealed vial in a dental amalgamator for 30–45 sec. to form a milky white solution.

Example 34

Synthesis of 2-({[4-(3-{N-[2-((2R)-3-Sulfo-2-{2-[1,4,7,10-tetraaza-4,7,10-tris(carboxymethyl)cyclododecyl]acetylamino}propyl)ethyl]carbamoyl}propoxy)-2,6-dimethylphenyl]sulfonyl}amino)(2S)-3-({1-[3-(imidazol-2-ylamino)propyl](1H-indazol-5-yl)}carbonylamino)propanoic Acid Bis(trifluoroacetate) Salt

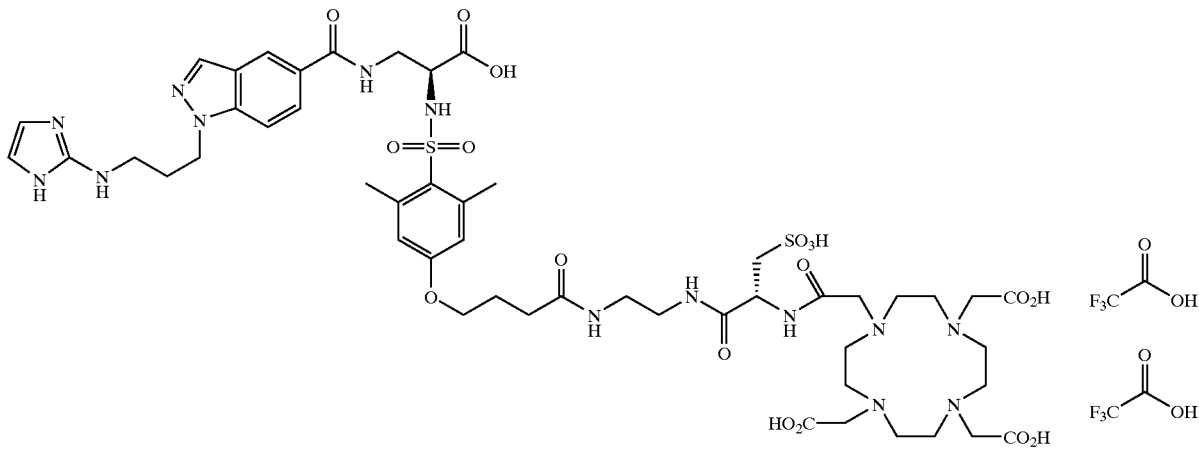

Part A—Preparation of Methyl (2S)-3-[(tert-Butoxy)carbonylamino]-2-[({2,6-dimethyl-4-[3-(N-{2-[(phenylmethoxy)carbonylamino]ethyl}carbamoyl)propoxy]phenyl}sulfonyl)amino]propanoate

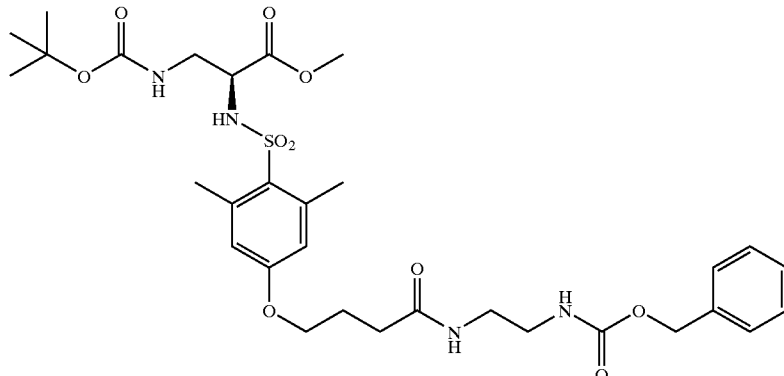

A solution of the product from Example 13, Part D (369 mg, 0.756 mmol), DIEA (0.52 mL, 3.0 mmol), and HBTU (315 mg, 0.832 mmol) in anhydrous DMF (14 mL) was stirred at ambient temperatures under nitrogen for 5 min, and treated with benzyl N-(2-aminoethyl)carbamate hydrochloride (192 mg, 0.832 mmol), and stirred an additional 1 h. The DMF was removed under vacuum, and the oily residue was taken up in EtOAc (150 mL), washed consecutively with 0.1 N HCl (40 mL), water (40 mL), and saturated NaCl (40 mL), dried (MgSO$_4$), and concentrated to give a colorless viscous oil. Flash chromatography on a 3×16 cm silica gel column (EtOAc) gave the title compound as a colorless viscous oil (450 mg, 89.6%). $^1$H NMR (CDCl$_3$): δ 7.34–7.27 (m, 5H), 6.58 (s, 2H), 6.31 (bs, 1H), 5.86 (bs, 1H), 5.36 (bs, 1H), 5.14–5.03 (m, 3H), 3.96 (t, J=6.0 Hz, 2H), 3.88–3.83 (m, 1H), 3.56 (s, 3H), 3.47–3.25 (m, 6H), 2.59 (s, 6H), 2.31 (t, J=6.9 Hz, 2H), 2.05 (p, J=6.6 Hz, 2H), 1.39 (s, 9H); $^{13}$C NMR (CDCl$_3$): δ 172.9, 170.5, 160.6, 157.3, 155.9, 141.8, 136.3, 128.5, 128.2, 128.0, 116.6, 79.9, 66.9, 55.5, 52.8, 43.1, 40.9, 40.3, 32.4, 28.2, 24.9, 23.3; MS: m/e 665.4 [M+H]; 687.3 [M+Na]; High Resolution MS: Calcd for C$_{31}$H$_{45}$N$_4$O$_{10}$S [M+H]: 665.2856, Found: 665.2883.

Part B—Preparation of Methyl (2S)-3-Amino-2-[({2,6-dimethyl-4-[3-(N-{2-[(phenylmethoxy)carbonylamino]ethyl}carbamoyl)propoxy]phenyl}sulfonyl)amino]propanoate Trifluoroacetate Salt

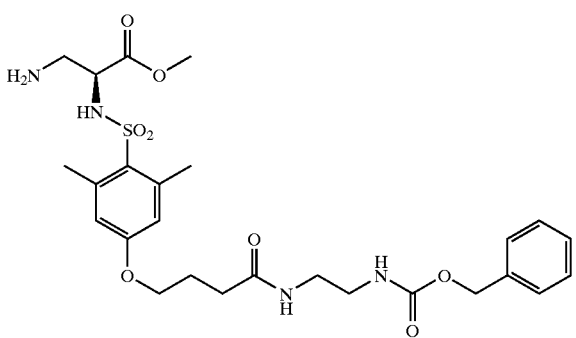

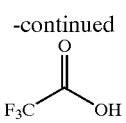

The product of Part A, above (420 mg, 0.632 mmol) was dissolved in 25/75 DCM/TFA (20 mL) and allowed to stand at ambient temperatures under nitrogen for 10 min. The solution was concentrated, and the resulting viscous oil was dissolved in 50% ACN and lyophilized to give the title compound as a colorless solid (437 mg, 102%). MS: m/e 565.3 [M+H].

Part C—Preparation of Methyl (2S)-2-[({2,6-Dimethyl-4-[3-(N-{2-[(phenylmethoxy)carbonylamino]ethyl}carbamoyl)propoxy]phenyl}sulfonyl)amino]-3-{[1-(3-{[1-(triphenylmethyl)imidazol-2-yl]amino}propyl)(1H-indazol-5-yl)]carbonylamino}propanoate

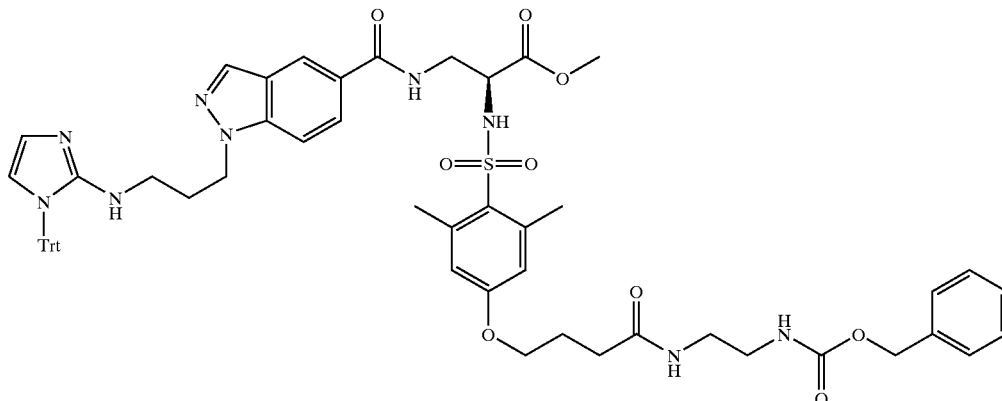

A solution of 1-(3-((1-(triphenylmethyl)imidazol-2-yl)amino)propyl)-1H-indazole-5-carboxylic acid (100 mg, 0.190 mmol), DIEA (0.099 mL, 0.57 mmol), and HBTU (91 mg, 0.24 mmol) in anhydrous DMF (2.0 mL) was stirred at ambient temperatures under nitrogen for 5 min, treated with the product of Step B, above (142 mg, 0.21 mmol) and additional DIEA (0.033 mL, 0.19 mmol), and stirred an additional 1 h. The DMF was removed under vacuum and the amber oil was purified by HPLC on a Vydac C-18 column (22×250 mm) using a 1.65%/min gradient of 18 to 67.5% ACN containing 0.1% TFA at a flow rate of 20 mL/min. The main product peak eluting at 23.2 min was lyophilized to give the title compound as a colorless powder (194 mg, 95.1%). $^1$H NMR(CDCl$_3$+D2O): δ 8.11 (s, 1H), 7.71 (s, 1H), 7.66 (d, J=8.75 Hz, 1H), 7.42–7.24 (m, 16H), 7.17–7.13 (m, 6H), 6.93 (d, J=2.81Hz, 1H), 6.52–6.47(m, 2H), 5.04 (s, 2H), 4.07–4.00 (mn, 3H), 3.93–3.78 (m, 3H), 3.69–3.64 (m, 4H), 3.37–3.27 (m, 4H), 3.14 (t, J=6.88 Hz, 2H), 2.57 (s, 6H), 2.29 (t, J=7.18), 2.01 (pentet, J=6.66, 2H), 1.73 (pentet, J=6.59, 2H); MS: m/e 1074.4 [M+H], 537.9 [M+2H]; High Resolution MS: Calcd for C$_{59}$H$_{64}$N$_9$O$_9$S [M+H]: 1074.4548; found: 1074.452.

Part D—Preparation of (2S)-2-{[(4-{3-[N-(2-Aminoethyl)carbamoyl]propoxy}-2,6-dimethylphenyl)sulfonyl]amino}-3-({1-[3-(imidazol-2-ylamino)propyl](1H-indazol-5-yl)}carbonylamino)propanoic Acid

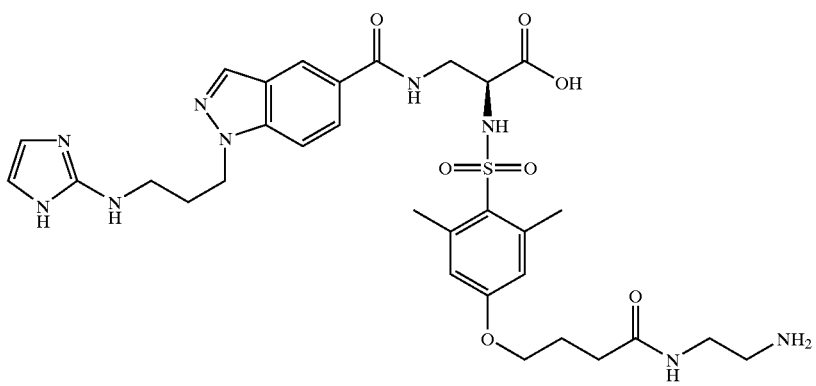

The product of Part C, above (194 mg, 0.180 mmol) was dissolved in peroxide-free THF (8.0 mL) and water (1.2 mL), and treated with 3 N LiOH (0.80 mL). The resulting mixture was stirred at ambient temperatures under nitrogen for 2 h. The THF was removed under vacuum and the resulting mixture was partitioned between water (25 mL) and CHCl₃ (25 mL). The aqueous layer was adjusted to pH 3 with 0.1 N HCl (22 mL) and extracted with additional CHCl₃ (2×25 mL). The combined CHCl₃ extracts were washed with saturated NaCl (25 mL), dried (MgSO₄), and concentrated to give the intermediate carboxylic acid as a colorless amorphous solid (171 mg). MS: m/e 1060.4 [M+H], 531.0 [M+2H].

The solid was dissolved in a solution of TFA (8.0 mL) and Et₃SiH (0.40 mL), and heated at 70° C. under nitrogen for 2 h. The solution was concentrated under vacuum and the resulting oily solid was partitioned between ether (20 mL) and water (20 mL). The aqueous layer was washed with a second portion of ether (20 mL). The combined ether washings were back-extracted with water (20 mL). The combined aqueous layers were lyophilized to give the title compound as a colorless solid (139 mg, 84.8%). MS: m/e 684.3 [M+H], 343.0 [M+2H].

Part E—Preparation of 2-{[(4-{3-[N-(2-{(2R)-2-[(tert-Butoxy)carbonylamino]-3-sulfopropyl}ethyl)carbamoyl]propoxy}-2,6-dimethylphenyl)sulfonyl]amino}(2S)-3-({1-[3-(imidazol-2-ylamino)propyl](1H-indazol-5-yl)}carbonylamino)propanoic Acid A solution of the product of Part D, above (91 mg, 0.10 mmol), the N-hydroxysuccinimide ester of Boc-L-cysteic acid (103 mg, 0.25 mmol), and DIEA (0.104 mL, 0.60 mmol) in anhydrous DMF (5.0 mL) was stirred at ambient temperatures under nitrogen for 19 h. The DMF was removed under vacuum and the resulting amber oil was purified by HPLC on a Vydac C-18 column (22×250 mm) using a 0.72%/min gradient of 0 to 36% ACN containing 0.1% TFA at a flow rate of 80 mu/min. The main product peak eluting at 40.0 min was lyophilized to give the title compound as a colorless fluffy solid (69 mg, 74.0%). MS: m/e 935.3 [M+H].

Part F—Preparation of 2-({[4-(3-{N-[2-((2R)-2-Amnino-3-sulfopropyl)ethyl]carbamoyl}propoxy)-2,6-dimethylphenyl]sulfonyl}amino)(2S)-3-({1-[3-(imidazol-2-ylamino)propyl](1H-indazol-5-yl)}carbonylamino)propanoic Acid Trifluoroacetate Salt

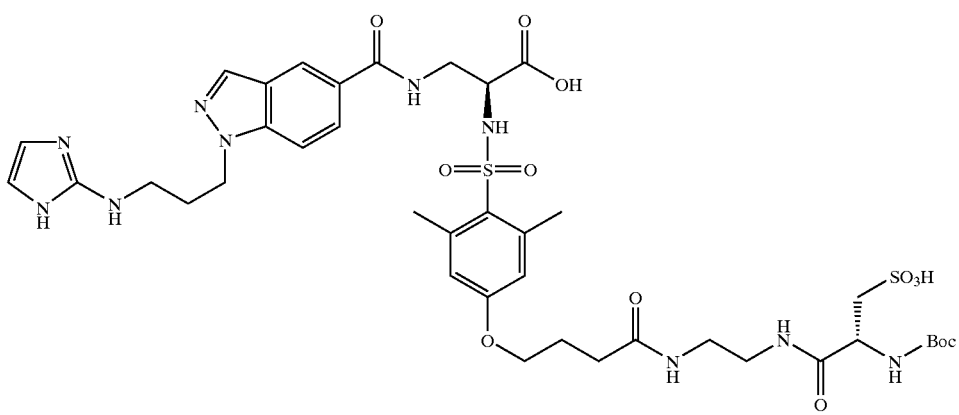

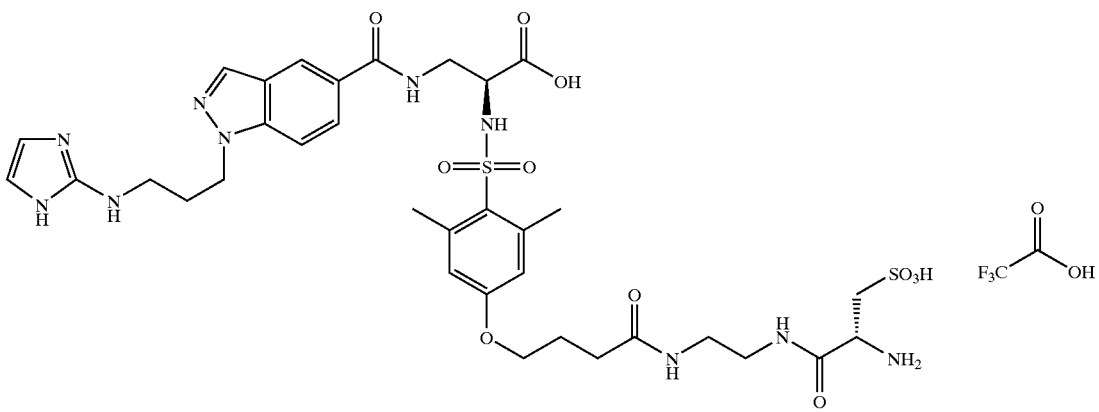

A solution of the product of Part E, above (130 mg, 0.139 mmol) in 50/50 TFA/DCM (16.0 mL) and allowed to stand at ambient temperatures under nitrogen for 10 min. The solution was concentrated under vacuum, and the resulting oily solid was purified by HPLC on a Vydac C-18 column (50×250 mm) using a 0.90%/min gradient of 0 to 27% ACN containing 0.1% TFA at a flow rate of 80 mL/min. The main product peak eluting at 22.6 min was lyophilized to give the title compound as a colorless solid (117 mg, 88.8%). $^1$H NMR (D$_2$O): □ 8.09 (s, 1H), 7.75 (s (unresolved X portion of ABX system) 1H), 7.39 (B portion of ABX system, Jab=8.9 Hz, Jbx=1.6 Hz, 1H), 7.34 (A portion of ABX system, Jab=8.9 Hz, 1H), 6.50 (s, 2H), 6.02 (s, 1H), 4.46 (t, J=6.3 Hz, 2H), 4.31 (X' portion of A'B'X' system, Ja'x'=7.8 Hz, J'x'=4.9 Hz, 1H), 4.16 (X portion of AMX system, Jax=10.9 Hz, Jmx=3.8 Hz, 1H), 3.70 (M portion of AMX system, Jam=14.1Hz, Jmx=3.8 Hz, 1H), 3.39–3.15 (m, 9H), 3.03 (t, J=6.3 Hz, 2H), 2.34 (s, 6H), 2.14 (pentet, J=6.3 Hz, 2H), 2.07 (t, J=7.4 Hz, 2H), 1.58 (pentet, J=7.4 Hz, 2H); MS: m/e 835.2 [M+H]; 857.3 [M+Na]; High Resolution MS: Calcd for C$_{34}$H$_{47}$N$_{10}$O$_{11}$S$_2$ [M+H]: 835.2867, found: 835.2888.

Part G—Preparation of 2-{[(4-{3-[N-(2-{(2R)-3-Sulfo-2-[2-(1,4,7,10-tetraaza-4,7,10-tris{[(tert-butyl)oxycarbonyl]methyl}cyclododecyl)acetylamino]propyl}ethyl)carbamoyl]propoxy}-2,6-dimethylphenyl)sulfonyl]amino}

(2S)-3-({1-[3-(imidazol-2-ylamino)propyl](1H-indazol-5-yl)}carbonylamino)propanoic Acid Bis(trifluoroacetate) Salt

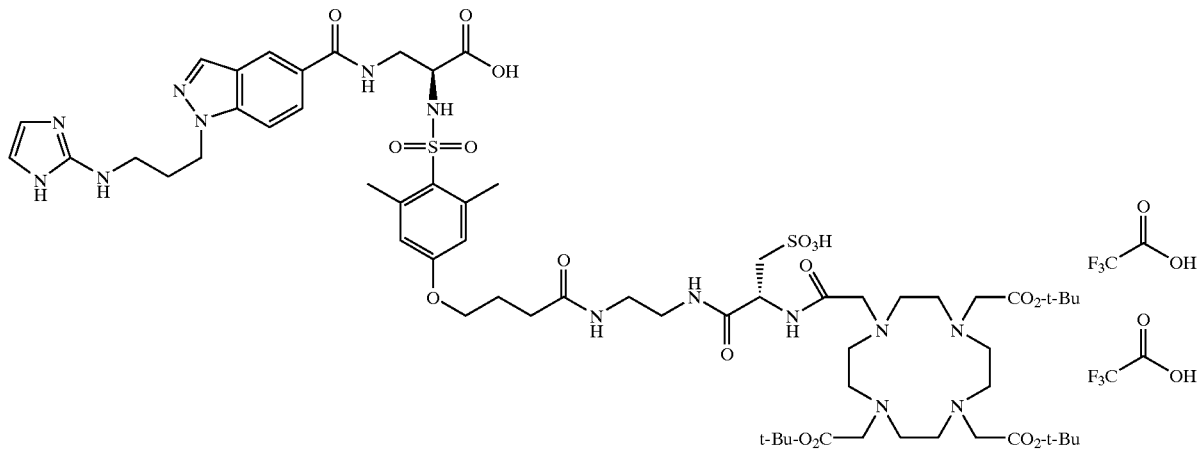

A solution of the product of Example 4, Part B (73.1 mg, 0.080 mmol), DIEA (0.083 mL, 0.480 mmol), and HBTU (22.7 mg, 0.060 mmol) in anhydrous DMF (4.0 mL) was stirred under nitrogen at ambient temperatures for 15 min and treated with the product of Part F, above (37.9 mg, 0.040 mmmol). The DMF was removed under vacuum after 4.5 h and the resulting amber oil was purified by HPLC in two steps. An initial HPLC purification was carried out on a Vydac C-18 column (22×250 mm) using a 0.9%/min gradient of 9 to 45% ACN containing 0.1% TFA at a flow rate of 20 mL/min. The main product peak eluting at 26.4 min was lyophilized to give a colorless solid. Final purification was accomplished on a Zorbax C-18 column (21.2×250 mm) under isocratic conditions using 33.3% ACN containing 0.1% TFA at a flow rate of 20 mL/min. The main product peak eluting at 5.2 min was lyophilized to give the title compound as a colorless fluffy solid (34.0 mg, 20.5%). MS: m/e 1389.6 [M+H]; High Resolution MS: Calcd for C$_{62}$H$_{97}$N$_{14}$O$_{18}$S$_2$ [M+H]: 1389.6547, Found: 1389.655.

Part H—Preparation of 2-({[4-(3-{N-[2-((2R)-3-Sulfo-2-{2-[1,4,7,10-tetraaza-4,7,10-tris(carboxymethyl)cyclododecyl]acetylamino}propyl)ethyl]carbamoyl}propoxy)-2,6-dimethylphenyl]sulfonyl}amino) (2S)-3-({1-[3-(imidazol-2-ylamino)propyl](1H-indazol-5-yl)}carbonylamino)propanoic Acid Bis(trifluoroacetate) Salt The product of Step G, above (32.0 mg, 0.0174 mmol) was dissolved in a solution of TFA (4.0 mL) and Et$_3$SiH (0.20 mL), and heated at 50° C. under nitrogen for 30 min. The solution was concentrated and the residue was purified by HPLC on a Zorbax C-18 column (21.2×250 mm) using a 0.90%/min gradient of 0 to 27% ACN containing 0.1% TFA at a flow rate of 20 mL/min. The main product peak eluting at 23.5 min was lyophilized to give the title compound as a colorless fluffy solid (22.2 mg, 88.1%). MS: m/e 1221.4 [M+H]; High Resolution MS: Calcd for C$_{50}$H$_{73}$N$_{14}$O$_{18}$S$_2$ [M+H]: 1221.4669, Found: 1221.469.

Example 35

Synthesis of DOTA/2-{[(4-{3-[N-(2-{(2R)-2-[4-(N-{(1R)-1-[N-(2-{4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]-2-sulfoethyl}carbamoyl)(4S)-4-amino-butanoylamino]-3-sulfopropyl}ethyl)carbamoyl]propoxy}-2,6-dimethylphenyl)sulfonyl]amino}2S)-3-({1-[3-(imidazol-2-ylamino)propyl](1H-indazol-5-yl)}carbonylamino)propanoic Acid Bis (trifluoroacetate) Conjugate Part A—Preparation of Di-2,3,5,6-tetrafluorophenyl (2S)-2-[(tert-Butoxy)carbonylamino]pentane-1,5-dioate

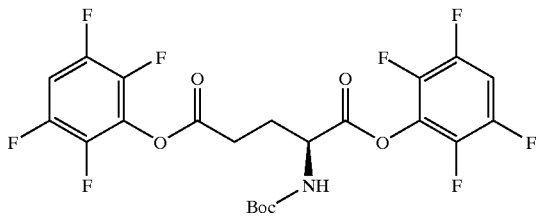

To a solution of Boc-L-Glu-OH (28.9 g, 117 mmol) in DMF (500 mL) at ambient temperatures and under nitrogen, was added a solution of 2,3,5,6-tetrafluorophenol (48.2 g, 290 mmol) in DMF (50 mL). After stirring for 10 min, EDC (55.6 g, 290 mmol) was added and the mixture was stirred for 96 h. The volatiles were removed under vacuum and the residue was triturated with 0.1 N HCl (750 mL). To this mixture was added EtOAc (600 mL) and the layers were separated. The aqueous layer was extracted with EtOAc (3×500 mL), and all EtOAc extracts were combined, washed consecutively with water (300 mL) and saturated NaCl (300 mL), dried (MgSO$_3$), and concentrated to give a tan solid (62 g). The tan solid was washed with ACN to give the title compound (45.5 g, 73.0%) in purified form. MS: m/e 566.0 [M+Na].

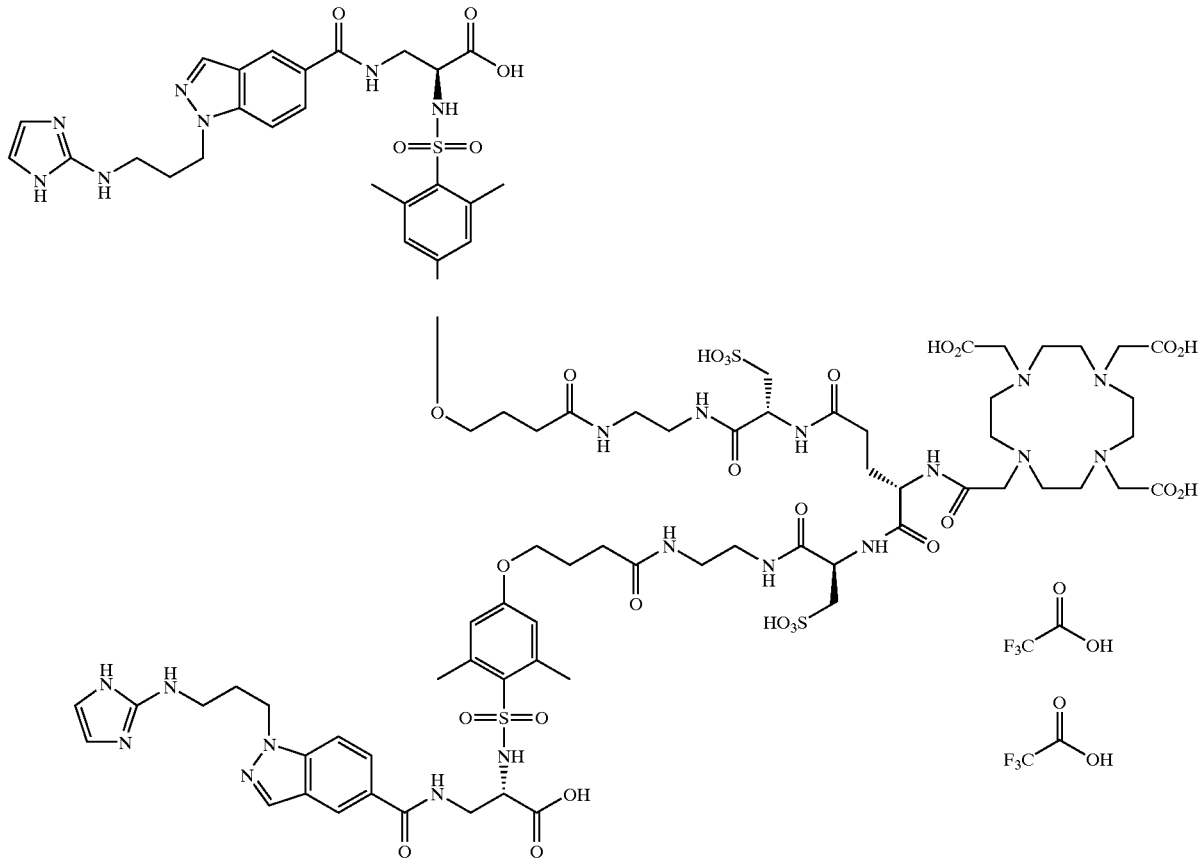

Part B—Preparation of 2-{[(4-{3-[N-(2-{(2R)-2-[4-(N-{(1R)-1-[N-(2-{4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]-2-sulfoethyl}carbamoyl)(4S)-4-[(tert-butoxy)carbonylamino]butanoylamino]-3-sulfopropyl}ethyl)carbamoyl]propoxy}-2,6-dimethylphenyl)sulfonyl]amino}2S)-3-{1-[3-(imidazol-2-ylamino)propyl](1H-indazol-5-yl)}carbonylamino)propanoic Acid

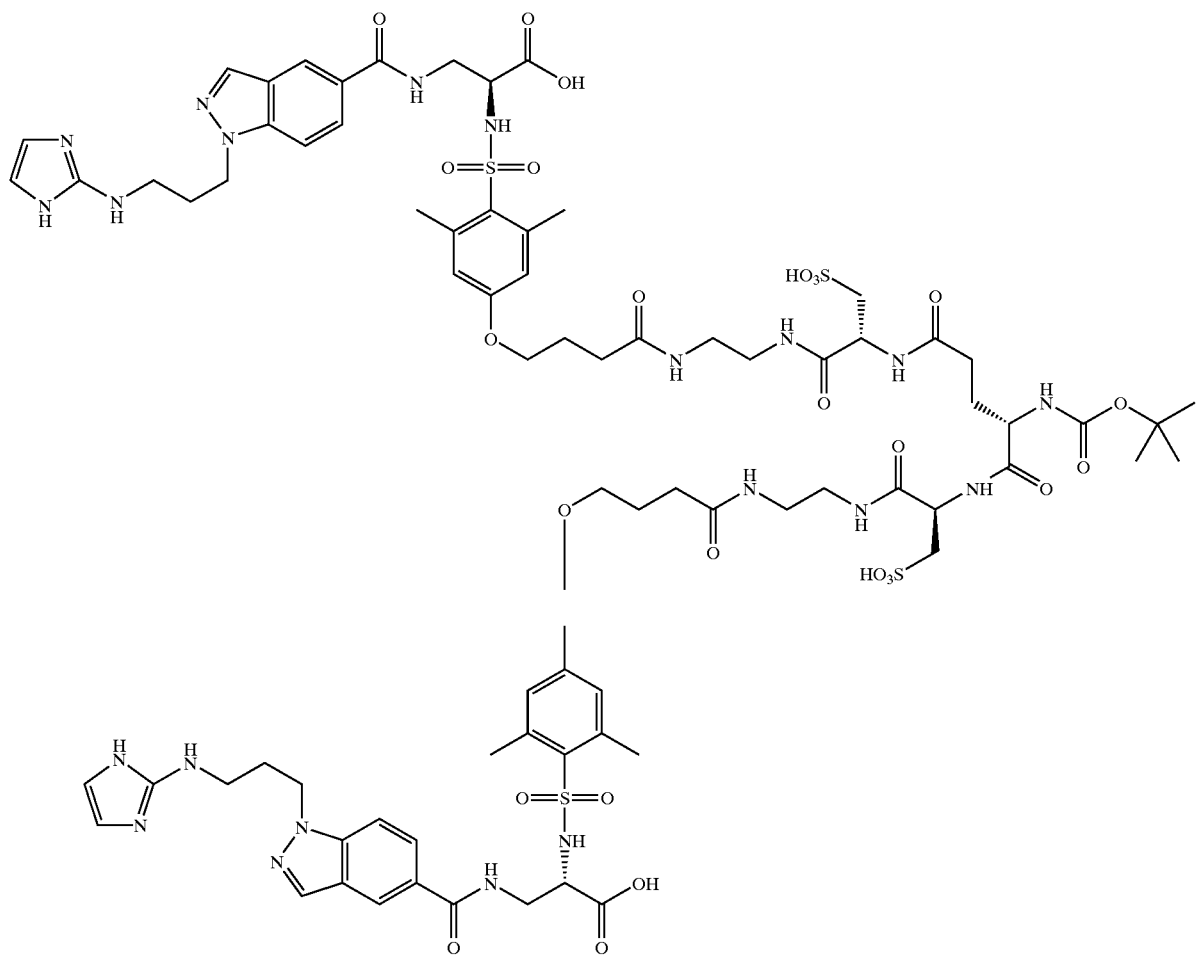

A solution of the product of Example 34, Part F (43.5 mg, 0.0459 mmol), the product of Part A, above (10.8 mg, 0.020 mmol), and DIEA 0.015 mL, 0.084 mmol) in anhydrous DMF (1.0 mL) was stirred at ambient temperatures under nitrogen for 23 h. The DMF was removed under vacuum and the resulting amber oil was purified by HPLC on a Vydac C-18 column (22×250 mm) using a 0.90%/min gradient of 9 to 45% ACN containing 0.1% TFA at a flow rate of 20 mL/min. The main product peak eluting at 20.9 min was lyophilized to give the title compound as a colorless fluffy solid (22.0 mg, 55.7%). MS: m/e 1880.7 [M+H], 941.4 [M+2H]; High Resolution MS: Calcd for $C_{78}H_{106}N_{21}O_{26}S_4$ [M+H]: 1880.6501; found: 1880.6530.

Part C—Preparation of 2-{[(4-{3-[N-(2-{(2R)-2-[4-(N-{(1R)-1-[N-(2-{4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]-2-sulfoethyl}carbamoyl)(4S)-4-amino-butanoylamino]-3-sulfopropyl}ethyl)carbamoyl]propoxy)-2,6-dimethylphenyl)sulfonyl]amino}2S)-3-({1-[3-(imidazol-2-ylamino)propyl](1H-indazol-5-yl)}carbonylamino)propanoic Acid

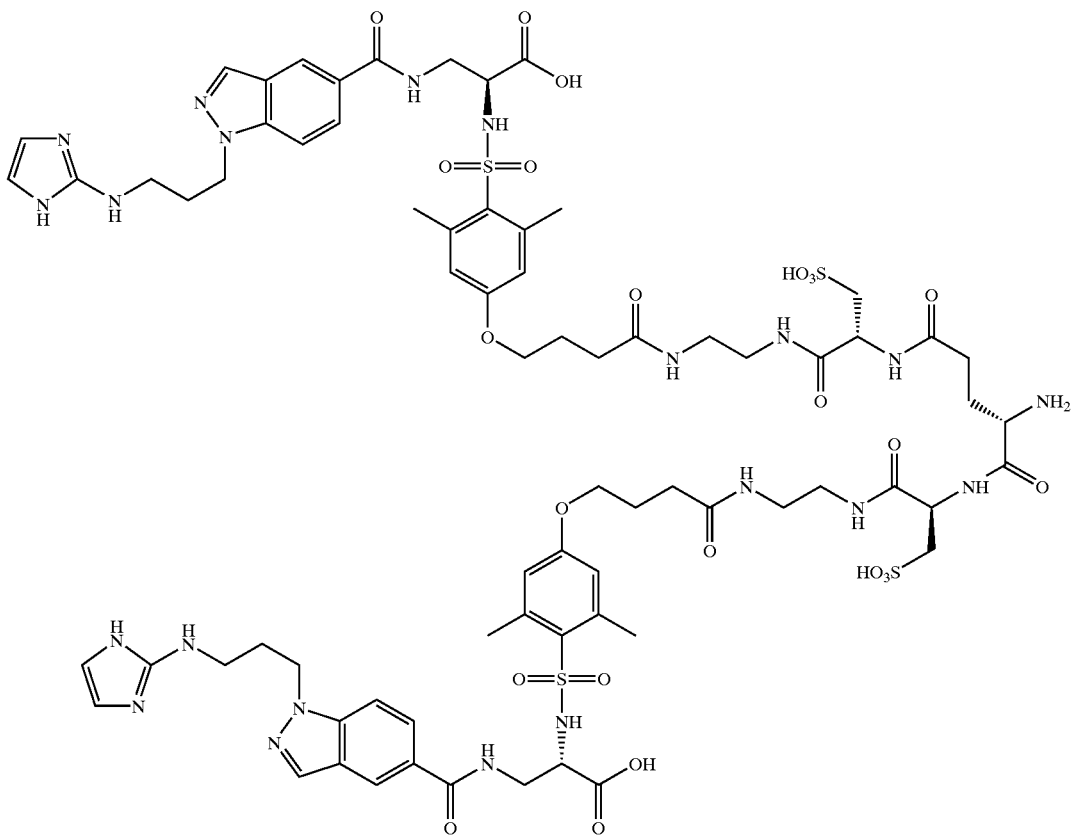

A solution of the product of Part B, above (22.0 mg, 0.0117 mmol) in 50/50 TFA/DCM (8.0 mL) was allowed to react at ambient temperatures under nitrogen for 10 min and concentrated to a pale amber oil. The oil was dissolved in 50% ACN (20 mL) and lyophilized to give the title compound as a colorless fluffy solid (21.2 mg, 95.6%). MS: m/e 1781.7 [M+H], 891.0 [M+2H], 594.4 [M+3H]; High Resolution MS: Calcd for $C_{73}H_{98}N_{21}O_{24}S_4$ [M+H]: 1780.5976; found: 1780.598.

Part D Preparation of DOTA Tris-t-butyl Ester/2-{[(4-{3-[N-(2-{(2R)-2-[4-(N-{(1R)-1-[N-(2-{[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}-ethyl)carbamoyl]-2-sulfoethyl}carbamoyl)(4S)-4-aminobutanoylamino]-3-sulfopropyl}ethyl)carbamoyl]propoxy}-2,6-dimethylphenyl)sulfonyl]amino}2S)-3-({1-[3-(imidazol-2-ylamino)propyl](1H-indazol-5-yl)}carbonylamino)propanoic Acid Bis(trifluoroacetate) Salt Conjugate

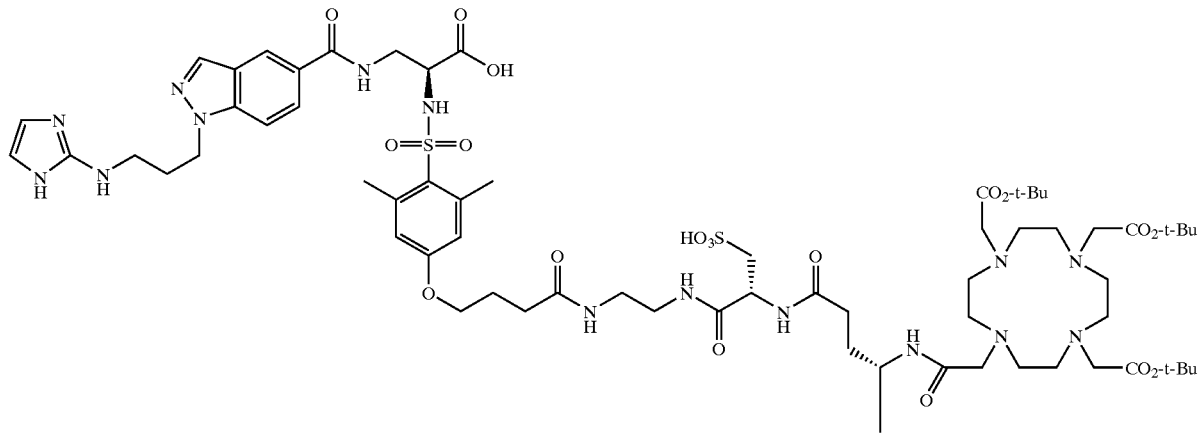

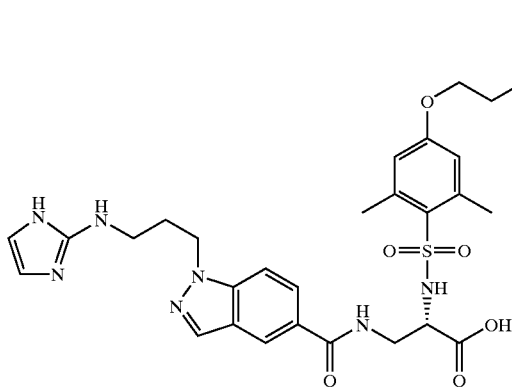

A solution of the product of Example 4, Part B (21.4 mg, 0.0234 mmol), DIEA (0.024 mL, 0.14 mmol), and HBTU (6.6 mg, 0.0176 mmol) in anhydrous DMF (1.0 mL) was stirred under nitrogen at ambient temperatures for 15 min and treated with the product of Part C, above 21.0 mg, 0.0111 mmol). After 23 h the solution was diluted with EtOH (5.0 mL) and water (3.0 mL) and treated with 0.5 N NaOH (0.30 mL). After 30 min the solution was adjusted to pH 3 with 1 N HCl (0.20 mL). The solution was diluted with water (135 mL) and the resulting solution was purified directly by HPLC on a Vydac C-18 column (22×250 mm) using a 0.90%/min gradient of 9 to 45% ACN containing 0.1% TFA at a flow rate of 20 mL/min. The main product peak eluting at 27.0 min was lyophilized to give the title compound as a colorless fluffy solid (11.5 mg, 37.1%). MS: m/e 1168.1 [M+2H], 779.3 [M+3H]; High Resolution MS: Calcd for $C_{101}H_{148}N_{25}O_{31}S_4$ [M+H]: 2334.9656, found: 2334.967.

Part E—Preparation of DOTA/2-{[(4-{3-[N-2-{(2R)-2-[4-(N-{(1R)-1-[N-(2-{4-[4-({[(1S)-1-carboxy-2-({1-[3-(imidazol-2-ylamino)propyl](1H-indazol-5-yl)}carbonylamino)ethyl]-amino}sulfonyl)-3,5-dimethylphenoxy]butanoylamino}ethyl)carbamoyl]-2-sulfoethyl}carbamoyl)(4S)-4-aminobutanoylamino]-3-sulfopropyl}ethyl)carbamoyl]propoxy}-2,6-dimethylphenyl)sulfonyl]amino}2S)-3-({1-[3-(imidazol-2-ylamino)propyl](1H-indazol-5-yl)}carbonylamino) propanoic Acid Bis(trifluoroacetate) Conjugate The product of Step D, above (11.5 mg, 0.00449 mmol) was dissolved in a solution of TFA (4.0 mL) and Et$_3$SiH (0.20 mL) and heated at 50° C. under nitrogen for 30 min. The solution was concentrated under vacuum and the residue was purified by HPLC on a Vydac C-18 column (22×250 mm) using a 0.90%/min gradient of 0 to 36% ACN containing 0.1% TFA at a flow rate of 20 mL/min. The main product peak eluting at 27.5 min was lyophilized to give the title compound as a colorless fluffy solid (9.3 mg, 86.5%). MS: m/e 1084.1 [M+2H], 723.1 [M+3H]; High Resolution MS: Calcd for $C_{89}H_{124}N_{25}O_{31}S_4$ [M+H]: 2166.7778; Found: 2166.778.

Example 36

Synthesis of 2-[({4-[4-({[2-((2R)-3-Sulfo-2-{2-[1,4,7,10-tetraaza-4,7,10-tris(carboxymethyl) cyclododecyl]acetylamino}propyl)ethyl]amino}sulfonyl)phenyl]phenyl}-sulfonyl)amino] (2S)-3-({1-[3-(imidazol-2-ylamino)propyl](1H-indazol-5-yl)}carbonylamino)propanoic Acid Bis (trifluoroacetate) Salt

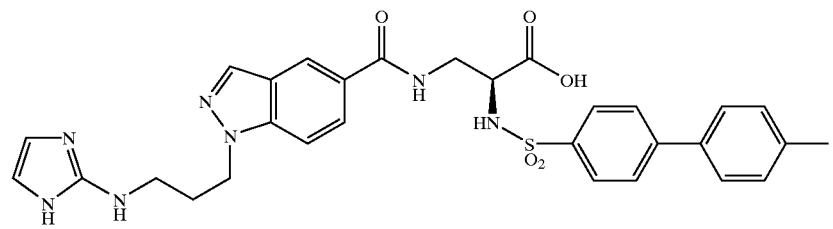

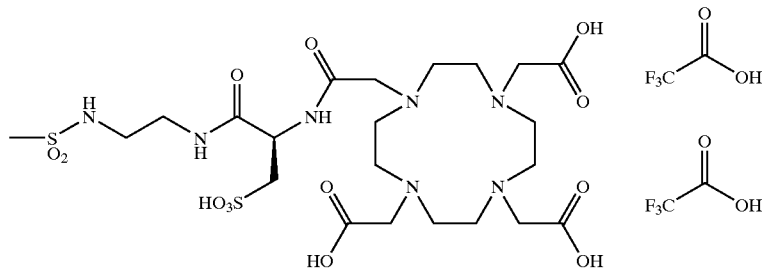

Part A—Preparation of Methyl (2S)-3-[(tert-Butoxy) carbonylamino]-2-{[(4-{4-[({2-[(phenylmethoxy) carbonylamino]ethyl}amino)sulfonyl]phenyl}phenyl) sulfonyl]-amino}propanoate Part B—Preparation of Methyl (2S)-3-Amino-2-{[(4-{4-[({2-[(phenylmethoxy)carbonylamino]ethyl}amino) sulfonyl]phenyl}phenyl)sulfonyl]amino}propanoate Trifluoroacetate Salt

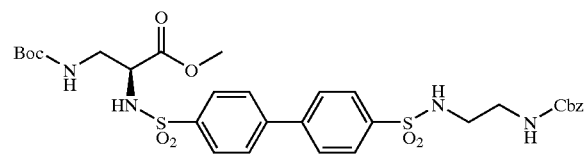

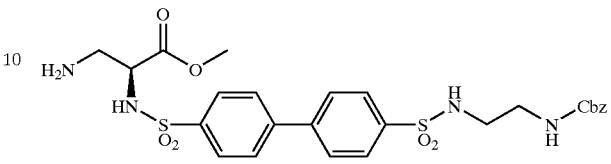

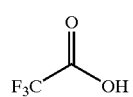

Biphenyl-4,4'-disulfonyl chloride (5.30 g, 15.0 mmol, freshly recrystallized from CHCl₃) and DCM (400 mL) were placed in a 100 mL 3-neck flask fitted with a thermometer, an addition funnel, and a nitrogen line. The addition funnel was charged with a solution of benzyl N-(2-aminoethyl) carbamate hydrochloride (2.30 g, 10.0 mmol) and DIEA (1.80 mL, 10.0 mmol) in DCM (40 mL). The contents of the flask were cooled below 5° C., and the contents of the addition funnel were added to the flask with rapid stirring over 30 min while keeping the temperature of the flask below 5° C. The addition funnel was then charged with a solution of N-β-Boc-L-α,β-diaminopropionic acid methyl ester hydrochloride (5.10 g, 20.0 mmol) and DIEA (7.60 mL, 44.0 mmol) in DCM (40 mL). This solution was added to the flask with stirring at 5° C. over 15 min, and stirred at ambient temperatures for an additional 4 days. The reaction was concentrated and the resulting residue was partitioned between EtOAc (6 L) and 0.1 N HCl (600 mL). The organic solution was washed consecutively with water (3 L), and saturated NaCl (2 L), dried (MgSO₄), and concentrated to give the title compound as a colorless solid (9.60 g). MS: m/e 591.2.

The product of Part A, above (8.80 g) was dissolved in 50/50 TFA/DCM (200 mL) and allowed to react at ambient temperatures under nitrogen for 1 h. The solution was concentrated under vacuum and the resulting viscous orange oil was purified by HPLC on a Vydac C-18 column (50×250 mm) using a 1.58%/min gradient of 0 to 63% ACN containing 0.1% TFA at a flow rate of 80 mL/min. The main product peak eluting at 22.7 min was lyophilized to give the title compound as a colorless solid (3.54 g, 54.9% for two steps from benzyl N-(2-aminoethyl)carbamate hydrochloride). MS: m/e 591.2 [M+H]; High Resolution MS: Calcd for $C_{26}H_{31}N_4O_8S_2$ [M+H]: 591.1583; Found: 591.1585.

Part C—Preparation of Methyl (2S)-2-{[(4-{4-[({2-[(Phenylmethoxy)carbonylamino]ethyl}amino)sulfonyl] phenyl}phenyl)sulfonyl]amino}-3-{[1-(3-{[1-(triphenylmethyl)imidazol-2-yl]amino}propyl)(1H-indazol-5-yl)]carbonylamino}propanoate

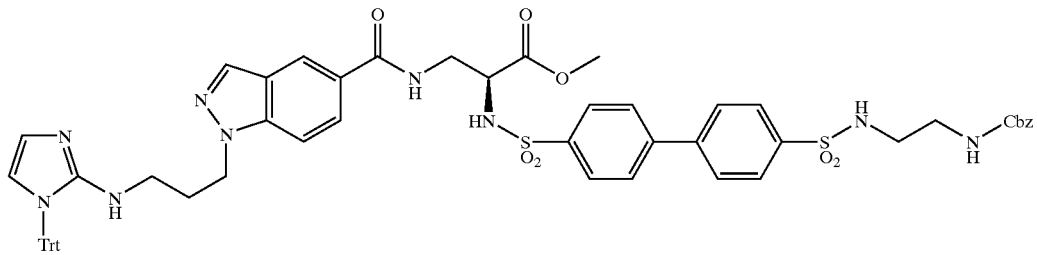

A solution of 1-(3-((1-(triphenylmethyl)imidazol-2-yl) amino)propyl)-1H-indazole-5-carboxylic acid (265 mg, 0.503 mmol), DIEA (0.099 mL, 0.42 mmol), and HBTU (158 mg, 0.417 mmol) in anhydrous DMF (10.2 mL) was stirred at ambient temperatures under nitrogen for 5 min, treated with the product of Step B, above (246 mg, 0.417 mmol), and stirred an additional 1 h. The DMF was removed under vacuum and the amber oil was purified by HPLC on a Vydac C-18 column (50×250 mm) using a 1.8%/min gradient of 18 to 72% ACN containing 0.1% TFA at a flow rate of 80 mL/min. The main product peak eluting at 24.8 min was lyophilized to give a colorless powder. This powder was repurified by HPLC using the same column and gradient conditions. Product fractions were lyophilized to give the title compound as a colorless fluffy powder (245 mg, 53.5%). MS: m/e 1100.3 [M+H]; High Resolution MS: Calcd for $C_{59}H_{57}N_9O_9S_2$ [M+H]: 1100.3799; Found: 1100.380.

Part D—Preparation of Methyl (2S)-2-({[4-(4-{[(2-Aminoethyl)amino]sulfonyl}phenyl)phenyl]sulfonyl}amino)-3-{[1-(3-{[1-(triphenylmethyl)imidazol-2-yl]amino}propyl)(1H-indazol-5-yl)]carbonylamino}propanoate tures under nitrogen for 18 h. Additional Boc-L-cysteic acid p-nitrophenyl ester (50.0 mg, 0.121 mmol) was added and stirring was continued an additional 24 h. The DMF was removed under vacuum and the oily solid residue was purified by HPLC on a Vydac C-18 column (22×250 mm) using a 1.12%/min gradient of 18 to 63% ACN containing 0.1% TFA at a flow rate of 20 mL/min. The main product peak was centered at 32.1 min. The earliest eluting product fractions contained an impurity which was removed by HPLC purification with the same column and flow conditions, but using a 1.0%/min gradient of 18 to 58% ACN containing 0.1% TFA. The main product peak eluted at 32.1 min. The product containing fractions from these two runs were combined and lyophilized to give the title compound as a colorless solid (174 mg, 65.6% from the product of Part C). MS: m/e 1217.3 [M+H], 1117.3 [M+H−Boc].

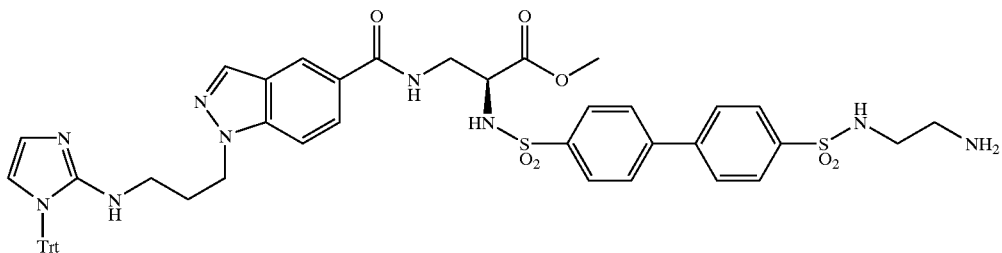

A solution of the product of Part C, above (240 mg, 0.218 mmol) in MeOH (22 mL) was hydrogenolyzed over 10% Pd/C at 55 psi for 3 h. The catalyst was removed by filtration through Celite® and the filtrate was concentrated to give the title compound as a colorless, viscous oil (240 mg). MS: m/e 966.3 [M+H], 724.2 [M+H-trityl].

Part E—Preparation of (2R)-N-[2-({[4-(4-{[((1S)-1-(Methoxycarbonyl)-2-{[1-(3-{[1-(triphenylmethyl)imidazol-2-yl]amino}propyl)(1H-indazol-5-yl)]carbonylamino}ethyl)amino]sulfonyl}phenyl)phenyl]sulfonyl}amino)ethyl]-2-[(tert-butoxy)carbonylamino]propanesulfonic Acid

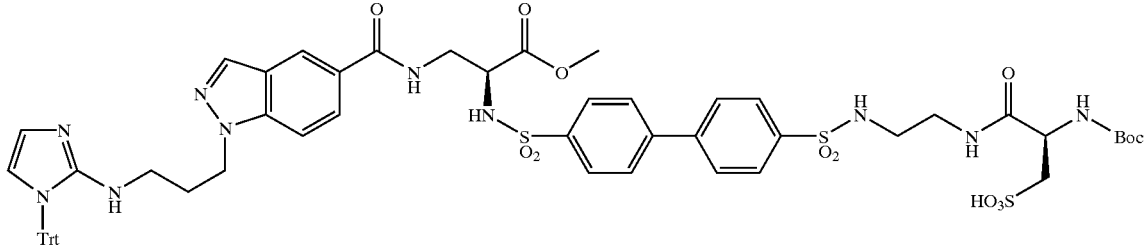

A solution of the product of Part D, above (240 mg) and DIEA (0.166 mL, 0.950 mmol) in anhydrous DMF (4.0 mL) was treated with the p-nitrophenyl ester of Boc-L-cysteic acid (149 mg, 0.362 mmol) and stirred at ambient tempera- Part F—Preparation of 2-[({4-[4-({[2-((2R)-2-Amino-3-sulfopropyl)ethyl]amino}sulfonyl)phenyl]phenyl}sulfonyl)amino](2S)-3-({1-[3-(imidazol-2-ylamino)propyl](1H-indazol-5-yl)}carbonylamino)propanoic Acid Trifluoroacetate Salt (5.3 mg, 0.014 mmol) in anhydrous DMF (1.5 mL) was stirred under nitrogen at ambient temperatures for 10 min and added to a solution of the product of Part F, above (10.0 mg, 0.0116 mmol) and DIEA (0.012 mL, 0.070 mmol) in anhydrous DMF (1.0 mL). The resulting solution was stirred

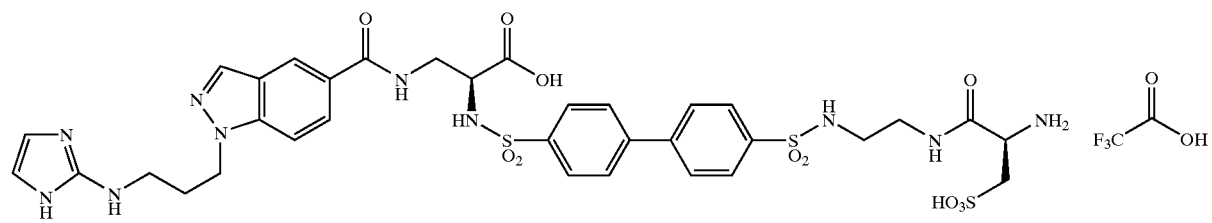

A mixture of the product of Part E, above (21.4 mg, 0.0176 mmol), peroxide-free THF (0.70 mL), water (0.063 mL), and 3 N LiOH (0.043 mL, 0.129 mmol) was stirred at ambient temperatures under nitrogen for 3 h, and concentrated under vacuum to a colorless solid.

The above solid was dissolved in 95/5 TFA/Et$_3$SiH (1.20 mL) and heated at reflux under nitrogen for 1 h. The solution was concentrated under vacuum and the oily solid was purified by HPLC on a Vydac C-18 column (22×250 mm) using a 1.2%/min gradient of 0 to 36% ACN containing 0.1% TFA at a flow rate of 20 mL/min. The main product peak eluting at 19.2 min was lyophilized to give the title compound as a colorless solid (11.0 mg, 64.2%). MS: m/e 861.2 [M+H]; High Resolution MS: Calcd for C$_{34}$H$_{41}$N$_{10}$O$_{11}$S$_3$ [M+H]: 861.21181; Found: 861.2132.

Part G—Preparation of 2-{[(4-{4-[({2-[(2R)-3-Sulfo-2-(2-{1,4,7,10-tetraaza-4,7,10-tris{[(tert-butyl)oxycarbonyl]methyl}cyclododecyl}acetylamino)propyl]ethyl}amino)sulfonyl]phenyl}phenyl)sulfonyl]amino}(2S)-3-({1-[3-(imidazol-2-ylamino)propyl](1H-indazol-5-yl)}carbonylaminopropanoic Acid Bis(trifluoroacetate) Salt at ambient temperatures under nitrogen for 18 h, and concentrated under vacuum. The resulting pale amber oil was purified by HPLC on a Vydac C-18 column (22×250 mm) using a 1.0%/min gradient of 9 to 49% ACN containing 0.1% TFA at a flow rate of 20 mL/min. The main product peak eluting at 30.0 min was lyophilized to give the title compound as a colorless fluffy solid (10.5 mg, 55.1%). MS: m/e 1415.4 [M+H].

Part H—Preparation of 2-[({4-[4-({[2-((2R)-3-Sulfo-2-{2-[1,4,7,10-tetraaza-4,7,10-tris(carboxymethyl)cyclododecyl]acetylamino}propyl)ethyl]amino}sulfonyl)phenyl]phenyl}-sulfonyl)amino](2S)-3-({1-[3-(imidazol-2-ylamino)propyl](1H-indazol-5-yl)}carbonylamino)propanoic Acid Bis(trifluoroacetate) Salt A solution of the product of Part G, above (10.5 mg, 0.00639 mmol) in 95/5 TFA/Et$_3$SiH (1.0 mL) was heated at reflux under nitrogen for 3 h. The solution was concentrated under vacuum and the resulting oily solid was purified by HPLC on a Vydac C-18 column (22×250 mm) using a 0.90%/min gradient of 0 to 27% ACN containing 0.1% TFA at a flow rate of 20 mL/min. The main product peak eluting

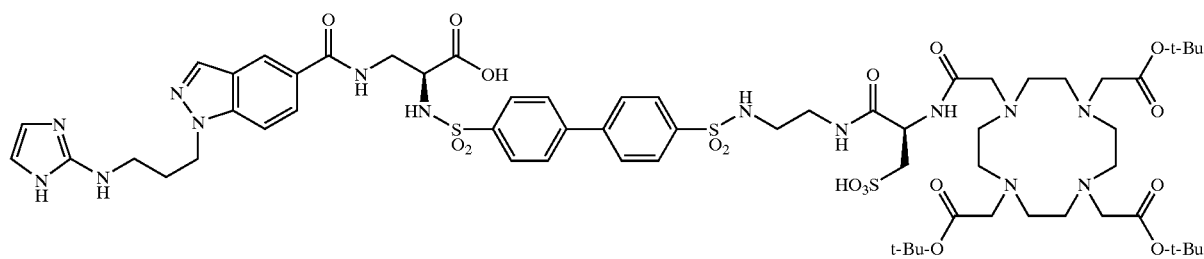

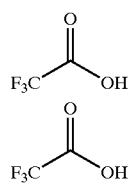

A solution of the product of Example 4, Part B (15.9 mg, 0.0174 mmol), DIEA (0.012 mL, 0.070 mmol), and HBTU at 28.0 min was lyophilized to give the title compound as a colorless fluffy solid (2.3 mg, 24.4%). MS: m/e 1247.3

[M+H]; High Resolution MS: Calcd for $C_{50}H_{67}N_{14}O_{18}S_3$ [M+H]: 1247.3919; Found: 1247.390.

Example 37

Synthesis of (4S)-4-(N-{1-[N-(2-{4-[4-({[(1S)-1-carboxy-2-({1-[3-(2-pyridylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid

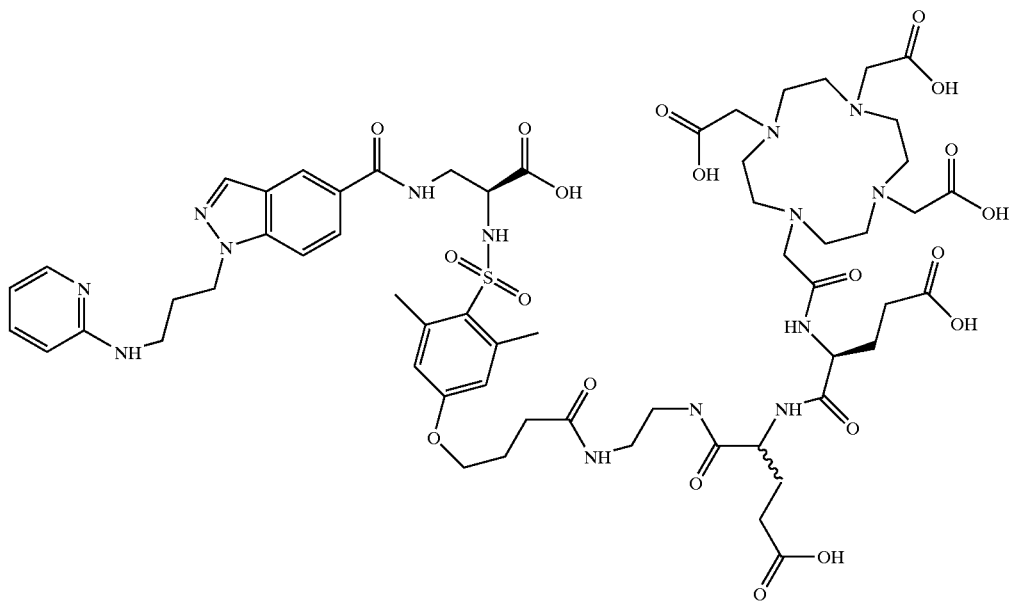

Step A: Synthesis of

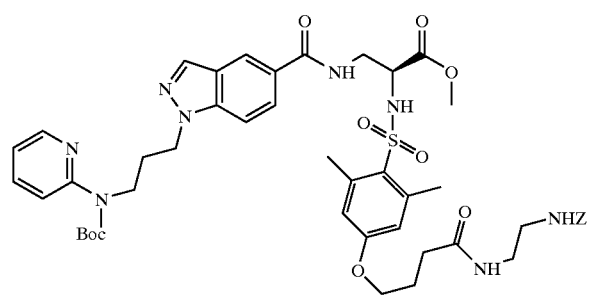

N-Boc-(1-[3-(2-pyridylamino)propyl]-1H-indazole)-5-carboxylic acid (prepared as described in Jadhav et al, U.S. Pat. No. 5,760,028) (217 mg, 0.548 mmol) was added to a solution of methyl (2S)-3-amino-2-[({2,6-dimethyl-4-[3-(N-{2[(phenylmethoxy)carbonylamino]ethyl}carbamoyl)propoxy]phenyl}sulfonyl)amino]propanoate (Prepared as in Example 34, Step B) and HBTU (250 mg, 0.658 mmol) in DMF (10 mL). Diisopropylethylamine (334 µL, 1.12 mmol) was added dropwise. The reaction was stirred for 45 min, the solvents concentrated, and the residue purified by flash chromatography (EtOAc/MeOH, from 0%->6% MEOH). The product fractions were combined and concentrated to afford 526 mg (102%) of the product as a golden oil. LRMS (ES): 943.5 [M+H]$^+$, 843.4 [M−Boc+H]$^+$.

Step B: Synthesis of

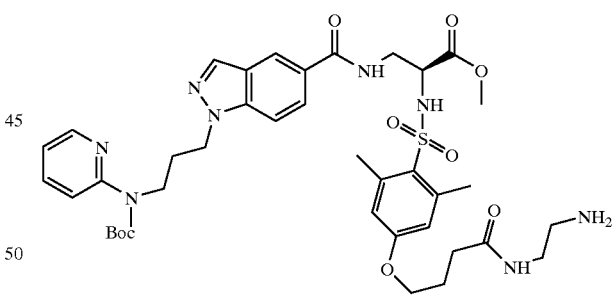

The product of step A (517 mg) in methanol (3 mL) was added to 10% palladium on carbon (200 mg) in methanol (7 mL) under nitrogen in a Parr bottle. It was hydrogenolyzed at 50 psi for 90 min, filtered through Celite, rinsed with methanol, and concentrated to afford a viscous oil. This was redissolved in 1:1 water/acetonitrile containing 0.1% TFA (mL) and lyophilized (1:1 acetontrile/water/0.1% TFA) to afford the product as a white powder (380 mg, 74% yield). LRMS (ES): 809.3 ([M+H]$^+$, 45%) 355.2 (100%). $^1$HNMR (600.1343 MHz, CDCl$_3$): 8.49 (t, 1H), 8.29 (m, 1H), 8.18 (d, 2H), 7.87 (t, 1H), 7.74 (m, 2H), 7.64 (d, 1H), 7.52 (d, 1H), 7.11 (t, 1H), 6.66 (d, 1H), 6.64 (s, 2H), 4.45 (t, 2H), 4.04 (t, 1H), 3.91 (t, 2H), 3.83 (t, 2H), 3.55 (m, 1H), 3.47 (m, 1H), 3.35 (s, 3H), 3.16 (m, under H2O peak, 2H), 2.71 (m, 2H), 2.52 (s, 3H) 2.50 (s, 3H), 2.21 (t, 2H), 2.15 (t, 2H), 1.88 (t, 2H), 1.33, s (9H).

Step C: Synthesis of

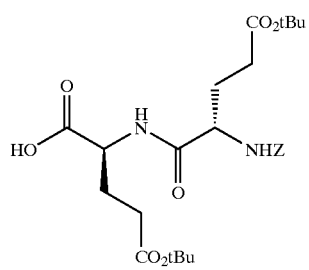

Gamma-tert-butoxy-Z-glutamic acid succinimide ester (2.0 g, 4.75 mmol) was dissolved in dimethylformamide, and gamma-tert-butoxyglutamic acid (0.98 g, 4.8 mmol) was added, followed by diisopropylethylamine (1.75 mL, 10.1 mmol). The solution was stirred 18 hr, concentrated, and the residue partitioned into ethyl acetate/10% citric acid. The aqueous fraction was extracted with ethyl acetate and the combined organics were washed with water, 10% potassium hydrogen sulfate, and brine, and then concentrated. The residual oil was purified by flash chromatography on silica (CH2Cl2/EtOAc/EtOH, 1:1:0.5%) and the product fractions combined and evaporated to yield the product (1.3 g, 53%) as a gummy solid. LRMS (ES): 523.4 [M+H]$^+$, 467.4; $^1$HNMR (600.1330 MHz, CDCl$_3$) 7.30 (m, 6H), 5.80 (d, 1H), 5.09 (m, 2H), 4.53 (m, 1H), 4.29 (m, 1H), 2.36 (m, 4H), 1.88–2.16 (m, 4H), 1.42 (s, 9 H), 1.41 (s, 9H).

Step D: Synthesis of

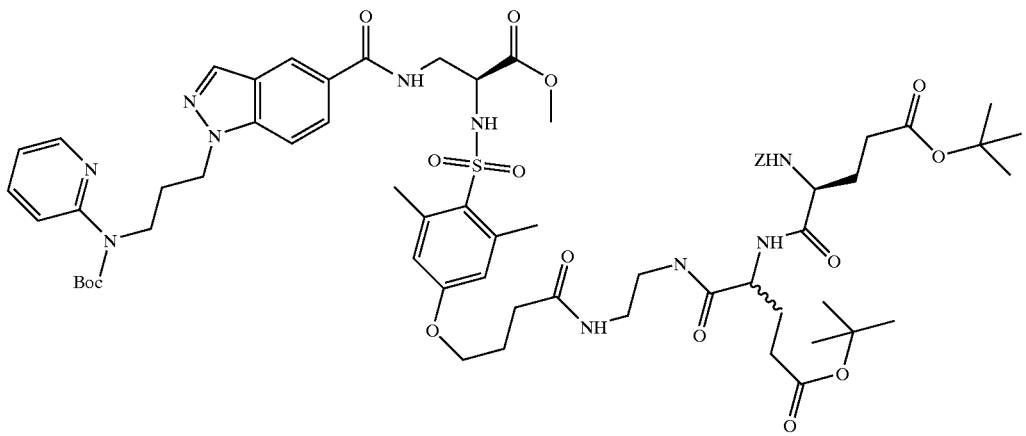

In a flask under nitrogen were added diisopropylethylamine (28 uL, 160 umol), the product XIC (62 mg, 120 umol), and HBTU (130 umol, 49 mg). This was stirred for 10 minutes and then the product of Step B (100 mg, 108 umol) was added, followed by diisopropylethylamine (50 uL, 288 umol). The reaction was stirred for 60 minutes and concentrated. The residue was purified by prep HPLC (Vydac C18, 21.2 mm×25 cm, 90% acetonitrile/water/0.1% TFA; 20–75% B over 40 minutes). The product fractions were combined and lyophilized to afford 135 mg (88%) of the product as a white solid. The product was contaminated with ~15% of the deBoc product after lyophilization, but this was not purified. LRMS (EI); 313.5 ([M+H]$^+$, 80%), 1213.5 ([M−Boc+H]$^+$, 45%) 551.3 (100%).

Step E: Synthesis of

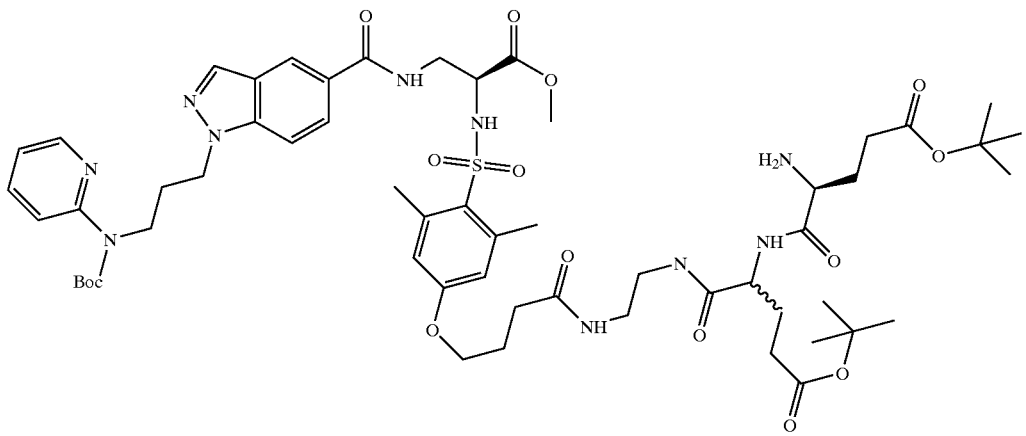

The product of step Step D (118 mg) was hydrogenolyzed and isolated as in step B. The lyophilized solid (110 mg) was not purified, but used directly in the following step. LRMS (EI); 1179.6 ([M+H]⁺, 20%), 1079.5 ([M−Boc+H]⁺, 25%) 540.3 (100%).

Step F: Synthesis of

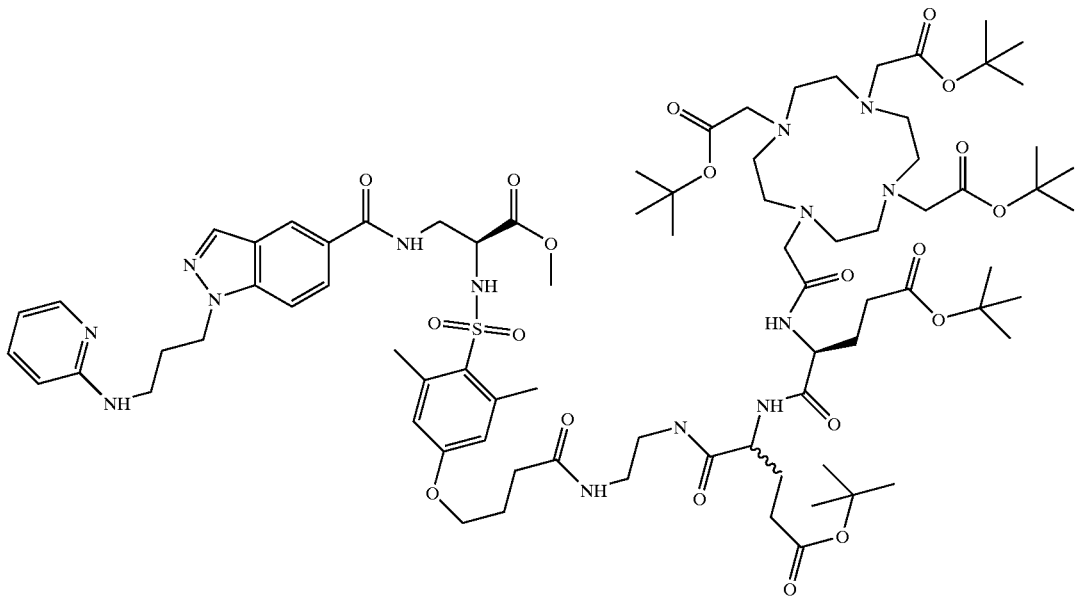

In dry glassware under nitrogen were mixed HBTU (35 mg, 90 μmol), DOTA(OtBu)₃—OH (49 mg, 85 μmol), and diisopropylethylamine (35 μL, 200 μmol) in dry DMF (7 mL). This was stirred for 10 minutes and then the product of step E (100 mg, 77 μmol) was added, along with additional diisopropylethylamine (45 μL, 250 μmol) to bring solution pH>9. After stirring for 30 min, the reaction was concentrated and purified by preparative HPLC (Vydac C18, 21.2 mm×25 cm, 90% acetonitrile/water/0.1% TFA; 20–70% B over 50 minutes). Four products were obtained after purification; a pair of glutamic acid isomers (60 mg) and the corresponding Boc deprotected compounds (29 mg) for a total yield of 66%.

Step G: Synthesis of 4-(N-{(1R)-1-[N-(2-{4-[4-({[(1S)-1-carboxy-2-({1-[3-(2-pyridylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)(4S)-4-{2-[1,4,7,10-tetraaza-4,7,10-tris(carboxymethyl)cyclododecyl]acetylamino}butanoic acid

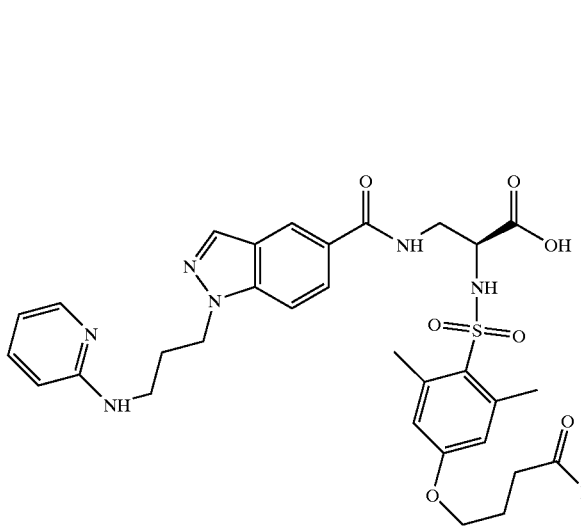

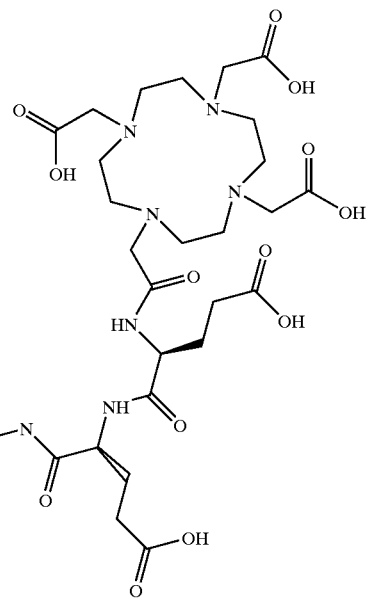

The combined Boc and Boc-deprotected D-Glutamic acid isomeric products of step F (45 mg, 23 umol) were dissolved in THF/methanol (1:1, 4 mL) and lithium hydroxide (3N in water, 75 uL, 225 umol) added with stirring. The solution was stirred for 4 hours, concentrated under vacuum, and the residue treated with dichloromethane (3 mL), trifluoroacetic acid (3 mL) and triethylsilane (300 uL) under nitrogen. The solution was stirred overnight, concentrated, and purified by preparative HPLC (Zorbax C8, 21.2 mm×25 cm, 50% acetonitrile/0.1% formic acid, 10–20% B over 180 min) $R_t$=100.4 minutes.

Step H: The synthesis of (4S)-4-(N-{(1S)-1-[N-(2-{4-[4-({[(1S)-1-carboxy-2-({1-[3-(2-pyridylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid

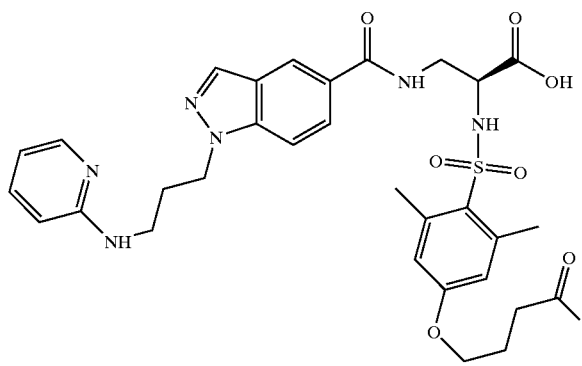

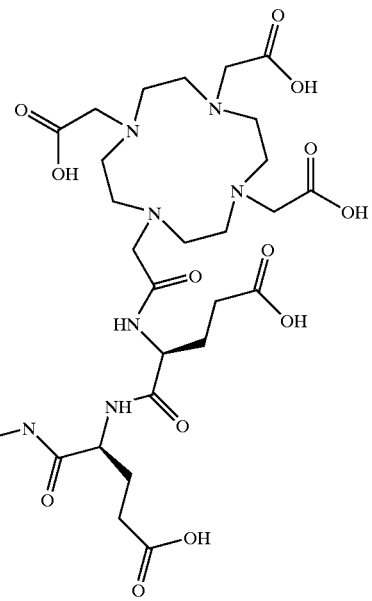

acetonitrile/water/0.1% formic acid; 15–30% B over 50 minutes). The product fractions were combined, frozen, and lyophilized to afford the product as a white solid (17.6 mg, 57%). LRMS (EI); 1339.5 ([M+H]$^+$, 15%), 670.4 ([M+2H]$^+$$_2$, 100%). HPLC (2×(4.6×21.2 mm Zorbax CN) Water/90%

The L-glutamic acid isomeric products of Step F (46 mg, 23 umol) were combined with the corresponding Boc deprotected analog and treated similarly to step G to afford the product as a white solid (15.5 mg, 50%). LRMS (EI); 1339.5 ([M+H]$^+$, 15%), 670.4 ([M+2H]$^{+2}$, 100%). HPLC (2×(4.6×

21.2 mm Zorbax CN) Water/90% acetonitrile/0.1% formic acid, 10–20% B over 180 min) $R_t$=101.3 minutes.

Example 38

Synthesis of (4S)-4-(N-{1-[N-(2-{4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid

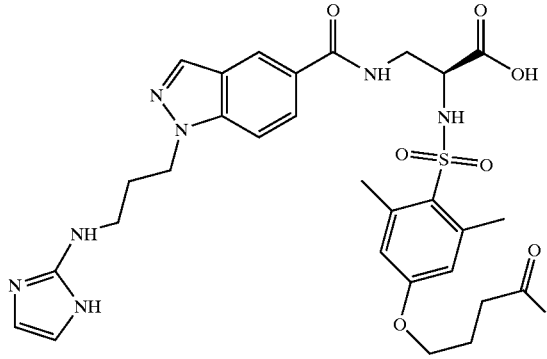
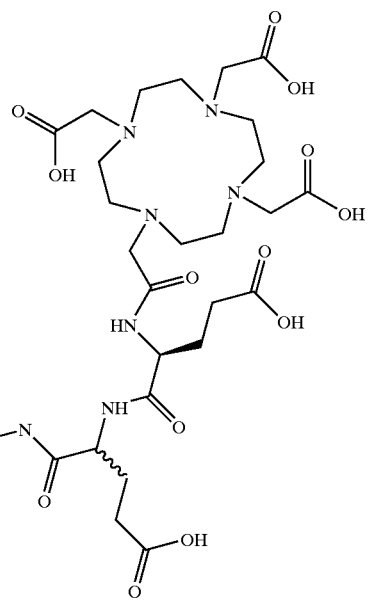

Step A: Synthesis of tert-butyl 2,3,5,6-tetrafluorophenyl (2S)-2-{(2S)-4-[(tert-butyl)oxycarbonyl]-2-[(phenylmethoxy)carbonylamino]butanoylamino}pentane-1,5-dioate

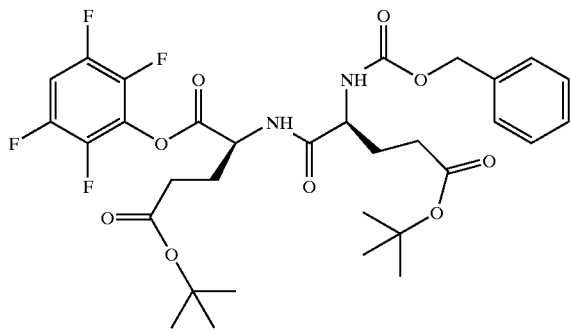

The product of Example 37, Step C (640 mg, 1.23 mmol) was dissolved in DMF (5 mL) with 2,3,5,6-tetrafluorophenol (286 mg, 1.7 mmol). To this was added (3-dimethylaminopropyl)ethyl carbodiimide hydrochloride (282 mg, 1.47 mmol) and the solution was stirred 18 hr. The reaction was concentrated and the residue partitioned between ethyl acetate and water. The aqueous layer was extracted twice with ethyl acetate, and the combined organic layer was washed with 0.1N HCl, 10% NaHCO₃, water, and brine. It was dried over sodium sulfate, filtered, concentrated, and purified by flash chromatography (5:1 hexane/ethyl acetate). The product was obtained as a clear oil (385 mg, 48%) LRMS (EI); 693.1 ([M+Na]⁺, 35%), 671.3 ([M+H]⁺, 100%), 615.2 ([(M–tBu)+H]⁺, 20%).

Step B: Synthesis of (2S)-2-({[4-(3-(N-[2-(2-{(2S)-4-[(tert-butyl)oxycarbonyl]-2-[(phenylmethoxy)carbonylamino] butanoylamino}-4-[(tert-butyl)oxycarbonyl] butanoylamino)ethyl]carbamoyl}propoxy)-2,6-dimethylphenyl]sulfonyl}amino)-3-({1-[3-(imidazol-2-ylamino)propyl](1H-indazol-5-yl)}carbonylamino)propanoic acid

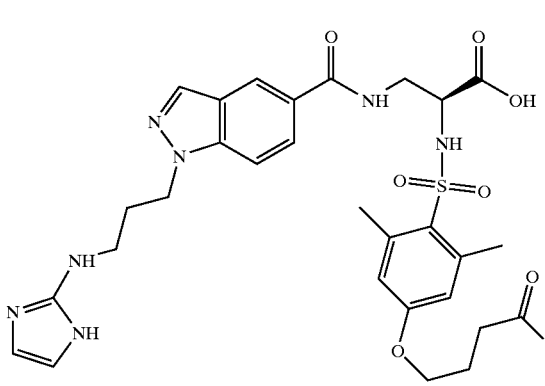
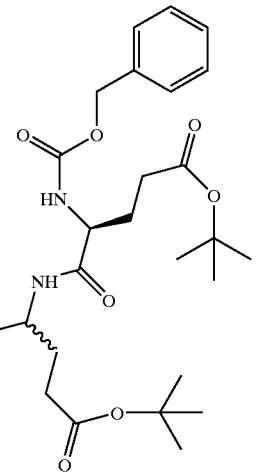

The product of Example 34, Step D (45 mg, 50 umol) was dissolved in DMF (1.5 mL) with the product of step A (44 mg, 65 umol) and diisopropylethylamine (30.5 uL, 175 umol) under nitrogen. The solution was stirred for 45 min, concentrated under vacuum, and purified by preparative HPLC (Vydac C18, 21.2 mm×25 cm, 90% acetonitrile/water/0.1% TFA; 20–70% B over 25 minutes). The product fractions were frozen and lyophilized to afford the product as a white powder (49 mg, 83%). LRMS (EI); 693.1 ([M+Na]$^+$, 35%), 1188.4 ([M+H]$^+$, 45%), 595.3 ([M+2H]$^{+2}$, 100%).

Step C: Synthesis of (2S)-2-({[4-(3-{N-[2-(2-{(2S)-2-amino-4-[(tert-butyl)oxycarbonyl]butanoylamino}4-[(tert-butyl)oxycarbonyl]butanoylamino)ethyl]carbamoyl}propoxy)-2,6-dimethylphenyl]sulfonyl}amino)-3-({1-[3-(imidazol-2-ylamino)propyl](1H-indazol-5-yl)}carbonylamino)propanoic acid hydrogenolyzed at 50 psi for 180 min, filtered through Celite, rinsed with methanol, and concentrated to afford a viscous oil. This was redissolved in 1:1 water/acetonitrile containing 0.1% TFA (nmL) and lyophilized (1:1 acetontrile/water/0.1% TFA) to afford the product as a white powder (29 mg, 100% yield) which analyzes for 2 equal peaks by HPLC (4.6×150 mm Zorbax C-18, 1 mL/min; Water/90% acetonitrile/0.1% trifluoroacetic acid, 2–100% B over 14 min) R$_t$=9.78 and 10.14 minutes. LRMS (ES): 1054.5 ([M+H]$^+$, 10%) 527.8 ([M+2H]$^{+2}$, 100%); identical for each peak. This was not further purified but taken into the next step as a mixture of two diastereomers.

Step D: Synthesis of (2S)-2-({[4-(3-{N-[2-(2-{(2S)-4-[(tert-butyl)oxycarbonyl]-2-[2-(1,4,7,10-tetraaza-4,7,10-tris{[(tert-butyl)oxycarbonyl]methyl}cyclododecyl)acetylamino]butanoylamino}-4-[(tert-butyl)oxycarbonyl]butanoylamino)ethyl]carbamoyl}propoxy)-2,6-

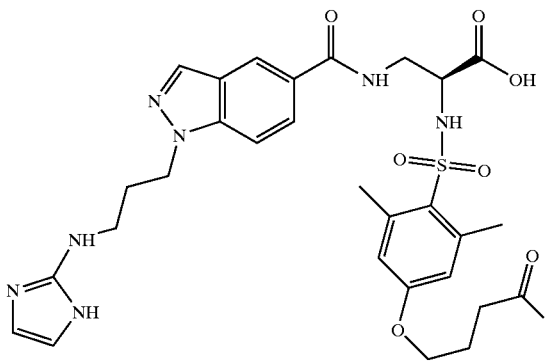
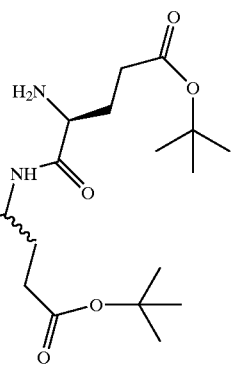

The product of step B (25 mg, 24 umol) in methanol (3 mL) was added to 10% palladium on carbon (14 mg) in methanol (3 mL) under nitrogen in a Parr bottle. It was dimethylphenyl]sulfonyl}amino)-3-({1-[3-(imidazol-2-ylamino)propyl](1H-indazol-5-yl)}carbonylamino)propanoic acid

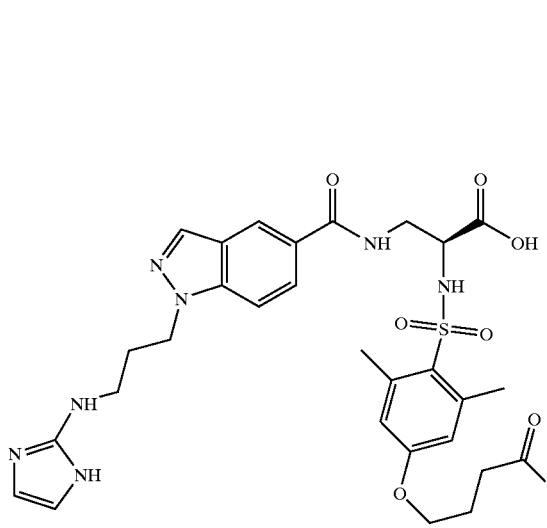
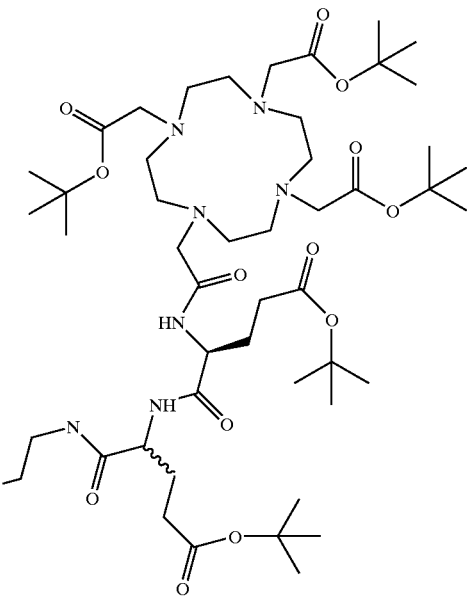

In dry glassware under nitrogen were mixed HBTU (16.4 mg, 43 μmol), DOTA(OtBu)$_3$—OH (36 mg, 52 μmol), and diisopropylethylamine (26 μL, 85 μmol) in dry DMF (0.6 mL). This was stirred for 10 minutes and then the product of step C (29 mg, 25 μmol) was added in DMF (0.8 mL), along with additional diisopropylethylamine (20 μL, 65 μmol) to bring solution pH>9. After stirring for 60 min, the reaction was concentrated and purified by preparative HPLC (Vydac C18, 21.2 mm×25 cm, 90% acetonitrile/water/0.1% TFA; 20–70% B over 50 minutes). Two products were obtained after purification, a pair of glutamic acid stereoisomers, which were each frozen and lyophilized to afford the products as white powders (8 mg each, 40%) with identical fragmentation patterns. LRMS (ES): 1609.0 ([M+H]$^+$, 5%), 805.0 ([M+2H]$^{+2}$, 30%), 537.4 ([M+3H]$^{+3}$, 100%); Using the HPLC method in Step X2C, R$_t$=11.54 min and 11.78 min.

Step E: Synthesis of (4S)-4-(N-{1-[N-(2-(4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid

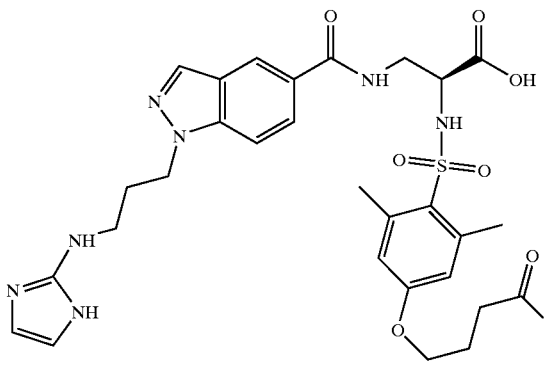
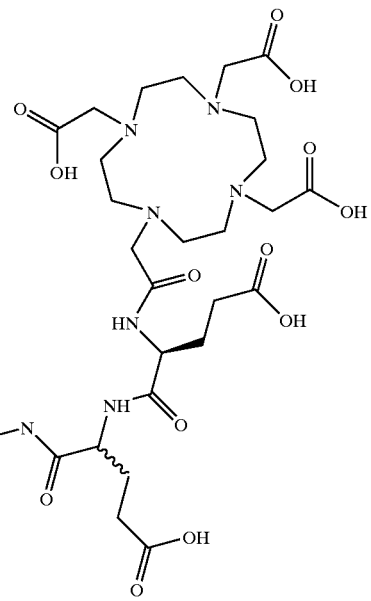

The products of step D were each individually dissolved in a mixture of dichloromethane (1 mL), trifluoroacetic acid (1 mL), and triethylsilane (0.2 mL) under nitrogen and stirred 16 hours. The solutions were concentrated and the residues purified by prep HPLC (Vydac C18, 21.2 mm×25 cm, 90% acetonitrile/water/0.1% TFA; 0–45% B over 45 minutes). The product fractions were frozen and lyophilized to afford the products as white solids (3.5 mg of each, ~50%) with identical fragmentation patterns LRMS (ES): 1328.5 ([M+H]$^+$, 5%), 664.8 ([M+2H]+$^2$, 100%), 372.2 (100%); Using the HPLC method in Step C, $R_t$=8.08 min and 8.09 min.

Example 39

Synthesis of (4S)-4-{N-[(1S)-1-(N-{1,3-bis[N-(2-{4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]propyl}carbamoyl)-3-carboxypropyl]carbamoyl}-4-(6-{2-[1,4,7,10-tetraaza-4,7,10-tris(carboxymethyl)cyclododecyl]acetylamino}hexanoylamino)butanoic acid

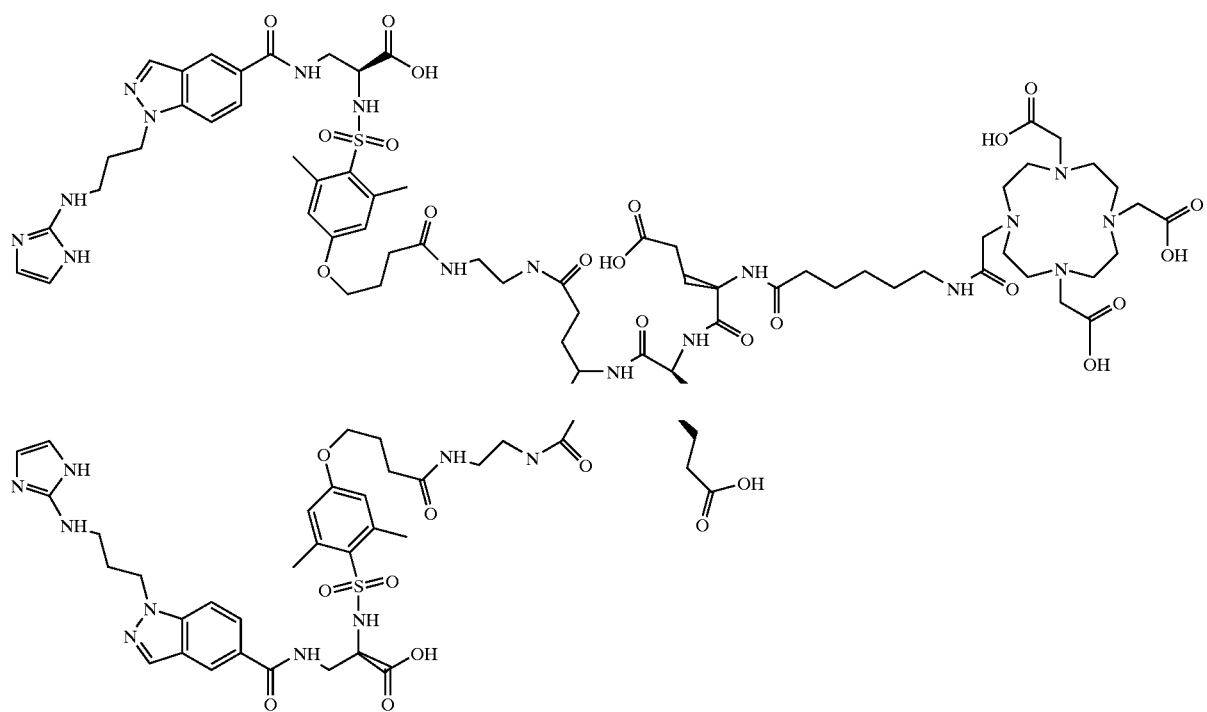

Step A: Synthesis of (2S)-2-{[(4-{3-[N-(2-{4-[N-(2-(4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]-4-[(tert-butoxy)carbonylamino]butanoylamino}ethyl)carbamoyl]propoxy}-2,6-dimethylphenyl)sulfonyl]amino)-3-({1-[3-(imidazol-2-ylamino)propyl](1H-indazol-5-yl)}carbonylamino)propanoic acid

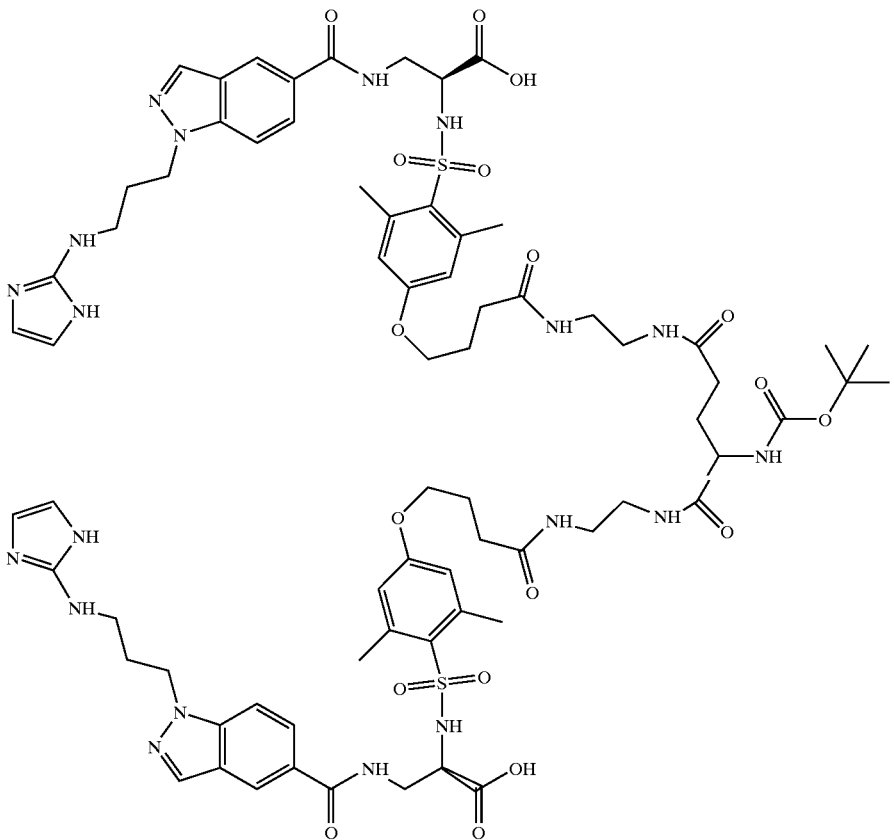

The product of Example 34, Step D (45 mg, 49.4 umol) was added along with Boc-Glu-(OTFP)-OTFP (13 mg, 24 umol) to DMF (1.5 mL) containing diisopropylethylamine (31 uL, 180 umol) and stirred for 18 hours. The solution was concentrated and purified by prep HPLC (Vydac C18, 21.2 mm×25 cm, 90% acetonitrile/water/0.1% TFA; 5–55% B over 25 minutes). The product fractions were frozen and lyophilized to afford the product as a white powder (31 mg, 82%). LRMS (ES): 1578.5 ([M+H]$^+$, 5%), 790.1 ([M+2H]$^+$2, 100%), 527.3 ([M+3H]$^{+3}$, 50%).

Step B: Synthesis of tert-butyl (4S)-4-{(2S)-4-[(tert-butyl)oxycarbonyl]-2-[(phenylmethoxy)carbonylamino]butanoylamino}-4-(N-{1,3-bis[N-(2-{4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylaamino}ethyl)carbamoyl]propyl}carbamoyl)butanoate

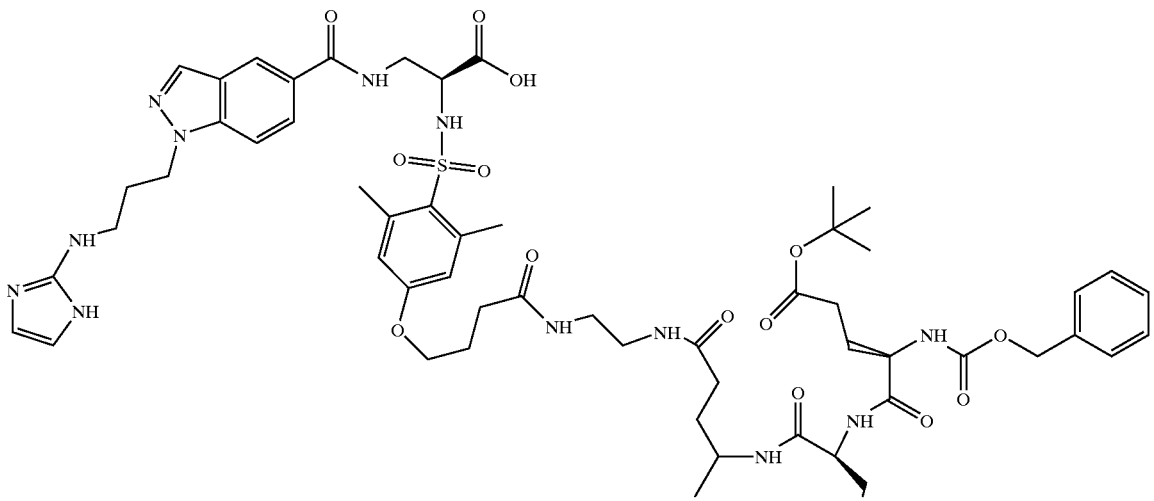

-continued

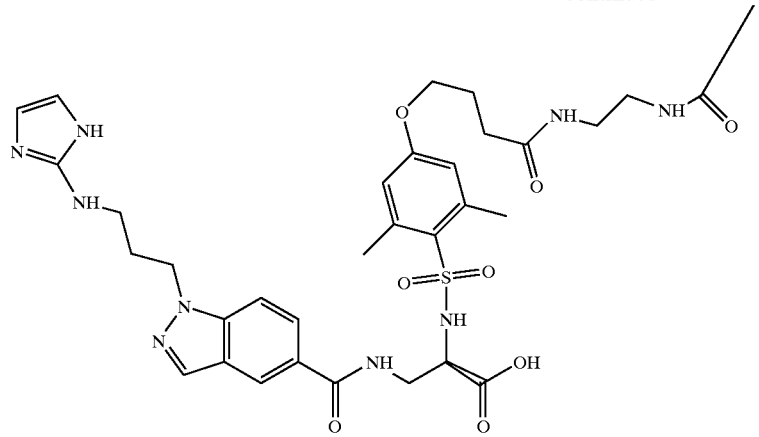

The product of Step A (30 mg, 19 umol) was added to a solution of trifluoroacetic acid (250 uL) in dichloromethane (500 uL) and stirred for 30 minutes under a nitrogen atmosphere. The solution was concentrated and left under vacuum for 1 hour. The residue was dissolved in DMF (800 uL) under nitrogen and the product of Example 38, Step A (16 mg, 24 umol) added, followed by diisopropylethylamine (75 uL, 730 umol) to adjust pH>9. The solution was stirred for 60 minutes, concentrated, and purified by prep HPLC (Vydac C18, 21.2 mm×25 cm, 90% acetonitrile/water/0.1% TFA; 20–60% B over 40 minutes). The product fractions were frozen and lyophilized to afford the product as a white powder (30 mg, 81%). LRMS (ES): 1983.6 ([M+H]$^+$, 10%), 992.0 ([M+2H]$^{+2}$, 100%), 661.8 ([M+3H]$^{+3}$, 80%), 643.2 ([(M−tBu)+3H]$^{+3}$, 40%), 624.4 ([(M−2tBu)+3H]$^{+3}$, 30%). HRMS: Calculated for $C_{93}H_{124}N_{21}O_{24}S_2$: 1982.857; Found: 1982.55.

Step C: Synthesis of (4S)-4-((2S)-2-{6-[(tert-butoxy)carbonylamino]hexanoylamino}-4-carboxybutanoylamino)-4-(N-{1,3-bis[N-(2-(4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]propyl)carbamoyl)butanoic acid

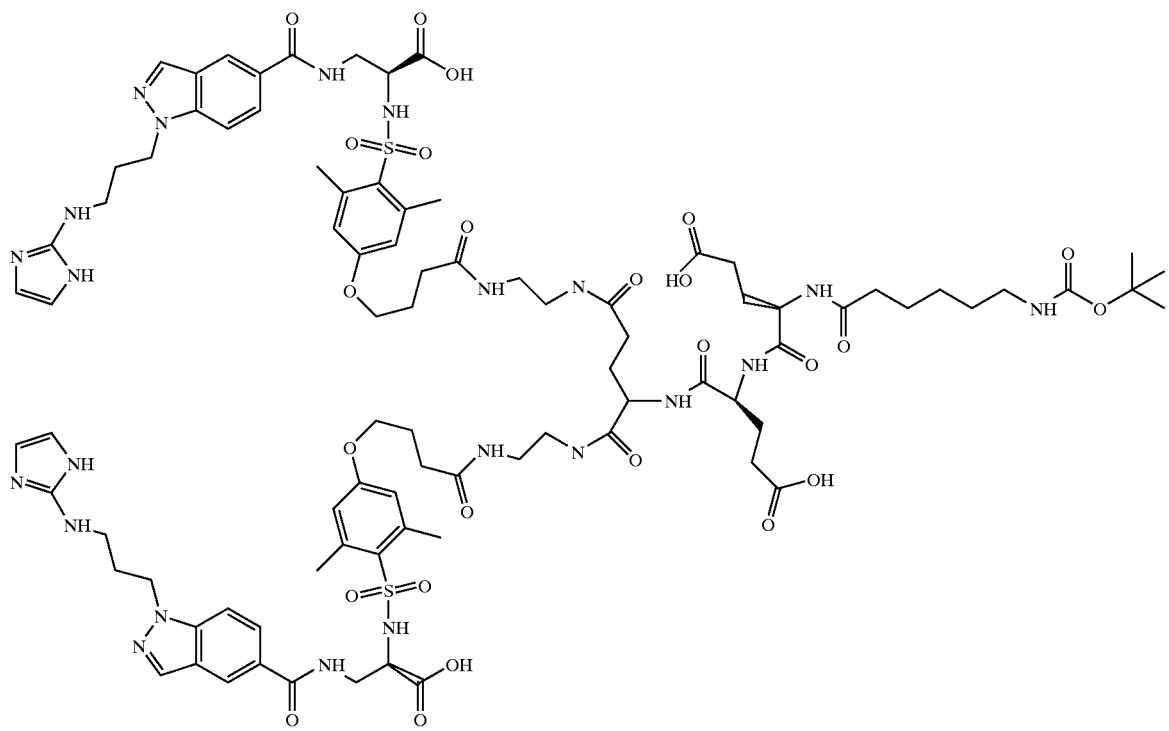

The product of step B (29 mg, 14.6 umol) was dissolved in neat trifluoroacetic acid (2 mL) and triethylsilane (250 uL) added. The reaction was heated with stirring under nitrogen to 70C for 3 hr, concentrated, reconcentrated with toluene (5 mL), dissolved in 1:1 water/acetonitrile, frozen, and lyophilized. The resulting powder (27 mg) was dissolved in DMF (0.8 mL) with 2,3,5,6-tetrafluorophenyl 6-[(tert-butoxy)carbonylamino]hexanoate (10 mg, 26 umol)

and diisopropylethylamine (18 uL, 100 umol) and stirred for 60 minutes. Additional 2,3,5,6-tetrafluorophenyl 6-[(tert-butoxy)carbonylamino]hexanoate (20 mg, 52 umol) was added and the reaction stirred 45 minutes. The reaction, containing primarily the tris-hexanoyl product, was concentrated, the residue dissolved in ethanol (2 mL), and sodium hydroxide (5N solution, 200 uL) added. The solution was stirred 25 minutes, neutralized to pH<5 with 1N HCl (~1.1 mL) and concentrated. The residue was purified by preparative HPLC (Vydac C18, 21.2 mm×25 cm, 90% acetonitrile/water/0.1% TFA; 15–55% B over 50 minutes). The product fraction was frozen and lyophilized to afford the product as a white powder (21 mg, 65%). LRMS (ES): 1951.3 ([M+H]+, 5%), 975.5 ([M+2H]+2, 90%), 617.5 ([(M−Boc)+3H]+3, 100%).

Step D: Synthesis of (4S)-4-[(2S)-2-(6-aminohexanoyl amino)-4-carboxybutanoylamino]-4-(N-{1,3-bis[N-(2-{4-[4-{[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]propyl}carbamoyl)butanoic acid

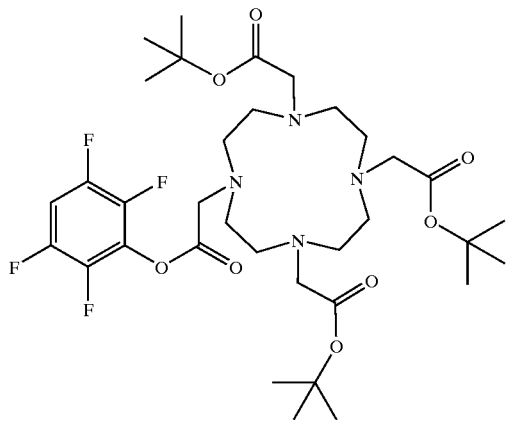

DOTA(OtBu)$_3$—OH (95 mg, 138 umol) was added to dry DMF (1 mL) along with HBTU (90 mg, 210 umol), diisopropylethylamine (103 uL, 740 umol), and 2,3,5,6-

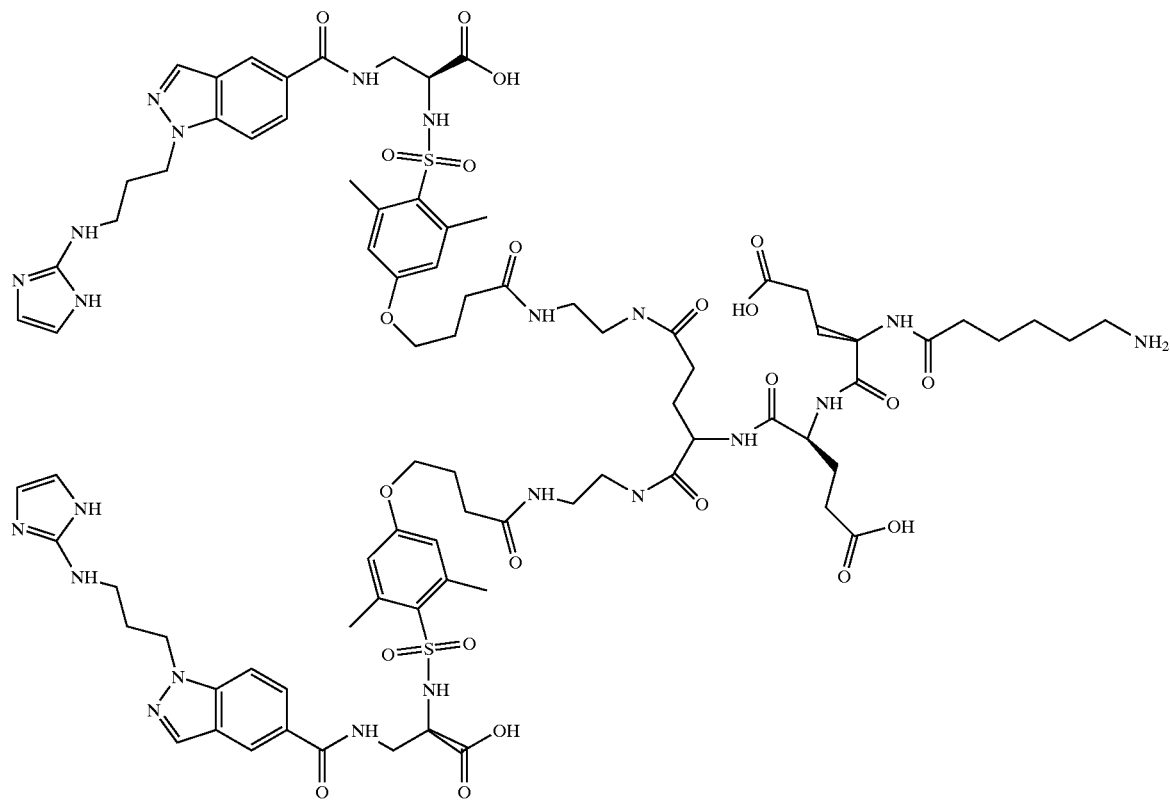

The product of C (19 mg, 9.7 umol) was added to trifluoroacetic acid (200 uL) and dichloromethane (600 uL) and stirred under nitrogen for 30 min, concentrated, and purified by prep HPLC (Vydac C18, 21.2 mm×25 cm, 90% acetonitrile/water/0.1% TFA; 5–35% B over 40 minutes). The product fractions were frozen and lyophilized to afford the product as a white powder (13 mg, 70%). LRMS (ES): 1850.3 ([M+H]+, 5%), 925.6 ([M+2H]+2, 25%), 617.7 ([M+3H]+3, 100%).

Step E: Synthesis of 2,3,5,6-tetrafluorophenyl 2-(1,4,7,10-tetraaza-4,7,10-tris{[(tert-butyl)oxycarbonyl]methyl}cyclododecyl)acetate tetrafluorophenol (32 mg, 270 umol). The solution was stirred under nitrogen for 18 hours, concentrated, and purified by preparative HPLC (Vydac C18, 21.2 mm×25 cm, 90% acetonitrile/water/0.1% TFA; 20–80% B over 30 minutes). The product fractions were frozen and lyophilized to afford the product as a white powder (81 mg, 70%). LRMS (ES): 721.5 ([M+H]+, 100%), 665.5 ([(M−tBu)+H]+, 70%).

Step F: Synthesis of (4S)-4-((2S)-4-carboxy-2-{6-[2-(1,4,7,10-tetraaza-4,7,10-tris{[(tert-butyl)oxycarbonyl]methyl}cyclododecyl)acetylamino]hexanoylamino}butanoylamino)-4-(N-{1,3-bis[N-(2-{4-[4-({[(1S)-1-carboxy-2-({1-[3-(imidazol-2-ylamino)propyl]

(1H-indazol-5-yl)}carbonylamino)ethyl]amino}sulfonyl)-3,
5-dimethylphenoxy]butanoylamino}ethyl)carbamoyl]
propyl}carbamoyl)butanoic acid

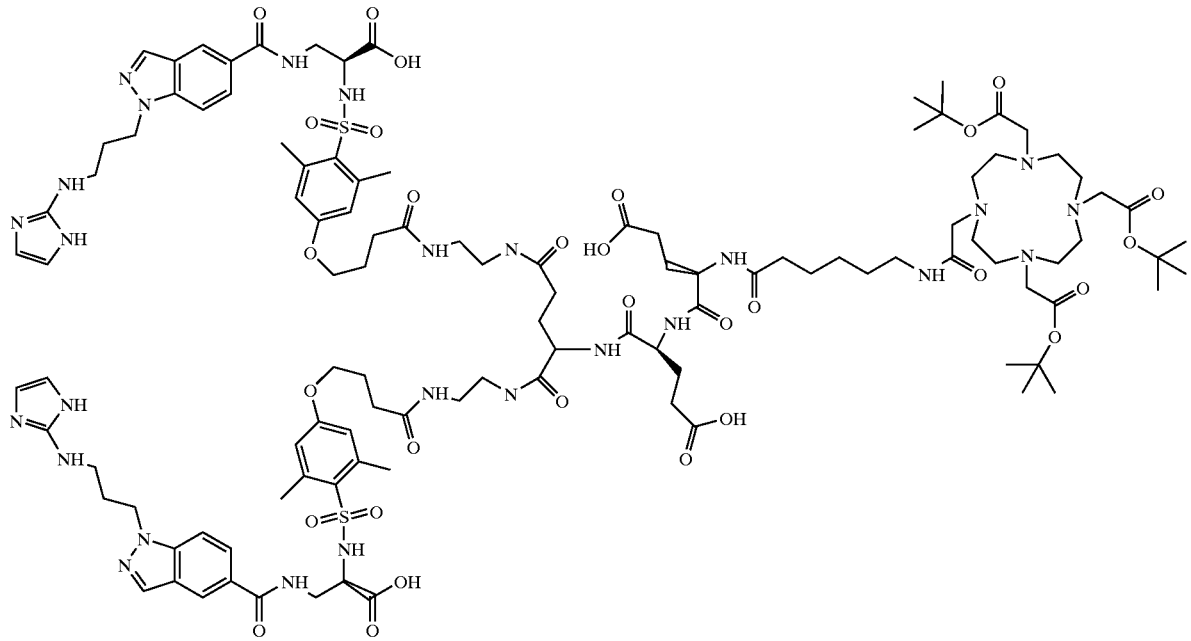

The product of step D (12 mg, 6.1 umol) and the product of step E (7.2 mg, 7.6 umol) were mixed together in dry DMF (600 uL) with diisopropylethylamine (13.2 uL, 76 umol) and stirred under nitrogen. At 90 minutes and 4 hours, additional amounts of step E (5 mg, 5.1 umol) were added. After 5 hours, the reaction was concentrated, dissolved in ethanol (2 mL) and treated with sodium hydroxide (540 uL of a 1N solution. After 45 minutes, the solution was acidified with 1N HCl (~600 uL), concentrated and purified by preparative HPLC (Vydac C18, 21.2 mm×25 cm, 90% acetonitrile/water/0.1% TFA; 10–55% B over 50 minutes).

The product fraction, which contained several impurities by HPLC analysis, was frozen and lyophilized to afford the product as a white powder (10.5 mg, 72%). LRMS (ES): 802.2 ([M+3H]$^{+3}$, 100%), 604.1 ([M+4H]$^{+4}$, 90%).

Step G: Synthesis of (4S)-4-{N-[(1S)-1-(N-{1,3-bis[N-(2-{4-[4-({[(1S)-1-carboxy-2-({1-[3-(imidazol-2-ylamino)propyl](1H-indazol-5-yl)}carbonylamino)ethyl]amino}sulfonyl)-3,5-dimethylphenoxy]butanoylamino}ethyl)carbamoyl]propyl}carbamoyl)-3-carboxypropyl]carbamoyl}-4-(6-{2-[1,4,7,10-tetraaza-4,7,10-tris(carboxymethyl)cyclododecyl]acetylamino}hexanoylamino)butanoic acid

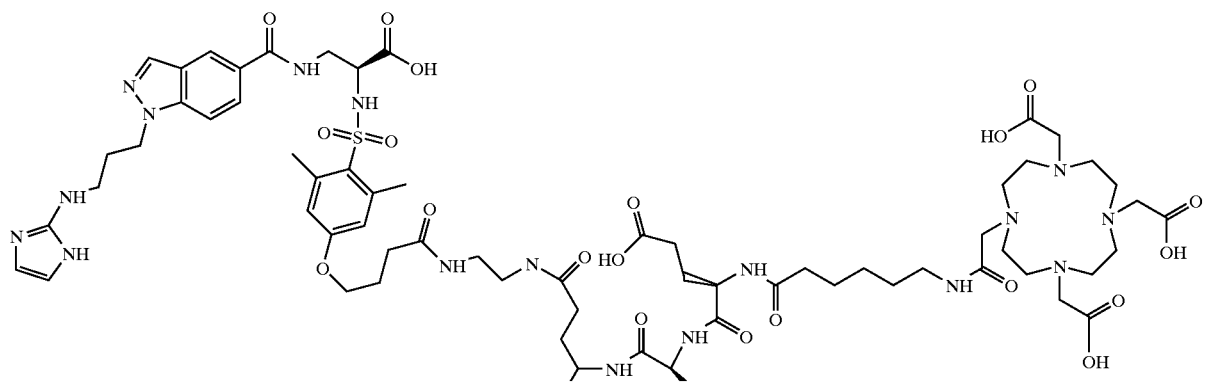

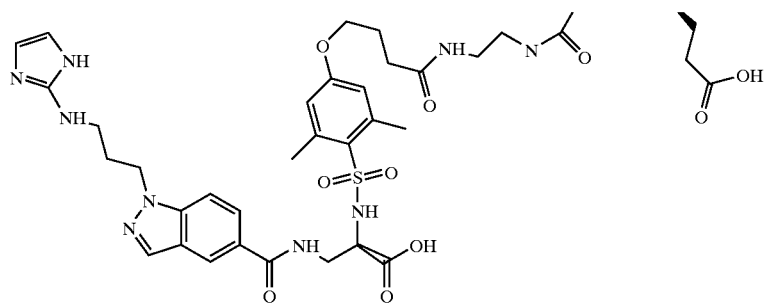

The product of F (10 mg) was added to dichloromethane (1 mL) containing trifluoroacetic acid (1 mL) and triethylsilane (200 uL) and stirred under nitrogen for 72 hours. The reaction was concentrated and purified by preparative HPLC (Vydac C18, 21.2 mm×25 cm, 90% acetonitrile/water/0.1% TFA; 15–55% B over 50 minutes). The product fraction was frozen and lyophilized to afford the product as a white powder (1 mg, 15%). LRMS (ES): 1118.7 ([M+2H]+$^{+2}$, 10%), 746.3 ([M+3H]$^{+3}$, 40%) 560.0 ([M+4H]$^{+4}$, 100%).

Example 40

Synthesis of (4S)-4-(N-{1-[N-(2-{4-[4-({[(1S)-1-carboxy-2-({1-[3-(3,4,5,6-tetrahydropyrimidin-2-ylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid Step A: Synthesis of ethyl 1-[3-(pyrimidin-2-ylamino)propyl]-1H-indazole-5-carboxylate

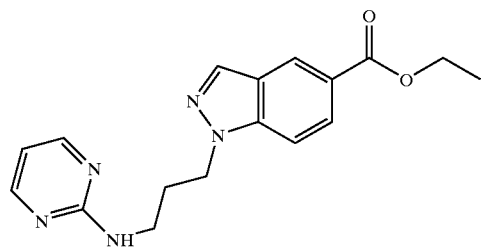

Ethyl 1-(3-oxopropyl)-1H-indazole-5-carboxylate (1.0 g, 4.06 mmol, prepared as described in Jadhav et al, U.S. Pat. No. 5,760,028) was dissolved in toluene (15 mL) and 2-aminopyrimidine (463 mg, 4.9 mmol) added, along with anhydrous magnesium sulfate (2.44 g, 20 mmmol) under nitrogen. The mixture was vigorously stirred for six hours, filtered under nitrogen, the solids washed (10 mL toluene), and the filtrate treated with sodium triacetoxyborohydride

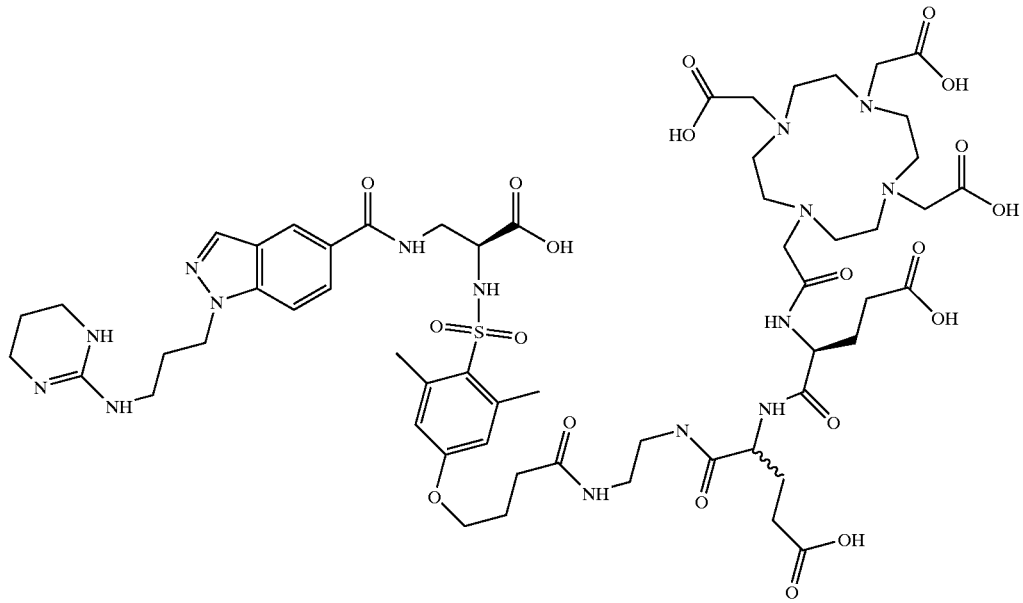

(8.6 g, 40 mmol). The reaction was stirred under nitrogen for 18 hours, diluted with toluene (25 mL), and poured into water (100 mL). Saturated sodium bicarbonate solution (80 mL) was added to adjust pH>8. The layers were separated and the aqueous layer extracted with three portions of ethyl acetate. The combined organics were washed with saturated bicarbonate solution, water, and brine, dried over sodium sulfate, filtered, and concentrated under vacuum to afford a golden oil (1.3 g). This purified by preparative HPLC (Vydac C18, 21.2 mm×25 cm, 90% acetonitrile/water/0.1% TFA; 10–70% B over 30 minutes). The product fractions were frozen and lyophilized to afford the desired product as a white powder (520 mg, 40%). LRMS (ES): 326.2 ([M+H]$^+$. HRMS: Calculated for $C_{17}H_{20}N_5O_2$: 326.1617; Found: 326.1605. $^1$HNMR (600.1343 MHz, CDCl$_3$): 9.68 (bs, 1H), 8.58 (m, 1H), 8.49 (s, 1H), 8.12 (s, 1H), 8.08 (m, 1H), 8.03, (t, 1H), 7.50 (d, 1H), 6.73 (t, 1H), 4.55 (m, 2H), 4.39 (q, 2H), 3.36 (m, 2H), 2.35 (m, 2H), 1.41 (t,3H).

Step B: Synthesis of 1-[3-(pyrimidin-2-ylamino)propyl]-1H-indazole-5-carboxylic acid

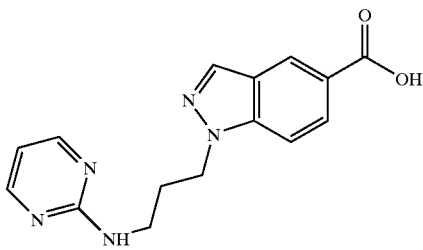

The product of step A (510 mg, 1.16 mmol) was dissolved in ethanol (50 mL) and sodium hydroxide (6.5 mL of a 1N solution, 6.5 mmol) added. The solution was heated at reflux for 1.5 hours, diluted with water (45 mL), and the ethanol removed under vacuum. The solution was acidified to pH=3 with 1N HCl (~7 mL) with stirring. The resulting solids were filtered, washed with water, and dried under vacuum to afford the product (308 mg, 89%). LRMS (ES): 298.1 ([M+H]$^+$. HRMS: Calculated for $C_{15}H_{16}N_5O_2$: 298.1304; Found: 298.1320. $^1$HNMR (600.1343 MHz, CDCl$_3$): 12.5 (b, H), 8.42 (s, 1H), 8.26 (d, 2H), 8.19 (s, 1H), 7.90 (d, 1H), 7.67, (d, 1H), 7.45 (m, 1H), 6.58 (s, 1H), 4.50 (t, 2H), 3.29 (m, 2H), 2.13 (t, 2H).

Step C: Synthesis of methyl (2S)-2-[({2,6-dimethyl-4-[3-(N-{2-[(phenylmethoxy)carbonylamino]ethyl}carbamoyl)propoxy]phenyl}sulfonyl)amino]-3-({1-[3-(pyrimidin-2-ylamino)propyl](1H-indazol-5-yl)}carbonylamino)propanoate

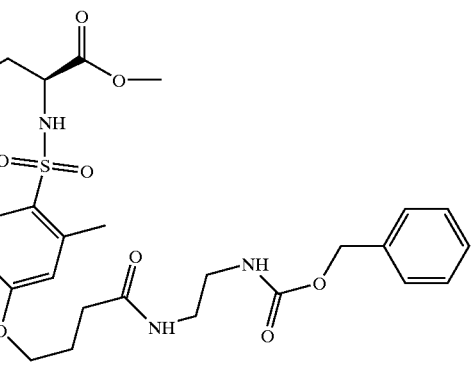

The product of step B (292 mg, 0.98 mmol) was treated as in Example 37, Step A to afford the crude product which was purified by preparative HPLC (Vydac C18, 21.2 mm×25 cm, 90% acetonitrile/water/0.1% TFA; 10–70% B over 30 minutes). The product fractions were frozen and lyophilized to afford the desired product as a white powder (825 mg, 88%). LRMS (ES): 844.3 ([M+H]$^+$.

Step D: Synthesis of methyl (2S)-2-{[(4-{3-[N-(2-aminoethyl)carbamoyl]propoxy}-2,6-dimethylphenyl)sulfonyl]amino}-3-({1-[3-(3,4,5,6-tetrahydropyrimidin-2-ylamino)propyl](1H-indazol-5-yl)}carbonylamino)propanoate

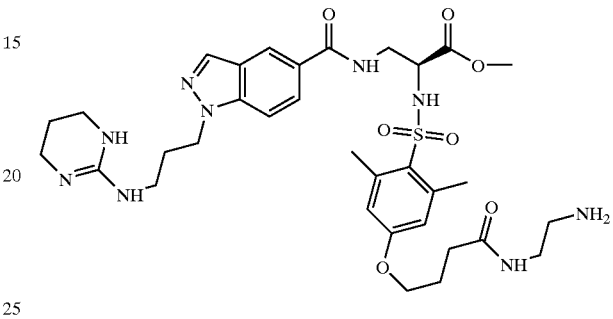

The product of Step C (250 mg, 260 umol) was treated as in Example 37, Step B to afford the product as a white powder (220 mg, 89%). LRMS (ES): 714.3 ([M+H]$^+$, 25%), 402.2 (30%), 357.1 ([M+2H]$^{+2}$, 100%). HRMS: Calculated for $C_{33}H_{48}N_7O_7S$: 714.3397; Found: 714.3374.

Step E: Synthesis of tert-butyl (4S)-4-[N-(2-{4-[4-({[(1S)-1-(methoxycarbonyl)-2-({1-[3-(3,4,5,6-tetrahydropyrimidin-2-ylamino)propyl](1H-indazol-5-yl)}carbonylamino)ethyl]amino}sulfonyl)-3,5-dimethylphenoxy]butanoylamino}ethyl)carbamoyl]-4-[(phenylmethoxy)carbonylamino]butanoate

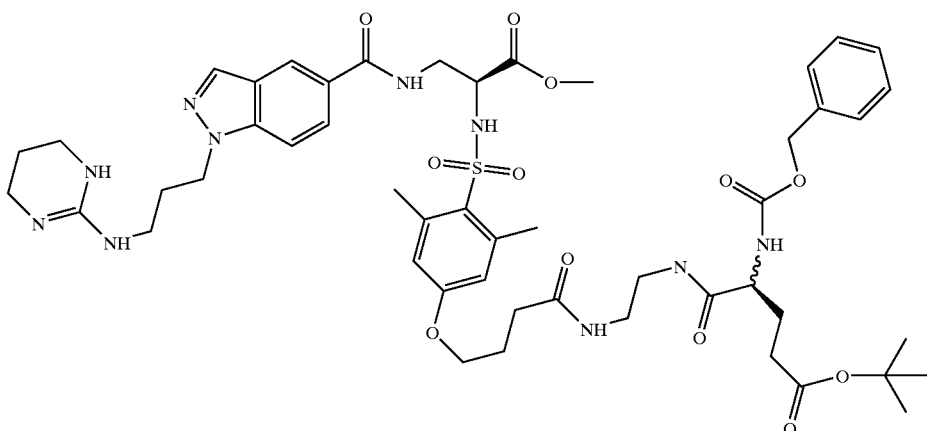

The product of step D (219 mg, 234 umol) was dissolved in DMF (2 mL) and tert-butyl 2,5-dioxopyrrolidinyl (2S)-2-[(phenylmethoxy)carbonylamino]pentane-1,5-dioate (108 mg, 250 umol) added, along with diisopropylamine (130 uL, 750 umol). The solution was stirred under nitrogen for 90 minutes, concentrated, and purified by preparative HPLC (Vydac C18, 21.2 mm×25 cm, 90% acetonitrile/water/0.1% TFA; 20–75% B over 40 minutes). The product fractions were frozen and lyophilized to afford the desired product as a white powder (242 mg, 81%). LRMS (ES): 1033.4 ([M+H]$^+$, 100%), 489.2 ([(M−tBu)+2H]$^{+2}$, 80%)

Step F: Synthesis of tert-butyl 4-[N-(2-{4-[4-({[(1S)-1-(methoxycarbonyl)-2-({1-[3-(3,4,5,6-tetrahydropyrimidin-2-ylamino)propyl](1H-indazol-5-yl)}carbonylamino)ethyl]amino}sulfonyl)-3,5-dimethylphenoxy]butanoylamino}ethyl)carbamoyl]-4-aminobutanoate

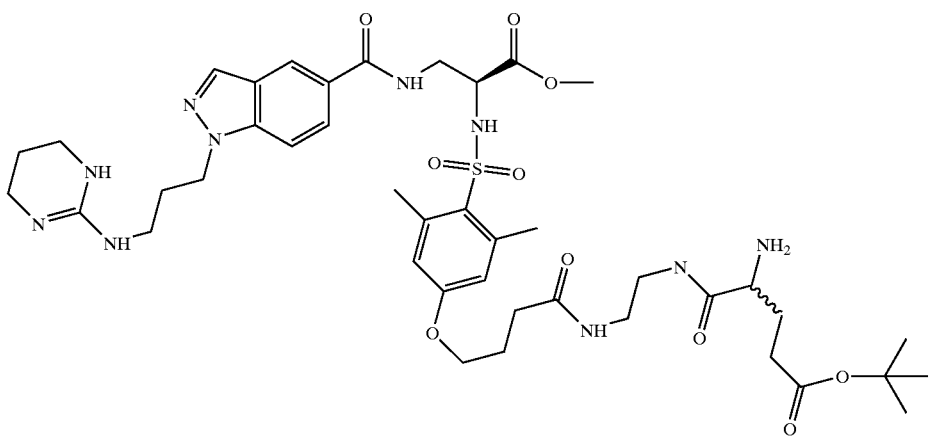

The product of C (228 mg, 198 umol) was treated as in Step D to afford the product as a white powder (176 mg, 79%). LRMS (ES): 899.5 ([M+H]$^+$, 50%), 450.2 ([M+2H]$^+$$_2$, 65%), 422.4 ([(M−tBu)+2H]$^{+2}$, 100%).

Step G: Synthesis of tert-butyl 4-{(2S)-4-[(tert-butyl)oxycarbonyl]-2-[(phenylmethoxy)carbonylamino]butanoylamino}-4-[N-(2-{4-[4-({[(1S)-1-(methoxycarbonyl)-2-({1-[3-(3,4,5,6-tetrahydropyrimidin-2-ylamino)propyl](1H-indazol-5-yl)}carbonylamino)ethyl]amino}sulfonyl)-3,5-dimethylphenoxy]butanoylamino}ethyl)carbamoyl]butanoate

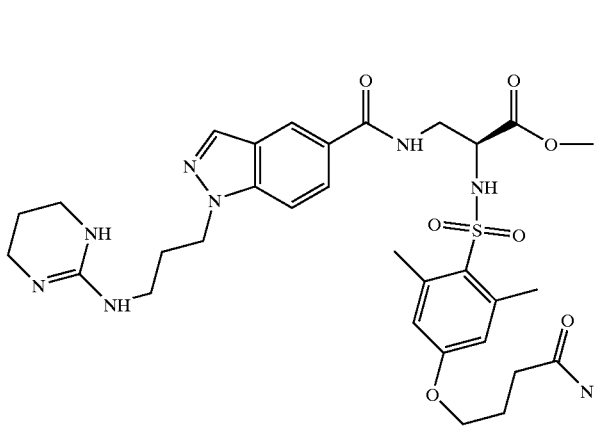
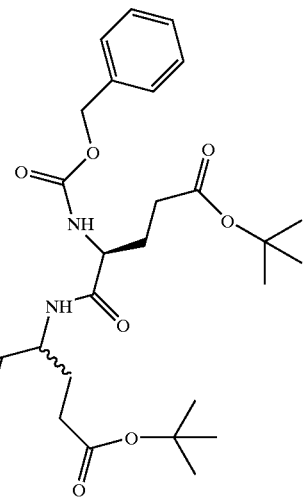

The product of step F (85 mg, 76 umol) was treated as in step E to afford the product after lyophilization (87 mg, 87%). LRMS (ES): 1218.6 ([M+H]$^+$, 100%), 610.0 ([M+2H]$^{+2}$, 20%), 581.8 ([(M−tBu)+2H]$^{+2}$, 30%), 553.8 ([(M−2tBu)+2H]$^{+2}$, 85%).

Step H: Synthesis of tert-butyl (4S)-4-(N-{1-[N-(2-{4-[4-({[(1S)-1-(methoxycarbonyl)-2-({1-[3-(3,4,5,6-tetrahydropyrimidin-2-ylamino)propyl](1H-indazol-5-yl)}carbonylamino)ethyl]amino}sulfonyl)-3,5-dimethylphenoxy]butanoylamino}ethyl)carbamoyl]-3-[(tert-butyl)oxycarbonyl]propyl}carbamoyl)-4-aminobutanoate }carbonylamino)ethyl]amino}sulfonyl)-3,5-dimethylphenoxy]butanoylamino}ethyl)carbamoyl]-3-[(tert-butyl)oxycarbonyl]propyl}carbamoyl)-4-[2-(1,4,7,10-tetraaza-4,7,10-tris{[(tert-butyl)oxycarbonyl]methyl}cyclododecyl)acetylamino]butanoate

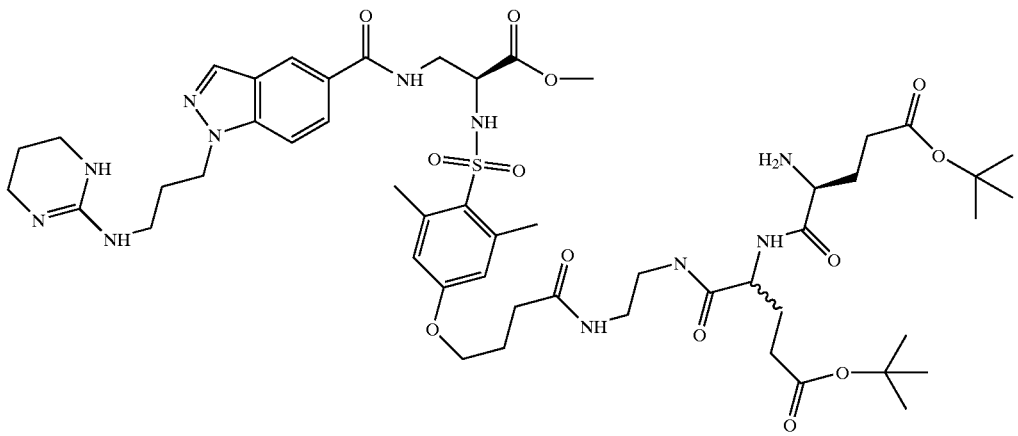

The product of step G (75 mg, 56 umol) was treated as in step F to afford the product as a white solid (72 mg, 97%). LRMS (ES): 1084.6 ([M+H]$^+$, 20%), 542.8 ([M+2H]$^{+2}$, 100%), 514.8 ([(M−tBu)+2H]$^{+2}$, 30%), 486.9 ([(M−2tBu)+2H]$^{+2}$, 20%).

Step I: Synthesis of tert-butyl (4S)-4-(N-{1-[N-(2-{4-[4-({[(1S)-1-(methoxycarbonyl)-2-({1-[3-(3,4,5,6-tetrahydropyrimidin-2-ylamino)propyl](1H-indazol-5-yl)

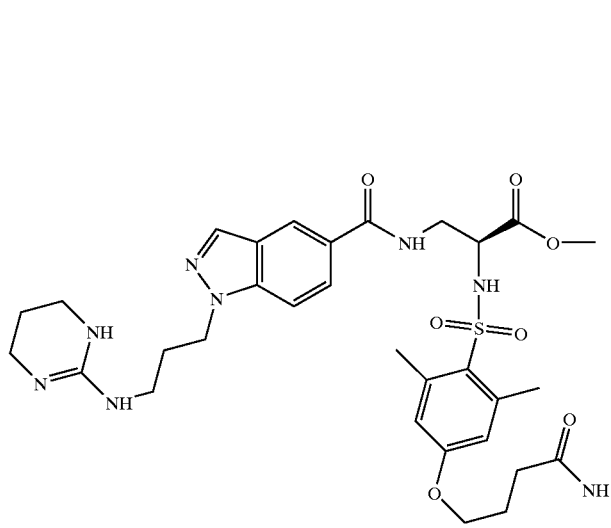
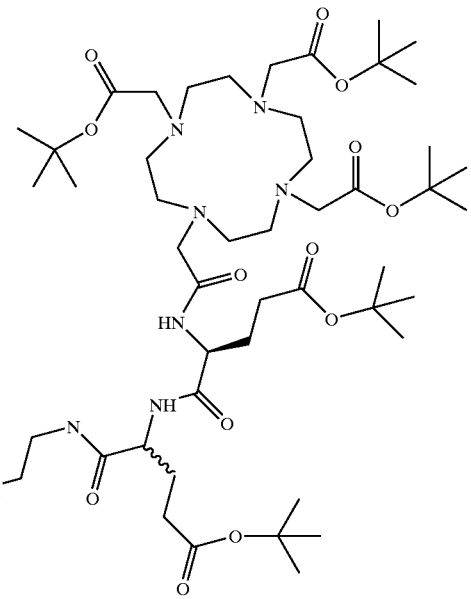

The product of step H (60 mg, 46 umol) was treated as in Example 37, Step G to afford the product as a single pure compound (40 mg, 54%) after lyophilization. LRMS (ES): 1638.7 ([M+H]$^+$, 10%), 820.1 ([M+2H]$^{+2}$, 30%), 528.5 ([(M−tBu)+3H]$^{+3}$, 30%), 509.8 ([(M−2tBu)+3H]$^{+3}$, 100%), 491.1 ([(M−3tBu)+3H]$^{+3}$, 50%).

Step J: Synthesis of (4S)-4-(N-{1-[N-(2-{4-[4-({[(1S)-1-carboxy-2-({1-[3-(3,4,5,6-tetrahydropyrimidin-2-ylamino)propyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid The product of step I (25 mg, 14.3 umol) was dissolved in THF (600 uL)/water (100 uL) and lithium hydroxide (3N in water, 60 uL, 180 umol) added with stirring. The solution was stirred for 100 min, acidified to pH=2 with trifluoroacetic acid (14 uL), and concentrated under vacuum. The residue was treated with dichloromethane (1 mL), trifluoroacetic acid (1 mL) and triethylsilane (100 uL) under nitrogen. The solution was stirred overnight, concentrated, and purified by preparative HPLC (Zorbax CN, 21.2 mm×25 cm, 50% acetonitrile/water/0.1% formic acid; 20–30% B over 50 minutes). The product fractions were combined, frozen, and lyophilized to afford the product as a white solid (13 mg, 57%). LRMS (EI); 1344.5 ([M+H]$^+$, 15%), 672.9 ([M+2H]$^{+2}$, 100%), 449.9 ([M+3H]$^{+3}$, 50%).

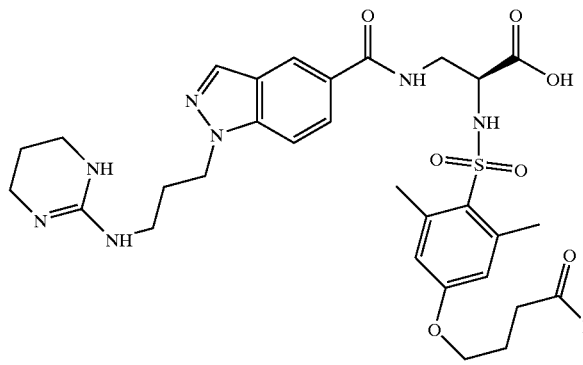
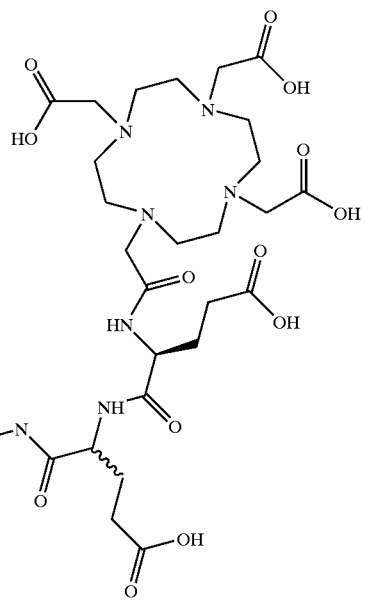

Exammle 41

Synthesis of (4S)-4-(N-{1-[N-(2-{4-[4-({[(1S)-1-carboxy-2-({1-methyl-3-[3-(2-3,4,5,6-tetrahydropyridylamino)propyl](1H-indazol-6-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid 1-Methyl-3-[3-(2-pyridylamino)propyl]-1H-indazole-6-carboxylic acid (79 mg, 256 umol, prepared as described in Jadhav et al, U.S. Pat. No. 5,760,028) was treated with the product of Example 34, Step B (223 mg 282 umol) as in example 37, Step A to afford the crude product which was purified by prep HPLC (Vydac C18, 21.2 mm×25 cm, 90% acetonitrile/water/0.1% TFA; 10–60% B over 30 minutes). The product fractions were frozen and lyophilized to afford the desired product as a white powder (122 mg, 49%). LRMS (ES): 857.3 ([M+H]$^+$, 100%). HRMS: Calculated for $C_{43}H_{53}N_8O_9$: 857.3656; Found: 857.3676.

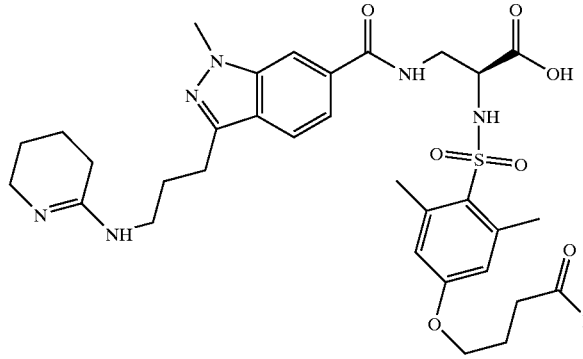
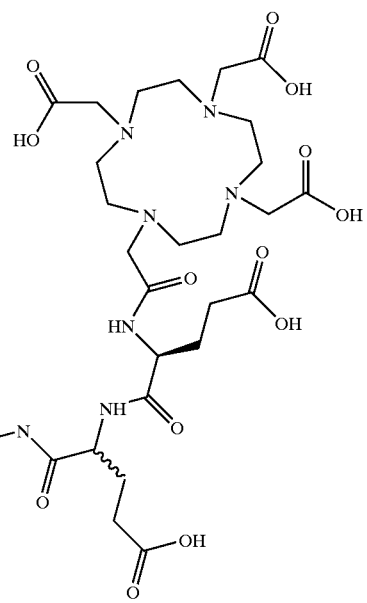

Step A: Synthesis of methyl (2S)-2-[({2,6-dimethyl-4-[3-(N-{2-[(phenylmethoxy)carbonylamino]ethyl}carbamoyl)propoxy]phenyl}sulfonyl)amino]-3-{1-methyl-3-[3-(2-pyridylamino)propyl](1H-indazol-6-yl)}carbonylamino)propanoate Step B: Synthesis of methyl (2S)-2-{[(4-{3-[N-(2-aminoethyl)carbamoyl]propoxy}-2,6-dimethylphenyl)sulfonyl]amino}-3-({1-methyl-3-[3-(2-3,4,5,6-tetrahydropyridyl amino)propyl](1H-indazol-6-yl)}carbonylamino)propanoate

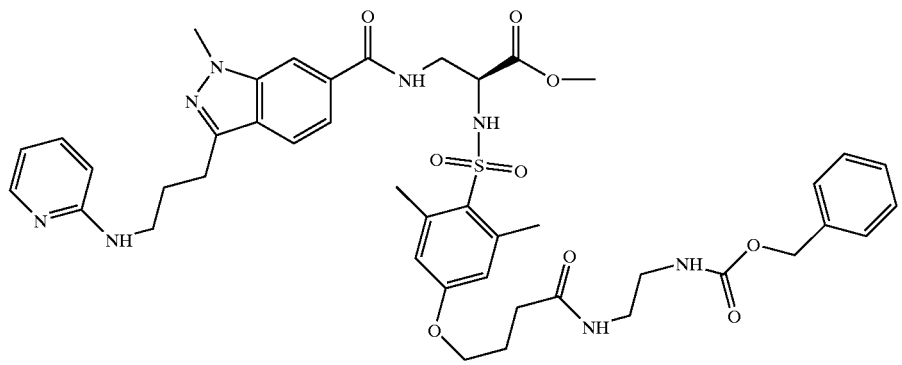

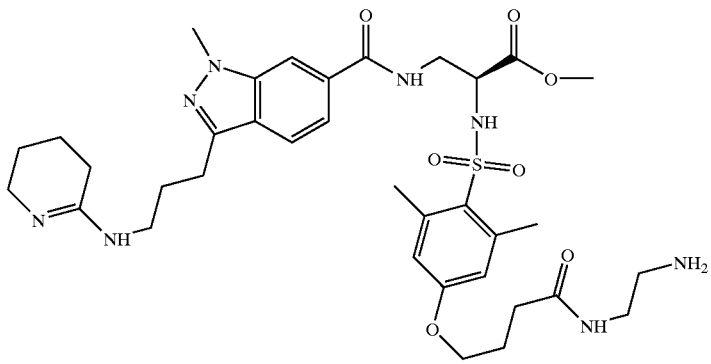

In a Parr bottle were added 10% Pd/C (50 mg) and methanol (5 mL) under nitrogen. The product of Step A (113 mg, 116 mmol) in methanol (5 mL) was added, along with 20 uL of trifluoroacetic acid. The mixture was hydrogenated at 50 psi with shaking for 7.5 hours, filtered through Celite, the Celite rinsed with methanol, and the combined filtrates concentrated. The residue was redissolved in 1:1 acetonitrile/water/0.1% TFA, frozen and lyophilized to afford the product as a white powder (98 mg, 88%). LRMS (ES): 727.3 ([M+H]$^+$, 25%), 364.2 ([M+2H]$^{+2}$, 100%). HRMS: Calculated for $C_{35}H_{51}N_8O_7S$: 727.3601; Found: 727.3613.

Step C: Synthesis of tert-butyl (4S)-4-[N-(2-{4-[4-({[1S)-1-(methoxycarbonyl)-2-({-methyl-3-[3-(2-3,4,5,6-tetrahydropyridylamino)propyl](1H-indazol-6-yl)}carbonylamino)ethyl]amino}sulfonyl)-3,5-dimethylphenoxy]butanoylamino}ethyl)carbamoyl]-4-[(phenylmethoxy)carbonylamino]butanoate Step D: Synthesis of tert-butyl (4S)-4-{(2S)-4-[(tert-butyl)oxycarbonyl]-2-[(phenylmethoxy)carbonylamino]butanoylamino}-4-[N-(2-{4-[4-({[(1S)-1-(methoxycarbonyl)-2-({1-methyl-3-[3-(2-3,4,5,6-tetrahydropyridylamino)propyl](1H-indazol-6-yl)}carbonylamino)ethyl]amino}sulfonyl)-3,5-dimethylphenoxy]butanoylamino}ethyl)carbamoyl]butanoate

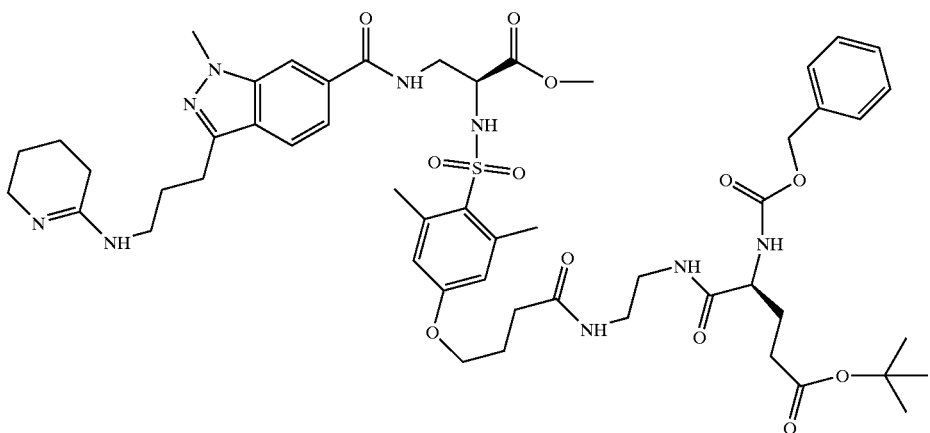

The product of step B (98 mg, 102 umol) is reacted as in Example 40, Step E cm, 90% acetonitrile/water/0.1%/TFA; 10–70% B over 25 minutes). The product fractions were frozen and lyophilized to afford the desired product as a white powder (103 mg, 96%). LRMS (ES): 1046.5 ([M+H]$^+$, 100%), 495.9 ([(M−tBu)+2H]$^{+2}$, 60%).

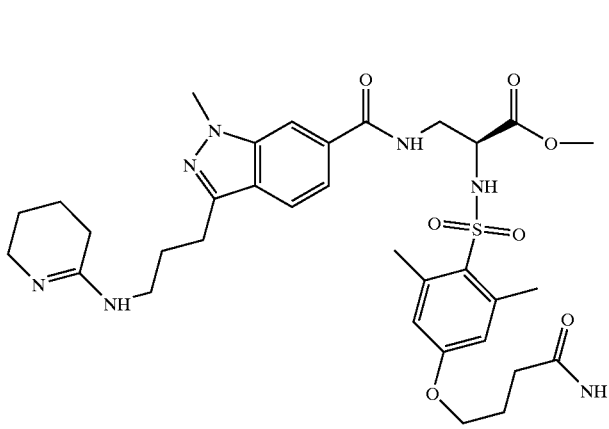
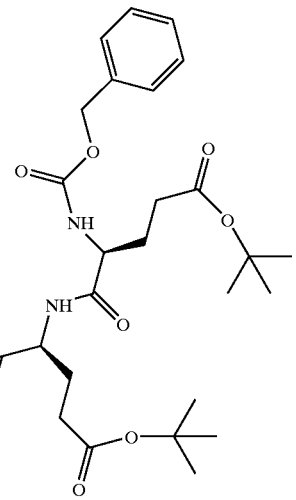

The product of step C (97 mg, 83 umol) was treated as in Example 37, StepB to afford the crude deprotected amine (87 mg). This was then reacted as in Example 40, Step E and purified by preparative HPLC (Zorbax C8, 21.2 mm×25 cm, 90% acetonitrile/water/0.1% TFA; 20–80% B over 30 minutes). The product fractions were frozen and lyophilized to afford the desired product as a white powder (77 mg, 76%). LRMS (ES): 1231.6 ([M+H]$^+$, 90%), 616.4 ([M+2H]$^+_2$, 40%), 588.4 ([(M−tBu)+2H]$^{+2}$, 50%), 495.9 ([(M−2tBu)+2H]$^{+2}$, 100%).

Step E: Synthesis of tert-butyl (4S)-4-(N-{(1S)-1-[N-(2-{4-[4-({[(1S)-1-(methoxycarbonyl)-2-({1-methyl-3-[3-(2-3,4,5,6-tetrahydropyridylamino)propyl](1H-indazol-6-yl)}carbonylamino)ethyl]amino}sulfonyl)-3,5-dimethylphenoxy]butanoylamino}ethyl)carbamoyl]-3-[(tert-butyl)oxycarbonyl]propyl)carbamoyl]-4-[2-(1,4,7,10-tetraaza-4,7,10-tris {([(tert-butyl)oxycarbonyl]methyl}cyclododecyl)acetylamino]butanoate The product of step D (71 mg, 53 umol) was treated as in Example 37, Step B to afford the crude deprotected amine (64 mg). This was then reacted with DOTA(OtBu)$_3$—OH (29.5 mg, 52 umol) as in Example 40, Step I and the crude product purified by preparative HPLC (Vydac C18, 21.2 mm×25 cm, 90% acetonitrile/0.1% TFA; 20–75% B over 45 minutes). The product fractions were frozen and lyophilized to afford the desired product as a white powder (62 mg, 75%). LRMS (ES): 1651.9 ([M+H]$^+$, 5%), 826.7 ([M+2H]$^+_2$, 30%), 532.8 ([(M−tBu)+3H]$^{+3}$, 25%), 514.9 ([(M−2tBu)+3H]$^{+3}$, 100%), 495.4 ([(M−3tBu)+3H]$^{+3}$, 60%).

Step F: Synthesis of (4S)-4-(N-{1-[N-(2-{4-[4-({[(1S)-1-carboxy-2-({1-methyl-3-[3-(2-3,4,5,6-tetrahydropyridylamino)propyl](1H-indazol-6-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid

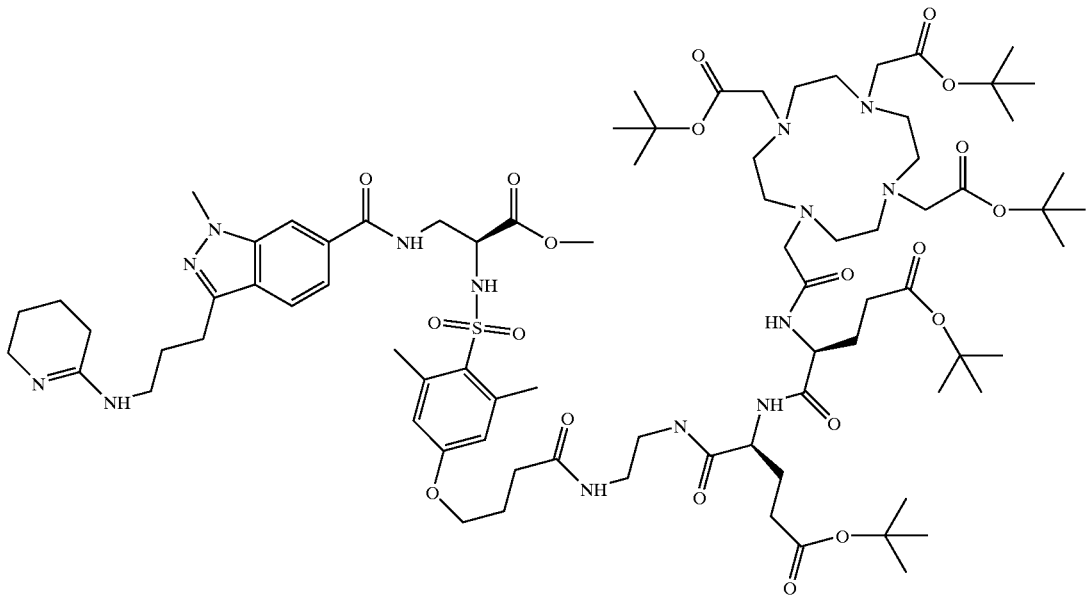

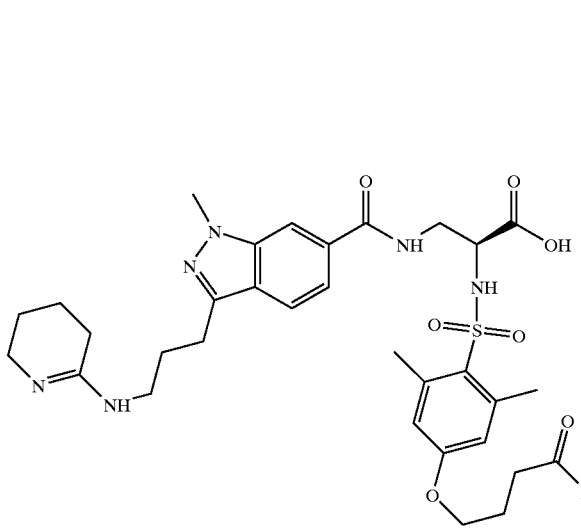
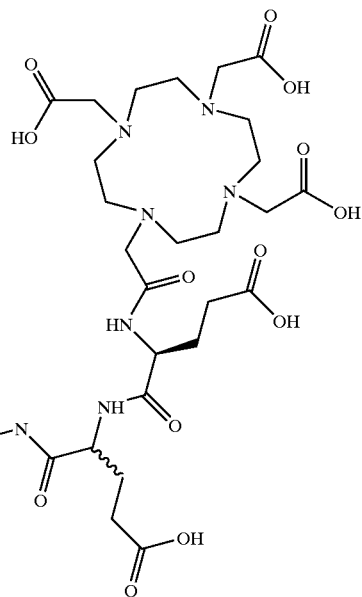

The product of step E (42 mg, 25 umol) was treated as in Example 40, Step J and the crude product purified by preparative HPLC (Zorbax CN, 21.2 mm×25 cm, 50% acetonitrile/water/0.1% formic acid; 20–35% B over 60 minutes). The product fractions were combined, frozen, and lyophilized to afford the product as a white solid (11 mg, 48%). LRMS (EI); 1357.6 ([M+H]$^+$, 15%), 679.5 ([M+2H]$^+_2$, 100%), 453.3 ([M+3H]$^{+3}$, 40%).

Example 42

Synthesis of (4S)-4-(N-{(1S)-1-[N-(2-{4-[4-({[(1S)-1-carboxy-2-({1-[2-(2-3,4,5,6-tetrahydropyridylamino)ethyl](1H-indazol-5-yl)}carbonylamino)ethyl]amino}sulfonyl)-3,5-dimethylphenoxy]butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid

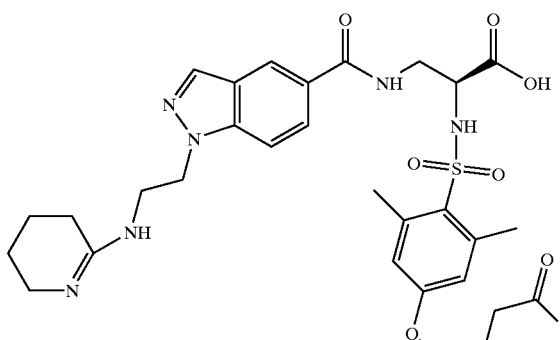
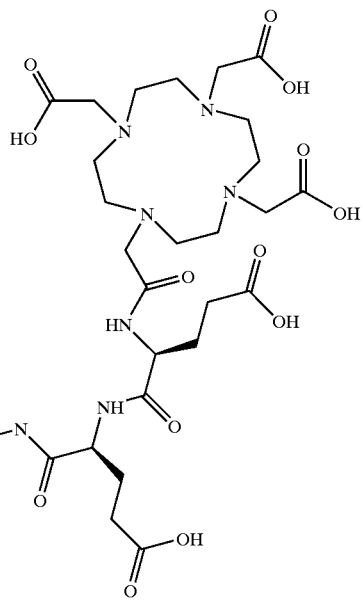

Step A: Synthesis of ethyl 1-[2-(1,3-dioxoisoindolin-2-yl)ethyl]-1H-indazole-5-carboxylate and ethyl 2-[2-(1,3-dioxoisoindolin-2-yl)ethyl]-1H-indazole-5-carboxylate

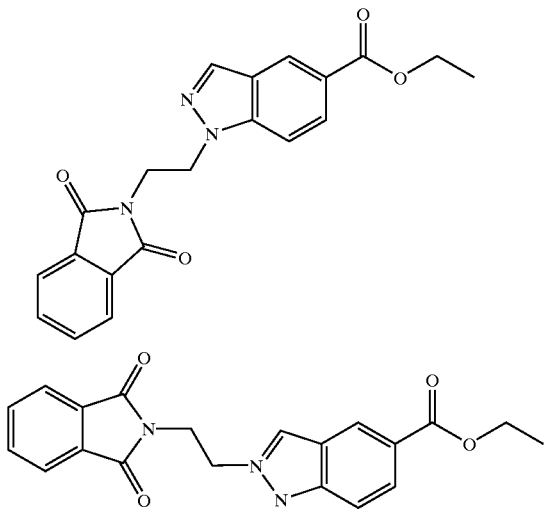

Ethyl 1H-indazole-5-carboxylate (1.5 g, 7.9 mmol) and 18-crown-6 (45 mg) were added to dry THF (45 mL) in flame-dried glassware under nitrogen. Sodium bis(trimethylsilyl)amide (8.7 mL of 1M solution in THF, 8.7 mmol) was added via syringe, followed by N-(2-bromoethyl)phthalimide (2.5 g, 9.8 mmol). The reaction was heated at reflux temperature for 22 hr, cooled, and concentrated under vacuum. The residue was partitioned between toluene and water, separated, and the aqueous layer extracted with ethyl acetate. The combined organics were washed with water and brine, dried over sodium sulfate, filtered and concentrated to afford 3.5 g of an oil. This was purified by flash chromatography (toluene—ethyl acetate gradient), collecting two separate products which were concentrated to yield the products as oils which solidified on standing. The 1-substituted indazole eluted first (980 mg), followed by the 2-substituted analog (600 mg) for a combined yield of 55%. Their mass spectra were identical. LRMS (ES): 364.1 ([M+H]$^+$, 100%), 386.1 ([M+Na]$^+$, 15%)

Step B: Synthesis of ethyl 1-(2-aminoethyl)-1H-indazole-5-carboxylate

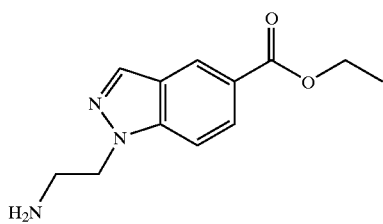

Ethyl 1-[2-(1,3-dioxoisoindolin-2-yl)ethyl]-1H-indazole-5-carboxylate (step A, 980 mg, 2.7 mmol) was dissolved in ethanol/THF (1:1, 35 mL) under nitrogen. Hydrazine (365 uL) was added and the reaction stirred 17 hours. THF (75 mL) was added and the resulting solids were filtered off. The filtrate was concentrated to an orange solid, which was purified by flash chromatography (dichoromethane/5% methanol/0.5% triethylamine). The product fractions were combined and concentrated to an orange solid (404 mg, 66%). LRMS (ES): 234.1 ([M+H]$^+$, 100%)

Step C: Synthesis of ethyl 1-{2-[(1-hydroxy-2-pyridyl)amino]ethyl}-1H-indazole-5-carboxylate

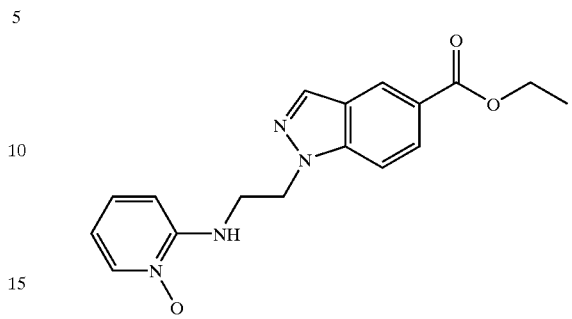

Ethyl 1-(2-aminoethyl)-1H-indazole-5-carboxylate (584 mg, 2.5 mmol, prepared as in step B), was added to dry n-butanol along with 2-chloropyridine-N-oxide hydrochloride (847 mg, 5.1 mmol) and anhydrous sodium bicarbonate (850 mg, 10.1 mmol). The reaction mixture was vigorously stirred and heated at 100C for 21 hr. Additional aliquots of 2-chloropyridine-N-oxide hydrochloride (847 mg, 5.1 mmol) and anhydrous sodium bicarbonate (850 mg, 10.1 mmol) were added and heating continued for 24 hours. The reaction was cooled and filtered and the filtrate concentrated. The residue was purified by flash chromatography (5% methanol-dichloromethane) and the product fractions concentrated to afford the product as an orange solid (358 mg, 44%). LRMS (ES): 327.1 ([M+H]$^+$, 100%), 653.3 ([2M+H]$^+$, 40%) $^1$HNMR (600.1343 MHz, CDCl$_3$): 8.44 (s, 1H), 8.12 (s, 1H), 7.97 (d of t, 2H), 7.56 (bs, 1H), 7.45 (d, 1H), 7.06, (m, 1H), 6.45 (m, 1H), 6.35 (t, 1H), 4.68 (t, 2H), 4.37 (q, 2H), 3.90 (q, 2H), 1.39 (t, 3H).

Step D: Synthesis of 1-{2-[(1-oxy-2-pyridyl)amino]ethyl}-1H-indazole-5-carboxylic acid

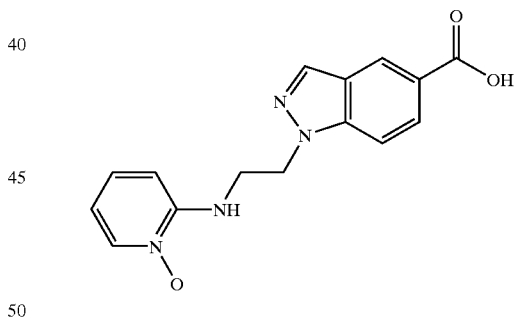

The product of step C (349 mg, 1.07 mmol) was dissolved in ethanol (35 mL) and 1N sodium hydroxide solution (6.0 mL, 6 mmol) added. The solution was heated at reflux for 75 min, the volume reduced by half, and water (30 mL) added. 1N hydrochloric acid was added to pH=3 and the remaining ethanol concentrated under vacuum. The resulting solids were filtered and dried under vacuum to afford the product as an off-white solid (163 mg, 51%). LRMS (ES): 299.2 ([M+H]$^+$, 100%).

Step E: Synthesis of methyl (2S)-2-[({2,6-dimethyl-4-[3-(N-{2-[(phenylmethoxy)carbonylamino]ethyl}carbamoyl)propoxy]phenyl}sulfonyl)amino]-3-[(1-{2-[(1-oxy(2-pyridyl))amino]ethyl}(1H-indazol-5-yl))carbonylamino]propanoate

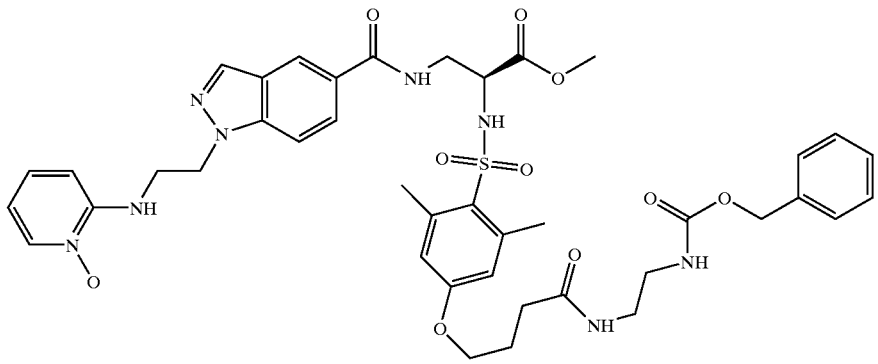

The product of step D (137 mg, 460 umol) was dissolved in DMF with the product of Example 34, Step B (312 mg, 460 umol), and HBTU (209 mg, 552 umol) under nitrogen. Diisopropylethylamine (240 uL, 1.4 mmol) was added and the reaction was stirred for 50 minutes. The solution was concentrated and purified by preparative HPLC (Vydac C-18, 5 cm×25 cm, 80 mL/min, 90% acetonitrile/water/ 0.1% trifluoroacetic acid; 20–55% B over 40 minutes). The product fractions were combined, frozen, and lyophilized to afford the product as a white solid (238 mg, 54%). LRMS (EI); 845.3 ([M+H]$^+$, 100%), 1690.6 ([2M+H]$^+$, 10%), 711.3 ([(M−Z)+H]$^+$, 30%).

Step F: Synthesis of (2S)-2-{[(4-{3-[1N-(2-aminoethyl) carbamoyl]propoxy}-2,6-dimethylphenyl)sulfonyl]amino}-3-({1-[2-(2-3,4,5,6-tetrahydropyridylamino)ethyl](1H-indazol-5-yl)}carbonylamino)propanoic acid and 3N lithium hydroxide solution (720 uL, 2.1 mmol) added. The solution was stirred for 1 hour, acidified to pH=2 with trifluoroacetic acid and concentrated. The residue was purified by preparative HPLC (Vydac C-18, 21.2 mm×25 cm, 90% acetonitrile/water/0.1% trifluoroacetic acid; 5–30% B over 50 minutes). The product fractions were combined, frozen, and lyophilized to afford the product as a white solid (38 mg, 26%). LRMS (EI); 685.3 ([M+H]$^+$, 100%).

Step G: Synthesis of (2S)-2-{[(4-{3-[N-(2-{(2S)-4-[(tert-butyl)oxycarbonyl]-2-[(phenylmethoxy)carbonylamino] butanoylamino}ethyl)carbamoyl]propoxy}-2,6-dimethylphenyl)sulfonyl]amino}-3-({1-[2-(2-3,4,5,6-tetrahydropyridylamino)ethyl](1H-indazol-5-yl) }carbonylamino)propanoic acid

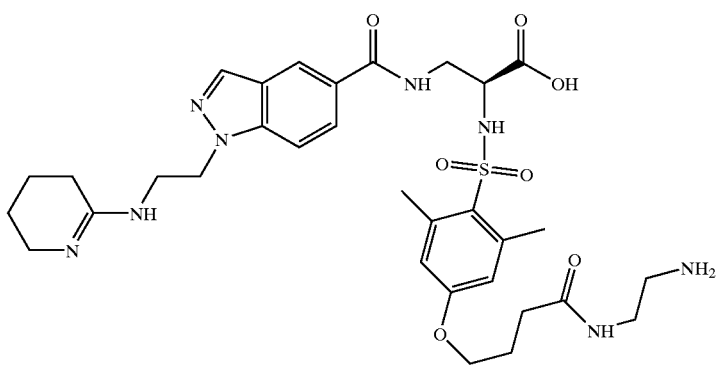

Into a Parr bottle under nitrogen was placed 10% palladium on carbon (100 mg), followed by methanol (10 mL). The product of step E (230 mg, 240 umol), dissolved in methanol (30 mL) was added and the reaction hydrogenated at 55 psi for 20 hours. Additional catalyst (50 mg) and trifluoroacetic acid (60 uL) were added and the hydrogenation continued for 34 hours. The reaction was filtered through Celite, rinsed, and the filtrates concentrated to yield 205 mg of an oil, which still contained some deprotected N-oxide. This oil was dissolved in water/THF (1:1, 1.5 mL)

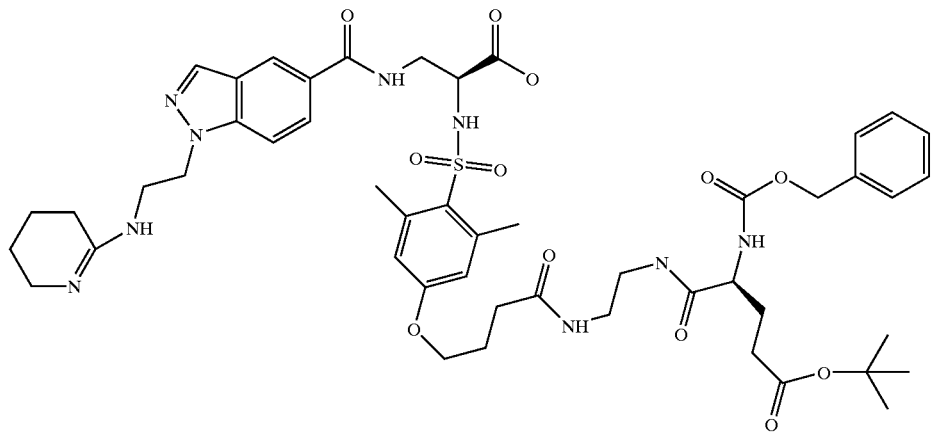

The product of Step F (125 mg, 183 umol) is treated as in Example 40, Step E. The product is obtained as a white solid after lyophilization.

Step H: Synthesis of (2S)-2-({[4-(3-{N-[2-((2S)-2-{(2S)-4-[(tert-butyl)oxycarbonyl]-2-[(phenylmethoxy)carbonylamino]butanoylamino}4-[(tert-butyl)oxycarbonyl]butanoylamino)ethyl]carbamoyl}propoxy)-2,6-dimethylphenyl]sulfonyl}amino)-3-({1-[2-(2-3,4,5,6-tetrahydropyridylamino)ethyl](1H-indazol-5-yl)}carbonylamino)propanoic acid

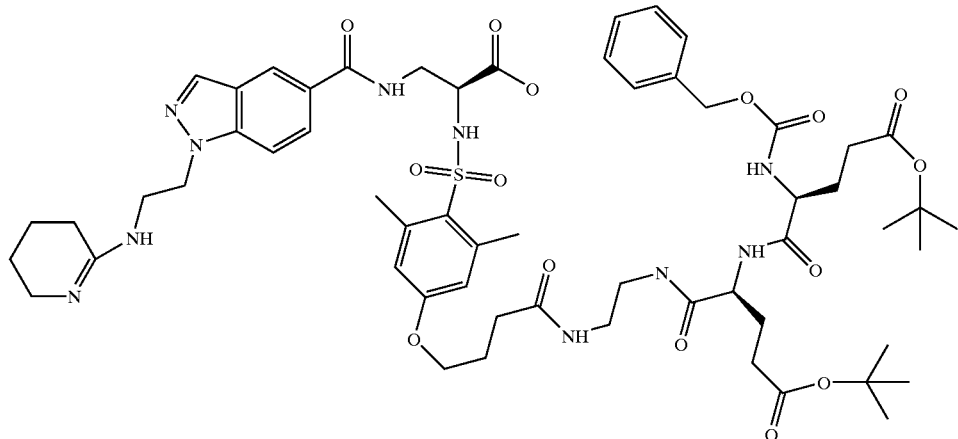

The product of Step G is treated as in Example 40, Step F. The residue is not purified but treated directly as in Example 40, Step G. The product is obtained as a white solid after lyophilization.

Step I: Synthesis of tert-butyl (4S)-4-(N-{(1S)-1-[N-(2-{4-[4-({[(1S)-1-(methoxycarbonyl)-2-({1-[2-(2-3,4,5,6-tetrahydropyridylamino)ethyl](1H-indazol-5-yl)}carbonylamino)ethyl]amino}sulfonyl)-3,5-dimethylphenoxy]butanoylamino}ethyl)carbamoyl]-3-[(tert-butyl)oxycarbonyl]propyl}carbamoyl)-4-[2-(1,4,7,10-tetraaza-4,7,10-tris{[(tert-butyl)oxycarbonyl]methyl}cyclododecyl)acetylamino]butanoate

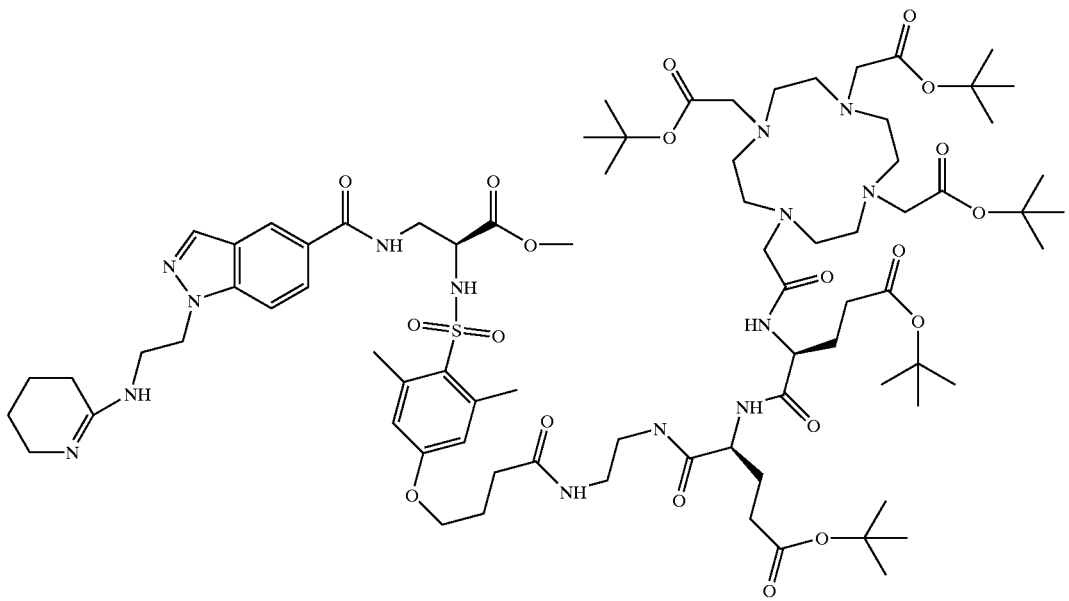

The product of Step H is treated as in Example 40, Step H. The residue is not purified but coupled directly with DOTA(OtBu)3—OH as in Example 40, step I. The product is obtained as a white solid after lyophilization.

Step J: Synthesis of (4S)-4-(N-{(1S)-1-[N-(2-{4-[4-({[(1S)-1-carboxy-2-({1-(2-(2-3,4,5,6-tetrahydropyridylamino) ethyl](1H-indazol-5-yl)}carbonylamino)ethyl] amino}sulfonyl)-3,5-dimethylphenoxy] butanoylamino}ethyl)carbamoyl]-3-carboxypropyl}carbamoyl)-4-{2-[1,4,7,10-tetraaza-4,7,10-tris(carboxymethyl)cyclododecyl]acetylamino}butanoic acid The product of step I is treated as in Example 40, Step J and the crude product is purified by preparative HPLC (Zorbax CN, 21.2 mm×25 cm, 50% acetonitrile/water/0.1% formic acid; 20–35% B over 60 minutes). The product fractions are combined, frozen, and lyophilized to afford the product as a white solid

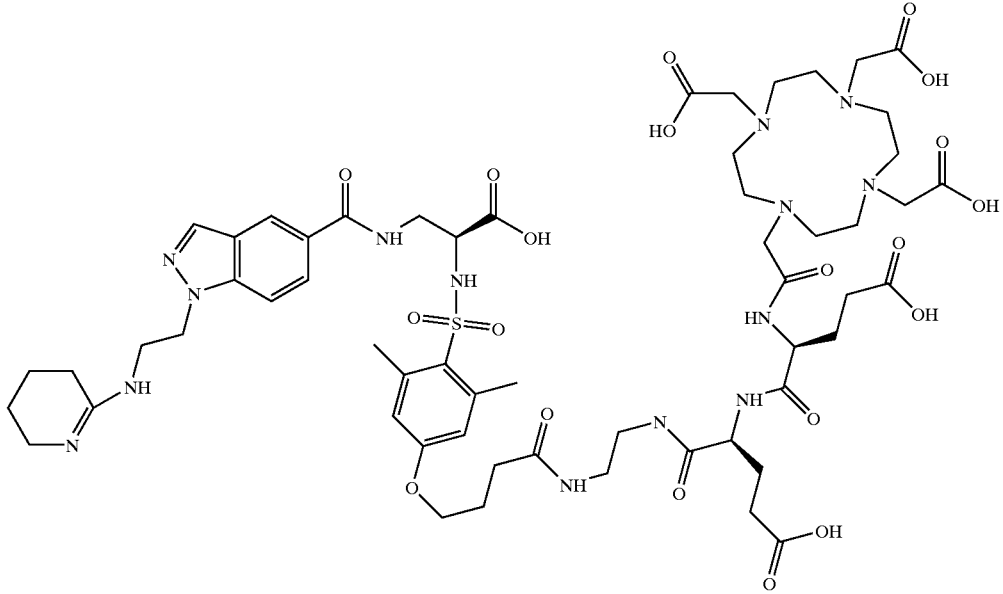

Example 43

Synthesis of (2S)-2-{[(2,6-dimethyl-4-{3-[N-(2-{2-[1,4,7,10tetraaza-4,7,10-tris(carboxymethyl)cyclododecyl]acetylamino}ethyl)carbamoyl]propoxy}phenyl)sulfonyl]amino}-3-({2-[2-(2-3,4,5,6-tetrahydropyridylamino)ethyl](2-hydro-1H-indazol-5-yl)}carbonylamino)propanoic acid

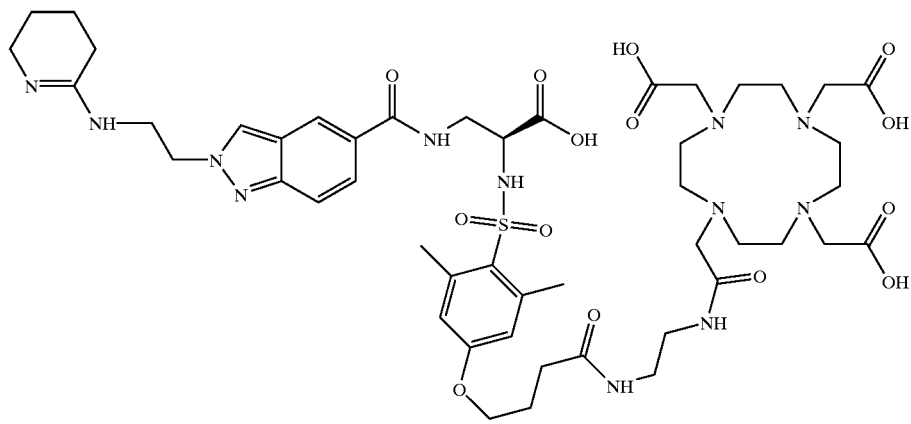

Step A: Synthesis of ethyl 2-(2-aminoethyl)-2-hydro-1H-indazole-5-carboxylate

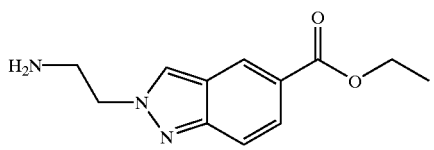

The slower eluting product of Example 42, Step A (600 mg, 1.65 mmol) was treated as in Example 42, Step B to afford the product as a single pure compound (164 mg, 43%). LRMS (ES): 234.2 ([M+H]$^+$, 100%).

Step B: Synthesis of ethyl 2-{2-[(1-hydroxy-2-pyridyl)amino]ethyl}-2-hydro-1H-indazole-5-carboxylate

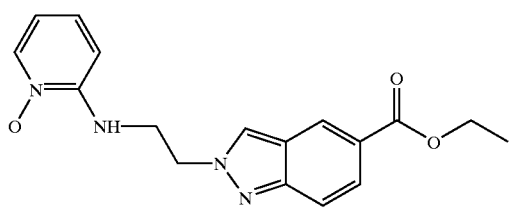

The product of step A (249 mg, 1.07 mmol) was treated as in Example 42, Step C to afford the product in 80% purity after flash chromatography. This was purified by preparative HPLC (Vydac C18, 21.2 mm×25cm, 90% acetonitrile/0.1% TFA; 10–55% B over 25 minutes). The product fractions were frozen and lyophilized to afford the desired product as a white powder (204 mg, 43%). LRMS (ES): 327.2 ([M+H]$^+$, 100%), 653.3 ([2M+H]$^+$, 40%).

Step C: Synthesis of 2-{2-[(1-hydroxy-2-pyridyl)amino]ethyl}-2-hydro-1H-indazole-5-carboxylic acid

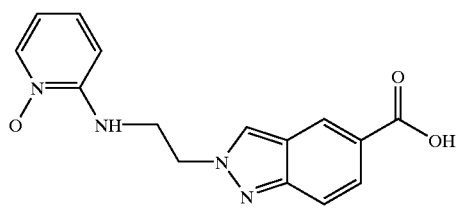

The product of step B (202 mg, 461 umol) was treated as in Example 42, Step D to afford the product as a white powder after filtration (138 mg, 100%). LRMS (ES): 299.2 ([M+H]$^+$, 100%).

Step D: Synthesis of methyl (2S)-2-[({2,6-dimethyl-4-[3-(N-{2-[(phenylmethoxy)carbonylamino]ethyl}carbamoyl)propoxy]phenyl}sulfonyl)amino]-3-[(2-{2-[(1-oxy(2-pyridyl))amino]ethyl}(2-hydro-1H-indazol-5-yl))carbonylamino]propanoate

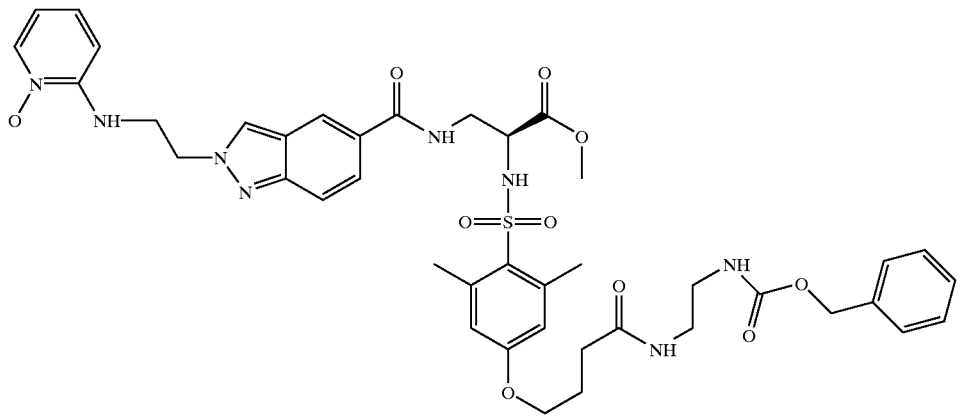

The product of step C (35mg, 116 umol) was treated as in Example 42, Step E to afford the product as a white powder after lyophilization (64 mg, 58%). LRMS (ES): 845.3 ([M+H]$^+$, 100%). HRMS: Calculated for $C_{41}H_{49}N_8O_{10}S$: 845.3292; Found: 845.3264.

Step E: Synthesis of methyl (2S)-2-{[(4-{3-[N-(2-aminoethyl)carbamoyl]propoxy}-2,6-dimethylphenyl) sulfonyl]amino}-3-({2-[2-(2-3,4,5,6-tetahydropyridylamino)ethyl](2-hydro-1H-indazol-5-yl) }carbonylamino)propanoate

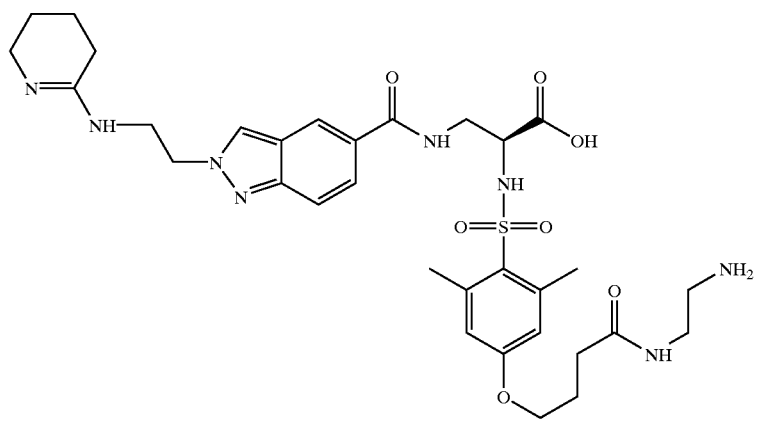

The product of step D (25 mg, 26 umol) was treated as in Example 42, Step F to afford the product as a white powder after lyophilization (11 mg, 52%). LRMS (ES): 685.3 ([M+H]$^+$, 100%).

Step F: Synthesis of methyl (2S)-2-[({2,6-dimethyl-4-[3-(N-{2-[2-(1,4,7,10-tetraaza-4,7,10-tris{[(tert-butyl) oxycarbonyl]methyl}cyclododecyl)acetylamino] ethyl}carbamoyl)propoxy]phenyl}sulfonyl)amino]-3-({2-[2-(2-3,4,5,6-tetrahydropyridylamino)ethyl](2-hydro-1H-indazol-5-yl)}carbonylamino) propanoate

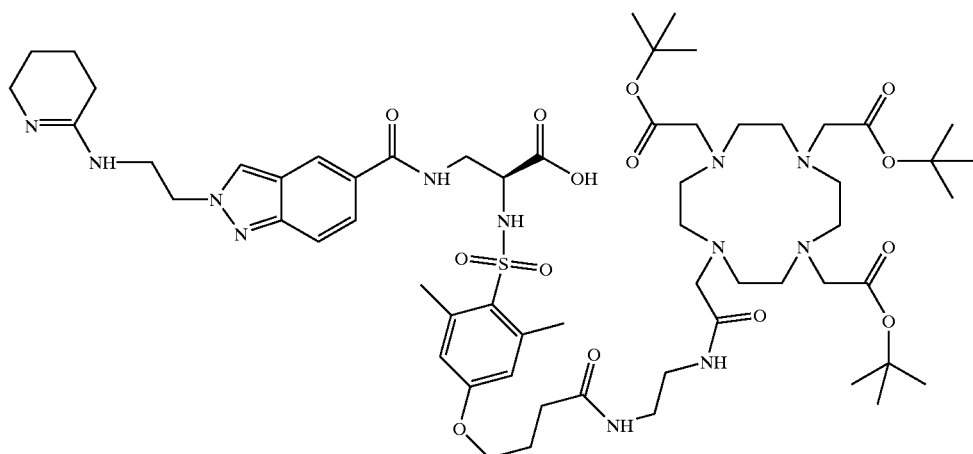

The product of Step E (11 mg, 15 umol) is reacted with DOTA(OtBu)3—OH (10 mg, 17 umol) as in Example 37, Step F, to afford the product as a pure compound after purification and lyophilization.

Step G: Synthesis of (2S)-2-{[(2,6-dimethyl-4-{3-[N-(2-{2-[1,4,7,10-tetraaza-4,7,10-tris(carboxymethyl)cyclododecyl]acetylamino}ethyl)carbamoyl]propoxy}phenyl)sulfonyl]amino}-3-({2-[2-(2-3,4,5,6-tetrahydropyridylamino)ethyl](2-hydro-1H-indazol-5-yl)}carbonylamino)propanoic acid

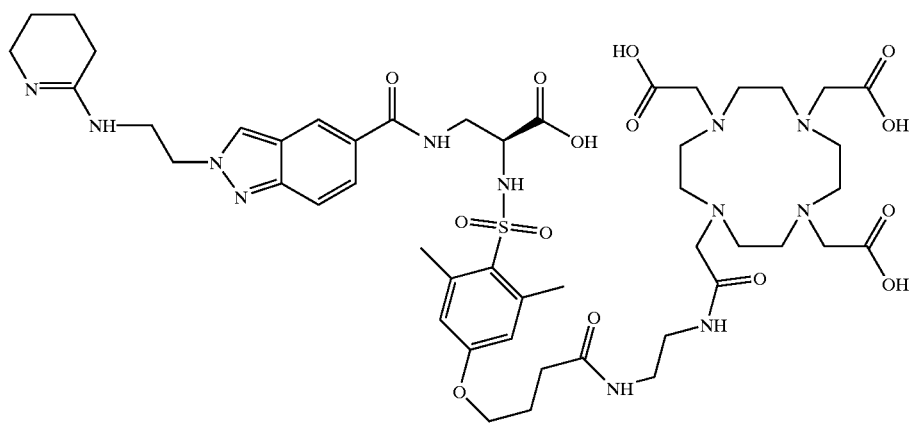

The product of Step F (12 mg, 9.7 umol) is deprotected as in Example 40, Step J, to afford the product as a pure compound after preparative HPLC purification and lyophilization of the product fractions.

Example 44

Synthesis of (4S)-4-{N-[(1S)-1-(N-{2-[({4-[4-({[(1S)-1-carboxy-2-({1-[2-(2-3,4,5,6-tetrahydropyridylamino)ethyl](1H-indazol-5-yl)}carbonylamino)ethyl]amino}sulfonyl)phenyl]phenyl}sulfonyl)amino]ethyl}carbamoyl)-3-carboxypropyl]carbamoyl)-4-{2-[1,4,7,10-tetraaza-4,7,10-tris(carboxy-methyl)cyclododecyl]acetylamino}butanoic acid

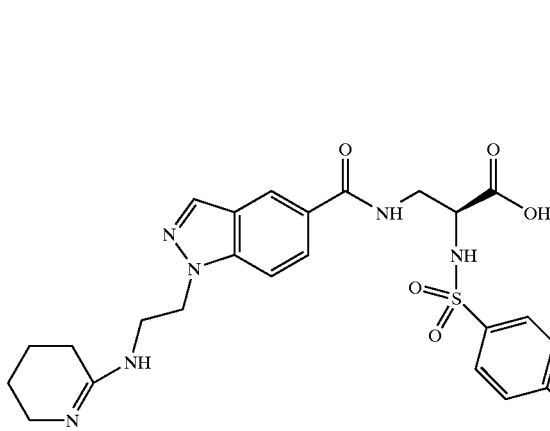
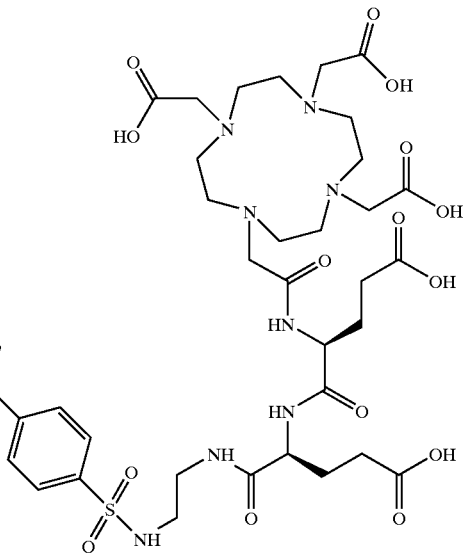

Step A: Synthesis of methyl (2S)-3-amino-2-{[(4-{4-[({2-[(phenylmethoxy)carbonylamino]ethyl}amino)sulfonyl]phenyl}phenyl)sulfonyl]amino}propanoate

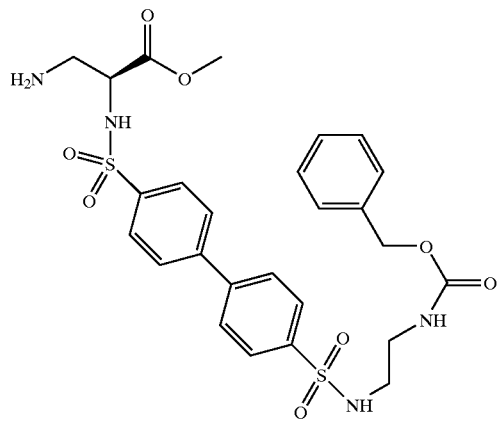

Biphenyl-4,4'-disulfonyl chloride (5.3 g, 15 mmol) was reacted with N-(2-aminoethyl)(phenylmethoxy) carboxamide (2.3 g, 10 mmol) and methyl (2S)-2-amino-3-[(tert-butoxy)carbonylamino]propanoate (5.1 g, 20 mmol) sequentially, in the same fashion as Step 1B, to afford 10.2 grams of the crude Boc-protected product after concentration of the organic extracts. This was directly dissolved in dichloromethane (100 mL) and trifluoroacetic acid (100 mL) added under nitrogen. The solution was stirred for 1 hour, concentrated and dissolved in acetonitrile. Addition of 0.1% trifluoroacetic acid resulted in a solid precipitate, which was filtered, and the filtrate was then purified by preparative HPLC (Vydac C-18, 5.5 cm×25 cm, 90% acetonitrile/water/0.1% trifluoroacetic acid, 80 mL/minute 0–70% B over 40 minutes). The product fractions were combined, frozen, and lyophilized to afford the product as a white solid (3.6 g, 50% for two steps). LRMS (ES): 591.1 ([M+H]$^+$, 100%). $^1$HNMR (600.1343 MHz, DMSO-d6): 8.1 (m, 3H), 7.97 (m, 4H), 7.91 (m, 4H), 7.83 (t, 1H), 7.30 (m, 5H), 4.98, (s, 2H), 4.25 (m, 1H), 3.35 (s, 3H), 3.15 (dd, 1H), 3.06 (m, 2H), 2.95 (dd, 1H), 2.83 (m, 2H).

Step B: Synthesis of methyl (2S)-3-[(1-{2-[(1-oxy(2-pyridyl))amino]ethyl}(1H-indazol-5-yl))carbonylamino]-2-{[(4-{4-[({2-[(phenylmethoxy)carbonylamino]ethyl}amino)sulfonyl]phenyl}phenyl)sulfonyl]amino}propanoate

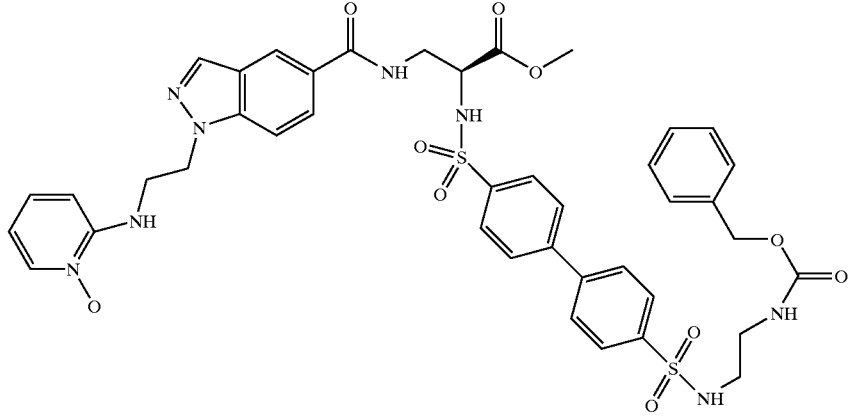

The product of Example 42, Step D (46 mg, 154 umol) was dissolved in dry DMF (2.5 mL) with the product of Step A (114 mg, 162 umol), HBTU (76 mg, 200 umol), and diisopropylethylamine (81 uL, 462 umol). The reaction was stirred for 1 hour, concentrated and the residue purified by preparative HPLC (Zorbax C-8, 21.2 mm×25 cm, 90% acetonitrile/water/0.1% trifluoroacetic acid; 20–60% B over 40 minutes). The product fractions were combined, frozen, and lyophilized to afford the product as a white solid (102 mg, 67%). LRMS (ES): 871.3 ([M+H]$^+$, 100%). HRMS: Calculated for $C_{41}H_{43}N_8O_{10}S_2$: 871.2544; Found: 871.2540.

Step C: Synthesis of methyl (2S)-2-({[4-(4-{[(2-aminoethyl)amino]sulfonyl}phenyl)phenyl]sulfonyl}amino)-3-({1-[2-(2-3,4,5,6-tetrahydropyridylamino)ethyl](1H-indazol-5-yl)}carbonylamino)propanoate

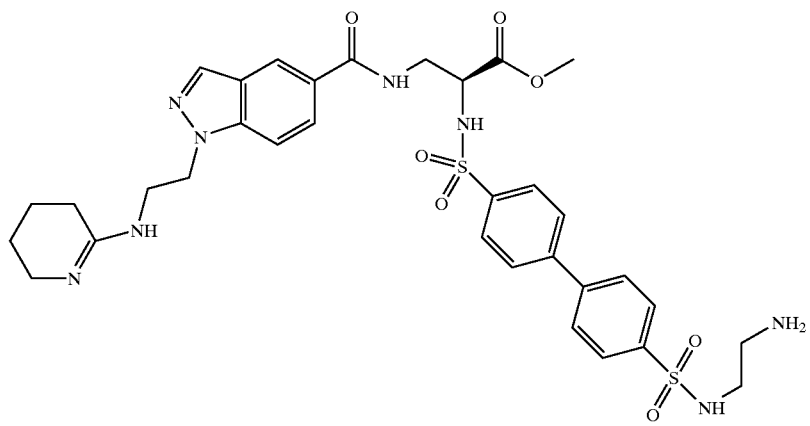

The product of Step B (75 mg, 76 umol) was treated as in Example 41, Step B and purified by preparative HPLC (Zorbax C-8, 21.2 mm×25 cm, 90% acetonitrile/water/0.1% trifluoroacetic acid; 15–25% B over 40 minutes). The product fractions were combined, frozen, and lyophilized to afford the product as a white solid (56 mg, 86%). LRMS (ES): 725.2 ([M+H]$^+$, 20%), 363.2 ([M+2H]$^{+2}$, 100%).

Step D: Synthesis of tert-butyl (4S)-4-(N-{2-[({4-[4-({[(1S)-1-(methoxycarbonyl)-2-(1-[2-(2-3,4,5,6-tetrahydropyridylamino)ethyl](1H-indazol-5-yl)}carbonylamino)ethyl]amino}sulfonyl)phenyl]phenyl}sulfonyl)amino]ethyl}carbamoyl)-4-[(phenylmethoxy)carbonylamino]butanoate

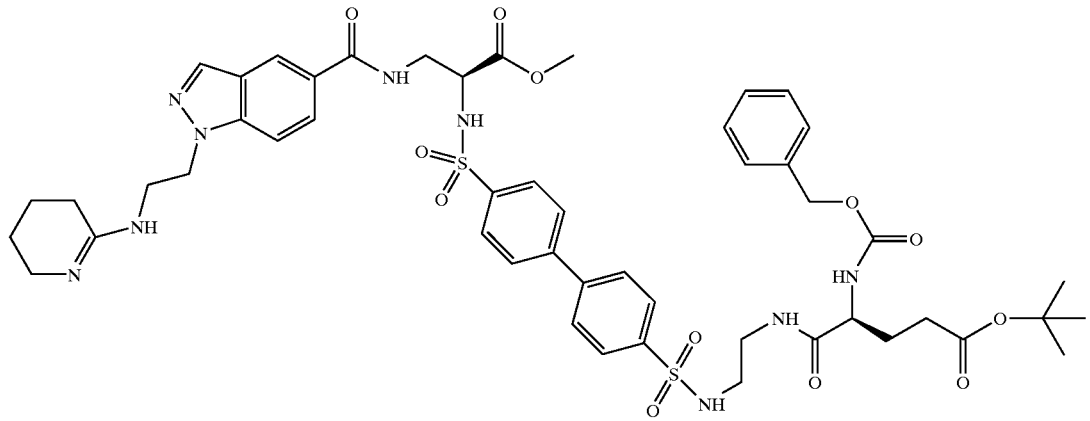

The product of Step C was reacted as in Example 40, Step E to afford the product as a white solid after lyophilization. LRMS Step E: Synthesis of tert-butyl (4S)-4-{(2S)-4-[(tert-butyl) oxycarbonyl]-2-[(phenytmethoxy)carbonylamino] butanoylamino}-4-(N-{2-[({4-[4-({[[(1S)-1-(methoxycarbonyl)-2-({1-[2-(2-3,4,5,6-tetrahydropyridylamino)ethyl](1H-indazol-5-yl)}carbonylamino)ethyl]amino}sulfonyl)phenyl]phenyl}sulfonyl)amino]ethyl}carbamoyl)butanoate Step G: Synthesis of (4S)-4-{N-[(1S)-1-(N-{2-[({4-[4-({[(1S)-1-carboxy-2-({1-[2-(2-3,4,5,6-tetrahydropyridylamino)ethyl](1H-indazol-5-yl)}carbonylamino)ethyl]amino}sulfonyl)phenyl]phenyl}sulfonyl)amino]ethyl}carbamoyl)-3-carboxypropyl]carbamoyl}-4-{2-[1,4,7,10-tetraaza-4,7,10-tris(carboxymethyl)cyclododecyl]acetylamino}butanoic acid

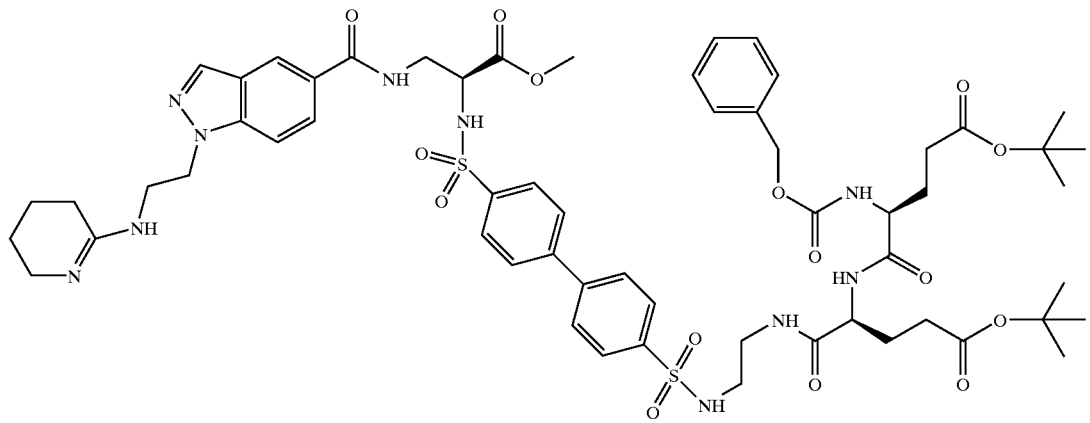

The product of Step D is treated as in Example 40, Step F to afford the product as a white solid after lyophilization.
Step F: Synthesis of tert-butyl (4S)-4-{N-[(1S)-1-(N-{2-[({4-[4-({[[(1S)-1-(methoxycarbonyl)-2-({1-[2-(2-(2,3,4,5,6-tetrahydropyridylamino)ethyl](1H-indazol-5-yl)}carbonylamino)ethyl]amino}sulfonyl)phenyl]phenyl}sulfonyl)amino]ethyl}carbamoyl)-3-[(tert-butyl)oxycarbonyl]propyl]carbamoyl}-4-[2-(1,4,7,10-tetraaza-4,7,10-tris{[(tert-butyl)oxycarbonyl]methyl}cyclododecyl)acetylamino]butanoate

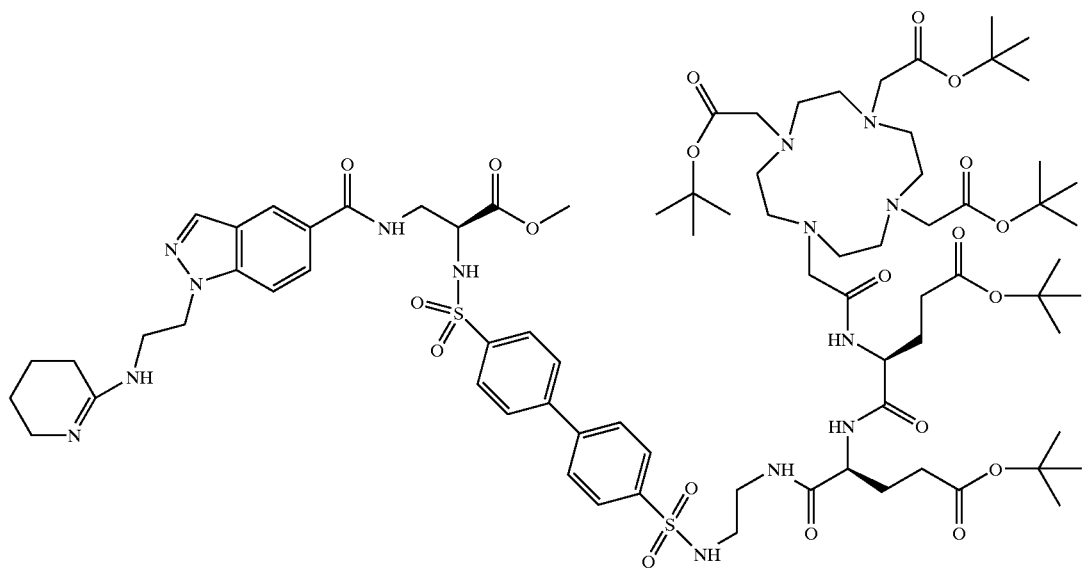

The product of Step E is treated as in Example 40, step G to afford the product as a white solid after lyophilization.

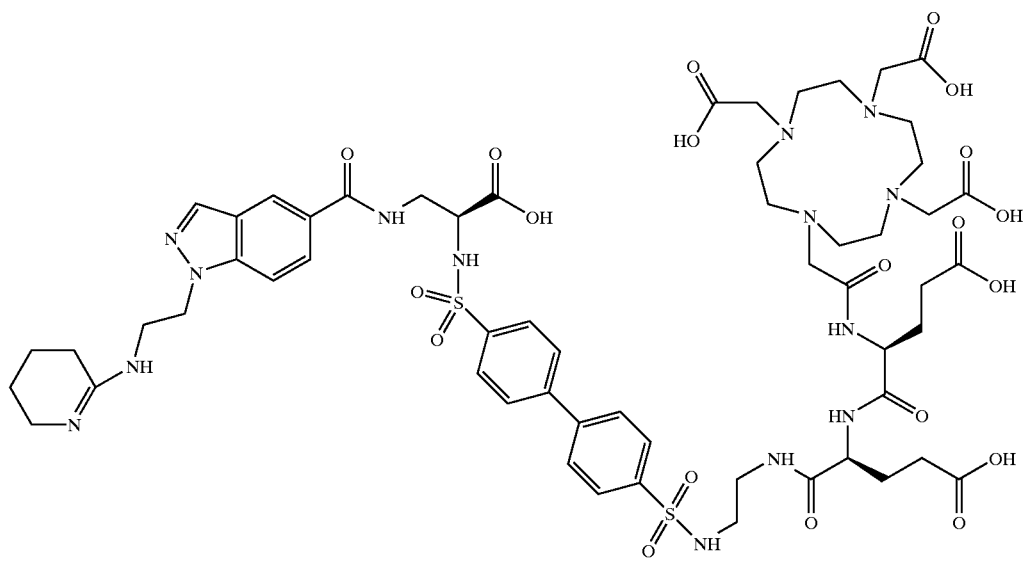

The product of Step F is treated as in Example 40, Step G to afford the product as a white solid after lyophilization.

Example 45

Synthesis of (4S)-4-{N-[(1S)-1-(N-{2-[({4-[4-({[(1S)-1-carboxy-2-({1-[3-(3,4,5,6-tetrahydropyrimidin-2-ylamino)propyl](1H-indazol-5-yl)}carbonylamino)ethyl]amino}sulfonyl)phenyl]phenyl}sulfonyl)amino]ethyl}carbamoyl)-3-carboxypropyl]carbamoyl}-4-{2-[1,4,7,10-tetraaza-4,7,10-tris(carboxymethyl)cyclododecyl]acetylamino}butanoic acid

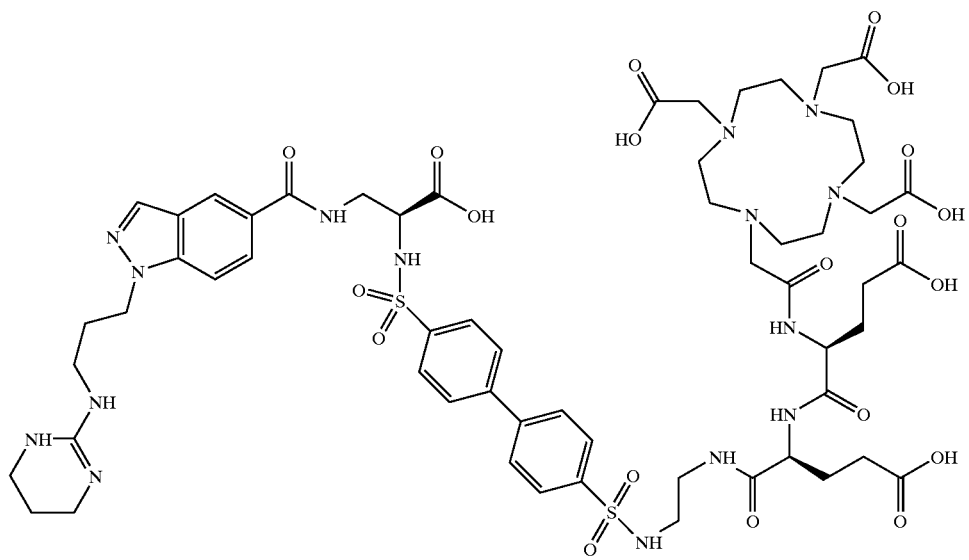

Step A: Synthesis of methyl (2S)-2-{[(4-{4-[({2-[(phenylmethoxy)carbonylamino]ethyl}amino)sulfonyl]phenyl}phenyl)sulfonyl]amino}-3-({1-[3-(pyrimidin-2-ylamino)propyl](1H-indazol-5-yl)}carbonylamino)propanoate

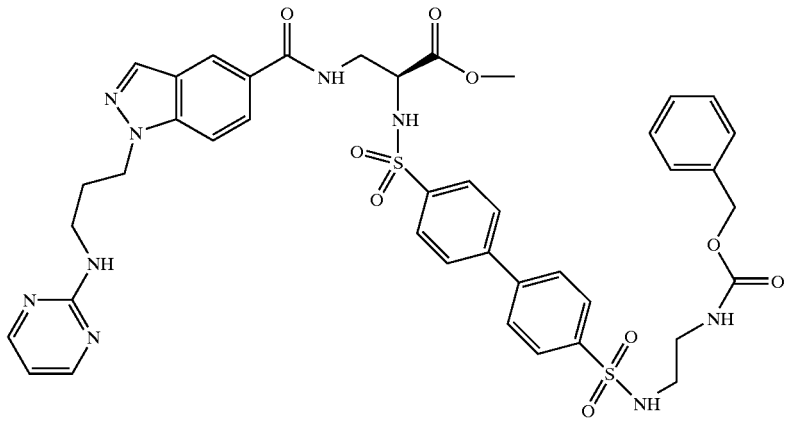

The product of Example 40, Step B (58 mg, 195 umol) was reacted with the product of Example 44, Step A (144 mg, 205 umol) as in Example 44, Step B and the residue purified by preparative HPLC (Vydac C-18, 21.2 mm×25 cm, 90% acetonitrile/water/0.1% trifluoroacetic acid; 10–70% B over 30 minutes). The product fractions were combined, frozen, and lyophilized to afford the product as a white solid (102 mg, 54%). LRMS (ES): 870.3 ([M+H]+, 100%). $^1$HNMR (600.1343 MHz, DMSO-d6): 8.52 (d, 1H), 8.51 (s, 1H), 8.29 (d, 1H), 8.17, (d, 1H), 7.82 (m, 9H), 7.74 (d, 1H), 7.64 (d, 1H), 7.49 (b, 1H), 7.31, (m, 6H), 6.61 (t, 1H), 4.98, (s, 2H), 4.46 (t, 2H), 4.19 (dd, 1H), 3.55 (m, 1H), 3.42 (m, 1H), 3.41 (s, 3H), 3.26 (t, 2H), 3.06 (t, 2H), 2.83 (m, 2H), 2.09 (m, 2H).

Step B: Synthesis of tert-butyl (4S)-4-(N-{2-[({4-[4-({[(1S)-1-(methoxycarbonyl)-2-({1-[3-(3,4,5,6-tetrahydropyrimidin-2-ylamino)propyl](1H-indazol-5-yl)}carbonylamino)ethyl]amino}sulfonyl)phenyl]phenyl}sulfonyl)amino]ethyl}carbamoyl)-4-[(phenylmethoxy)carbonylamino]butanoate The product of Step A (100 mg, 102 umol) was treated as in Example 41, Step B and the resulting solid (79 mg) directly reacted as in Example 40, Step E to afford the crude product as an oil, which was purified by preparative HPLC (Vydac C-18, 21.2 mm×25 cm, 90% acetonitrile/water/0.1% trifluoroacetic acid; 10–70% B over 40 minutes). The product fractions were combined, frozen, and lyophilized to afford the product as a white solid (98 mg, 80%). LRMS (ES): 1059.3 ([M+H]+, 100%).

Step C: Synthesis of tert-butyl (4S)-4-{(2S)-4-[(tert-butyl)oxycarbonyl]-2-[(phenylmethoxy)carbonylamino]butanoylamino}-4-(N-{2-[({4-[4-({[(1S)-1-(methoxycarbonyl)-2-({1-[3-(3,4,5,6-tetrahydropyrimidin-2-ylamino)propyl](1H-indazol-5-yl)}carbonylamino)ethyl]amino}sulfonyl)phenyl]phenyl}sulfonyl)amino]ethyl}carbamoyl)butanoate

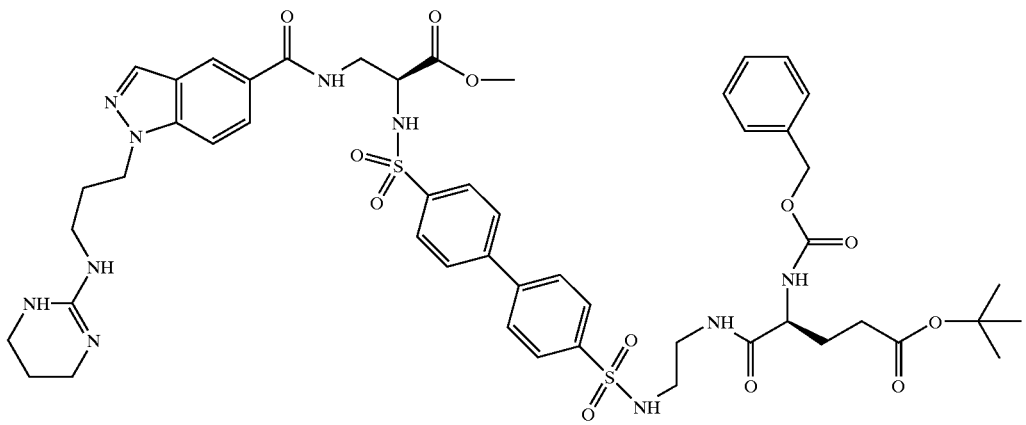

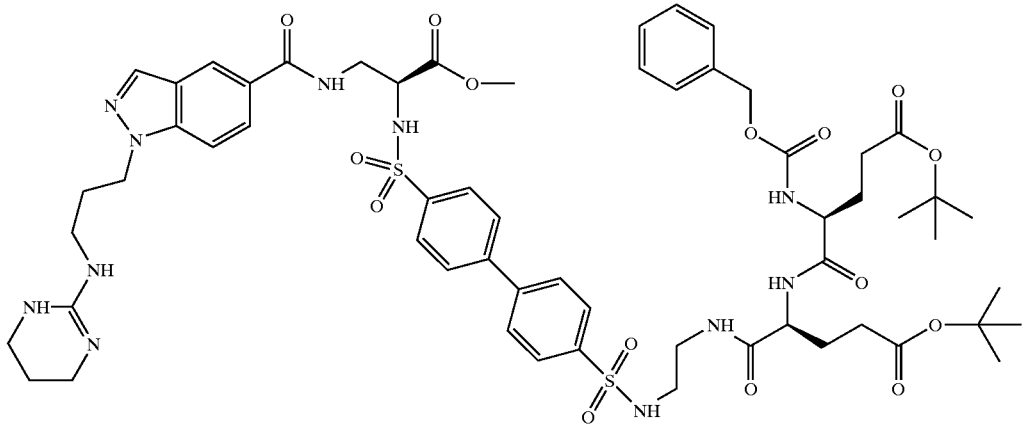

The product of Step B (96 mg, 82 umol) was treated as in Example 41, Step D to afford the product as a white solid (48 mg, 42%) after lyophilization. LRMS (ES): 1244.4 ([M+H]$^+$, 100%), 566.8 ([M−2tBu)+2H]$^{+2}$, 45%).

Step D: Synthesis of tert-butyl (4S)-4-{N-[(1S)-1-(N-{2-[({4-[4-({[(1S)-1-(methoxycarbonyl)-2-({1-[3-(3,4,5,6-tetrahydropyrimidin-2-ylamino)propyl](1H-indazol-5-yl)}carbonylamino)ethyl]amino}sulfonyl)phenyl]phenyl}sulfonyl)amino]ethyl}carbamoyl)-3-[(tert-butyl)oxycarbonyl]propyl]carbamoyl}-4-[2-(1,4,7,10-tetraaza-4,7,10-tris{[(tert-butyl)oxycarbonyl]methyl}cyclododecyl)acetylamino]butanoate ethyl}carbamoyl)-3-carboxypropyl]carbamoyl}-4-{2-[1,4,7,10-tetraza-4,7,10-tris(carboxymethyl)cyclododecyl]acetylamino}butanoic acid

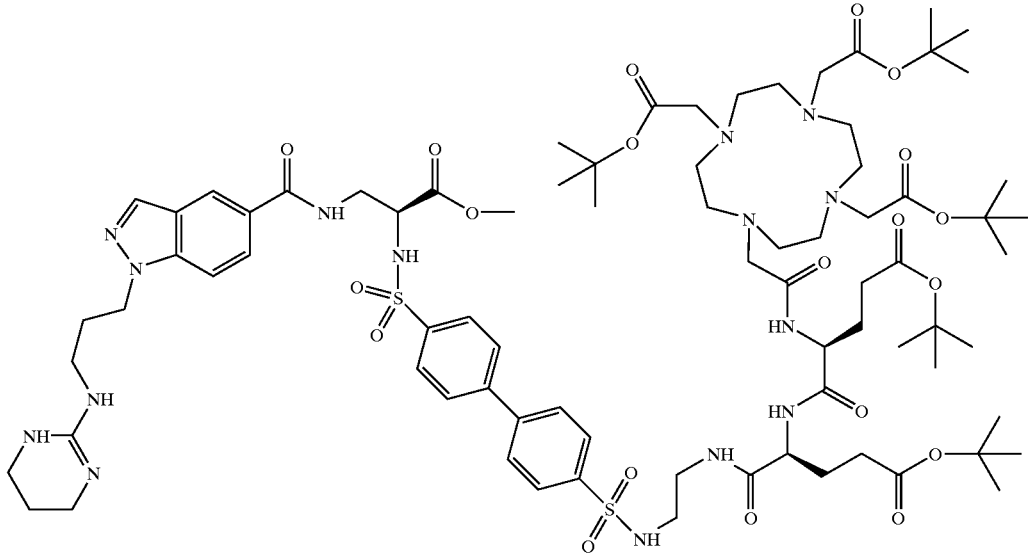

The product of Step C (47 mg, 35 umol) was treated as in Example 41, Step E to afford the product as a white solid (36 mg, 62%) after lyophilization. LRMS (ES): 1664.6 ([M+H]$^+$, 5%), 833.2 ([(M+2H]$^{+2}$, 60%), 518.4 ([(M−2tBu)+3H]$^{+3}$, 100%).

Step E: Synthesis of (4S)-4-{N-[(1S)-1-(N-{2-[({4-[4-({[(1S)-1-carboxy-2-({1-[3-(3,4,5,6-tetrahydropyrimidin-2-ylamino)propyl](1H-indazol-5-yl)}carbonylamino)ethyl]amino}sulfonyl)phenyl]phenyl}sulfonyl)amino]

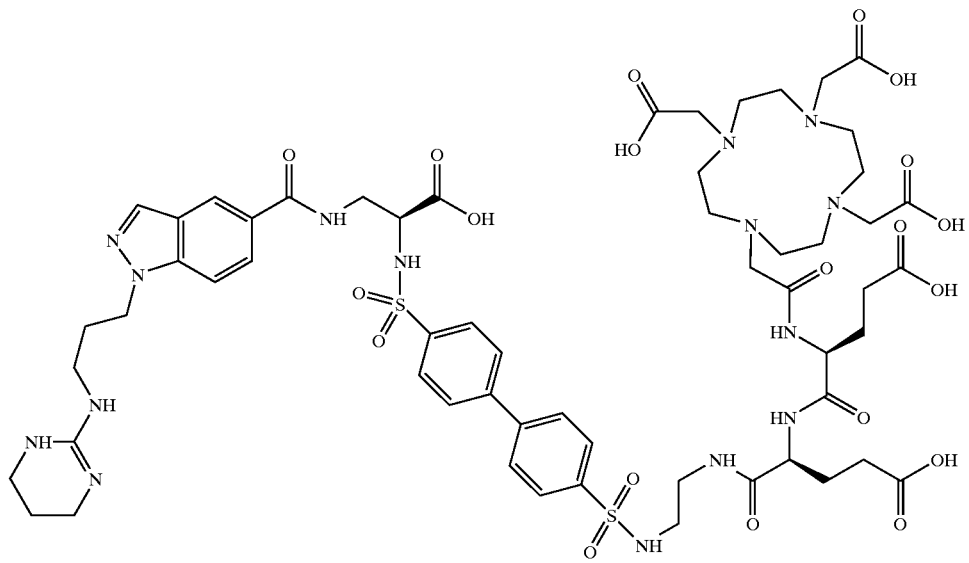

The product of Step D (29 mg, 15 umol) was treated as in Example 40, Step J to afford the crude product which was purified by preparative HPLC (Vydac C-18, 21.2 mm×25 cm, 90% acetonitrile/water/0.1% trifluoroacetic acid; 5–35% B over 35 minutes). The product fractions were combined, frozen, and lyophilized to afford the product as a white solid (11 mg, 46%) after lyophilization. LRMS (ES): 1370.4 ([M+H]$^+$, 10%), 685.8 ([(M+2H]$^{+2}$, 90%), 457.6 ([M+3H]$^{+3}$, 100%).

Example 46

Synthesis of (2S)-3-({3-[(imidazol-2-ylamino)methyl]-1-methyl(1H-indazol-6-yl)}carbonylamino)-2-({[4-(4-{[(2-{2-[1,4,7,10-tetraaza-4,7,10-tris(carboxymethyl)cyclododecyl]acetylamino}ethyl)amino]sulfonyl}phenyl)phenyl]sulfonyl}amino)propanoic acid

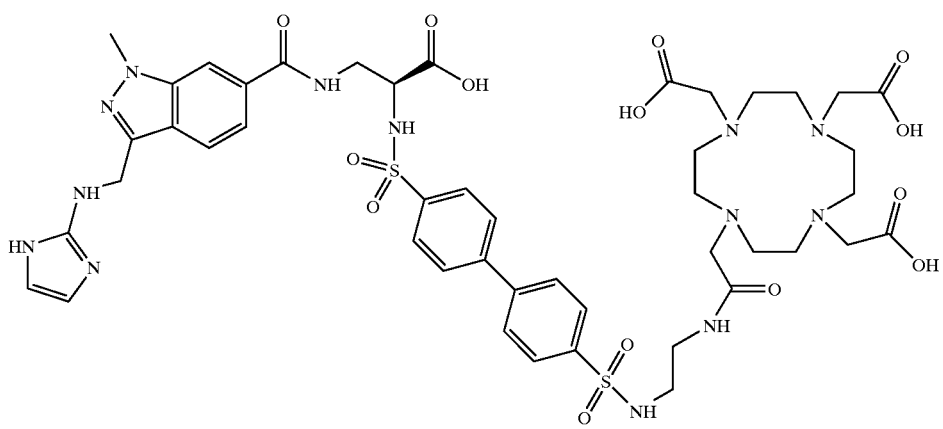

Step A: Synthesis of methyl 3-formyl-1-methyl-1H-indazole-6-carboxylate

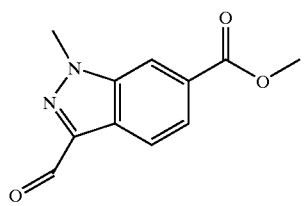

In a dry flask under nitrogen is added dry DMF (1.6 mL) and the solution cooled to −5C in an ice/ethanol bath. Phosphorous oxychloride (530 uL, 5.7 mmol) is added via syringe and the solution is allowed to stir for 30 minutes in the bath. Methyl 1-methyl-1H-indazole-6-carboxylate, (500 mg, 2.84 mmol, prepared as in Jadhav et al, U.S. Pat. No. 5,760,028) dissolved in DMF (3 mL) is added slowly to the cold solution. The reaction is then warmed to 35C, stirred for four hours, and then poured onto crushed ice. The resulting slurry is neutralized with 1N NaOH to pH=7, heated rapidly to boiling for 1 minute, cooled quickly to room temperature, and the solution extracted with ethyl acetate. The combined organics are washed with water and brine, dried, filtered and concentrated. The resulting oil is purified by flash chromatography to afford the product.

Step B: Synthesis of methyl 1-methyl-3-({[1-(triphenylmethyl)imidazol-2-yl]amino}methyl)-1H-indazole-6-carboxylate

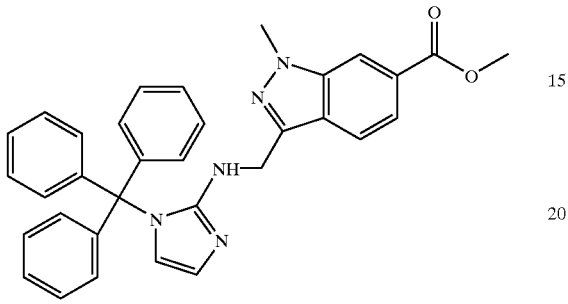

The product of Step A (204 mg, 1 mmol) is dissolved in toluene (10 mL) with N-trityl-2-aminoimidazole (357 mg, 1.1 mmol) and heated to reflux with a Dean-Stark trap. Four aliquots of toluene (3 mL each) are removed via distillation at 1.5 hour intervals, being replaced by dry toluene each time, and then the solution is left to reflux for 18 hours. The reaction is cooled to room temperature and sodium triacetoxyborohydride (1 gram, 5 mmol) is added in one portion. The reaction is stirred at room temperature for 24 hours, poured into water, and the layers separated. The aqueous layer is extracted with ethyl acetate and the combined organic layers are washed with saturated bicarbonate, water, and brine, dried over magnesium sulfate, concentrated, and purified by flash chromatography to afford the product.

Step C: Synthesis of 1-({[1-(triphenylmethyl)imidazol-2-yl]amino}methyl)-1H-indazole-5-carboxylic acid

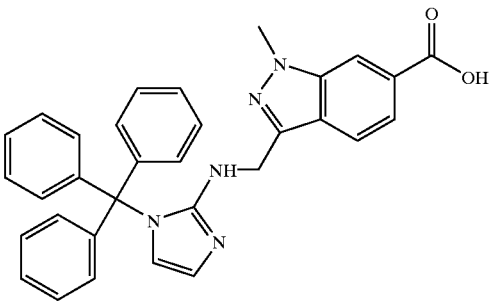

The product of Step B (250 mg, 474 umol) is added to THF/water (1:1, 15 mL) along with lithium hydroxide (3N, 0.8 mL, 2.4 mmol) and the solution stirred, following by TLC until the starting material has disappeared, when the THF is removed under vacuum. The reaction is acidified to pH=2 with 1N HCl and the resulting solids are filtered, washed with water, and dried under vacuum to afford the product.

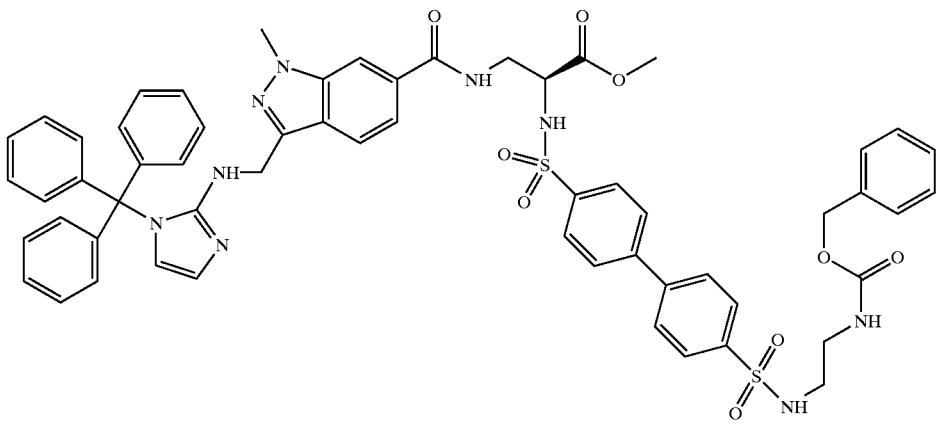

The product of Step C (190 mg, 370 umol) is reacted with the product of Example 44, Step A (285 mg, 407 umol) as in Example 44, Step B and the residue is purified by preparative HPLC (Vydac C-18, 21.2 mm×25 cm, 90% acetonitrile/water/0.1% trifluoroacetic acid; 10–70% B over 30 minutes). The product fractions are combined, frozen, and lyophilized to afford the product.

Step E: Synthesis of methyl (2S)-2-({[4-(4-{[(2-aminoethyl)amino]sulfonyl}phenyl)phenyl]sulfonyl}amino)-3-{[1-methyl-3-({[1-(triphenylmethyl)imidazol-2-yl]amino}methyl)(1H-indazol-6-yl)]carbonylamino}propanoate Step D: Synthesis of

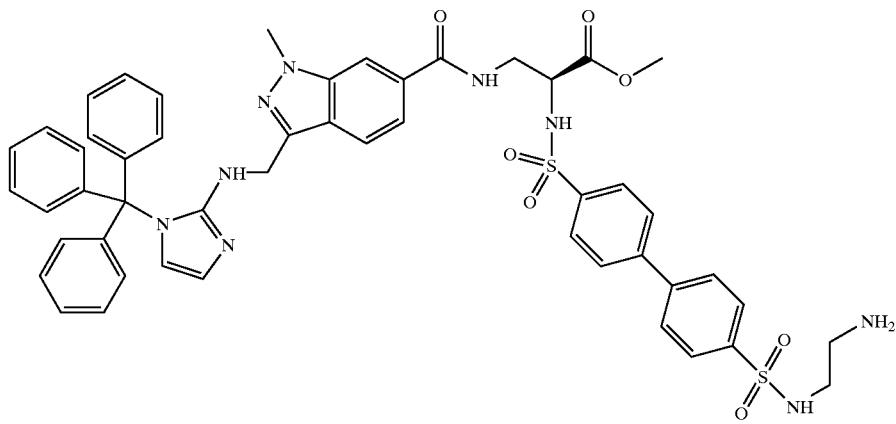

The product of Step D (100 mg) in methanol (10 mL) is added to a slurry of 10% palladium on carbon (50 mg) in methanol (8 mL) in a Parr bottle under nitrogen. The solution is hydrogenated at 50 psi for 1.5 hours, filtered through Celite, washed with methanol, and the combined filtrates concentrated. The resulting oil is not purified but carried directly into the next step.

Step F: Synthesis of methyl (2S)-3-{[1-methyl-3-({[1-(triphenylmethyl)imidazol-2-yl]amino}methyl)(1H-indazol-6-yl)]carbonylamino}-2-{[(4-{(4-[({2-[2-(1,4,7,10-tetraaza-4,7,10-tris{[(tert-butyl)oxycarbonyl]methyl}cyclododecyl)acetylamino]ethyl}amino)sulfonyl]phenyl}phenyl)sulfonyl]amino}propanoate

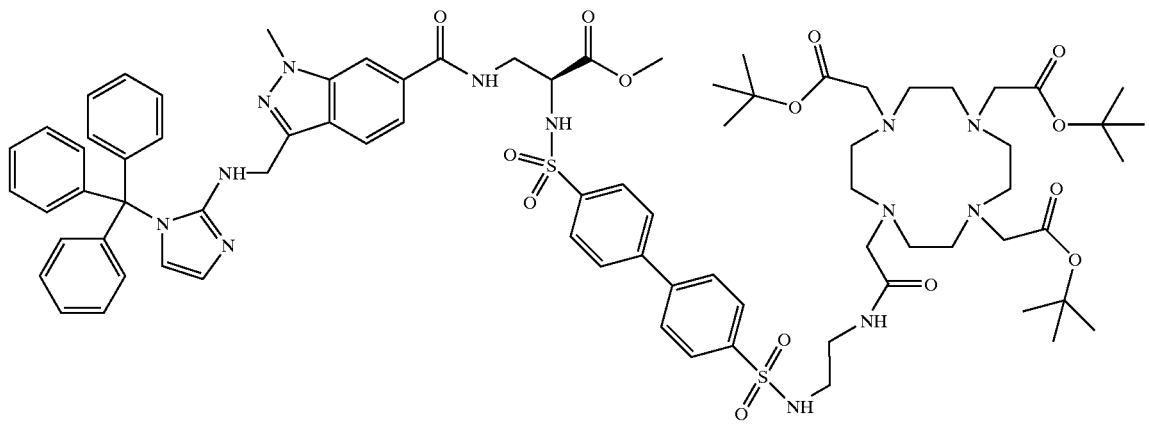

The product of Step E (73 mg, 77 umol) is reacted with DOTA(OtBu)3—OH (49 mg, 85 umol) as in Example 37, Step F, to afford the product as a pure compound after purification and lyophilization.

Step G: Synthesis of (2S)-3-({3-[(imidazol-2-ylamino)methyl]-1-methyl(1H-indazol-6-yl)}carbonylamino)-2-({[4-(4-{[(2-{2-[1,4,7,10-tetraaza-4,7,10-tris(carboxymethyl)cyclododecyl]acetylamino}ethyl)amino]sulfonyl}phenyl)phenyl]sulfonyl}amino)propanoic acid

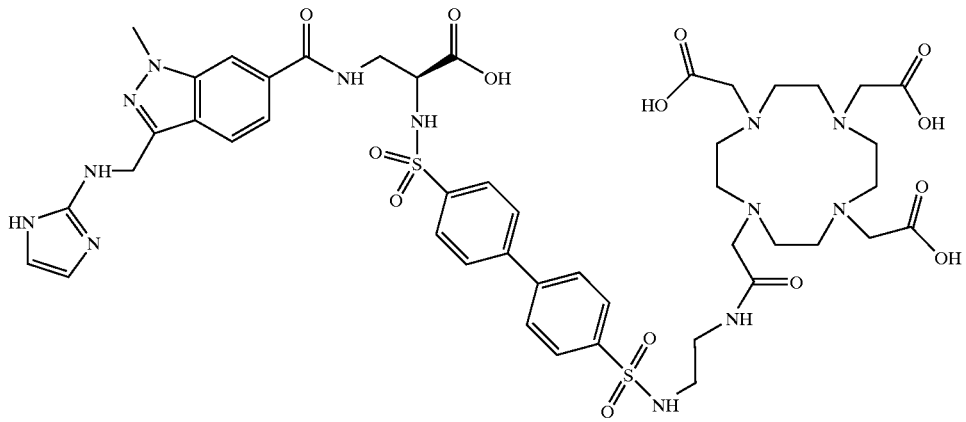

The product of Step F (73 mg, 77 umol) is deprotected as in Example 40, Step J, to afford the product as a pure compound after preparative HPLC purification and lyophilization of the product ractions.

Example 47

Synthesis of 3-[(7-{3-[(6-{[(1E)-1-aza-2-(2-sulfophenyl)vinyl]amino}(3-pyridyl))carbonylamino]propoxy}-1-[3-(imidazol-2-ylamino)propyl](1H-indazol-5-yl))carbonylamino](2S)-2-{[(2,4,6-trimethylphenyl)sulfonyl]-amino}propanoic acid

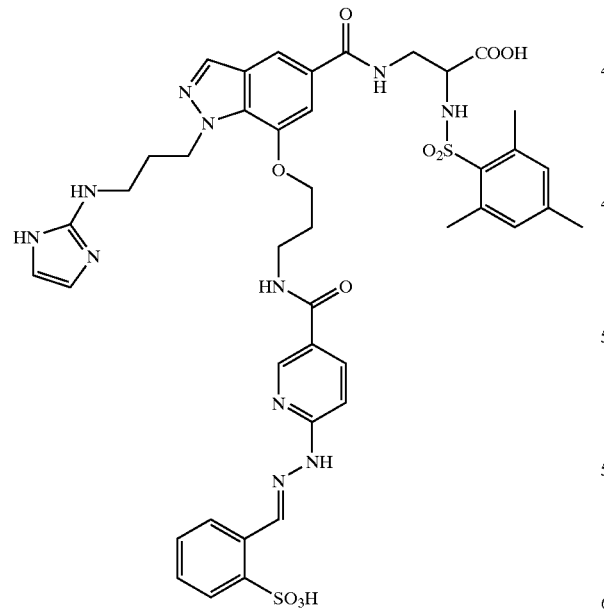

Part A. Preparation of ethyl 7-{3-[(tert-butoxy)-carbonylamino]propoxy}-1-benzyl-1H-indazole-5-carboxylate

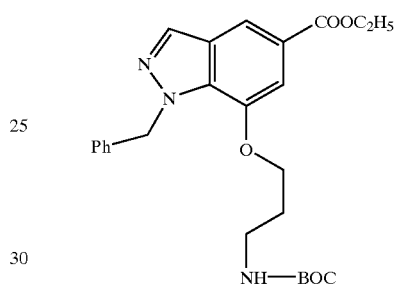

A solution of ethyl 7-hydroxy-1-benzyl-1H-indazole-5-carboxylate (P. Baraldi et. al, Il. Farmaco, 52(12), 717 (1997)) in ethanol is treated with sodium ethoxide, followed by commercially available boc-3-aminopropylbromide, and refluxed for 2–5 hours. The volatiles are removed and the crude residue is extracted with ethyl acetate. The crude residue is obtained after removal of ethyl acetate and is purified by chromatography to give the title compound.

Part B. Preparation of 7-{3-[(tert-butoxy)carbonylamino]-propoxy}-1-(3-{[1-(triphenylmethyl)imidazol-2-yl]amino}-propyl)-1H-indazole-5-carboxylic acid

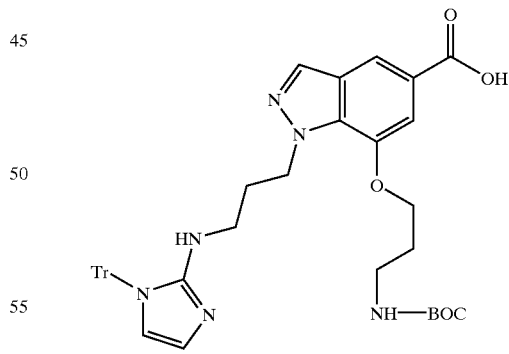

Ethyl 7-{3-[(tert-butoxy)carbonylamino]propoxy}-1-benzyl-1H-indazole-5-carboxylate is subjected to hydrogenolysis to give the debenzylated derivative. Using the procedure described in U.S. Pat. No. 5,760,028, Example 1050e, parts D, E, J, and K ethyl 7-{3-[(tert-butoxy)carbonylamino]propoxy}-1H-indazole-5-carboxylate is converted to the title compound in four steps.

Part C. Preparation of (2S)-3-({7-(3-aminopropoxy)-1-[3-(imidazol-2-ylamino)propyl](1H-indazol-5-yl)}carbonylamino)-2-{[(2,4,6-trimethylphenyl)sulfonyl]amino}propanoic acid

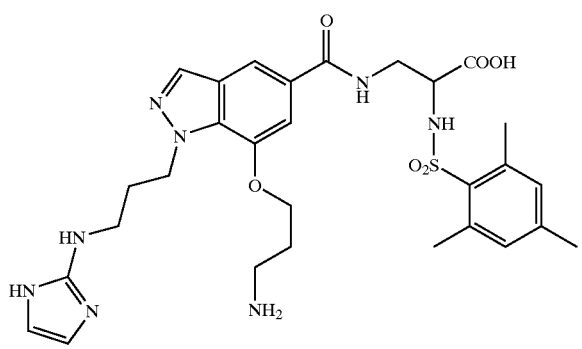

A solution of 7-{3-[(tert-butoxy)carbonylamino]-propoxy}-1-(3-{[1-(triphenylmethyl)imidazol-2-yl]amino}-propyl)-1H-indazole-5-carboxylic acid is treated with Hunig's base and HBTU, then is stirred for about 10 min. The reaction mixture is treated with methyl 3-amino-2(S) (2,4,6-trimethyl-benzenesulfonyl)aminopropionate. The product is then isolated via chromatography.

The methyl ester is saponified using LiOH in THF, and the trityl and boc protecting groups are removed by treatment with trifluoroacetic acid to give the title compound. It is purified by reversed phase preparative HPLC.

Part D. Preparation of 3-[(7-{3-[(6-{[(1E)-1-aza-2-(2-sulfophenyl)vinyl]amino}(3-pyridyl))carbonylamino] propoxy}-1-[3-(imidazol-2-ylamino)propyl](1H-indazol-5-yl))carbonylamino](2S)-2-{[(2,4,6-trimethylphenyl) sulfonyl]amino}-propanoic acid (2S)-3-({7-(3-Aminopropoxy)-1-[3-(imidazol-2-ylamino)-propyl](1H-indazol-5-yl)}carbonylamino)-2-{[(2,4,6-trimethylphenyl)sulfonyl]amino}propanoic acid is dissolved in N,N-dimethylformamide. Triethylamine (3 eq)is added, and the reaction is stirred for 5 min. 2-[[[5-[[(2,5-Dioxo-1-pyrrolidinyl)oxy]carbonyl]-2-pyridinyl] hydrazono]-methyl]-benzenesulfonic acid, monosodium salt (1.1 eq.) is added, and the reaction is stirred overnight. The reaction mixture is concentrated under high vacuum and the crude is purified by reversed phase preparative HPLC to give the title compound.

Example 48

Synthesis of 3-{[1-[3-(imidazol-2-ylamino)propyl]-7-(3-{2-[1,4,7,10-tetraaza-4,7,10-tris (carboxymethyl)cyclododecyl]-acetylamino}propoxy)(1H-indazol-5-yl)] carbonylamino}-2-{[(2,4,6-trimethylphenyl) sulfonyl]amino}propanoic acid

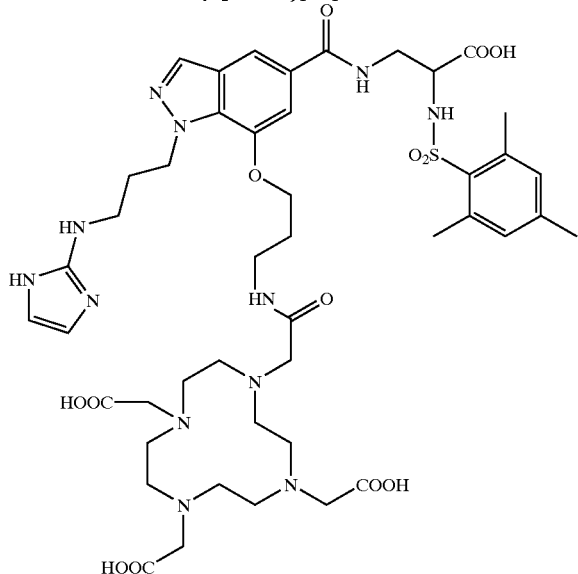

To asolution of tris(t-butyl)-1,4,7,10-tetra-azacyclododecane-1,4,7,10-tetraacetic acid (1 eq) and Hunig's base (3 eq.) in DMF is added HBTU (0.8 eq) and the mixture is stirred for 5 min. To this is added a solution of (2S)-3-({7-(3-Aminopropoxy)-1-[3-(imidazol-2-ylamino)propyl](1H-indazol-5-yl)}carbonylamino)-2-{[(2, 4,6-trimethylphenyl)sulfonyl]-amino}propanoic acid (0.75 eq) in DMF and the reaction mixture is allowed to stir under nitrogen at room temperature for 4 h. The solvent is removed in vacuo and the residue is purified by preparative RP-HPLC to obtain the conjugate. A solution of the conjugate in TFA is stirred at room temperature under nitrogen for 5 h. The solution is concentrated in vacuo and the residue is purified by preparative RP-BPLC to obtain the title compound as a lyophilized solid.

Examples 49–55

Synthesis of In-111 Complex of the Conjugate of Example 34

To a lead shielded and crimped 1 cc autosampler vial was added 40–50 μg of the conjugate of Example 34 dissolved in 100 μL ammonium citrate buffer (0.4 M, pH 4.7) followed by the addition of 2 mCi, (5 μL) In-111 in 0.05 N HCl (specific activity: 25 μg/mCi). The reaction mixture was heated at 90–100° C. for 30 min and analyzed by HPLC. Yield: 97.3%; Ret. Time: 8.1 min.

| HPLC Method | |
|---|---|
| Column: | Zorbax Rx C18, 25 cm × 4.6 mm |
| Column Temperature: | Ambient |
| Flow: | 1.0 ml/min |
| Solvent A: | 25 mM sodium phosphate buffer at pH 6 |
| Solvent B: | Acetonitrile |
| Detector: | Sodium iodide (NaI) radiometric probe, and UV at 220 nm wavelength. |

| Gradient | | | | | | |
|---|---|---|---|---|---|---|
| t (min) | 0 | 25 | 26 | 35 | 36 | 45 |
| % B | 10 | 20 | 60 | 60 | 10 | 10 |

Example 50

Synthesis of In-111 Complex of the Conjugate of Example 35

To a lead shielded and crimped 2 cc autosampler vial was added 100 μg of the conjugate of Example 35 dissolved in 200 μL ammonium citrate buffer (0.4 M, pH 4.8) followed by the addition of 2.5 mCi, (7.5 μL) In-111 (NEN) in 0.05 N HCl (specific activity: 40 μg/mCi). The reaction mixture was heated at 100° C. for 30 min and analyzed by HPLC. Yield: 74.7%, Ret. Time: 13.2 min.

HPLC Method
Column: Zorbax Rx C18, 25 cm × 4.6 mm
Column Temperature: Ambient
Flow: 1.0 ml/min
Solvent A: 25 mM sodium phosphate buffer at pH 6
Solvent B: Acetonitrile
Detector: Sodium iodide (NaI) radiometric probe, and UV at 220 nm wavelength.
Gradient

| t (min) | 0  | 25 | 26 | 35 | 36 | 45 |
|---------|----|----|----|----|----|----|
| % B     | 14 | 16 | 60 | 60 | 14 | 14 |

Example 51

Synthesis of In-111 Complex of the Conjugate of Example 36

To a lead shielded and crimped 2 cc autosampler vial was added 70 μg of the conjugate of Example 36 dissolved in 140 μL ammonium acetate buffer (0.5 M, pH 4.7) followed by the addition of 1 mg of gentisic acid (sodium salt) dissolved in 10 μL of $H_2O$, and 1.7 mCi, (9 μL) In-111 (NEN) in 0.05 N HCl (specific activity: 41 μg/mCi). The reaction mixture was heated at 100° C. for 20 min and analyzed by HPLC. Yield: 87%, Ret. Time: 17–18 min.

HPLC Method
Column: Zorbax Rx C18, 25 cm × 4.6 mm
Column Temperature: Ambient
Flow: 1.0 ml/min
Solvent A: 10 mM ammonium acetate
Solvent B: Acetonitrile
Detector: IN-US β-ram, and UV at 220 nm wavelength.
Gradient

| t (min) | 0 | 25 | 26 | 35 | 36 | 45 |
|---------|---|----|----|----|----|----|
| % B     | 7 | 7  | 60 | 60 | 7  | 7  |

Example 52

Synthesis of In-111 Complex of the Conjugate of Example 37

To a shielded and crimped 2 cc autosampler vial was added 40–60 μg of the conjugate of Example 37 dissolved in 80–120 μl 0.5 M ammonium acetate buffer (pH 4.8) followed by the addition of 1 mg gentisic acid sodium salt and 1–1.3 mCi (6 μl) In-111 in 0.05M HCl. The reaction mixture was heated at 100° C. for 15 minutes and analyzed by HPLC. Yield: 75.3%; Ret. Time: 16.8 min.

HPLC Method
Column: Zorbax Rx C18, 25 cm × 4.6 mm
Column Temperature: Ambient
Flow: 1.0 ml/min
Solvent A: 10 mM ammonium acetate
Solvent B: Acetonitrile
Detector: IN-US β-ram, and UV at 220 nm wavelength.
Gradient

| t (min) | 0  | 25 | 26 | 35 | 36 | 45 |
|---------|----|----|----|----|----|----|
| % B     | 10 | 13 | 60 | 60 | 10 | 10 |

Example 53

Synthesis of In-111 Complex of the Conjugate of Example 38

To a lead shielded and crimped 1 cc autosampler vial was added 40–50 μg of the conjugate of Example 38 dissolved in 100 μL ammonium citrate buffer (0.4 M, pH 4.7) followed by the addition of 2 mCi, (5 μL) In-111 in 0.05 N HCl (specific activity: 25 μg/mCi). The reaction mixture was heated at 90–100° C. for 30 min and analyzed by HPLC. Each of the two diasteromers of the conjugate of Example 38 forms an In-111 complex. Yield: 92.5 and 95.6%; Ret. Time: 13 and 14.7 min.

HPLC Method
Column: Zorbax Rx C18, 25 cm × 4.6 mm
Column Temperature: Ambient
Flow: 1.0 ml/min
Solvent A: 25 mM sodium phosphate buffer at pH 6
Solvent B: Acetonitrile
Detector: Sodium iodide (NaI) radiometric probe, and UV at 220 nm wavelength.
Gradient

| t (min) | 0 | 25 | 26 | 35 | 36 | 45 |
|---------|---|----|----|----|----|----|
| % B     | 9 | 9  | 60 | 60 | 9  | 9  |

Example 54

Synthesis of In-111 Complex of the Conjugate of Example 40

To a shielded and crimped 2 cc autosampler vial was added 40–60 μg of the conjugate of Example 40 dissolved in 80–120 μl 0.5 M ammonium acetate buffer (pH 4.8) followed by the addition of 1 mg gentisic acid sodium salt and 1–1.3 mCi (6 μl) In-111 in 0.05M HCl. The reaction mixture was heated at 100° C. for 15 minutes and analyzed by HPLC. Yield: 82%; Ret. Time: 11 min.

HPLC Method
Column: Zorbax Rx C18, 25 cm × 4.6 mm
Column Temperature: Ambient
Flow: 1.0 ml/min
Solvent A: 10 mM ammonium acetate
Solvent B: Acetonitrile
Detector: IN-US β-ram, and UV at 220 nm wavelength.
Gradient

| t (min) | 0 | 25 | 26 | 35 | 36 | 45 |
|---------|---|----|----|----|----|----|
| % B     | 9 | 10 | 60 | 60 | 9  | 9  |

Example 55

Synthesis of In-111 Complex of the Conjugate of Example 41

To a shielded and crimped 2 cc autosampler vial was added 40–60 μg of the conjugate of Example 41 dissolved in 80–120 μl 0.5 M ammonium acetate buffer (pH 4.8) followed by the addition of 1 mg gentisic acid sodium salt and 1–1.3 mCi (6 μl) In-111 in 0.05M HCl. The reaction mixture was heated at 100° C. for 15 minutes and analyzed by HPLC. Yield: 71.2%; Ret. Time: 12.2 min.

HPLC Method
Column: Zorbax Rx C18, 25 cm × 4.6 mm
Column Temperature: Ambient
Flow: 1.0 ml/min
Solvent A: 10 mM ammonium acetate -continued

| Solvent B: Acetonitrile<br>Detector: IN-US β-ram, and UV at 220 nm wavelength.<br>Gradient | | | | | |
|---|---|---|---|---|---|
| t (min) | 0 | 25 | 26 | 35 | 36 | 45 |
| % B | 10 | 10 | 60 | 60 | 10 | 10 |

Examples 56–58

Synthesis of Y-90 Complexes of the Conjugates of Examples 34, 36, and 38

To a clean sealed 5 mL vial was added 0.5–1.0 mL of the appropriate conjugate solution (200 μg/mL in 0.5 M ammonium acetate buffer, pH 7.0–8.0), followed by 0.05 mL of sodium gentisate (10 mg/mL in 0.5 M ammonium acetate buffer, pH 7.0–8.0) solution, and 10–40 μL of $^{90}YCl_3$ in 0.05 N HCl. The reaction mixture was heated at 100° C. for 5–10 min. After cooling to room temperature, a sample of the resulting solution was analyzed by HPLC and by ITLC.

| Complex Ex # | Conjugate Ex. # | Ret. Time (min) | % Yield | HPLC Method |
|---|---|---|---|---|
| 56 | 34 | 14.0 | 90 | C |
| 57 | 36 | 15.5 | 70 | E |
| 58* | 38 | 9.5, 10.0 | 89, 68 | B |

*Example 58 is a mixture of two diasteromers

HPLC Method B: The HPLC method using a reverse phase $C_{18}$ Zorbax column (4.6 mm×25 cm, 80 Å pore size) at a flow rate of 1.0 mL/min with a gradient mobile phase from 90% A (25 mM pH 6.0 phosphate buffer) and 10% B (acetonitrile) to 80% A and 20% B at 20 min.
HPLC Method C: The HPLC method using a reverse phase $C_{18}$ Zorbax column (4.6 mm×25 cm, 80 Å pore size) at a flow rate of 1.0 mL/min with a gradient mobile phase from 92% A (25 mM pH 6.0 phosphate buffer) and 8% B (acetonitrile) to 85% A and 15% B at 20 min.
HPLC Method E: The HPLC method using a reverse phase $C_{18}$ Zorbax column (4.6 mm×25 cm, 80 Å pore size) at a flow rate of 1.0 mL/min with a gradient mobile phase from 90% A (25 mM ammonium acetate buffer, pH=6.8) and 10% B (acetonitrile) to 85% A and 15% B at 20 min.

Utility

The pharmaceuticals of the present invention are useful for imaging angiogenic tumor vasculature, therapeutic cardiovascular angiogenesis, and cardiac pathologies associated with the expression of vitronectin receptors in a patient or for treating cancer in a patient. The radiopharmaceuticals of the present invention comprised of a gamma ray or positron emitting isotope are useful for imaging of pathological processes involving angiogenic neovasculature, including cancer, diabetic retinopathy, macular degeneration, restenosis of blood vessels after angioplasty, and wound healing, as well as atherosclerotic plaque, myocardial reperfusion injury, and myocardial ischemia, stunning or infarction. The radiopharmaceuticals of the present invention comprised of a beta, alpha or Auger electron emitting isotope are useful for treatment of pathological processes involving angiogenic neovasculature, by delivering a cytotoxic dose of radiation to the locus of the angiogenic neovasculature. The treatment of cancer is affected by the systemic administration of the radiophamaceuticals resulting in a cytotoxic radiation dose to tumors.

The compounds of the present invention comprised of one or more paramagnetic metal ions selected from gadolinium, dysprosium, iron, and manganese, are useful as contrast agents for magnetic resonance imaging (MRI) of pathological processes involving angiogenic neovasculature, as well as atherosclerotic plaque, myocardial reperfusion injury, and myocardial ischemia, stunning or infarction.

The compounds of the present invention comprised of one or more heavy atoms with atomic number of 20 or greater are useful as X-ray contrast agents for X-ray imaging of pathological processes involving angiogenic neovasculature, as well as atherosclerotic plaque, myocardial reperfusion injury, and myocardial ischemia, stunning or infarction.

The compounds of the present invention comprised of an echogenic gas containing surfactant microsphere are useful as ultrasound contrast agents for sonography of pathological processes involving angiogenic neovasculature, as well as atherosclerotic plaque, myocardial reperfusion injury, and myocardial ischemia, stunning or infarction.

Representative compounds of the present invention were tested in the following in vitro assays and in vivo models and were found to be active.

Immobilized Human Placental $\alpha_v\beta_3$ Receptor Assay

The assay conditions were developed and validated using [I-125] vitronectin. Assay validation included Scatchard format analysis (n=3) where receptor number (Bmax) and Kd (affinity) were determined. Assay format is such that compounds are preliminarily screened at 10 and 100 nM final concentrations prior to IC50 determination. Three standards (vitronectin, anti-$\alpha_v\beta_3$ antibody, LM609, and anti-avB5, $PIF_6$) and five reference peptides have been evaluated for IC50 determination. Briefly, the method involves immobilizing previously isolated receptors in 96 well plates and incubating overnight. The receptors were isolated from normal, fresh, non-infectious (HIV, hepatitis B and C, syphilis, and HTLV free) human placenta. The tissue was lysed and tissue debris removed via centrifugation. The lysate was filtered. The receptors were isolated by affinity chromatography using the immobilized $\alpha_v\beta_3$ antibody. The plates are then washed 3× with wash buffer. Blocking buffer is added and plates incubated for 120 minutes at room temperature. During this time compounds to be tested and [I-125] vitronectin are premixed in a reservoir plate. Blocking buffer is removed and compound mixture pipetted. Competition is carried out for 60 minutes at room temperature. Unbound material is then removed and wells are separated and counted via gamma scintillation.

Oncomouse® Imaging

The study involves the use of the c-Neu Oncomouse® and PVB mice simultaneously as controls. The mice are anesthetized with sodium pentobarbital and injected with approximately 0.5 mCi of radiopharmaceutical. Prior to injection, the tumor locations on each Oncomouse® are recorded and tumor size measured using calipers. The animals are positioned on the camera head so as to image the anterior or posterior of the animals. 5 Minute dynamic images are acquired serially over 2 hours using a 256×256 matrix and a zoom of 2×. Upon completion of the study, the images are evaluated by circumscribing the tumor as the target region of interest (ROI) and a background site in the neck area below the carotid salivary glands.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the rate of growth of the tumors in control mice versus those in the mice administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the tumors. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the tumors in the animal can be imaging using an ultrasound probe held proximate to the tumors. The effectiveness of the contrast agents can be readily seen by comparison to the images obtain from animals that are not administered a contrast agent.

Rabbit Matrigel Model

This model was adapted from a matrigel model intended for the study of angiogenesis in mice. Matrigel (Becton & Dickinson, USA) is a basement membrane rich in laminin, collagen IV, entactin, HSPG and other growth factors. When combined with growth factors such as bFGF [500 ng/ml] or VEGF [2 µg/ml] and injected subcutaneously into the mid-abdominal region of the mice, it solidifies into a gel and stimulates angiogenesis at the site of injection within 4–8 days. In the rabbit model, New Zealand White rabbits (2.5–3.0 kg) are injected with 2.0 ml of matrigel, plus 1 µg bFGF and 4 µg VEGF. The radiopharmaceutical is then injected 7 days later and the images obtained.

This model can also be used to assess the effectiveness of the radiopharmaceuticals of the present invention comprised of a beta, alpha or Auger electron emitting isotope. The radiopharmaceuticals are administered in appropriate amounts and the uptake at the angiogenic sites can be quantified either non-invasively by imaging for those isotopes with a coincident imageable gamma emission, or by excision of the angiogenic sites and counting the amount of radioactivity present by standard techniques. The therapeutic effect of the radiopharmaceuticals can be assessed by monitoring the rate of growth of the angiogenic sites in control rabbits versus those in the rabbits administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the angiogenic sites. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the angiogenic sites. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the angiogenic sites in the animal can be imaging using an ultrasound probe held proximate to the tumors. The effectiveness of the contrast agents can be readily seen by comparison to the images obtain from animals that are not administered a contrast agent.

Canine Spontaneous Tumor Model

Adult dogs with spontaneous mammary tumors were sedated with xylazine (20 mg/kg)/atropine (1 ml/kg). Upon sedation the animals were intubated using ketamine (5 mg/kg)/diazepam (0.25 mg/kg) for full anethesia. Chemical restraint was continued with ketamine (3 mg/kg)/xylazine (6 mg/kg) titrating as necessary. If required the animals were ventilated with room air via an endotrachael tube (12 strokes/min, 25 ml/kg) during the study. Peripheral veins were catheterized using 20G I.V. catheters, one to serve as an infusion port for compound while the other for exfusion of blood samples. Heart rate and EKG were monitored using a cardiotachometer (Biotech, Grass Quincy, MA) triggered from a lead II electrocardiogram generated by limb leads. Blood samples are generally taken at ~10 minutes (control), end of infusion, (1 minute), 15 min, 30 min, 60 min, 90 min, and 120 min for whole blood cell number and counting. Radiopharmaceutical dose was 300 µCi/kg administered as an i.v. bolus with saline flush. Parameters were monitored continuously on a polygraph recorder (Model 7E Grass) at a paper speed of 10 mm/min or 10 mm/sec.

Imaging of the laterals were for 2 hours with a 256×256 matrix, no zoom, 5 minute dynamic images. A known source is placed in the image field (20–90 µCi) to evaluate region of interest (ROI) uptake. Images were also acquired 24 hours post injection to determine retention of the compound in the tumor. The uptake is determined by taking the fraction of the total counts in an inscribed area for ROI/source and multiplying the known µCi. The result is µCi for the ROI.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopbarmaceuticals can be assessed by monitoring the size of the tumors over time. This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the tumors. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the tumors in the animal can be imaging using an ultrasound probe held proximate to the tumors. The effectiveness of the contrast agents can be readily seen by comparison to the images obtain from animals that are not administered a contrast agent.

Cardiovascular disease models that can be used to assess the diagnostic radiopharmaceuticals, magnetic resonance, X-ray and ultrasound contrast agents of the present invention are reviewed in J. Nucl. Cardiol., 1998, 5, 167–83. There are several well established rabbit models of atherosclerosis; one model produces predominantly proliferating smooth muscle cells by balloon deendothelialization of infradiaphragmitic abdominal aorta to simulate restenotic lesions; another model that produces simulated advanced human atherosclerotic plaque by balloon deendothelialization followed by a high cholesterol diet.

A model of congestive heart failure is described in Am. J. Physiol., 1998, 274, H1516-23. In general, Yorkshire pigs are randomly assigned to undergo 3 wks of rapid atrial pacing at 240 beats/min. or to be sham controls. The pigs are chronically instrumented to measure left ventricular function in the conscious state. The pigs are anesthetized. A shielded stimulating electrode is sutured onto the left atrium, connected to a modified programmable pace maker and buried in a subcutaneous pocket. The pericardium is closed loosely, the thoracotomy is closed, and the pleural space is evacuated of air. After a recovery period of 7–10 days, the pacemaker is activated in the animals selected to undergo chronic rapid pacing. The animals are sedated, the pacemaker is deactivated (pacing groups only. After a 30 min stabilization period, indexes of LV function and geometry are determined (by echocardiography as a control) by injecting the radiolabeled compound. For biodistribution, the animals are anesthetized, the heart extirpate and the LV apex and midventricular regions are evaluated.

A rat model of reversible coronary occlusion and reperfusion is described in McNulty et al., J. Am. Physiol., 1996, H2283-9.

Obviously, numerous modifications and variations of the present invention are possible in light of the above teachings. It is therefore to be understood that within the scope of the appended claims, the invention may be practiced otherwise that as specifically described herein.

What is claimed is described below:

1. A compound of the formula:

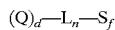

wherein,

Q is independently a compound of Formulae (Ia) or (Ib):

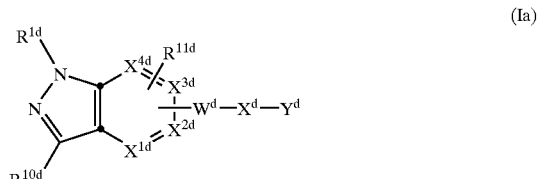

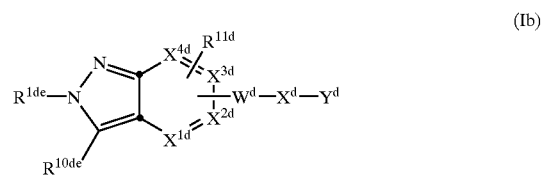

or stereoisomeric forms thereof, or mixtures of stereoisomeric forms thereof, or pharmaceutically acceptable salt or prodrug forms thereof wherein:

$X^{1d}$ is CH, C—$W^d$—$X^d$—$Y^d$, or C—$L_n$;

$X^{2d}$ is CH, or C—$W^d$—$X^d$—$Y^d$;

$X^{3d}$ is $CR^{11d}$, or C—$W^d$ $X^d$—$Y^d$;

$X^{4d}$ is $CR^{11d}$;

provided that when $R^{1d}$ is $R^{10de}$ then one of $X^{1d}$ and $X^{2d}$ is C—$W^d$—$X^d$—$Y^d$, and when $R^{10d}$ is $R^{10de}$ then $X^{3d}$ is C—$W^d$—$X^d$—$Y^d$;

$R^{1d}$ is selected from: $R^{1de}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)-substituted with 0–1 $R^{15d}$ or 0–2 $R^{11d}$ or 0–1 $R^{21d}$;

$R^{1de}$ is selected from:

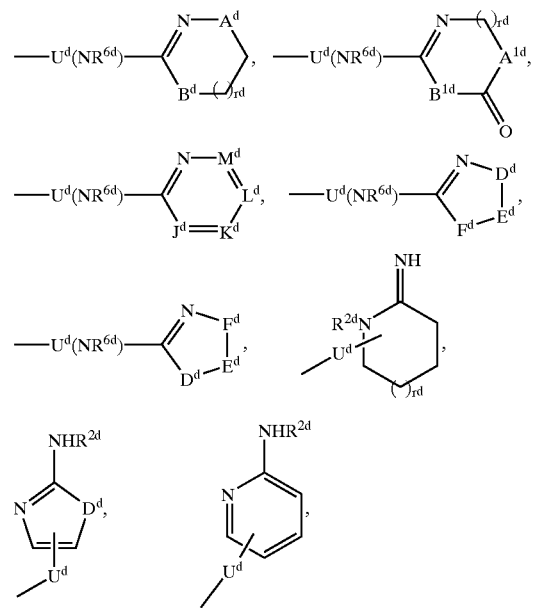

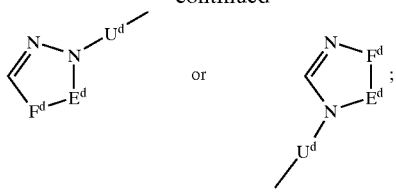

$A^d$ and $B^d$ are independently —$CH_2$—, —O—, —$N(R^{2d})$—, or —C(=O)—;

$A^{1d}$ and $B^{1d}$ are independently —$CH_2$— or —$N(R^{3d})$—;

$D^d$ is —$N(R^{2d})$—, —O—, —S—, —C(=O)— or —$SO_2$—;

$E^d$—$F^d$ is —$C(R^{4d})=C(R^{5d})$—, —$N=C(R^{4d})$—, —$C(R^{4d})=N$—, or —$C(R^{4d})_2C(R^{5d})_2$—;

$J^d$, $K^d$, $L^d$ and $M^d$ are independently selected from: —$C(R^{4d})$—, —$C(R^{5d})$— and —N—, provided that at least one of $J^d$, $K^d$, $L^d$ and $M^d$ is not —N—;

$R^{2d}$ is selected from: H, $C_1$–$C_6$ alkyl, ($C_1$–$C_6$ alkyl)carbonyl, ($C_1$–$C_6$ alkoxy)carbonyl; ($C_1$–$C_6$ alkyl)aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl($C_1$–$C_6$ alkyl)-, ($C_1$–$C_6$ alkyl)carbonyl-, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^{3d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;

$R^{4d}$ and $R^{5d}$ are independently selected from: H, $C_1$–$C_4$ alkoxy, $NR^{2d}R^{3d}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl)carbonyl, ($C_1$–$C_6$ alkoxy)carbonyl, arylcarbonyl, or alternatively, when substituents on adjacent atoms, $R^{4d}$ and $R^{5d}$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, and $NO_2$;

$U^d$ is selected from: —$(CH_2)_n{}^d$—, —$(CH_2)_n{}^d(CR^{7d}=CR^{8d})(CH_2)_m{}^d$—, —$(CH_2)_n{}^d(C \equiv C)(CH_2)_m{}^d$—, —$(CH_2)_t{}^dQ(CH_2)_m{}^d$—, —$(CH_2)_n{}^dO(CH_2)_m{}^d$—, —$(CH_2)_n{}^dN(R^{6d})(CH_2)_m{}^d$—, —$(CH_2)_n{}^dC(=O)(CH_2)_m{}^d$—, —$(CH_2)_n{}^d(C=O)N(R^{6d})(CH_2)_m{}^d$—, —$(CH_2)_n{}^dN(R^{6d})(C=O)(CH_2)_m{}^d$—, and —$(CH_2)_n{}^dS(O)_p{}^d(CH_2)_m{}^d$—;

wherein one or more of the methylene groups in $U^d$ is optionally substituted with $R^{7d}$;

$Q^d$ is selected from 1,2-cycloalkylene, 1,2-phenylene, 1,3-phenylene, 1,4-phenylene, 2,3-pyridinylene, 3,4-pyridinylene, 2,4-pyridinylene, and 3,4-pyridazinylene;

$R^{6d}$ is selected from: H, $C_1$–$C_4$ alkyl, or benzyl;

$R^{7d}$ and $R^{8d}$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_0$–$C_6$ alkyl)-;

$R^{10d}$ is selected from: H, $R^{1de}$, $C_1$–$C_4$ alkoxy substituted with 0–1 $R^{21d}$, $N(R^{6d})_2$, halogen, $NO_2$, CN, $CF_3$, $CO_2R^{17d}$, $C(=O)R^{17d}$, $CONR^{17d}R^{20d}$, —$SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{10de}$ is selected from: H, $C_1$–$C_4$ alkoxy substituted with 0–1 $R^{21d}$, $N(R^{6d})_2$, halogen, $NO_2$, CN, $CF_3$, $CO_2R^{17d}$, $C(=O)R^{17d}$, $CONR^{17d}R^{20d}$, $SO_2R^{17d}$, —$SO_2NR^{17d}R^{20d}$, $C_1$–$C_6$ alkyl substituted with 0–1 $R^{15d}$ or 0–1 $R^{21d}$, $C_3$–$C_6$ alkenyl substituted with 0–1 $R^{15d}$ or 0–1 $R^{21d}$, $C_3$–$C_7$ cycloalkyl substituted with 0–1 $R^{15d}$ or 0–1 $R^{21d}$, $C_4$–$C_{11}$ cycloalkylalkyl substituted with 0–1 $R^{15d}$ or 0–1 $R^{21d}$, aryl substituted with 0–1 $R^{15d}$ or 0–2 $R^{11d}$ or 0–1 $R^{21d}$, and aryl($C_1$–$C_6$ alkyl)- substituted with 0–1 $R^{15d}$ or 0–2 $R^{11d}$ or 0–1 $R^{21d}$;

$R^{11d}$ is selected from H, halogen, $CF_3$, CN, $NO_2$, hydroxy, $NR^{2d}R^{3d}$, $C_1$–$C_4$ alkyl substituted with 0–1 $R^{21d}$, $C_1$–$C_4$ alkoxy substituted with 0–1 $R^{21d}$, aryl substituted with 0–1 $R^{21d}$, aryl($C_1$–$C_6$ alkyl)- substituted with 0–1 $R^{21d}$, ($C_1$–$C_4$ alkoxy)carbonyl substituted with 0–1 $R^{21d}$, ($C_1$–$C_4$ alkyl)carbonyl substituted with 0–1 $R^{21d}$, $C_1$–$C_4$ alkylsulfonyl substituted with 0–1 $R^{21d}$, and $C_1$–$C_4$ alkylaminosulfonyl substituted with 0–1 $R^{21d}$;

$W^d$ is selected from: —$(C(R^{12d})_2)_q{}^dC(=O)N(R^{13d})$—, and —$C(=O)$—$N(R^{13d})$—$(C(R^{12d})_2)_q{}^d$—;

$X^d$ is —$C(R^{12d})(R^{14d})$—$C(R^{12d})(R^{15d})$—; or alternatively, $W^d$ and $X^d$ can be taken together to be

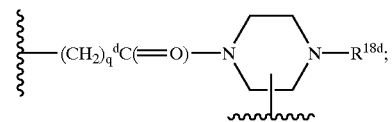

$R^{12d}$ is selected from H, halogen, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, and aryl($C_1$–$C_6$ alkyl)-;

$R^{13d}$ is selected from H, $C_1$–$C_6$ alkyl, $C_3$–$C_7$ cycloalkylmethyl, and aryl($C_1$–$C_6$ alkyl)-;

$R^{14d}$ is selected from: H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17d}$, $C(=O)R^{17d}$, and $CONR^{17d}R^{20d}$, provided that any of the above alkyl, cycloalkyl, aryl or heteroaryl groups may be substituted independently with 0–1 $R^{16d}$ or 0–2 $R^{11d}$;

$R^{15d}$ is selected from: H, $R^{16d}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl($C_1$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17d}$, $C(=O)R^{17d}$, $CONR^{17d}R^{20d}$, $SO_2R^{17d}$, and $SO_2NR^{17d}R^{20d}$, provided that any of the above alkyl, cycloalkyl, aryl or heteroaryl groups may be substituted independently with 0–2 $R^{11d}$;

$Y^d$ is selected from: —$COR^{19d}$, —$SO_3H$, —$PO_3H$, tetrazolyl, —$CONHNHSO_2CF_3$, —$CONHSO_2R^{17d}$, —$CONHSO_2NHR^{17d}$, —$NHCOCF_3$, —$NHCONHSO_2R^{17d}$, —$NHSO_2R^{17d}$, —$OPO_3H_2$, —$OSO_3H$, —$PO_3H_2$, —$SO_3H$, —$SO_2NHCOR^{17d}$, —$SO_2NHCO_2R^{17d}$,

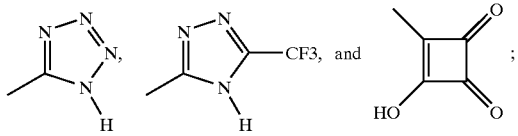

$R^{16d}$ is selected from: —$N(R^{20d})$—$C(=O)$—$O$—$R^{17d}$, —$N(R^{20d})$—$C(=O)$—$R^{17d}$, —$N(R^{20d})$—$C(=O)$—$NH$—$R^{17d}$, —$N(R^{20d})SO_2$—$R^{17d}$, and —$N(R^{20d})SO_2$—$NR^{20d}R^{17d}$;

$R^{17d}$ is selected from: $C_1$–$C_{10}$ alkyl optionally substituted with a bond to $L_n$, $C_3$–$C_{11}$ cycloalkyl optionally substituted with a bond to $L_n$, aryl($C_1$–$C_6$ alkyl)- optionally substituted with a bond to $L_n$, ($C_1$–$C_6$ alkyl)aryl optionally substituted with a bond to $L_n$, heteroaryl ($C_1$–$C_6$ alkyl)- optionally substituted with a bond to $L_n$, ($C_1$–$C_6$ alkyl)heteroaryl optionally substituted with a bond to $L_n$, biaryl($C_1$–$C_6$ alkyl)- optionally substituted with a bond to $L_n$, heteroaryl optionally substituted with a bond to $L_n$, aryl optionally substituted with a bond to $L_n$, biaryl optionally substituted with a bond to $L_n$, and a bond to $L_n$, wherein said aryl, biaryl or heteroaryl groups are also optionally substituted with 0–3 substituents selected from the group: $C_1$–$C_4$ alkyl, $C_1$–$C_4$ alkoxy, aryl, heteroaryl, halo, cyano, amino, $CF_3$, and $NO_2$;

$R^{18d}$ is selected from: —H, —$C(=O)$—$O$—$R^{17d}$, —$C(=O)$—$R^{17d}$, —$C(=O)$—$NH$—$R^{17d}$, —$SO_2$—$R^{17d}$, and —$SO_2$—$NR^{20d}R^{17d}$;

$R^{19d}$ is selected from: hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$
alkylcarbonyloxyalkyloxy, $C_3$–$C_{10}$
alkoxycarbonyloxyalkyloxy, $C_2$–$C_{10}$
alkoxycarbonylalkyloxy, $C_5$–$C_{10}$
cycloalkylcarbonyloxyalkyloxy, $C_5$–$C_{10}$
cycloalkoxycarbonyloxyalkyloxy, $C_5$–$C_{10}$
cycloalkoxycarbonylalkyloxy, $C_7$–$C_{11}$
aryloxycarbonylalkyloxy, $C_8$–$C_{12}$
aryloxycarbonyloxyalkyloxy, $C_8$–$C_{12}$
arylcarbonyloxyalkyloxy, $C_5$–$C_{10}$
alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, and $(R^{11d})(R^{12d})N$—($C_1$–$C_{10}$ alkoxy)-;

$R^{20d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;

$R^{21d}$ is selected from: COOH and $NR^{6d}_2$;

$m^d$ is 0–4;

$n^d$ is 0–4;

$t^d$ is 0–4;

$p^d$ is 0–2;

$q^d$ is 0–2; and $r^d$ is 0–2;

with the following provisos:

(1) $t^d$, $n^d$, $m^d$ and $q^d$ are chosen such that the number of atoms connecting $R^{1d}$ and $Y^d$ is in the range of 10–14; and (2) $n^d$ and $m^d$ are chosen such that the value of $n^d$ and $m^d$ is greater than one unless $U^d$ is —$(CH_2)_t^d Q^d (CH_2)_m^d$—;

or Q is a peptide selected from the group:

$R^1$ is L-valine, D-valine or L-lysine optionally substituted on the □ amino group with a bond to $L_n$;

$R^2$ is L-phenylalanine, D-phenylalanine, D-1-naphthylalanine, 2-aminothiazole-4-acetic acid or tyrosine, the tyrosine optionally substituted on the hydroxy group with a bond to $L_n$;

$R^3$ is D-valine;

$R^4$ is D-tyrosine substituted on the hydroxy group with a bond to $L_n$;

provided that one of $R^1$ and $R^2$ in each Q is substituted with a bond to $L_n$, and further provided that when $R^2$ is 2-aminothiazole-4-acetic acid, K is N-methylarginine;

provided that at least one Q is a compound of Formula Ia or Ib;

d is selected from 1, 2, 3, 4, 5, 6, 7, 8, 9, and 10;

$L_n$ is a linking group having the formula:

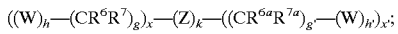

W is independently selected at each occurrence from the group: O, S, NH, NHC(=O), C(=O)NH, $NR^8C(=O)$, C(=O)N $R^8$, C(=O), C(=O)O, OC(=O), NHC(=S)NH, NEC(=O)NH, $SO_2$, $SO_2NH$, $(OCH_2CH_2)_{20-200}$, $(CH_2CH_2O)_{20-200}$, $(OCH_2CH_2CH_2)_{20-200}$, $(CH_2CH_2CH_2O)_{20-200}$, and $(aa)_r$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system having 1–4 heteroatoms independently selected from N, S, and O and substituted with 0–3 $R^{10}$;

$R^6$, $R^{6a}$, $R^7$, $R^{7a}$, and $R^8$ are independently selected at each occurrence from the group: H, =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)NH$R^{11}$, NHC(=O)NH$R^{11}$, NH$R^{11}$, $R^{11}$, and a bond to $S_f$;

$R^{10}$ is independently selected at each occurrence from the group: a bond to $S_f$, COOR$^{11}$, C(=O)NHR$^{11}$, NHC (=O)R$^{11}$, OH, NHR$^{11}$, $SO_3H$, $PO_3H$, —$OPO_3H_2$, —$OSO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system having 1–4 heteroatoms independently selected from N, S, and O and substituted with 0–3 $R^{11}$;

$R^{11}$ is independently selected at each occurrence from the group: H, alkyl substituted with 0–1 $R^{12}$, aryl substituted with 0–1 $R^{12}$, a 5–10 membered heterocyclic ring system having 1–4 heteroatoms independently selected from N, S, and O and substituted with 0–1 $R^{12}$, $C_{3-10}$ cycloalkyl substituted with 0–1 $R^{12}$, and a bond to $S_f$;

$R^{12}$ is a bond to $S_f$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

$S_f$ is a surfactant which is a lipid or a compound of the formula:

$A^9$ is selected from the group: OH and $OR^{27}$;

$A^{10}$ is $OR^{27}$;

$R^{27}$ is $C(=O)C_{1-20}$ alkyl;

$E^1$ is $C_{1-10}$ alkylene substituted with 1–3 $R^{28}$;

$R^{28}$ is independently selected at each occurrence from the group: $R^{30}$, —$PO_3H$—$R^{30}$, =O, —$CO_2R^{29}$, —$C(=O)R^{29}$, —$C(=O)N(R^{29})_2$, —$CH_2OR^{29}$, —$OR^{29}$, —$N(R^{29})_2$, $C_1$–$C_5$ alkyl, and $C_2$–$C_4$ alkenyl;

$R^{29}$ is independently selected at each occurrence from the group: $R^{30}$, H, $C_1$–$C_6$ alkyl, phenyl, benzyl, and trifluoromethyl;

$R^{30}$ is a bond to $L_n$;

or a pharmaceutically acceptable salt thereof.

2. A compound according to claim 1, wherein the compound is of the formula:

$$Q-L_n-S_f$$

wherein:

Q is a compound of Formula (Ia) or (Ib):

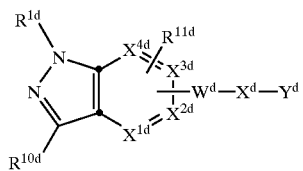
(Ia)

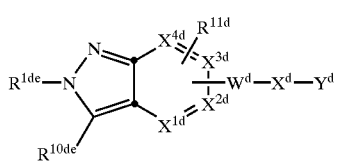
(Ib)

$R^{10de}$ is selected from:

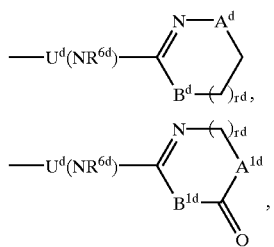

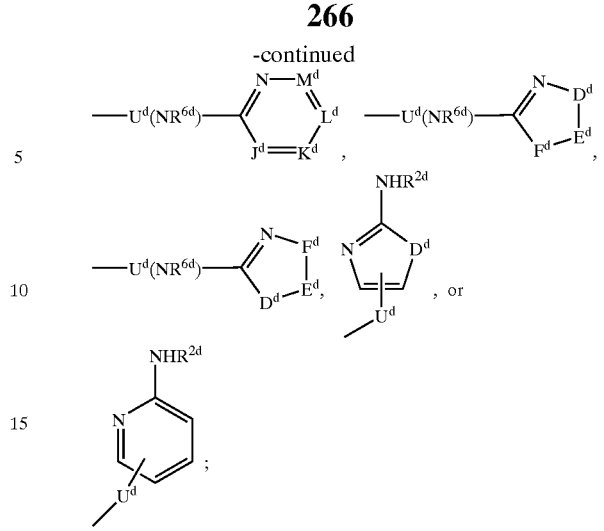

$A^d$ and $B^d$ are independently —$CH_2$—, —O—, —$N(R^{2d})$—, or —$C(=O)$—;

$A^{1d}$ and $B^{1d}$ are independently —$CH_2$— or —$N(R^{3d})$—;

$D^d$ is —$N(R^{2d})$—, —O—, —S—, —$C(=O)$— or —$SO_2$—;

$E^d$—$F^d$ is —$C(R^{4d})=C(R^{5d})$—, —$N=C(R^{4d})$—, —$C(R^{4d})=N$—, or —$C(R^{4d})_2C(R^{5d})_2$;

$J^d$, $K^d$, $L^d$ and $M^d$ are independently selected from: —$C(R^{4d})$—, —$C(R^{5d})$— and —N—, provided that at least one of $J^d$, $K^d$, $L^d$ and $M^d$ is not —N—;

$R^{2d}$ is selected from: H, $C_1$–$C_6$ alkyl, ($C_1$–$C_6$ alkyl)carbonyl, ($C_1$–$C_6$ alkoxy)carbonyl, $C_1$–$C_6$ alkylaminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl($C_1$–$C_6$ alkyl)-, ($C_1$–$C_6$ alkyl)carbonyl, arylcarbonyl, alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, and aryl($C_1$–$C_6$ alkoxy)carbonyl, wherein said aryl groups are substituted with 0–2 substituents selected from the group: $C_1$–$C_4$ alkyl, $C_1$–$C_4$ alkoxy, halo, $CF_3$, and nitro;

$R^{3d}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_1$–$C_6$ alkyl)-;

$R^{4d}$ and $R^{5d}$ are independently selected from: H, $C_1$–$C_4$ alkoxy, $NR^{2d}R^{3d}$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, $C_2$–$C_7$ alkylcarbonyl, and arylcarbonyl or alternatively, when substituents on adjacent atoms, $R^{4d}$ and $R^{5d}$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, and $NO_2$;

$U^d$ is selected from: —$(CH_2)_n{}^d$—, —$(CH_2)_n{}^d(CR^{7d}=CR^{8d})(CH_2)_m{}^d$—, —$(CH_2)_n{}^dQ^d(CH_2)_m{}^d$—, —$(CH_2)_n{}^dO(CH_2)_m{}^d$—, —$(CH_2)_n{}^dN(R^{6d})(CH_2)_m{}^d$—, —$(CH_2)_n{}^dC(=O)(CH_2)_m{}^d$—, and —$(CH_2)_n{}^dS(O)_p{}^d(CH_2)_m{}^d$—;

wherein one or more of the methylene groups in $U^d$ is optionally substituted with $R^{7d}$;

$Q^d$ is selected from 1,2-phenylene, 1,3-phenylene, 2,3-pyridinylene, 3,4-pyridinylene, and 2,4-pyridinylene;

$R^{6d}$ is selected from: H, $C_1$–$C_4$ alkyl, and benzyl;

$R^{7d}$ and $R^{8d}$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, and heteroaryl($C_0$–$C_6$ alkyl)-;

$W^d$ is —C(=O)—N($R^{13d}$)—(C($R^{12d}$)$_2$)$_q{}^d$—;

$X^d$ is —C($R^{12d}$)($R^{14d}$)—C($R^{12d}$)($R^{15d}$)—;

alternatively, $W^d$ and $X^d$ can be taken together to be

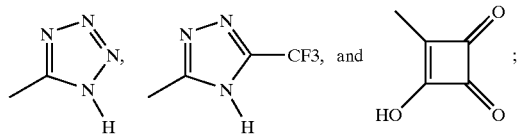

$R^{12d}$ is H or $C_1$–$C_6$ alkyl;

$Y^d$ is selected from: —COR$^{19d}$, —SO$_3$H,

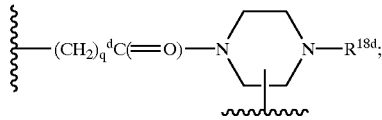

Z is selected from the group: aryl substituted with 0–1 $R^{10}$, $C_{3-10}$ cycloalkyl substituted with 0–1 $R^{10}$, and a 5–10 membered heterocyclic ring system having 1–4 heteroatoms independently selected from N, S, and O and substituted with 0–1 $R^{10}$;

$R^6$, $R^{6a}$, $R^7$, $R^{7a}$, and $R^8$ are independently selected at each occurrence from the group: H, =O, COOH, SO$_3$H, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)$R^{11}$, C(=O)NHR$^{11}$, NHC(=O)NHR$^{11}$, NHR$^{11}$, $R^{11}$, and a bond to $S_f$;

k is 0 or 1;

$S_f$ is a surfactant which is a lipid or a compound of the formula:

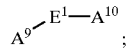

$A^9$ is OR$^{27}$;

$A^{10}$ is OR$^{27}$;

$R^{27}$ is C(=O)$C_{1-5}$ alkyl;

$E^1$ is $C_{1-4}$ alkylene substituted with 1–3 $R^{28}$;

$R^{28}$ is independently selected at each occurrence from the group: $R^{30}$, —PO$_3$H—$R^{30}$, =O, —CO$_2R^{29}$, —C(=O)$R^{29}$, —CH$_2$OR$^{29}$, —OR$^{29}$, and $C_1$–$C_5$ alkyl;

$R^{29}$ is independently selected at each occurrence from the group: $R^{30}$, H, $C_1$–$C_6$ alkyl, phenyl, and benzyl;

$R^{30}$ is a bond to $L_n$;

or a pharmaceutically acceptable salt thereof.

3. A compound according to claim 2, wherein the present invention provides a compound selected from the group:

DPPE-2-(6-aminohexanoylamino)-3-((1-(3-(imidazol-2-ylamino)propyl)(1H-indazol-5-yl))carbonylamino) propanoic acid-dodecanoate conjugate;

ω-amino-PEG$_{3400}$-2-(6-aminohexanoylamino)-3-((1-(3-(imidazol-2-ylamino)propyl)(1H-indazol-5-yl)) carbonyl-amino)propanoic acid; and ω-amino-PEG$_{3400}$-Glu-(2-(6-amindohexanoylamino)-3-((1-(3-(imidazol-2-ylamino)-propyl)(1H-indazol-5-yl)) carbonyl-amino)propanoic acid)$_2$.

* * * * *